(12) United States Patent
Alessi et al.

(10) Patent No.: US 7,122,360 B1
(45) Date of Patent: Oct. 17, 2006

(54) POLYPEPTIDES, POLYNUCLEOTIDES AND USES THEREOF

(75) Inventors: Dario Alessi, Dundee (GB); Marin Deak, Dundee (GB); Philip Cohen, Dundee (GB); Matilde Caivano, Dundee (GB)

(73) Assignee: University of Dundee, Dundee (GB)

( * ) Notice: Subject to any disclaimer, the term of this patent is extended or adjusted under 35 U.S.C. 154(b) by 0 days.

(21) Appl. No.: 09/720,582

(22) PCT Filed: Jun. 8, 1999

(86) PCT No.: PCT/GB99/01660

§ 371 (c)(1),
(2), (4) Date: Jul. 26, 2001

(87) PCT Pub. No.: WO99/67283

PCT Pub. Date: Dec. 29, 1999

(30) Foreign Application Priority Data

Jun. 24, 1998 (GB) ............................ 9813467.9
Aug. 10, 1998 (GB) ............................ 9817303.2

(51) Int. Cl.
- C12N 9/12 (2006.01)
- C12N 1/20 (2006.01)
- C12N 15/00 (2006.01)
- C07K 1/00 (2006.01)
- C07H 21/04 (2006.01)

(52) U.S. Cl. .................... 435/194; 435/4; 435/7.1; 435/69.1; 435/183; 435/252.3; 435/320.1; 435/810; 530/300; 530/324; 530/350; 536/23.2

(58) Field of Classification Search ............... 435/183, 435/194, 4, 7.1, 69.1, 252.3, 320.1, 810; 530/300, 324, 350; 536/23.2
See application file for complete search history.

(56) References Cited

U.S. PATENT DOCUMENTS 5,643,758 A * 7/1997 Guan et al. ............... 435/69.7

FOREIGN PATENT DOCUMENTS

| WO | WO 93/14081 | 7/1993 |
| WO | WO 93/19752 | 10/1993 |
| WO | WO 94/14977 | 7/1994 |
| WO | WO 95/02591 | 1/1995 |
| WO | WO 96/41645 | 12/1996 |
| WO | WO 97/44467 | 11/1997 |
| WO | WO 98/03662 | 1/1998 |

OTHER PUBLICATIONS

Wilkinson. Accession Q18846. Nov. 1, 1996.*
Alcorta et al. Accession P18652. Nov. 1, 1990.*
Bjoerbaek et al. Accession P51812. Oct. 1, 1996.*
Chrestensen et al. Acession P18654; Q03140; Q8K3J8. Nov. 1, 1990.*
Grove et al. Accession A53300. Jul. 2, 1996.*
Broun et al. Science. Nov. 13, 1998;282(5392):1315-7.*
Zhao et al. Mol Cell Biol. Aug. 1995;15(8):4353-63.*
Zhao et al. Accession A57459. Feb. 16, 1996 (RESULT 2).*
Zhao et al. Accession A57459. Feb. 16, 1996 (RESULT 7).*
Database EMEST2 Accession No. AA678670 (Dec. 4, 1997).
Database EMEST27 Accession No. AA314565 (Apr. 18, 1997).
Database EMEST28 Accession No. AA472165 (Jun. 21, 1997).
Sequence database (GenBank) entries listed on Appendix 1.
Alessi et al., Methods in Enzymol 255:279-290 (1995).
Alessi et al., J Biol Chem 270:27489-27494 (1995).
Alessi et al., FEBS Lett 399:333-338 (1996).
Alessi et al., EMBO J 15:6541-6551 (1996).
Alessi, FEBS Lett 402:121-123 (1997).
Andersson et al., J Biol Chem 264:8222-8229 (1989).
Appleby et al., Biochem J 302:723-727 (1994).
Ben-Levy et al., EMBO J 14:5920-5930 (1995).
Bjorbaek et al., J Biol Chem 270:18848-18852 (1995).
Botting, DN&P 9(2):123-128 (1996).
Caivano, FEBS Lett 429:249-253 (1998).
Chandra et al., J Immunol 155:4535-4543 (1995).
Chen et al., Mol Cell Biol 12:915-927 (1992).
Clifton et al., FEBS Lett 392:209-214 (1996).
Cohen, Trends Cell Biol 7:353-361 (1997).
Cross et al., Biochem J 303:21-26 (1994).
Cross et al., Nature 378:785-789 (1995).
Cuenda et al., FEBS Lett 364-229-233 (1995).
Cuenda et al., EMBO J 16:295-305 (1997).
Dalby et al., J Biol Chem 273:1496-1505 (1998).
Davis et al., FEBS Lett 259:61-63 (1989).
Deak et al., EMBO J 17:4426-4441 (1998).
Dubois et al., FASEB J 12:1063-1073 (1998).
Engelman et al., J Biol Chem 273:32111-32120 (1998).
Favata et al., J Biol Chem 273:18623-18632 (1998).
Freshney et al., Cell 78:1039-1049 (1994).
Fukunaga et al., EMBO J 16:1921-1933 (1997).
Gallagher et al., Bioorg Med Chem 5:49-64 (1997).
Ginty et al., Cell 77:713-725 (1994).
Goedert et al., EMBO J 16:3563-3571 (1997).
Gonzalez et al., Nature 337:749-752 (1989).
Gonzalez et al., Cell 59:675-680 (1989).
Guan et al., J Biol Chem 273:12901-12908 (1998).
Hanks et al., Science 241:42-52 (1988).

(Continued)

Primary Examiner—Tekchand Saidha
Assistant Examiner—Christian L. Fronda
(74) Attorney, Agent, or Firm—Rogalskyj & Weyand, LLP

(57) ABSTRACT

Substantially pure two kinase domain protein kinases comprising the amino acid sequences provided in the description, variants, fusions, fragments, or derivatives thereof useful in screening assays for drugs. Applications thereof in the modulation of CREB, COX2 and IL2 activities.

17 Claims, 34 Drawing Sheets

OTHER PUBLICATIONS

Figure 4:
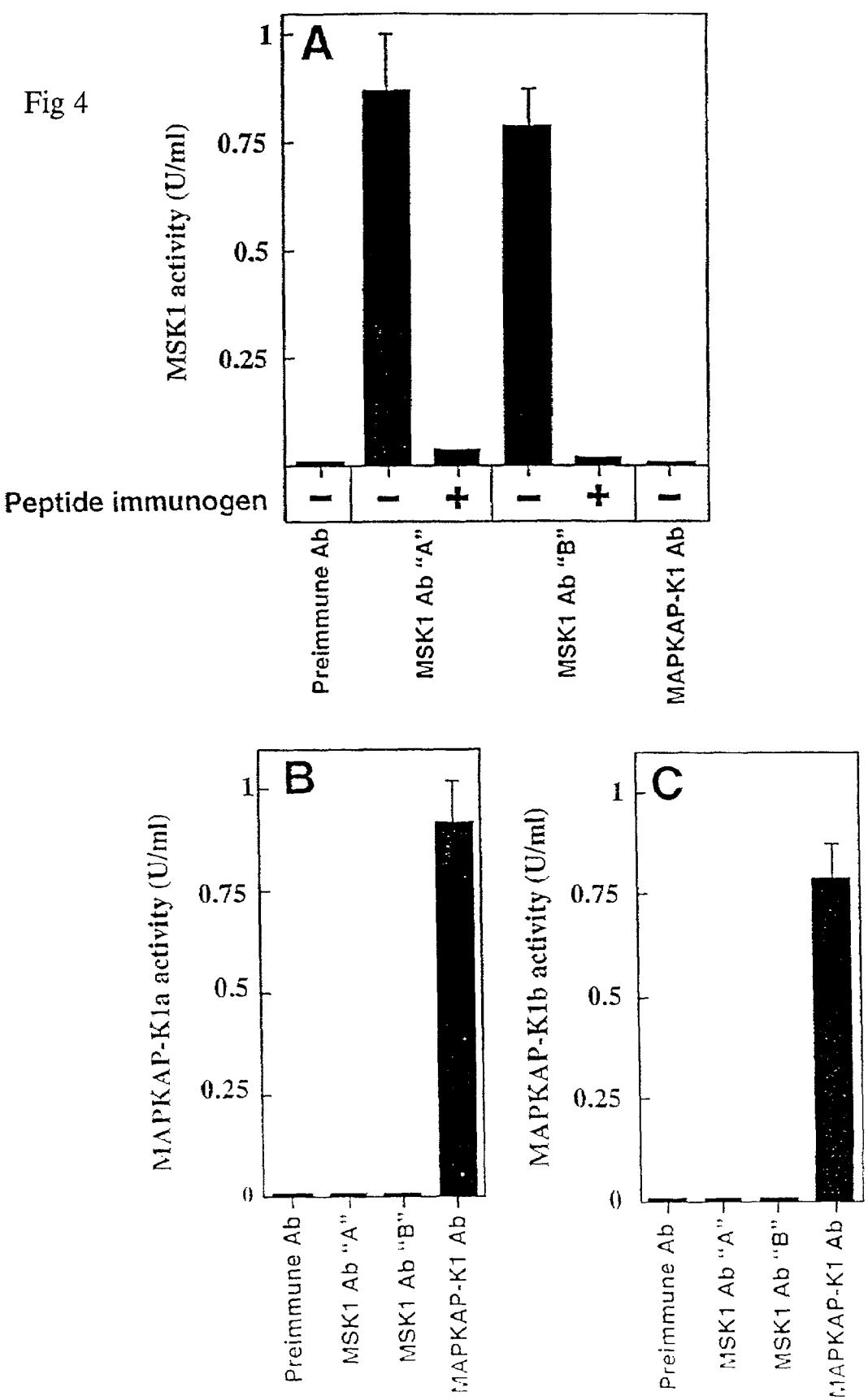

Hwang et al., Biochem Pharmacol 54:87-96 (1997).
Iordanov et al., EMBO J 16:1009-1022 (1997).
Kim et al., J Biol Chem 273:27686-27694 (1998).
Lapointe et al., Hypertension 33:276-282 (1999).
Lawler et al., FEBS Lett 414:153-158 (1997).
Leighton et al., FEBS Lett 375:289-293 (1995).
Lennon et al., Genomics 33:151-152 (1996).
Marshall et al., J Biol Chem 262:3510-3517 (1987).
McLaughlin et al., J Biol Chem 271:8488-8492 (1996).
Mitchell et al., Proc Natl Acad Sci USA 90:11693-11697 (1994).
Montminy, Annu Rev Biochem 66:807-822 (1997).
Nakajima et al., Proc Natl Acad Sci USA 90:2207-2211 (1993).
New et al., J Biol Chem 274:1026-1032 (1999).
Pende et al., J Neurosci 17:1291-1301 (1997).
Pierrat et al., J Biol Chem 273:29661-29671 (1998).
Pouliot et al., J Immunol 158:4930-4937 (1997).
Pulkkinen, Drugs 46(suppl 1):129-133 (1993).
Reiser et al., Biochem J 330:1107-1114 (1998).
Robbins et al., Cell 64:615-623 (1991).
Rouse et al., Cell 78:1027-1037 (1994).
Sanchez et al., Nature 372:794-798 (1994).
Slater et al., Biochem Biophys Res Commun 198:304-308 (1994).
Slater et al., Biochem Biophys Res Commun 203:67-71 (1994).
Slater et al., Am J Obstet Gynecol 172:77-82 (1995).
Stokoe et al., Biochem J 296:843-849 (1993).
Sturgill et al., Nature 334:715-718 (1988).
Sutherland et al., Eur J Biochem 212:581-588 (1993).
Tan et al., EMBO J 15:4629-4642 (1996).
Teixeira et al., J Clin Endocrinol Metabol 78:1396-1402 (1994).
Tong et al., Nature Struct Biol 4:311-316 (1997).
Trivier et al., Nature 384:567-570 (1996).
Tsukada et al., Mol Cell Biol 14:7285-7297 (1994).
Vik et al., Biochem Biophys Res Commun 235:398-402 (1997).
Wang et al., J Biol Chem 273:9373-9377 (1998).
Waskiewicz et al., EMBO J 16:1909-1920 (1997).
Xing et al., Science 273:959-963 (1996).
Xing et al., Mol Cell Biol 18:1946-1955 (1998).
Zhao et al., Mol Cell Biol 15:4353-4363 (1995).

* cited by examiner

Fig 2A page 2 of 2

```
(46)   IENFELLKVLGTGAYGKVFLVRKISGHDTGKLYAMKVLKKATIVQKAKTTEHTRTERQVLEHIRQSPFLVTLHYAFQ (1)
(423)  YDEDLKDKPLGEGSFSICRKCVHKK---SNQAFAVKIISKRM---EANT----QKEITALKLCEGHENLVKLHEVSH (2)
(43)   YKVT--SQVMGLGINGKVLQIFNKR----TQEKFALKMLQDCP-------KA--RREVELHWRASQCEHIVRIVDVYE (3)
(63)   YQES--KQVLGLGVNGKVLECFHRR----TGQKCALKLLYDSP-------KA--RQEVDHHWQASGEHIVCILDVYE (4)
(48)   YKLT---SELIGEGAYAKVQGAVSLQ---NGKEYAVKIIEKQAGHSRSRV----FREVETEYQCQGNKILEIEFEE (5)

TETK----LHLILDYINGGELFTHLSQR----ERFTEHEVQIYVGEIVLALEHLQKLGFIYRDIKLENILLDS---NGHVVLTDE (1)
DQLH----TFEVMELENGGELRFHLSERIKKK--KHFSEIASYIMRKLVSAVSHMHDVGVVHRDLKPENLIFTDENDLEIKLIDE (2)
NLYAGRKCLIVMECLDGGELFSRIQDRGDQAFTEREASEIVKSLGEAIQYLHSINIAHRDVKPENLLYTSKRPNAILKLTDE (3)
NMHHGKRCLIIMECMEGGELFSRIQERGDQAFTEREAAEINRDLGTAIQFLHSHNIAHRDVKPENLLYTSKEKDAVLKLTDE (4)
DDTR----FYLVFEKLQGGSILAHIQKQ--KHGNEREASRVVRDVAAALDFLHTKGIAHRDLKPENILCESPEKVSPVKICDE (5)

GLSKEFVADET-----ERAYSFCGTIEYMAPDIVRGGDSG---HDKAVDWWSLGVLMYELTGASPET-VDGEKNSQ----- (1)
GEFARLKPPDNQ----PLKTPCFTLHYAAPELEN--QNG---YDESCDLMSIGVILYTMLSGQVPFQSHDRSLICTS---- (2)
GEFAKETTSHN----SLTTPCYTPYYVAPEVLG--PEK---YDKSCDMMSLGVIMYILLCGYPPFYSNHGLAISP----- (3)
GEFAKETT-QN----ALQTPCYTPYYVAPEVLG--PEK---YDKSCDMMSLGVIMYIMLCGFPPFYSNTGQAISP----- (4)
DLGSGMKLNSCTPITTPELTTPCGSAEYMAPEVVEVFTDQATFYDKRCDLISLGVVLYIMLSGYPPFYGADCGWDR---- (5)

-------AEISRRILKSEPPYP-----QEMSALAKDITQRELMKDFKKLGCGPRDADEIKEHLFFQKINWDDLAAKK (1)
AVEIMKKILKGDFSEGEAWKNVSQEAKDILQGILLTVDPNKRLKMSGLRYNEWLQDGSQLSSNFLMTPDIL (2)
--------MKTRIRMGQYEFPNPEWSEVSEEVKMLIRNLLKTEPTQRMTITEFMNHPWIMQSTKVFQTPLHTSRVL (3)
--------MKRRIRLGQKGEPNPEWSEVSEDAKVIRLLLKTDPTERLTITQFMNHPWINQSMVVFQTPLHTARVL (4)
G-------GEVCRVCQNKLFESLQEGKYEFPDKDWAHISSEAKYMAPEVVRDAKQRLSAAQVLQHPWIVQG--QAFEKGLPTPQVL (5)

(1) MSK1-N    (SEQ ID NO:32)
(2) MSK1-C    (SEQ ID NO:33)
(3) MAPKAP-K2 (SEQ ID NO:41)
(4) MAPKAP-K3 (SEQ ID NO:42)
(5) MNK1      (SEQ ID NO:43)
```

Fig 2B

```
MSK1    MEEEGGSSGGAAGTSADGGDGGEQLLTVKHELRTANILTGHAEKVGIENHELLKVLGTGAYKVFLVRKISGHDTGKLYAMK
mMSK2   --------------------HASGDEDEGCAVELQITEANILTGHEEKVSVENPALLKVLGTGAYKVFLVRKTGHDAGKLYAMK
MSK2    --------------------------------------------------------------------------------

MSK1    VLKKATIVQKAKTTEHTRTERQVLEHIRQSPFLVTLHYA 120 FQTETKLHLILDYINGGELFTHLSQREREFTEHEVQIYVG
mMSK2   VLRKATVQKAKTQEHTRTERSVLELVRQAPFLVTLHYA 106 FQTDAKLHLILDYVSGGEMFTHLYQRQYEKEAEVRVYGG
MSK2    --------------------------------------------------------------------------------

MSK1    EIVLALEHLHKLGIIYRDIKLENIELDSNGHVLTDFGLSKEFVADETERAYSFCGTIEYMAPDIVRGGDSGHDKAVDWWS
mMSK2   EIVLALEHLHKLGIIYRDLKLENVLLDSEGHIVLTDFGLSKEELTEEKERTFSFCGTIEYMAPEIIRS-KAGHGKAVDWWS
MSK2    --------------------------------------------------------------------------------

MSK1    LGVLMYELITGASPFTVDGEKNSQAEISRRIILKSEPPYPQEMSALAKDLIQRLLMKDPKKRLGCPPRDADEIKEHLFE
mMSK2   LGILFELLTGASPFTLEGERNTQAEVSRRIILKCSPPFPLRIGPVAQDLLQRLLCKDPKKRLGAGPQGAQEVKSHPFF
MSK2    --------------------QTEVSRRIILKCSPPFPPRIGPVAQDLLQRLLCKDPKKRLGAGPQGAQEVRNHPFF

MSK1    QK-INTDDLAAKKVPAPEKPVIRDELDVSNFAEEFTEMDPTY 359 SPAALPQSSE-KIFQGYSFVAPSILFKRNAAVI-Dp
mMSK2   RVWTGW-ALAARKIPAPFRPQIRSELDVGNFAEEFTRLEPVY 344 SPAGSPPPGDPRIFQGYSFVAPSILFDHNNAVMADV
MSK2    QGL-DWVALAARKIPAPFRPQIRSELDVGNEAEEFTRLEPVY 96 SPPGSPPPGDPRIFQGYSFVAPSILFDHNNAVMTDG

MSK1    LQFHMGVERPGVTNVARSAMKDSPFYQHYDLKDKPLGEGSFSICRKCVHKKSNQAFAVKIISKRMEANTQKEITALKI
mMSK2   LQAPGAGYRPGRAAVARSAMQDSPFFQQYEIDLIREPALGQGSFEAVKILSRRLEENTQREVAALRL
MSK2    LEAPGAGDRPGRAAVARSAMQDSPFFQQYEIDLIREPALGQGSFEAVKILSRRLEANTQREVAALRI

MSK1    CEG 477 HPNIVKLHEVFHDQLHTFLVMELLNGGELFERIKKKHFSETEASYIMRKLVSAVSHMHD-VGVVHRDLKPENLL
mMSK2   CQS 464 HPNVVNLHEVLHDQLHTYLVLELLRGGELLEHIRKKHFSESEASQILRSLVSAVSFMHEEAGVVHRDLKPENIL
MSK2    CQS 216 HPNVVNLHEVHHDQLHTYIVLELLRGGELLEHIRKKRHFSESEASQILRSLVSAVSFMHEEAGVVHRDLKPENIL
```

Fig 2C page 1 of 2

```
MSK1   FTDENDNLEIKIIDEGEARLKPPD-NQPLKTPCFFTLHYAAPELLN 595
nMSK2  YADDTPGAPVKIIDEGFARLRPQSPAEPMQTPCFTLQYAAPELLA 584
MSK2   YADDTPGAPVKIIDEGFARLRPQSPGVPMQTPCFTLQYAAPELLA 336
                                  *

MSK1   LTCTSAVEIMKKIKKGDFSPEGEAWKNVSQEAKDLIQGLLTVDPNKRLKMSGLRYNEWLQDGSQLSSNPIMTPDILGSSG
nMSK2  GGQSQAAEIMCKIREGRFSILDGEAMQGVSEEAKELVRGLLTVDPAKRLKLEGLRSSSWLQDGSARSSPPLRTPDVLESSG
MSK2   GGQXQAAEIMCKIREGRFSILDGEAMQGVSEEAKELVRGLLTVDPAKRLKLEGLRGSSWLQDGSARSSPPLRTPDVLESSG

MSK1   AAVHTCV 715  KATEHAENKYKREGFCLQNVDKAPIAKRRKMKKTSTSTETRSSSESSHSSSSHSGKTTPTKTLQPSNP
mMSK2  PAVRSGL 704  NATEMAFNRGKREGFFLKSVENAPIAKRRKQKLRSA                                 740  (SEQ ID NO:44)
MSK2   PAVRSGL 456  NATEMAFNRGKREGFFLKSVENAPINCHFMDCLCNYVHQRPVLGVLKERPWGTL               510  (SEQ ID NO:45)

MSK1   ADSNNPETLFQFSDSVA  802  (SEQ ID NO:1)
```

Fig 2C page 2 of 2

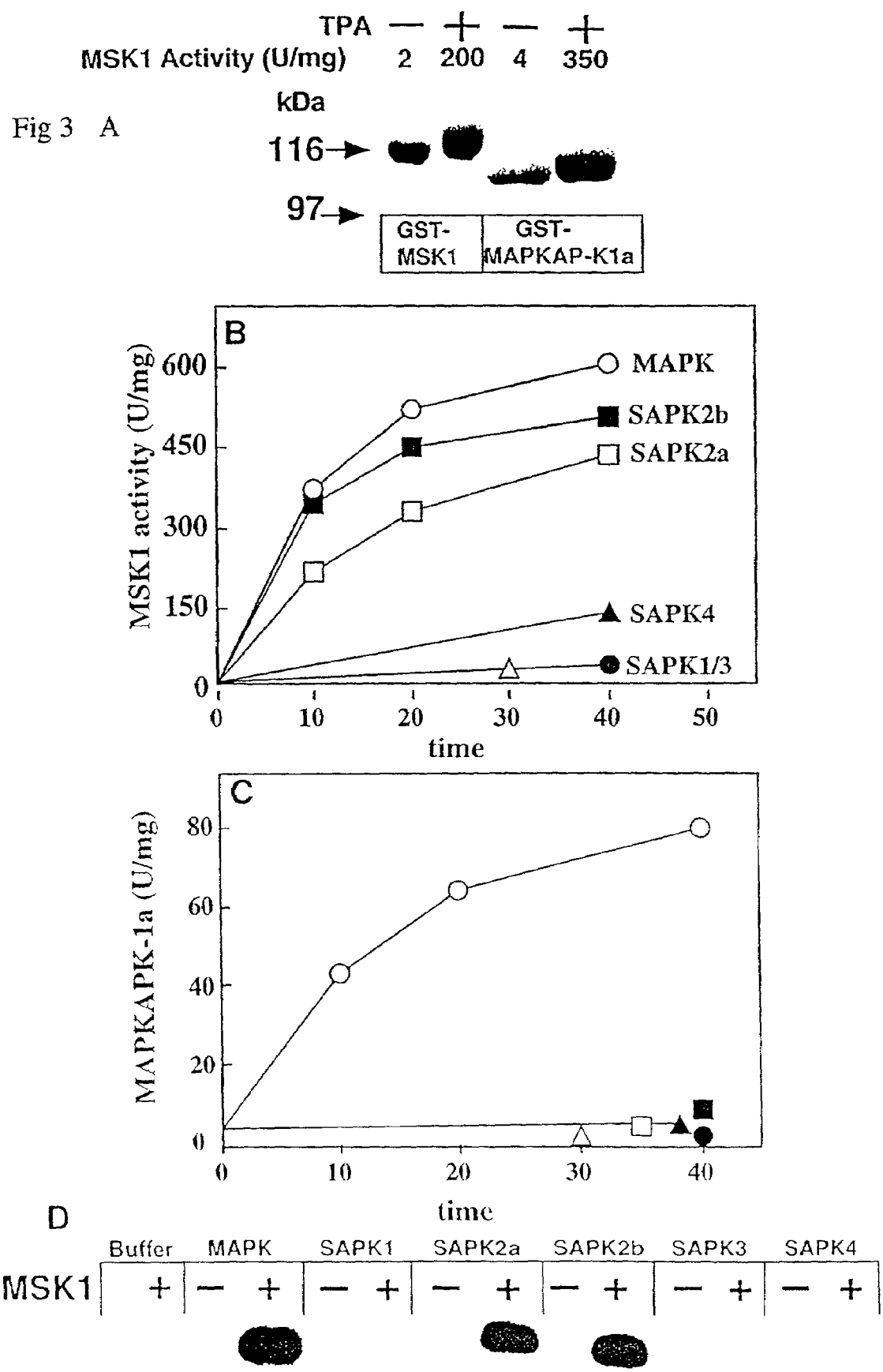

Figure 8:
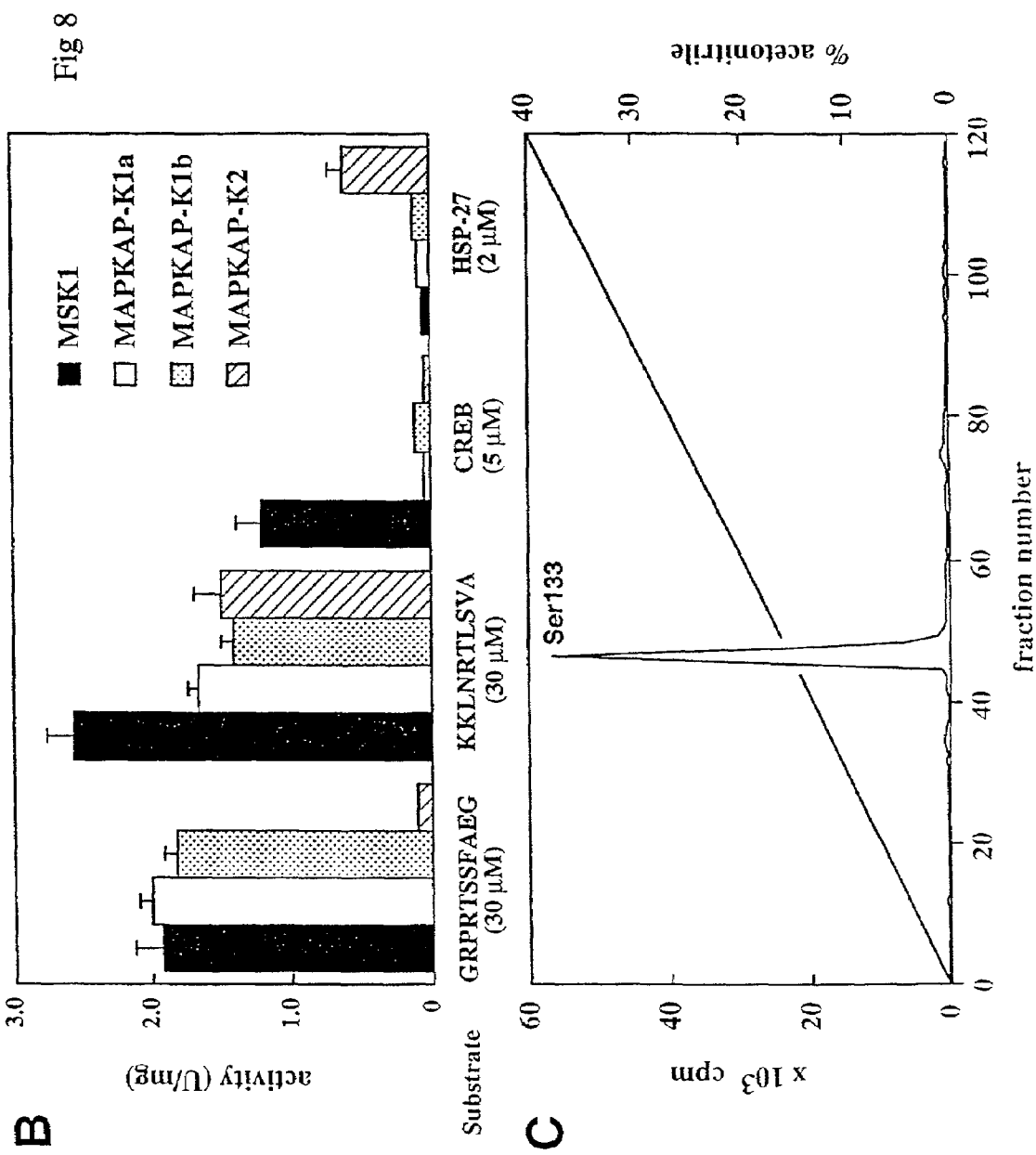

Fig 8  page 1 of 2

A

| | | MSK1 | | MAPKAP-K1a | | MAPKAP-K1b | |
|---|---|---|---|---|---|---|---|
| | | Km (µM) | Vmax (%) | Km (µM) | Vmax (%) | Km (µM) | Vmax (%) |
| 1. | GRPRTSSFAEG | 2 | 100 | 3 | 100 | 2 | 100 |
| 2. | KKRNRTLSVA | 0.2 | 100 | 3 | 100 | 1 | 225 |
| 3. | KKRNKTLSVA | 25 | 75 | 250 | 86 | 160 | 106 |
| 4. | KKLNRTLSVA | 0.3 | 150 | 15 | 100 | 5 | 175 |
| 5. | EILSRRPSYRK | <0.1 | 100 | 20 | 64 | 25 | 188 |
| 6. | CREB PROTEIN | 2.5 | 80 | >50 | ~15 | 30 | ~20 |

(1.) SEQ ID NO:16
(2.) SEQ ID NO:17
(3.) SEQ ID NO:34
(4.) SEQ ID NO:35
(5.) SEQ ID NO:18

Fig 12
A 5 min
TNF   − + + + + + + + +
SB   − − − + + − − + +
PD   − − − − − + + + +
10 sec exp. 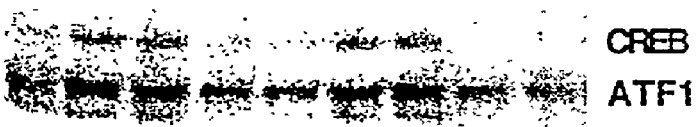 CREB / ATF1
30 sec exp.  CREB / ATF1
B 15 min
TNF   − + + + + + + + +
SB   − − − + + − − + +
PD   − − − − − + + + +
10 sec exp.  CREB / ATF1
C 15 min
TNF   − + + + +
Ro   − − − + +
10 sec exp. 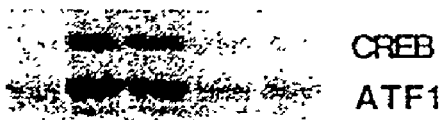 CREB / ATF1

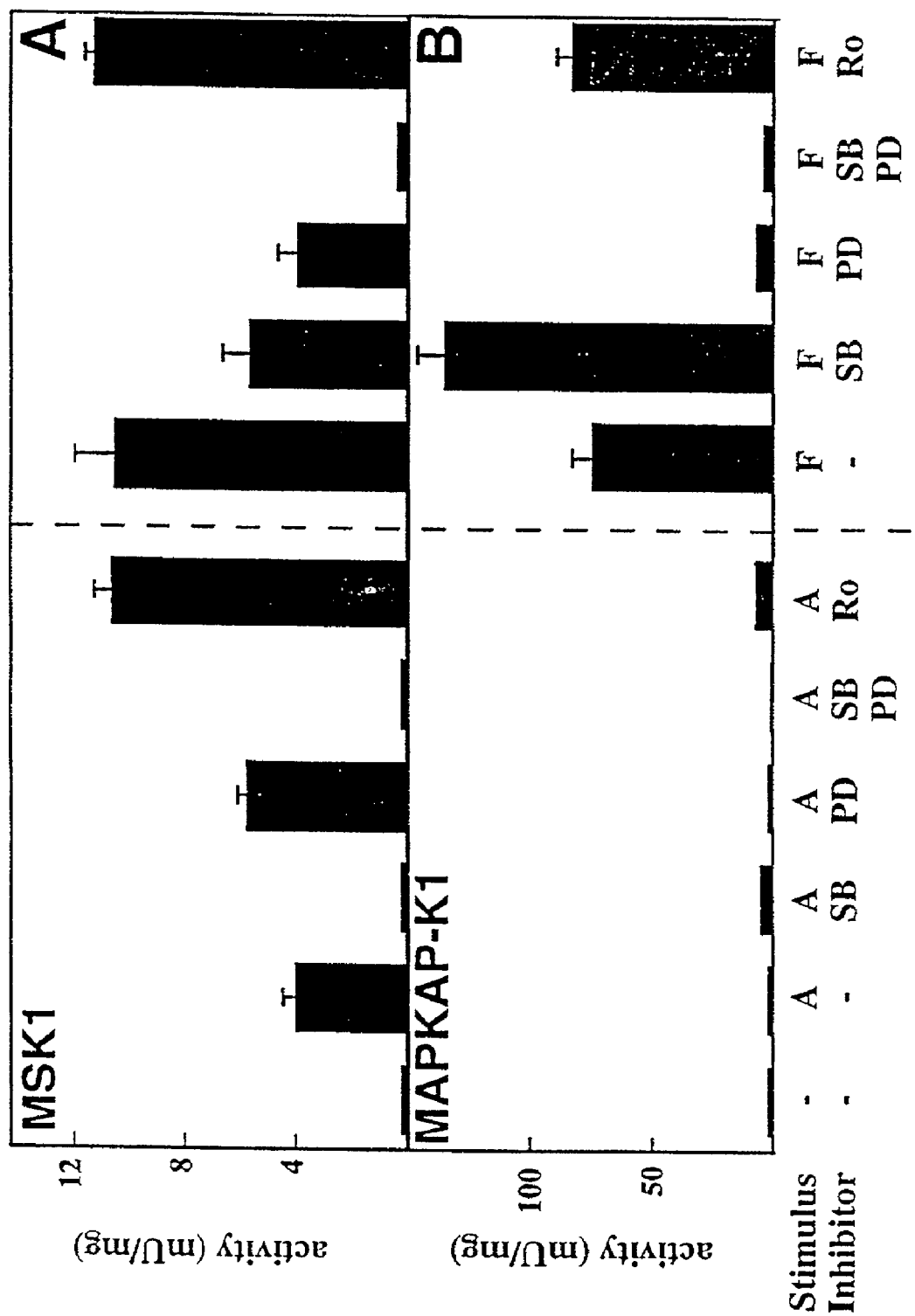
Fig 14 page 1 of 2

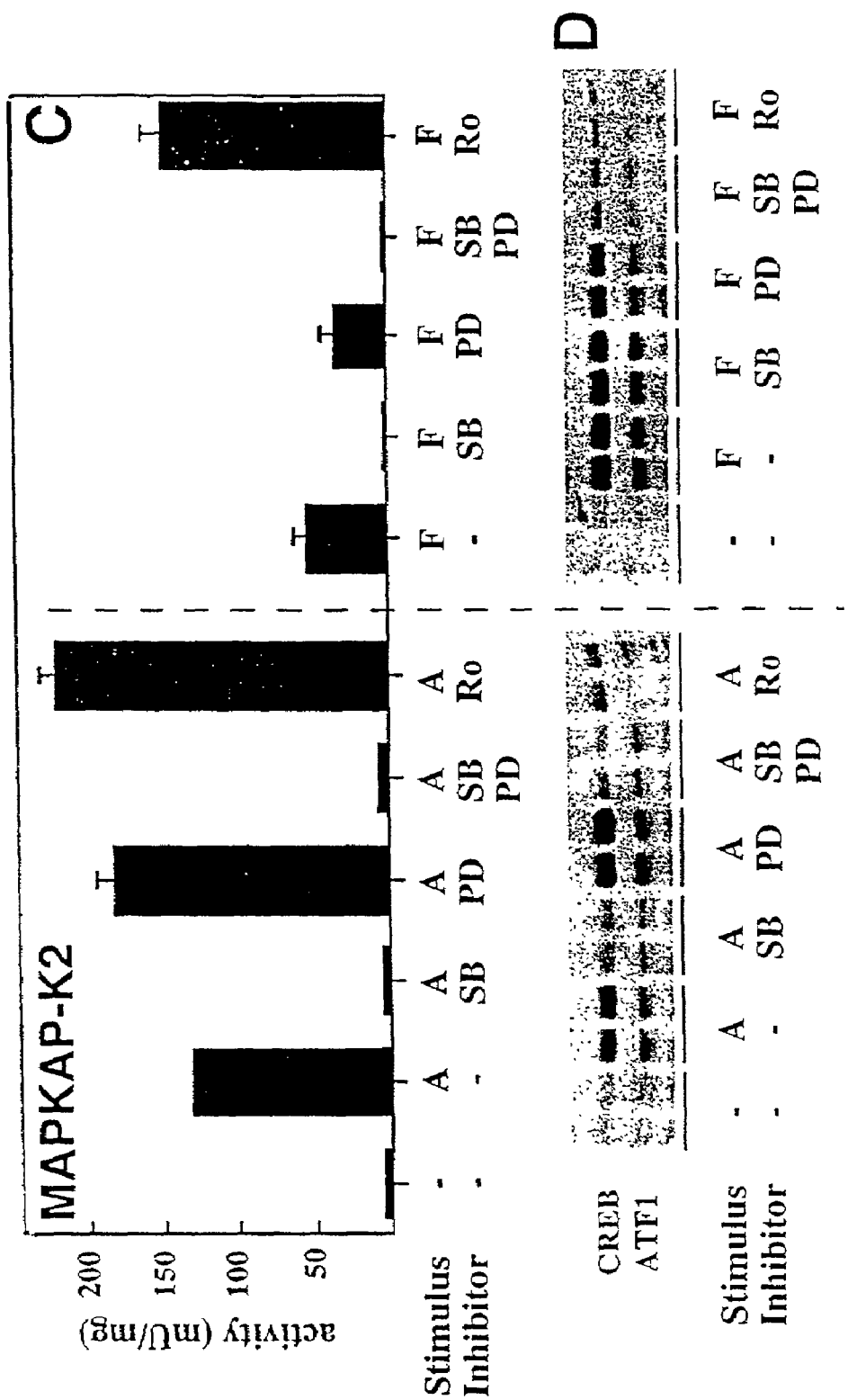
Fig 14 page 2 of 2

Figure 16 page 1 of 4

MSK2 amino acid sequence ( 705 aa) (SEQ ID NO:2)

TEANLTGHEEKVSVENFELLKVLGTGAYGKVFLVRKAGGHDAGKLYA
MKVLRKAALVQRAKTQEHTRTERSVLELVRQAPFLVTLHYAFQTDAK
LHLILDYVSGGEMFTHLYQRQYFKEAEVRVYGGEIVLALEHLHKLGI
IYRDLKLENVLLDSEGHIVLTDFGLSKEFLTEEKERTFSFCGTIEYM
APEIIRSKTGHGKAVDWWSLGILLFELLTGASPFTLEGERNTQAEVS
RRILKCSPPFPPRIGPVAQDLLQRLLCKDPKKRLGAGPQGAQEVRNH
PFFQGLDWVALAARKIPAPFRPQIRSELDVGNFAEEFTRLEPVYSPP
GSPPPGDPRIFQGYSFVAPSILFDHNNAVMTDGLEAPGAGDRPGRAA
VARSAMMQQYELDLREPALGQGSFSVCRRCRQRQSGQEFAVKILSRR
LEANTQREVAALRLCQSHPNVVNLHEVHHDQLHTYLVLELLRGGELL
EHIRKKRHFSESEASQILRSLVSAVSFMHEEAGVVHRDLKPENILYA
DDTPGAPVKIIDFGFARLRPQSPGVPMQTPCFTLQYAAPELLAQQGY
DESCDLWSLGVILYMMLSGQVPFQGASGQGGQSQAAEIMCKIREGRF
SLDGEAWQGVSEEAKELVRGLLTVDPAKRLKLEGLRGSSWLQDGSAR
SSPPLRTPDVLESSGPAVRSGLNATFMAFNRGKREGFFLKSVENAPL

MSK2 DNA sequence ( 2116 bp) (SEQ ID NO:11)

ACCGAAGCCAACCTGACCGGGCACGAGGAGAAGGTGAGCGTGGAGAA
CTTCGAGCTGCTCAAGGTGCTGGGCACGGGAGCCTACGGCAAGGTGT
TCCTGGTGCGGAAGGCGGGCGGGCACGACGCGGGGAAGCTGTACGCC
ATGAAGGTGCTGCGCAAGGCGGCGCTGGTGCAGCGCGCCAAGACGCA
AGAGCACACGCGCACCGAGCGCTCGGTGCTGGAGCTGGTGCGCCAGG
CGCCCTTCCTGGTCACGCTGCACTACGCTTTCCAGACGGATGCCAAG
CTGCACCTCATCCTGGACTATGTGAGCGGCGGGGAGATGTTCACCCA
CCTCTACCAGCGCCAGTACTTCAAGGAGGCTGAGGTGCGCGTGTATG
GGGGTGAGATCGTGCTGGCCCTGGAACACCTGCACAAGCTCGGCATC
ATTTACCGAGACCTGAAACTGGAGAATGTGCTGCTGGACTCCGAGGG
CCACATTGTCCTCACGGACTTCGGGCTGAGCAAGGAGTTCCTGACGG
AGGAGAAGAGCGGACCTTCTCCTTCTGTGGCACCATCGAGTACATG
GCCCCCGAAATCATCCGTAGCAAGACGGGGCATGGCAAGGCTGTGGA
CTGGTGGAGCCTGGGCATCTTGCTCTTCGAGCTGCTGACGGGGGCCT
CGCCCTTCACCCTGGAGGGCGAGAGGAACACGCAGGCTGAGGTGTCT
CGACGGATCCTGAAGTGCTCCCCTCCCTTCCCCCCTCGGATCGGGCC
CGTGGCGCAGGACCTGCTGCAGCGGCTGCTTTGTAAGGATCCTAAGA
AGCGATTGGGCGCGGGGCCCCAGGGGGCACAAGAAGTCCGGAACCAT
CCCTTCTTCCAGGGCCTCGATTGGGTGGCTCTGGCTGCCAGGAAGAT
TCCAGCCCCATTCCGGCCCCAAATCCGCTCAGAGCTGGATGTGGGCA
ACTTTGCGGAGGAATTCACTCGGCTGGAGCCTGTCTACTCACCCCCT
GGCAGCCCCCCACCTGGGGACCCCCGAATCTTTCAGGGATACTCCTT
TGTGGCACCCTCCATTCTCTTTGACCACAACAACGCGGTGATGACCG
ATGGGCTGGAAGCGCCTGGTGCTGGAGACCGGCCAGGTCGGGCAGCG

```
GTGGCCAGGAGCGCTATGATGCAGCAGTACGAGCTGGACCTGCGGGA
GCCTGCGCTGGGCCAGGGCAGCTTTTCTGTGTGTCGCCGCTGCCGCC
AGCGCCAGAGCGGCCAGGAGTTCGCAGTCAAGATCCTCAGTCGCAGG
CTGGAGGCGAACACGCAGCGCGAAGTGGCTGCCCTGCGCCTGTGCCA
GTCACACCCCAACGTGGTGAATCTGCACGAGGTGCATCACGACCAGC
TGCACACGTACCTGGTCCTGGAGCTGCTGCGGGGCGGGAGCTGCTG
GAGCACATCCGCAAGAAGCGGCACTTCAGCGAGTCGGAAGCAAGCCA
GATCCTGCGCAGCCTCGTGTCGGCCGTGAGCTTCATGCACGAGGAGG
CGGGCGTGGTGCACCGCGACCTCAAGCCGGAGAACATCCTGTACGCC
GACGACACGCCCGGGGCCCCGGTGAAAATCATCGACTTCGGGTTCGC
GCGGTTGCGGCCGCAGAGTCCCGGGGTGCCCATGCAGACGCCCTGCT
TCACGCTGCAGTACGCTGCCCCCGAGCTGCTGGCGCAGCAGGGCTAC
GACGAGTCCTGCGACCTCTGGAGCCTGGGCGTCATTCTGTACATGAT
GCTGTCGGGGCAGGTCCCCTTCCAGGGGGCCTCTGGCCAGGGCGGGC
AGAGCCAGGCGGCCGAGATCATGTGCAAAATCCGCGAGGGGCGCTTC
TCCCTTGACGGGGAGGCCTGGCAGGGTGTATCCGAGGAAGCCAAGGA
GCTGGTCCGAGGGCTCCTGACCGTGGACCCCGCCAAGCGGCTGAAGC
TCGAGGGACTGCGGGGCAGCTCGTGGCTGCAGGACGGCAGCGCGCGC
TCCTCGCCCCGCTCCGGACGCCCGACGTGCTCGAGTCCTCTGGGCC
CGCAGTGCGCTCGGGTCTCAACGCCACCTTCATGGCATTCAACCGGG
GCAAGCGGGAGGGCTTCTTCCTGAAGAGCGTGGAGAATGCACCCCTC
A
``` longer splicing variant of MSK2

(SEQ ID NO:3)

(711 AA)

TEANLTGHEEKVSVENFELLKVLGTGAYGKVFLVRKAGGHDAGKLYA
MKVLRKAALVQRAKTQEHTRTERSVLELVRQAPFLVTLHYAFQTDAK
LHLILDYVSGGEMFTHLYQRQYFKEAEVRVYGGEIVLALEHLHKLGI
IYRDLKLENVLLDSEGHIVLTDFGLSKEFLTEEKERTFSFCGTIEYM
APEIIRSKTGHGKAVDWWSLGILLFELLTGASPFTLEGERNTQAEVS
RRILKCSPPFPPRIGPVAQDLLQRLLCKDPKKRLGAGPQGAQEVRNH
PFFQGLDWVALAARKIPAPFRPQIRSELDVGNFAEEFTRLEPVYSPP
GSPPPGDPRIFQGYSFVAPSILFDHNNAVMTDGLEAPGAGDRPGRAA
VARSAMMQDSPFFQQYELDLREPALGQGSFSVCRRCRQRQSGQEFAV
KILSRRLEANTQREVAALRLCQSHPNVVNLHEVHHDQLHTYLVLELL
RGGELLEHIRKKRHFSESEASQILRSLVSAVSFMHEEAGVVHRDLKP
ENILYADDTPGAPVKIIDFGFARLRPQSPGVPMQTPCFTLQYAAPEL
LAQQGYDESCDLWSLGVILYMMLSGQVPFQGASGQGGQSQAAEIMCK
IREGRFSLDGEAWQGVSEEAKELVRGLLTVDPAKRLKLEGLRGSSWL
QDGSARSSPPLRTPDVLESSGPAVRSGLNATFMAFNRGKREGFFLKS
VENAPL

Fig 16 page 2 of 4

Nucleotide sequence of longer splicing variant
2134 bp MSK2 (SEQ ID NO:12)

```
ACCGAAGCCAACCTGACCGGGCACGAGGAGAAGGTGAGCGTGGAGAA
CTTCGAGCTGCTCAAGGTGCTGGGCACGGGAGCCTACGGCAAGGTGT
TCCTGGTGCGGAAGGCGGGCGGGCACGACGCGGGGAAGCTGTACGCC
ATGAAGGTGCTGCGCAAGGCGGCGCTGGTGCAGCGCGCCAAGACGCA
AGAGCACACGCGCACCGAGCGCTCGGTGCTGGAGCTGGTGCGCCAGG
CGCCCTTCCTGGTCACGCTGCACTACGCTTTCCAGACGGATGCCAAG
CTGCACCTCATCCTGGACTATGTGAGCGGCGGGGAGATGTTCACCCA
CCTCTACCAGCGCCAGTACTTCAAGGAGGCTGAGGTGCGCGTGTATG
GGGGTGAGATCGTGCTGGCCCTGGAACACCTGCACAAGCTCGGCATC
ATTTACCGAGACCTGAAACTGGAGAATGTGCTGCTGGACTCCGAGGG
CCACATTGTCCTCACGGACTTCGGGCTGAGCAAGGAGTTCCTGACGG
AGGAGAAAGAGCGGACCTTCTCCTTCTGTGGCACCATCGAGTACATG
GCCCCCGAAATCATCCGTAGCAAGACGGGGCATGGCAAGGCTGTGGA
CTGGTGGAGCCTGGGCATCTTGCTCTTCGAGCTGCTGACGGGGGCCT
CGCCCTTCACCCTGGAGGGCGAGAGGAACACGCAGGCTGAGGTGTCT
CGACGGATCCTGAAGTGCTCCCCTCCCTTCCCCCCTCGGATCGGGCC
CGTGGCGCAGGACCTGCTGCAGCGGCTGCTTTGTAAGGATCCTAAGA
AGCGATTGGGCGCGGGGCCCCAGGGGGCACAAGAAGTCCGGAACCAT
CCCTTCTTCCAGGGCCTCGATTGGGTGGCTCTGGCTGCCAGGAAGAT
TCCAGCCCCATTCCGGCCCCAAATCCGCTCAGAGCTGGATGTGGGCA
ACTTTGCGGAGGAATTCACTCGGCTGGAGCCTGTCTACTCACCCCCT
GGCAGCCCCCCACCTGGGGACCCCCGAATCTTTCAGGGATACTCCTT
TGTGGCACCCTCCATTCTCTTTGACCACAACAACGCGGTGATGACCG
ATGGGCTGGAAGCGCCTGGTGCTGGAGACCGGCCAGGTCGGGCAGCG
GTGGCCAGGAGCGCTATGATGCAGGACTCGCCCTTCTTCCAGCAGTA
CGAGCTGGACCTGCGGGAGCCTGCGCTGGGCCAGGGCAGCTTTTCTG
TGTGTCGCCGCTGCCGCCAGCGCCAGAGCGGCCAGGAGTTCGCAGTC
AAGATCCTCAGTCGCAGGCTGGAGGCGAACACGCAGCGCGAAGTGGC
TGCCCTGCGCCTGTGCCAGTCACACCCCAACGTGGTGAATCTGCACG
AGGTGCATCACGACCAGCTGCACACGTACCTGGTCCTGGAGCTGCTG
CGGGGCGGGGAGCTGCTGGAGCACATCCGCAAGAAGCGGCACTTCAG
CGAGTCGGAAGCAAGCCAGATCCTGCGCAGCCTCGTGTCGGCCGTGA
GCTTCATGCACGAGGAGGCGGGCGTGGTGCACCGCGACCTCAAGCCG
GAGAACATCCTGTACGCCGACGACACGCCCGGGGCCCCGGTGAAAAT
CATCGACTTCGGGTTCGCGCGGTTGCGGCCGCAGAGTCCCGGGGTGC
CCATGCAGACGCCCTGCTTCACGCTGCAGTACGCTGCCCCCGAGCTG
CTGGCGCAGCAGGGCTACGACGAGTCCTGCGACCTCTGGAGCCTGGG
CGTCATTCTGTACATGATGCTGTCGGGCAGGTCCCCTTCCAGGGGG
CCTCTGGCCAGGGCGGGCAGAGCCAGGCGGCCGAGATCATGTGCAAA
ATCCGCGAGGGCGCTTCTCCCTTGACGGGGAGGCCTGGCAGGGTGT
ATCCGAGGAAGCCAAGGAGCTGGTCCGAGGGCTCCTGACCGTGGACC
CCGCCAAGCGGCTGAAGCTCGAGGGACTGCGGGGCAGCTCGTGGCTG
CAGGACGGCAGCGCGCGCTCCTCGCCCCGCTCCGGACGCCCGACGT
```

```
GCTCGAGTCCTCTGGGCCCGCAGTGCGCTCGGGTCTCAACGCCACCT
TCATGGCATTCAACCGGGGCAAGCGGGAGGGCTTCTTCCTGAAGAGC
GTGGAGAATGCACCCCTCA
```

Fig 16  page 4 of 4

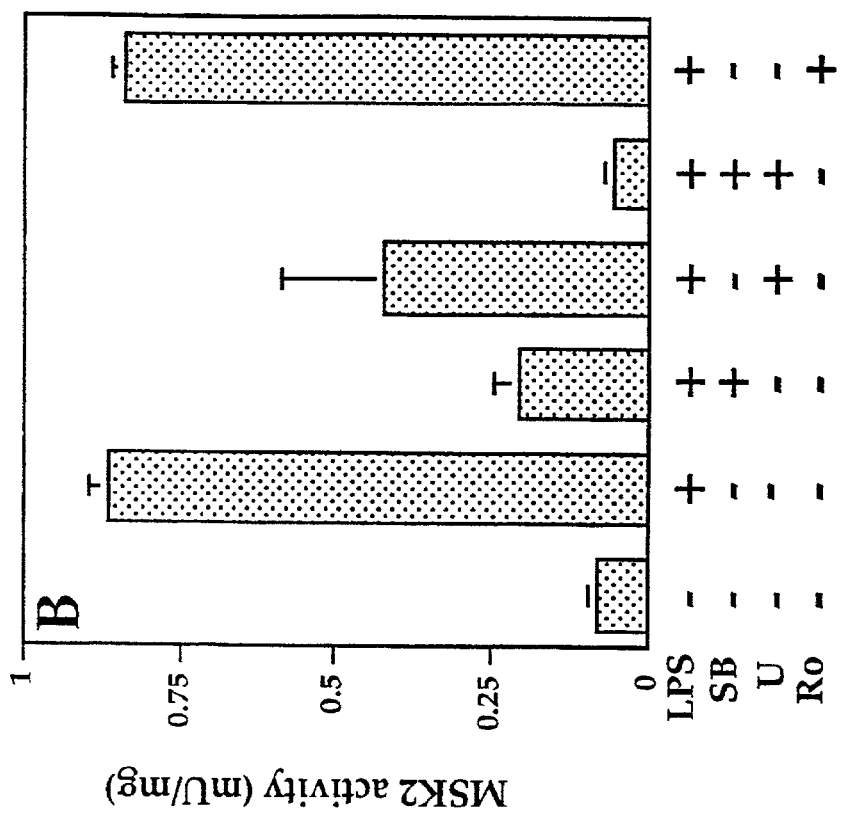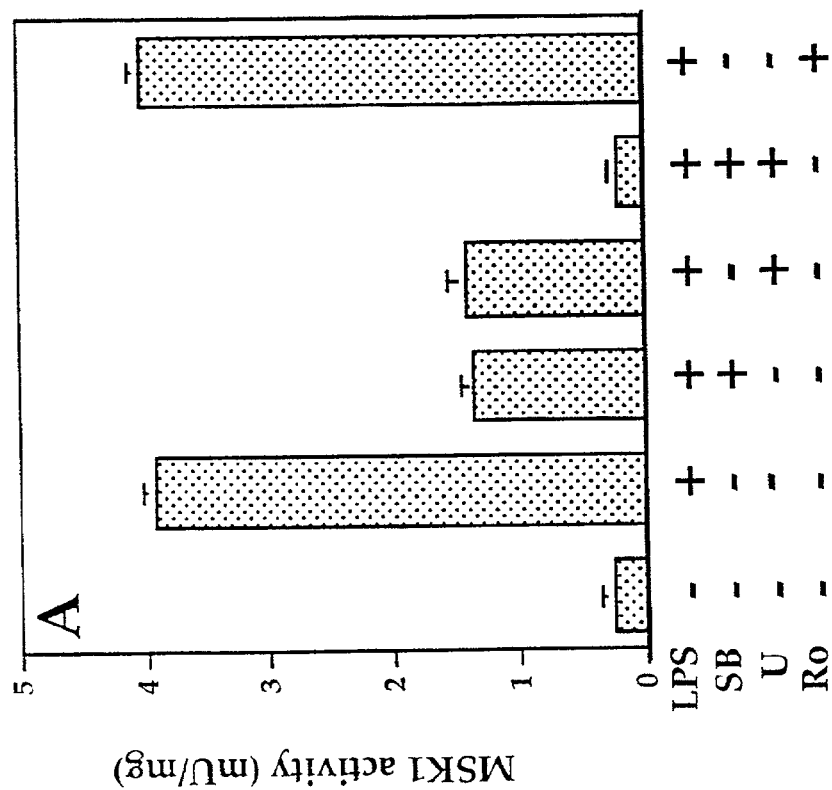
Fig 18 page 1 of 2

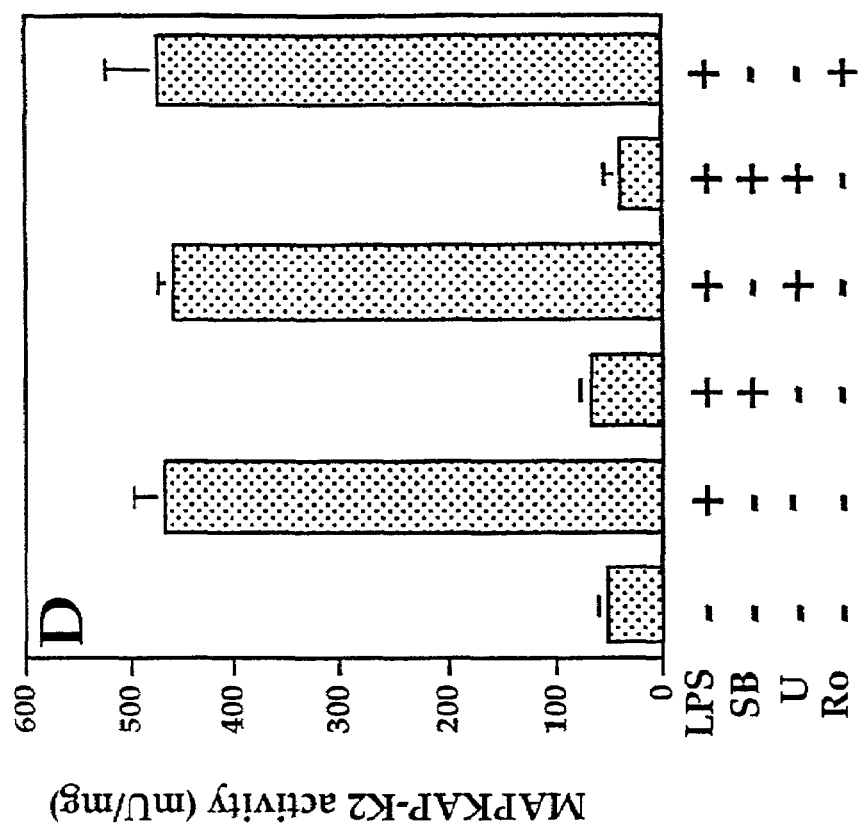
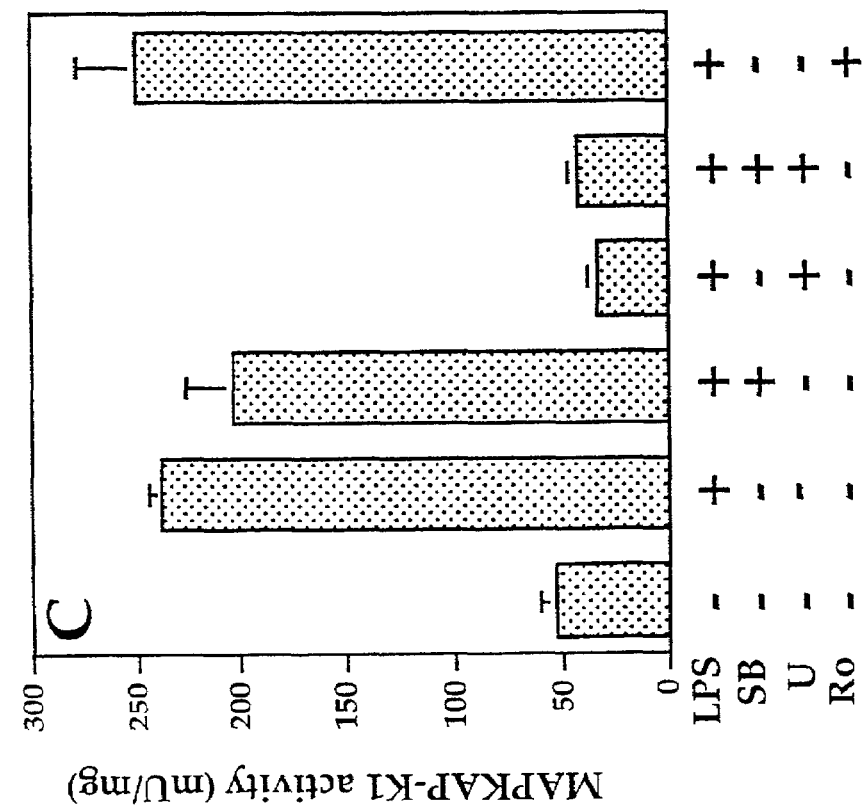
Fig 18 page 2 of 2

POLYPEPTIDES, POLYNUCLEOTIDES AND USES THEREOF

The present application is a US national stage filing of PCT Application No. PCT/GB99/01660, filed Jun. 8, 1999, which claims foreign priority of UK 9813467.9, filed Jun. 24, 1998 and UK 9817303.2, filed Aug. 10, 1998.

The present invention relates to polypeptides, polynucleotides and uses thereof, in particular to members of the two-kinase domain protein kinase family.

Ten mitogen-activated protein kinase (MAPK) family members have been identified in mammalian cells (reviewed in Cohen, 1997). Two of these, MAPK1/ERK1 and MAPK2/ERK2, are activated strongly by polypeptide growth factors whose receptors are protein tyrosine kinases and by tumour promoting phorbol esters, but much more weakly (in most cell contexts) by stress stimuli and proinflammatory cytokines. In contrast, the other MAPK family members are strongly activated by stress signals and proinflammatory cytokines, but only weakly (in most cell contexts) by polypeptide growth factors and phorbol esters. For this reason, they are frequently referred to as stress-activated protein kinases (SAPKs).

A major challenge in this field is to identify the physiological substrates and roles of each of the MAPKs and SAPKs, but this problem is compounded by the finding that a number of the substrates are themselves protein kinases that are likely to have numerous physiological roles. Thus MAPK1/ERK1 and MAPK2/ERK2 activate three closely related protein kinases known as MAPK-activated protein kinases-1a, 1b and 1c (MAPKAP-K1a/b/c, also known as RSK1/2/3) (Sturgill et al., 1988 & Zhao et al 1995), while SAPK2a/p38 and SAPK2b/p38β activate two closely related enzymes termed MAPKAP-K2 (Freshney et al., 1994; Rouse et al, 1994) and MAPKAP-K3 (Clifton et al., 1996; McLaughlin et al., 1996). Several lines of evidence indicate that the MAPKAP-K1 isoforms are in vivo substrates for the MAPKs/ERKs and that MAPKAP-K2/K3 are in vivo substrates for the SAPK2/p38 isoforms. For example, the drug PD 98059, which suppresses the activation of MAPKs/ERKs by preventing activation of their upstream activator MAPK kinase-1 (MKK1), also inhibits activation of the MAPKAP-K1 isoforms (Alessi et al., 1995), but not MAP-KAP-K2/K3 (Clifton et al., 1996).

Conversely, the drug SB 203580, which is a specific inhibitor of SAPK2a/p38 and SAPK2b/p38β, prevents the activation of MAPKAP-K2/K3 (Cuenda et al., 1995; Clifton et al., 1996).

The MAPKAP-K1 isoforms are unusual in that they each contain two protein kinase domains within a single polypeptide and one role of the C-terminal kinase domain is to activate the N-terminal kinase domain allowing the latter to phosphorylate exogenous substrates (Bjorbaek et al., 1995; Vik and Ryder, 1997; Dalby et al., 1998). The phorbol ester-induced activation of MAPKAP-K1a in COS1 cells is accompanied by the phosphorylation of six residues (Ser222, Thr360, Ser364, Ser381, Thr574 and Ser737), four of which (Ser222, Ser364, Ser381 and Thr574) are critical for activation. The MAPKs/ERKs phosphorylate Thr574 in the C-terminal domain and Thr360 and Ser364, which are located between the two kinase domains. The phosphorylation of Thr574 activates the C-terminal domain, which then phosphorylates Ser381. The combined phosphorylation of Ser364 and Ser381 triggers activation of the N-terminal domain, provided that Ser222 is also phosphorylated (Dalby et al., 1998). The identity of the Ser222 kinase is unclear.

The importance of MAPKAP-K1 in cell function is indicated by the finding that inactivating mutations in the MAPKAP-K1b (RSK2) gene are the cause of Coffin Lowry Syndrome, a disease associated with progressive skeletal abnormalities and severe mental retardation (Trivier et al., 1996). However, although the MAPKAP-K1 isoforms phosphorylate many proteins in vitro, their physiological role(s) has yet to be defined. MAPKAP-K1 phosphorylates the transcription factor CREB (Cyclic AMP Response Element Binding protein) in vitro and at the residue (Ser133) known to trigger activation in vivo (Xing et al., 1996). MAPKAP-K1b is also reported to be the major kinase acting on CREBtide (a synthetic peptide corresponding to the sequence surrounding Ser133) that can be detected in lysates prepared from NGF-stimulated PC 12 cells (Ginty et al., 1994; Xing et al., 1996). Moreover, the phosphorylation of CREB at Ser133 is induced by signals that activate the MAPK/ERK cascade and prevented by PD 98059 (Pende et al., 1997). These findings suggest that CREB may be a physiological substrate for MAPKAP-K1, but the possibility that CREB is phosphorylated by another protein kinase that lies "downstream" of MAPKs/ERKs is not excluded.

MAPKAP-K2/K3 also phosphorylates CREB at Ser133 in vitro (Tan et al., 1996) and MAPKAP-K2 is the major CREBtide kinase detected in lysates prepared from SK-N-MC cells that have been stimulated with fibroblast growth factor or stressed by incubation with sodium arsenite (Tan et al., 1996). Moreover, these stimuli induce the phosphorylation of Ser133 in SK-N-MC cells and phosphorylation is prevented by SB 203580 (Tan et al., 1996). These findings suggest that CREB may be a physiological substrate for MAPKAP-K2/K3, but the possibility that CREB is phosphorylated by another protein kinase that lies "downstream" of SAPK2/p38 is not excluded by these data. MAPK1/ERK1 and MAPK2/ERK2 phosphorylate MAPKAP-K1 isoforms in vivo (but not MAPKAP-K2/K3), and SAPK2a/p38 and SAPK2b/p38β phosphorylate MAPKAP-K2/K3 in vivo, (but not MAPKAP-K1). However, two closely-related protein kinases have been identified more recently that are activated in vitro and in vivo by both MAPKs/ERKs and SAPK2/p38. For these reasons they have been termed MAPK-integrating kinases-1 and –2 (MNK1, MNK2) (Fukunaga & Hunter, 1997; Waskiewicz et al., 1997). Like MAPKAPK2/K3, MNK1 and MNK2 are single kinase domain enzymes. One physiological substrate of MNK1 may be the protein synthesis initiation factor eIF4E. MNK phosphorylates eIF4E at Ser209 in vitro (Waskiewicz et al., 1997), the residue whose phosphorylation is induced by growth factors or phorbol esters in vivo. Growth factor induced phosphorylation of Ser209 is prevented by PD 98059, while the phosphorylation of Ser209 induced by stress signals is suppressed by SB 203580 (Wang et al., 1998).

We now describe the identification and characterisation of two novel protein kinases, that resemble the MAPKAP-K1 isoforms in containing two protein kinase domains within a single polypeptide. However, unlike MAPKAP-K1 (but like MNKs) they are activated in vitro and in vivo by either MAPKs/ERKs or SAPK2/p38 and, for this reason they have been termed Mitogen and Stress-activated protein Kinases-1 and –2 (MSK 1, MSK2). We also present evidence which suggests that MSK1 and/or MSK2, rather than MAPKAP-K1 or MAPKAP-K2/K3, may mediate the activation of the transcription factors CREB and ATF1 by growth factors and stress signals.

Inflammatory mediators, such as prostaglandins, leukotrienes, interleukin-1 (IL-1) and TNF are produced in macrophages during bacterial infection by signal transduction pathways that are triggered when liopolysaccharide (LPS; endotoxin), a component of the cell wall of gram-negative bacteria, interacts with the CD14 receptor. These inflammatory mediators play key roles in mounting immune responses needed to fight the bacterial infection. However, their overproduction can also be the cause of chronic inflammatory disease and septic shock. For these reasons, drugs that are capable of suppressing the production of inflammatory mediators may be useful in treating these conditions. Cyclooxygenase-2 (COX-2) catalyses a rate limiting step in the production of prostaglandins and leukotrienes and is synthesised when macrophages are exposed to LPS (Dubois et al(1998) FASEB J 12, 1063–1073).

CREB may be involved in the transcription of the inducible cyclooxygenase-2 (COX2) gene. COX2 appears to be regulated at the transcription or translation levels. The COX2 protein appears to be inactivated or degraded rapidly (see for example, Marshall et al(1979) "Constraints on prostaglandin synthesis in tissues" *J Biol Chem* 262, 3510–3517). The mRNA may also be unstable: the long 3' untranslated portion of COX2 mRNA contains multiple copies of the Shaw-Kamen sequence (AUUUA) which are a feature of early response genes with rapid mRNA degradation (Kosaka et al(1994) *Eur J Biochem* 221, 889–897).

CREB control of COX2 expression is discussed in Montminy (1997) *Ann Rev Biochem* 66, 807–822.

CREB may also induce expression of the c-Fos (or Fos) gene. This gene is important in the control of proliferation and differentiation. Aberrant control of c-Fos may be involved in cancer, and inhibition of Fos transcription may be useful as an anticancer treatment applicable to most cancers.

The promoter for IL-1 contains a cyclic AMP-response element (Chandra et al (1995) *J Immunol* 155, 4535–4543).

ATF1 appears to perform a similar role to CREB and may be interchangeable with CREB.

We have identified a novel mitogen and stress-activated protein kinase (which we call MSK1) and a closely related homologue (which we call MSK2) that contain two protein kinase domains in a single polypeptide. MSK1 (802 residues) displays 40% overall amino acid sequence identity to MAP kinase-activated protein kinase-1 (MAPKAP-K1, also termed p90 RSK), another "two kinase domain" enzyme. The N- and C-terminal kinase domains of MSK1 are 54% and 44% identical to the corresponding domains in MAPKAP-K1, and the four key activating phosphorylation sites in MAPKAP-K1 are conserved in MSK1. Like MAPKAP-K1 (Sturgill et al (1988)), MSK1 is activated in vitro by MAPK2/ERK2 but, unlike MAPKAP-K1, it is also activated by stress-activated protein kinase2a (SAPK2a, also termed p38β and SAPK2b/p38β2. Consistent with these findings, endogenous MSK1 is activated in 293 cells by either polypeptide growth factor/phorbol ester stimulation or by exposure to UV radiation, oxidative and chemical stress, whereas MAPKAP-K1 is only activated significantly by growth factor/phorbol ester stimulation. The activation of MSK1 by growth factor/phorbol ester stimulation is prevented by the drug PD 98059, which suppresses activation of the MAPK cascade, while the activation of MSK1 by UV radiation, oxidative and chemical stress is largely prevented by SB 203580, a specific inhibitor of SAPK2a/p38 and SAPK2b/p38β. In HeLa cells, both PD 98059 and SB 203580 are required to suppress the activation of MSK1 by TNF because this agonist activates both the MAPK/ERK and the SAPK2/p38 cascades. The activation of MSK1 by either phorbol esters or UV radiation is abolished by making single inactivating mutations in either the N-terminal or C-terminal kinase domain. MSK1 is localised in the nucleus of cells and phosphorylates the transcription factor CREB at Ser133. CREB is a much better substrate in vitro for MSK1 than MAPKAP-K1 and MAPKAP-K2 which also phosphorylate CREB at Ser133. A synthetic peptide corresponding to the sequence surrounding Ser133 is phosphorylated with a remarkably low Km value (<0.1 µM). We demonstrate that the effects of SB 203580 and PD 98059 on the EGF, UV and TNF-induced activation of CREB and ATF1 mirror the effects of these inhibitors on MSK1 activation. These findings together with other observations, suggest that MSK1 and MSK2 may mediate the growth factor and stress-induced activation of CREB.

We present evidence that MSK1 and MSK2 may regulate the transcription of the genes for proinflammatory mediators COX-2 and IL-1 and the induction of the proinflammatory COX-2 protein. We demonstrate that MSK1 and MSK2 are both activated when macrophages are stimulated with LPS. Compounds which suppress the activation or activity of MSK1 and MSK2 may prevent the LPS-induced phosphorylation of CREB and ATF1 and/or the transcription factor C/EBPβ, the transcription of the COX-2 and IL-1 genes and the induction of the COX-2 protein.

CREB/ATF1 appears to be necessary for the transcription of COX-2; inhibitors of MSK1 may be useful in treating diseases or conditions in which COX2 has been implicated or in which non-steroidal antiinflammatories (NSAIDs), in particular COX2 selective inhibitors, have been found to be useful. Such diseases or conditions may include those in which inflammatory processes are thought to be involved or in which analgesia may be beneficial.

CREB/ATF1 may be necessary for the transcription of c-Fos and therefore inhibitors of MSK1/MSK2 may be useful in treating diseases or conditions in which c-Fos has been implicated. Such diseases or conditions may include cancer.

A first aspect of the invention provides a substantially pure polypeptide comprising the amino acid sequence

```
MEEEGGSSGGAAGTSADGGDGGEQLLTVKHELRTANLTGHAEKVGIENFEL
LKVLGTGAYGKVFLVRKISGHDTGKLYAMKVLKKATIVQKAKTTEHTRTER
QVLEHIRQSPFLVTLHYAFQTETKLHLILDYINGGELFTHLSQRERFTEHE
VQIYVGEIVLALEHLHKLGIIYRDIKLENILLDSNGHVVLTDFGLSKEFVA
DETERAYSFCGTIEYMAPDIVRGGDSGHDKAVDWWSLGVLMYELLTGASPF
TVDGEKNSQAEISRRILKSEPPYPQEMSALAKDLIQRLLMKDPKKRLGCGP
RDADEIKEHLFFQKINWDDLAAKKVPAPFKPVIRDELDVSNFAEEFTEMDP
TYSPAALPQSSEKLFQGYSFVAPSILFKRNAAVIDPLQFHMGVERPGVTNV
ARSAMMKDSPFYQHYDLDLKDKPLGEGSFSICRKCVHKKSNQAFAVKIISK
RMEANTQKEITALKLCEGHPNIVKLHEVFHDQLHTFLVMELLNGGELFERI
KKKKHFSETEASYIMRKLVSAVSHMHDVGVVHRDLKPENLLFTDENDNLEI
KIIDFGFARLKPPDNQPLKTPCFTLHYAAPELLNQNGYDESCDLWSLGVIL
YTMLSGQVPFQSHDRSLTCTSAVEIMKKIKKGDFSFEGEAWKNVSQEAKDL
IQGLLTVDPNKRLKMSGLRYNEWLQDGSQLSSNPLMTPDILGSSGAAVHTC
```

-continued

VKATFHAFNKYKREGFCLQNVDKAPLAKRRKMKKTSTSTETRSSSSESSHS

SSSHSHGKTTPTKTLQPSNPADSNNPETLFQFSDSVA (SEQ ID NO:1)

or

TEANLTGHEEKVSVENFELLKVLGTGAYGKVFLVRKAGGHDAGKLYAMKVL

RKAALVQRAKTQEHTRTERSVLELVRQAPFLVTLHYAFQTDAKLHLILDYV

SGGEMFTHLYQRQYFKEAEVRVYGGEIVLALEHLHKLGIIYRDLKLENVLL

DSEGHIVLTDFGLSKEFLTEEKERTFSFCGTIEYMAPEIIRSKTGHGKAVD

WWSLGILLFELLTGASPFTLEGERNTQAEVSRRILKCSPPFPPRIGPVAQD

LLQRLLCKDPKKRLGAGPQGAQEVRNHPFFQGLDWVALAARKIPAPFRPQI

RSELDVGNFAEEFTRLEPVYSPPGSPPPGDPRIFQGYSFVAPSILFDHNNA

VMTDGLEAPGAGDRPGRAAVARSAMMQQYELDLREPALGQGSFSVCRRCRQ

RQSGQEFAVKILSRRLEANTQREVAALRLCQSHPNVVNLHEVTHHDQLHTY

LVLELLRGGELLEHIRKKRHFSESEASQILRSLVSAVSFMHEEAGVVHRDL

KPENILYADDTPGAPVKIIDFGFARLRPQSPGVPMQTPCFTLQYAAPELLA

QQGYDESCDLWSLGVILLTVDQVPFQGASGQGGQSQAAEIMCKIREGRFSL

DGEAWQGVSEEAKELVRGLLTVDPAKRLKLEGLRGSSWLQDGSARSSPPLR

TPDVLESSGPAVRSGLNATFMAFNRGKREGFFLKSVENAPL (SEQ ID
NO:2)

or

TEANLTGHEEKVSVENFELLKVLGTGAYGKVFLVRKAGGHDAGKLYAMKVL

RKAALVQRAKTQEHTRTERSVLELVRQAPFLVTLHYAFQTDAKLHLILDYV

SGGEMFTHLYQRQYFKEAEVRVYGGEIVLALEHLHKLGIIYRDLKLENVLL

DSEGHIVLTDFGLSKEFLTEEKERTFSFCGTIEYMAPEIIRSKTGHGKAVD

WWSLGILLFELLTGASPFTLEGERNTQAEVSRRILKCSPPFPPRIGPVAQD

LLQRLLCKDPKKRLGAGPQGAQEVRNHPFFQGLDWVALAARKIPAPFRPQI

RSELDVGNFAEEFTRLEPVYSPPGSPPPGDPRIFQGYSFVAPSILFDHNNA

VMTDGLEAPGAGDRPGRAAVARSAIVIMQDSPFFQQYELDLREPALGQGSF

SVCRRCRQRQSGQEFAVKILSRRLEANTQREVAALRLCQSHPNVVNLHEVH

HDQLHTYLVLELLRGGELLEHIRKKRHFSESEASQILRSLVSAVSFMHEEA

GVVHRDLKPENILYADDTPGAPVKIIDFGFARLRPQSPGVPMQTPCFTLQY

AAPELLAQQGYDESCDLWSLGVILYMMLSGQVPFQGASGQGGQSQAAEIMC

KIREGRFSLDGEAWQGVSEEAKELVRGLLTVDPAKRLKLEGLRGSSWLQDG

SARSSPPLRTPDVLESSGPAVRSGLNATFMAFNRGKREGFFLKSVENAPL (SEQ ID NO:3)

or

RILKCSPPFPPRIGPVAQDLLQRLLCKDPKKRLGAGPQGAQEVRNHPFFQG

LDWVALAARKIPAPFRPQIRSELDVGNFAEEFTRLEPVYSPPGSPPPGDPR

-continued

IFQGYSFVAPSILFDHNNAVMTDGLEAPGAGDRPGRAAVARSAMMQDSPFF

QQYELDLREPALGQGSFSVCRRCRQRQSGQEFAVKILSRRLEANTQREVAA

LRLCQSHPNVVNLHEVHHDQLHTYLVLELLRGGELLEHIRKKRHFSESEAS

QILRSLVSAVSFMHEEAGVVHRDLKPENILYADDTPGAPVKIIDFGFARLR

PPGVPMQTPCFTLQYAAPELLAQQGYDESCDLWSLGVILYMMLSGQVPFQG

ASGQGGQXQAAEIMCKIREGRFSLDGEAWQGVSEEAKELVRGLLTVDPAKR

LKLEGLRGSSWLQDGSARSSPPLRTPDVLESSGPAVRSGLNATFMAFNRGK

REGFFLKSVENAPL (SEQ ID NO:4)

or

HASGDEDEDEGCAVELQITEANLTGHEEKVSVENFALLKVLGTGAYGKVFL

VRKTGGHDAGKLYAMKVLRKAALVQRAKTQEHTRTERSVLELVRQAPFLVT

LHYAFQTDAKLHLILDYVSGGEMFTHLYQRQYFKEAEVRVYGGEIVLALEH

LHKLGIIYRDLKLENVLLDSEGHIVLTDFGLSKEFLTEEKERTFSFCGTIE

YMAPEIIRSKAGHGKAVDWWSLGILLFELLTGASPFTLEGERNTQAEVSRR

ILKCSPPFPPLRIGPVAQDLLQRLLCKDPKKRLGAGPQGAQEVKSHPFFRVW

TGWALAARKIPAPFRPQIRSELDVGNFAEEFTRLEPVYSPAGSPPPGDPRI

FQGYSFVAPSILFDHNNAVMADVLQAPGAGYRPGRAAVARSAMMQDSPFFQ

QYELDLREPALGQGSFSVCRRCRQRQSGQEFAVKILSRRLEENTQREVAAL

RLCQSHPNVVNLHEVLHDQLHTYLVLELLRGGELLEHIRKKRLFSESEASQ

ILRSLVSAVSFMHEEAGVVHRDLKPENILYADDTPGAPVKIIDFGFARLRP

QSPAEPMQTPCFTLQYAAPELLAQQGYDESCDLWSLGVILYMMLSGQVPFQ

GASGQGGQSQAAEIMCKIREGRFSLDGEAWQGVSEEAKELVRGLLTVDPAK

RLKLEGLRSSSWLQDGSARSSPPLRTPDVLESSGPAVRSGLNATFMAFNRG

KREGFFLKSVENAPLAKRRKQKLRSA (SEQ ID NO:5)

or a variant, fragment, fusion or derivative thereof, or a fusion of a said variant or fragment or derivative. The polypeptide whose amino acid sequences are shown above are considered to be mitogen and stress activated protein kinases.

The polypeptides with the amino acid sequences as shown above are herein referred to as MSK1 (mitogen and stress-activated protein kinase 1; the first sequence shown) or MSK2 (mitogen and stress-activated protein kinase 2; the second sequence is a partial sequence of a human MSK2, the third a partial sequence of a splice variant of human MSK2, the fourth a partial sequence of a human MSK2 and the fifth a partial sequence of mouse MSK2).

Figure 1:
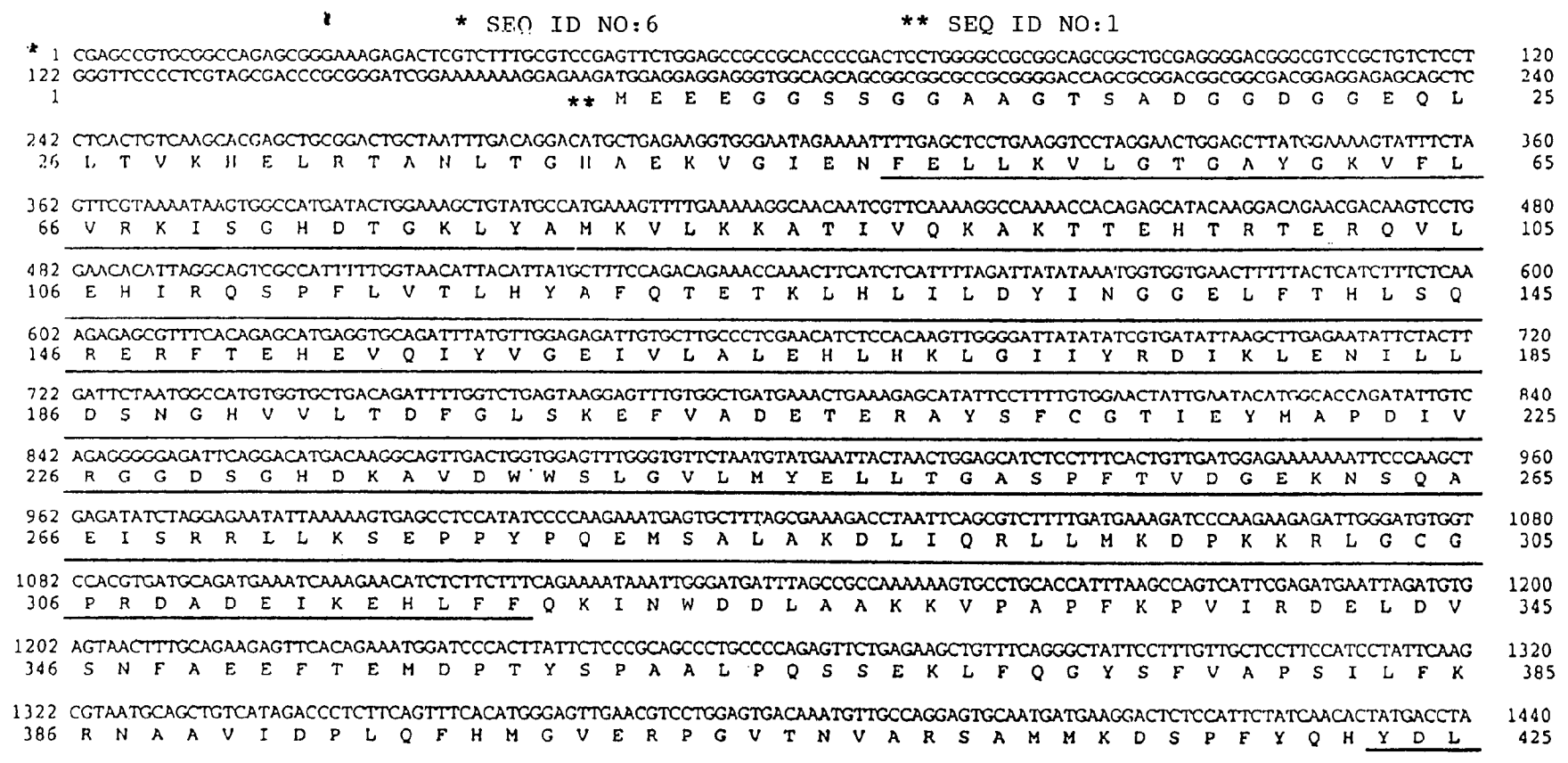
Figure 1:
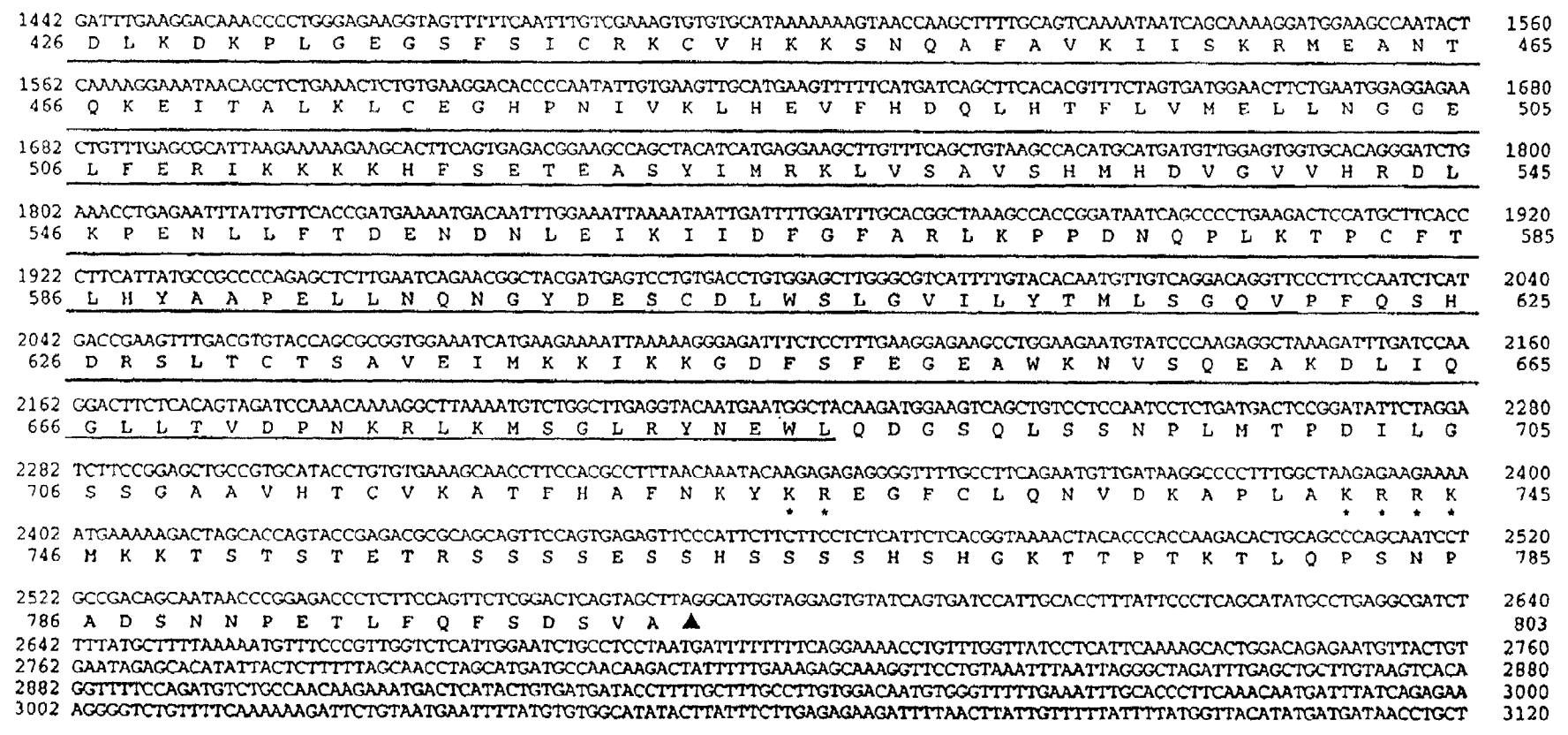

The amino acid sequence of MSK1 is also shown in FIG. 1 (MSK1). A partial amino acid sequence of a human MSK2 are also shown in FIG. 2C. The mouse MSK2 is a variant of the human MSK2 and is also shown in FIG. 2C.

By "substantially pure" we mean that the said polypeptide is substantially free of other proteins. Thus, we include any composition that includes at least 30% of the protein content by weight as the said polypeptide, preferably at least 50%, more preferably at least 70%, still more preferably at least 90% and most preferably at least 95% of the protein content is the said polypeptide.

Thus, the invention also includes compositions comprising the said polypeptide and a contaminant wherein the contaminant comprises less than 70% of the composition by weight, preferably less than 50% of the composition, more preferably less than 30% of the composition, still more preferably less than 10% of the composition and most preferably less than 5% of the composition by weight.

The invention also includes the substantially pure said polypeptide when combined with other components ex vivo, said other components not being all of the components found in the cell in which said polypeptide is found.

Variants (whether naturally-occurring or otherwise) may be made using the methods of protein engineering and site-directed mutagenesis well known in the art using the recombinant polynucleotides described below.

By "fragment of said polypeptide" we include any fragment which retains activity or which is useful in some other way, for example, for use in raising antibodies or in a binding assay.

By "fusion of said polypeptide" we include said polypeptide fused to any other polypeptide. For example, the said polypeptide may be fused to a polypeptide such as glutathione-S-transferase (GST) or protein A in order to facilitate purification of said polypeptide. Examples of such fusions to GST are given in Example 1. Similarly, the said polypeptide may be fused to an oligo-histidine tag such as His6 or to an epitope recognised by an antibody such as the well known Myc tag epitope. Fusions to any variant, fragment or derivative of said polypeptide are also included in the scope of the invention.

By "variants" of the polypeptide we include insertions, deletions and substitutions, either conservative or non-conservative. In particular we include variants of the polypeptide where such changes do not substantially alter the activity of the said polypeptide. Variants of MSK1 or MSK2 do not include polypeptides which have the amino acid sequence of human MAPKAP-K1a/b/c, also known as Rsk1/2/3. Variants of MSK1 or MSK2 also do not include polypeptides which have the amino acid sequence of *Drosphila melanogaster* p70 S6 kinase, as described in WO 98/03662. This polypeptide is approximately 55% identical to MSK1 or MSK2 in the N-terminal domain, and is approximately 20% identical overall.

It will be appreciated that a variant that comprises substantially all of a sequence shown above (ie substantially full-length MSK1) or substantially full-length human or mouse MSK2 comprising substantially all of a human or mouse MSK2 sequence shown above may be particularly useful. By "substantially all" is meant at least 80%, preferably 90%, still more preferably 95%, 98% or 100% (ie all) of the said sequence. By "substantially full-length" is meant comprising at least 80%, preferably 90%, still more preferably 95%, 98% or 100% (ie all) of the sequence of the full length polypeptide.

By "conservative substitutions" is intended combinations such as Gly, Ala; Val, Ile, Leu; Asp, Glu; Asn, Gln; Ser, Thr; Lys, Arg; and Phe, Tyr.

It is particularly preferred if the polypeptide variant has an amino acid sequence which has at least 65% identity with the amino acid sequence given above, more preferably at least 75%, still more preferably at least 80%, yet more preferably at least 90%, and most preferably at least 95% or 99% identity with the amino acid sequence given above.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (Thompson et al., 1994). The parameters used may be as follows: Fast pairwise alignment parameters: K-tuple(word) size; 1, window size; 5, gap penalty; 3, number of top diagonals; 5. Scoring method:xpercent. Multiple alignment parameters: gap open penalty; 10, gap extension penalty; 0.05.

Scoring matrix: BLOSUM.

Thus, using these parameters, MKS1 may have 42–44% overall identity with the closest homologues in the NCBI database; MAPKAP-K1a,b and c.

A particular embodiment of the invention provides a substantially pure human MSK1 polypeptide which consists of the amino acid sequence

MEEEGGSSGGAAGTSADGGDGGEQLLTVKHELRTANLTGHAEKVGIENFEL

LKVLGTGAYGKVFLVRKISGHDTGKLYAMKVLKKATIVQKAKTTEHTRTER

QVLEHIRQSPFLVTLHYAFQTETKLHLILDYINGGELFTHLSQRERFTEHE

VQIYVGEIVLALEHLHKLGIIYRDIKLENILLDSNGHVVLTDFGLSKEFVA

DETERAYSFCGTIEYMAPDIVRGGDSGHDKAVDWWSLGVLMYELLTGASPF

TVDGEKNSQAEISRRILKSEPPYPQEMSALAKDLIQRLLMKDPKKRLGCGP

RDADEIKEHLFFQKINWDDLAAKKVPAPFKPVIRDELDVSNFAEEFTEMDP

TYSPAALPQSSEKLFQGYSFVAPSILFKRNAAVIDPLQFHMGVERPGVTNV

ARSAMMKDSPFYQHYDLDLKDKPLGEGSFSICRKCVHKKSNQAFAVKIISK

RMEANTQKEITALKLCEGHPNIVKLHEVFHDQLHTFLVMELLNGGELFERI

KKKKHFSETEASYIMRKLVSAVSHMHDVGVVHRDLKPENLLFTDENDNLEI

KIIDFGFARLKPPDNQPLKTPCFTLHYAAPELLNQNGYDESCDLWSLGVIL

YTMLSGQVPFQSHDRSLTCTSAVEIMKKIKKGDFSFEGEAWKNVSQEAKDL

IQGLLTVDPNKRLKMSGLRYNEWLQDGSQLSSNPLMTPDILGSSGAAVHTC

VKATFHAFNKYKREGFCLQNVDKAPLAKRRKMKKTSTSTETRSSSSESSHS

SSSHSHGKTTPTKTLQPSNPADSNNPETLFQFSDSVA (SEQ ID NO:1)

or naturally occurring allelic variants thereof. The amino acid sequence is also shown as the translation of a polynucleotide sequence in FIG. 1.

A further particular embodiment of the invention provides a substantially pure MSK2 polypeptide which consists of the amino acid sequence

TEANLTGHEEKVSVENFELLKVLGTGAYGKVFLVRKAGGHDAGKLYAMKVL

RKAALVQRAKTQEHTRTERSVLELVRQAPFLVTLHYAFQTDAKLHLILDYV

SGGEMFTHLYQRQYFKEAEVRVYGGEIVLALEHLHKLGIIYRDLKLENVLL

DSEGHIVLTDFGLSKEFLTEEKERTFSFCGTTEYMAPEIIRSKTGHGKAVD

WWSLGILLFELLTGASPFTLEGERNTQAEVSRRILKCSPPFPPRIGPVAQD

LLQRLLCKDPKKRLGAGPQGAQEVRNHPFFQGLDWVALAARKIPAPFRPQI

RSELDVGNFAEEFTRLEPVYSPPGSPPPGDPRIFQGYSFVAPSILFDHNNA

VMTDGLEAPGAGDRPGRAAVARSAMMQQYELDLREPALGQGSFSVCRRCRQ

-continued

RQSGQEFAVKILSRRLEANTQREVAALRLCQSHPNVVNLHEVHHDQLHTYL
VLELLRGGELLEHIRKKRHFSESEASQILRSLVSAVSFMHEEAGVVHRDLK
PENILYADDTPGAPVKIIDFGFARLRPQSPGVPMQTPCFTLQYAAPELLAQ
QGYDESCDLWSLGVILYMMLSGQVPFQGASGQGGQSQAAEIMCKIREGRFS
LDGEAWQGVSEEAKELVRGLLTVDPAKRLKLEGLRGSSWLQDGSARSSPPL
RTPDVLESSGPAVRSGLNATFMAFNRGKREGFFLKSVENAPL (SEQ ID
NO:2)

or

TEANLTGHEEKVSVENFELLKVLGTGAYGKVFLVRKAGGHDAGKLYAMKV
LRKAALVQRAKTQEHTRTERSVLELVRQAPFLVTLHYAFQTDAKLHLILD
YVSGGEMFTHLYQRQYFKEAEVRVYGGEIVLALEHLHKLGIIYRDLKLEN
VLLDSEGHIVLTDFGLSKEFLTEEKERTFSFCGTIEYMAPEIIRSKTGHG
KAVDWWSLGILLFELLTGASPFTLEGERNTQAEVSRRILKCSPPFPPRIG
PVAQDLLQRLLCKDPKKRLGAGPQGAQEVRNHPFFQGLDWVALAARKIPA
PFRPQIRSELDVGNFAEEFTRLEPVYSPPGSPPPGDPRIFQGYSFVAPSI
LFDHNNAVMTDGLEAPGAGDRPGRAAVARSAMMQDSPFFQQYELDLREPA
LGQGSFSVCRRCRQRSGQEFAVKILSRRLEANTQREVAALRLCQSHPNV
VNLHEVHHDQLHTYLVLELLRGGELLEHIRKKRHFSESEASQILRSLVSA
VSFMHEEAGVVHRDLKPENILYADDTPGAPVKIIDFGFARLRPQSPGVPM
QTPCFTLQYAAPELLAQQGYDESCDLWSLGVILYMMLSGQVPFQGASGQG
GQSQAAEIMCKIREGRFSLDGEAWQGVSEEAKELVRGLLTVDPAKRLKLE
GLRGSSWLQDGSARSSPPLRTPDVLESSGPAVRSGLNATFMAFNRGKREG
FFLKSVENAPL (SEQ ID NO:3)

or

HASGDEDEDEGCAVELQITEANLTGHEEKVSVENFALLKVLGTGAYGKVF
LVRKTGGHDAGKLYAMKVLRKAALVQRAKTQEHTRTERSVLELVRQAPFL
VTLHYAFQTDAKLHLILDYVSGGEMFTHLYQRQYFKEAEVRVYGGEIVLA
LEHLHKLGIIYRDLKLENVLLDSEGHIVLTDFGLSKEFLTEEKERTFSFC
GTIEYMAPEIIRSKAGHGKAVDWWSLGILLFELLTGASPFTLEGERNTQA
EVSRRILKCSPPFPLRIGPVAQDLLQRLLCKDPKKRLGAGPQGAQEVKSH
PFFRVWTGWALAARKIPAPFRPQIRSELDVGNFAEEFTRLEPVYSPAGSP
PPGDPRIFQGYSFVAPSILFDHNNAVMADVLQAPGAGYRPGRAAVARSAM
MQDSPFFQQYELDLREPALGQGSFSVCRRCRQRQSGQEFAVKILSRRLEE
NTQREVAALRLCQSHPNVVNLHEVLHDQLHTYLVLELLRGGELLEHIRKK
RLFSESEASQTLRSLVSAVSFMHEEAGVVHRDLKPENILYADDTPGAPVK
IIDFGFARLRPQSPAEPMQTPCFTLQYAAPELLAQQGYDESCDLWSLGVI
LYMMLSGQVPFQGASGQGGQSQAAEIMCKIREGRFSLDGEAWQGVSEEAK

-continued

ELVRGLLTVDPAKRLKLEGLRSSSWLQDGSARSSPPLRTPDVLESSGPAV
RSGLNATFMAFNRGKREGFFLKSVENAPLAKRRKQKLRSA (SEQ ID NO:5)

or naturally occurring allelic variants thereof.

A further particular embodiment of the invention provides a substantially pure full-length human MSK2 polypeptide which comprises the amino acid sequence TEANLTGHEEKVSVENFELLKVLGTGAYGKVFLVRKAGGHDAGKLYAMKV
LRKAALVQPAKTQEHTRTERSVLELVRQAPFLVTLHYAFQTDAKLHLILD
YVSGGEMFTHLYQRQYFKEAEVRVYGGEIVLALEHLHKLGIIYRDLKLEN
VLLDSEGHIVLTDFGLSKEFLTEEKERTFSFCGTIEYMAPEIIRSKTGHG
KAVDWWSLGILLFELLTGASPFTLEGERNTQAEVSRRILKCSPPFPPRIG
PVAQDLLQRLLCKDPKKRLGAGPQGAQEVRNHPFFQGLDWVALAARKIPA
PFRPQIRSELDVGNFAEEFTRLEPVYSPPGSPPPGDPRIFQGYSFVAPSI
LFDHNNAVMTDGLEAPGAGDRPGRAAVARSAMMQQYELDLREPALGQGSF
SVCRRCRQRQSGQEFAVKILSRRLEANTQREVAALRLCQSHPNVVNLHEV
HHDQLHTYLVLELLRGGELLEHIRKKRHFSESEASQILRSLVSAVSFMHE
EAGVVHRDLKPENILYADDTPGAPVKIIDFGFARLRPQSPGVPMQTPCFT
LQYAAPELLAQQGYDESCDLWSLGVILYMMLSGQVPFQGASGQGGQSQAA
EIMCKIREGRFSLDGEAWQGVSEEAKELVRGLLTVDPAKRLKLEGLRGSS
WLQDGSARSSPPLRTPDVLESSGPAVRSGLNATFMAFNRGKREGFFLKSV
ENAPL (SEQ ID NO:2)

or

TEANLTGHEEKVSVENFELLKVLGTGAYGKVFLVRKAGGHDAGKLYAMKV
LRKAALVQRAKTQEHTRTERSVLELVRQAPFLVTLHYAFQTDAKLHLILD
YVSGGEMFTHLYQRQYFKEAEVRVYGGEIVLALEHLHKLGIIYRDLKLEN
VLLDSEGHIVLTDFGLSKEFLTEEKERTFSFCGTIEYMAPEIIRSKTGHG
KAVDWWSLGILLFELLTGASPFTLEGERNTQAEVSRRILKCSPPFPPRIG
PVAQDLLQRLLCKDPKKRLGAGPQGAQEVRNHPFFQGLDWVALAARKIPA
PFRPQIRSELDVGNFAEEFTRLEPVYSPPGSPPPGDPRIFQGYSFVAPSI
LFDHNNAVMTDGLEAPGAGDRPGRAAVARSAMMQDSPFFQQYELDLREPA
LGQGSFSVCRRCRQRQSGQEFAVKILSRRLEANTQREVAALRLCQSNPNV
VNLHEVHHDQLHTYLVLELLRGGELLEHIRKKRHFSESEASQILRSLVSA
VSFMHEEAGVVHRDLKPENILYADDTPGAPVKIIDFGFARLRPQSPGVPM
QTPCFTLQYAAPELLAQQGYDESCDLWSLGVILYMMLSGQVPFQGASGQG
GQSQAAEIMCKIREGRFSLDGEAWQGVSEEAKELVRGLLTVDPAKRLKLE
GLRGSSWLQDGSARSSPPLRTPDVLESSGPAVRSGLNATFMAFNRGKREG
FFLKSVENAPL (SEQ ID NO:3)

or naturally occurring allelic variants thereof. It will be appreciated that each of the above sequences is not the entire amino acid sequence of full-length human MSK2.

A further particular embodiment of the invention provides a substantially pure full-length mouse MSK2 polypeptide which comprises the amino acid sequence

```
HASGDEDEDEGCAVELQITEANLTGHEEKVSVENFALLKVLGTGAYGKVF

LVRKTGGHDAGKLYAMKVLRKAALVQRAKTQEHTRTERSVLELVRQAPFL

VTLHYAFQTDAKLHLILDYVSGGEMFTHLYQRQYFKEAEVRVYGGEIVLA

LEHLHKLGIIYRDLKLENVLLDSEGHIVLTDFGLSKEFLTEEKERTFSFC

GTIEYMAPEIIRSKAGHGKAVDWWSLGILLFELLTGASPFTLEGERNTQA

EVSRRILKCSPPFPLRIGPVAQDLLQRLLCKDPKKRLGAPQGAQEVKSH

PFFRVWTGWALAARKIPAPFRPQIRSELDVGNFAEEFTRLEPVYSPAGSP

PPGDPRIFQGYSFVAPSILFDHNNAVMADVLQAPGAGYRPGRAAVARSAN

MQDSPFFQQYELDLREPALGQGSFSVCRRCRQRQSGQEFAVKILSRRLEE

NTQREVAALRLCQSHPNVVNLHEVLHDQLHTYLVLELLRGGELLEHIRKK

RLFSESEASQILRSLVSAVSFMHEEAGVVHRDLKPENILYADDTPGAPVK

IIDFGFARLRPQSPAEPMQTPCFTLQYAAPELLAQQGYDESCDLWSLGVI

LYMMLSGQVPFQGASGQGGQSQAAEIMCKIREGRFSLDGEAWQGVSEEAK

ELVRGLLTVDPAKRLKLEGLRSSSWLQDGSARSSPPLRTPDVLESSGPAV

RSGLNATFMAFNRGKREGFFLKSVENAPLAKRRKQKLRSA (SEQ ID NO:5)
``` or naturally occurring allelic variants thereof. It will be appreciated that the above sequence is not the entire amino acid sequence of full-length mouse MSK2.

It is particularly preferred, although not essential, that the variant or fragment or derivative or fusion of the said polypeptide, or the fusion of the variant or fragment or derivative has at least 30% of the enzyme activity of MSK1 with respect to the phosphorylation of Crosstide (GR-PRTSSFAEG; (SEQ ID NO:16)see Example 1), CREB or CREBtide (a synthetic peptide corresponding to the sequence surrounding Ser 133 (EILSRRPSYRK (SEQ ID NO:18); see Example 1) or (preferably) with respect to the phosphorylation of a GST-CREB fusion protein, for example that described in Example 1, or of MSK2 with respect to the phosphorylation of Crosstide, CREB, a GST-CREB fusion protein as referred to above or CREBtide as appropriate. It is more preferred if the variant or fragment or derivative or fusion of the said polypeptide, or the fusion of the variant or fragment or derivative has at least 50%, preferably at least 70% and more preferably at least 90% of the enzyme activity of MSK1 with respect to the phosphorylation of CREB or the alternatives described above, or MSK2 with respect to the phosphorylation of Crosstide or the alternatives described above, as appropriate. However, it will be appreciated that variants or fusions or derivatives or fragments which are devoid of enzymatic activity may nevertheless be useful, for example by interacting with another polypeptide, or as antigens in raising antibodies.

A further aspect of the invention provides a recombinant polynucleotide encoding a polypeptide as defined in the first aspect of the invention or encoding a variant or fragment or derivative of fusion of said polypeptide or a fusion of a said variant or fragment or derivative. Preferences and exclusions for the said polynucleotide variant are the same as in the first aspect of the invention, except that the following Expressed Sequence Tags (ESTs) are also excluded:

ESTs related to human MSK1: AA158572, AA158571, AA255846, AA699729, AA134359, AA314565, N31641, AA305163, WO4930, AA134358, AA322270, H09985, AA255996, R11235, N57096, T97538, T97584, H09986, R11183, HSC0JE081, AA472165, AA897221, AA389168, AA061016, AA444366.

ESTs related to human MSK2: AA568895, AA857431, H41647, AA443601, AA678670, H53714, AA627558, H46268, R17109, AA955129.

ESTs related to mouse MSK2: AA267490, AA444366, AA061016, AA389168, AA472165, AA657108.

All ESTs are identified by the Genbank accession number, as described in Example 1.

A further aspect of the invention provides a recombinant polynucleotide suitable for expressing a polypeptide as defined in the first aspect of the invention or suitable for expressing a variant or fragment or derivative of fusion of said polypeptide or a fusion of a said variant or fragment or derivative. Preferences and exclusions for the said polynucleotide variant are the same as in the first aspect of the invention.

By "suitable for expressing" is mean that the polynucleotide is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

It is not considered that any of the ESTs listed above are polynucleotides as defined above; however, for the avoidance of doubt, the ESTs excluded above are further excluded from this aspect of the invention.

Thus a further aspect of the invention is a replicable vector suitable for expressing a polypeptide as defined in the first aspect of the invention or suitable for expressing a variant or fragment or derivative of fusion of said polypeptide or a fusion of a said variant or fragment or derivative. Preferences and exclusions for the said polynucleotide variant are the same as in the first aspect of the invention. For example, the replicable vector may be suitable for expressing a fusion of the polypeptide as defined in the first aspect of the invention, in particular a GST fusion, for example as described in Example 1.

A further aspect of the invention is a polynucleotide encoding a fusion of the polypeptide as defined in the first aspect of the invention, or a fusion of a variant or fragment or derivative, in particular a GST fusion. A still further aspect is a vector suitable for replication in a mammalian/eukaryotic cell, comprising a polynucleotide encoding the polypeptide, or a variant or fragment or derivative or a fusion of the polypeptide, as defined in the first aspect of the invention, or a fusion of a variant or fragment or derivative, in particular a GST fusion. The following ESTs clones may be vectors which may be suitable for replication in a mammalian/eukaryotic cell and are excluded from this aspect of the invention: AA389168; AA678670. It is not considered that any other of the ESTs excluded from other aspects of the invention are vectors as defined above; however, it will be appreciated that any other of the ESTs clones that may be such a vector are also excluded.

Characteristics of vectors suitable for replication in mammalian/eukaryotic cells are well known to those skilled in the art, and examples are given below. It will be appreciated that a vector may be suitable for replication in both prokaryotic and eukaryotic cells.

In one preferred embodiment the polynucleotide comprises the nucleotide sequence (SEQ ID NO:6)

CGAGCCGTGCGGCCAGAGCGGGAAAGAGACTCGTCTTTGCGTCCGAGTTC

TGGAGCCGCCGCACCCCGACTCCTGGGGCCGCGGCAGCGGCTGCGAGGGG

ACGGGCGTCCGCTGTCTCCTGGGTTCCCCTCGTAGCGACCCGCGGGATCG

GAAAAAAAGGAGAAGATGGAGGAGGAGGGTGGCAGCAGCGGCGGCGCCGC

GGGGACCAGCGCGGACGGCGGCGACGGAGGAGAGCAGCTCCTCACTGTCA

AGCACGAGCTGCGGACTGCTAATTTGACAGGACATGCTGAGAAGGTGGGA

ATAGAAAATTTTGAGCTCCTGAAGGTCCTAGGAACTGGAGCTTATGAAA

AGTATTTCTAGTTCGTAAAATAAGTGGCCATGATACTGGAAAGCTGTATG

CCATGAAAGTTTTGAAAAAGGCAACAATCGTTCAAAAGGCCAAAACCACA

GAGCATACAAGGACAGAACGACAAGTCCTGGAACACATTAGGCAGTCGCC

ATTTTTGGTAACATTACATTATGCTTTCCAGACAGAAACCAAACTTCATC

TCATTTTAGATTATATAAATGGTGGTGAACTTTTTACTCATCTTTCTCAA

AGAGAGCGTTTCACAGAGCATGAGGTGCAGATTTATGTTGGAGAGATTGT

GCTTGCCCTCGAACATCTCCACAAGTTGGGGATTATATATCGTGATATTA

AGCTTGAGAATATTCTACTTGATTCTAATGGCCATGTGGTGCTGACAGAT

TTTGGTCTGAGTAAGGAGTTTGTGGCTGATGAAACTGAAAGAGCATATTC

CTTTTGTGGAACTATTGAATACATGGCACCAGATATTGTCAGAGGGGAG

ATTCAGGACATGACAAGGCAGTTGACTGTGGAGTTTGGGTGTTCTAATG

TATGAATTACTAACTGGAGCATCTCCTTTCACTGTTGATGGAGAAAAAA

TTCCCAAGCTGAGATATCTAGGAGAATATTAAAAAGTGAGCCTCCATATC

CCCAAGAAATGAGTGCTTTAGCGAAAGACCTAATTCAGCGTCTTTTGATG

AAAGATCCCAAGAAGAGATTGGGATGTGGTCCACGTGATGCAGATGAAAT

CAAAGAACATCTCTTCTTTCAGAAAATAAATTGGGATGATTTAGCCGCCA

AAAAAGTGCCTGCACCATTTAAGCCAGTCATTCGAGATGAATTAGATGTG

AGTAACTTTGCAGAAGAGTTCACAGAAATGGATCCCACTTATTCTCCCGC

AGCCCTGCCCCAGAGTTCTGAGAAGCTGTTTCAGGGCTATTCCTTTGTTG

CTCCTTCCATCCTATTCAAGCGTAATGCAGCTGTCATAGACCCTCTTCAG

TTTCACATGGGAGTTGAACGTCCTGGAGTGACAAATGTTGCCAGGAGTGC

AATGATGAAGGACTCTCCATTCTATCAACACTATGACCTAGATTTGAAGG

ACAAACCCCTGGGAGAAGGTAGTTTTTCAATTTGTCGAAAGTGTGTGCAT

AAAAAAAGTAACCAAGCTTTTGCAGTCAAAATAATCAGCAAAAGGATGGA

AGCCAATACTCAAAAGGAAATAACAGCTCTGAAACTCTGTGAAGGACACC

CCAATATTGTGAAGTTGCATGAAGTTTTTCATGATCAGCTTCACACGTTT

CTAGTGATGGAACTTCTGAATGGAGGAGAACTGTTTGAGCGCATTAAGAA

AAAGAAGCACTTCAGTGAGACGGAAGCCAGCTACATCATGAGGAAGCTTG

TTTCAGCTGTAAGCCACATGCATGATGTTGGAGTGGTGCACAGGGATCTG

AAACCTGAGAATTTATTGTTCACCGATGAAAATGACAATTTGGAAATTAA

AATAATTGATTTTGGATTTGCACGGCTAAAGCCACCGGATAATCAGCCCC

TGAAGACTCCATGCTTCACCCTTCATTATGCCGCCCAGAGCTCTTGAAT

CAGAACGGCTACGATGAGTCCTGTGACCTGTGGAGCTTGGGCGTCATTTT

GTACACAATGTTGTCAGGACAGGTTCCCTTCCAATCTCATGACCGAAGTT

TGACGTGTACCAGCGCGGTGGAAATCATGAAGAAAATTAAAAAGGGAGAT

TTCTCCTTTGAAGGAGAAGCCTGGAAGAATGTATCCAAGAGGCTAAAGA

TTTGATCCAAGGACTTCTCACAGTAGATCCAAACAAAAGGCTTAAAATGT

CTGGCTTGAGGTACAATGAATGGCTACAAGATGGAAGTCAGCTGTCCTCC

AATCCTCTGATGACTCCGGATATTCTAGGATCTTCCGGAGCTGCCGTGCA

TACCTGTGTGAAAGCAACCTTCCACGCCTTTAACAAATACAAGAGAGAGG

GGTTTTGCCTTCAGAATGTTGATAAGGCCCCTTTGGCTAAGAGAAGAAAA

ATGAAAAAGACTAGCACCAGTACCGAGACGCGCAGCAGTTCCAGTGAGAG

TTCCCATTCTTCTTCCTCTCATTCTCACGGTAAAACTACACCCACCAAGA

CACTGCAGCCCAGCAATCCTGCCGACAGCAATAACCCGGAGACCCTCTTC

CAGTTCTCGGACTCAGTAGCTTAGGCATGGTAGGAGTGTATCAGTGATCC

ATTGCACCTTTATTCCCTCAGCATATGCCTGAGGCGATCTTTTATGCTTT

TAAAAATGTTTCCCGTTGGTCTCATTGGAATCTGCCTCCTAATGATTTTT

TTTCAGGAAAACCTGTTTGGTTATCCTCATTCAAAAGCACTGGACAGAGA

ATGTTACTGTGAATAGAGCACATATTACTCTTTTTAGCAACCTAGCATGA

TGCCAACAAGACTATTTTTGAAAGAGCAAAGGTTCCTGTAAATTTAATTA

GGGCTAGATTTGAGCTGCTTGTAAGTCACAGGTTTTCCAGATGTCTGCCA

ACAAGAAATGACTCATACTGTGATGATACCTTTTGCTTTGCCTTGTGGAC

AATGTGGGTTTTTGAAATTTGCACCCTTCAAACAATGATTTATCAGAGAA

AGGGGTCTGTTTTCAAAAAAGATTCTGTAATGAATTTTATGTGTGGCATA

TACTTATTTCTTGAGAGAAGATTTTAACTTATTGTTTTTATTTTATGGTT

ACATATGATGATAACCTGCTATTATTAAACT or a variant, fragment, fusion or derivative thereof. The nucleotide sequence encoding MSK1 is shown in FIG. 1 together with the translation of the relevant open reading frame.

In another preferred embodiment the polynucleotide comprises the nucleotide sequence (SEQ ID NO:11)

ACCGAAGCCAACCTGACCGGGCACGAGGAGAAGGTGAGCGTGGAGAACTT

CGAGCTGCTCAAGGTGCTGGGCACGGGAGCCTACGGCAAGGTGTTCCTGG

TGCGGAAGGCGGGCGGGCACGACGCGGGGAAGCTGTACGCCATGAAGGTG

CTGCGCAAGGCGGCGCTGGTGCAGCGCGCCAAGACGCAAGAGCACACGCG

CACCGAGCGCTCGGTGCTGGAGCTGGTGCGCCAGGCGCCCTTCCTGGTCA

CGCTGCACTACGCTTTCCAGACGGATGCCAAGCTGCACCTCATCCTGGAC

TATGTGAGCGGCGGGGAGATGTTCACCCACCTCTACCAGCGCCAGTACTT

CAAGGAGGCTGAGGTGCGCGTGTATGGGGGTGAGATCGTGCTGGCCCTGG

-continued

```
AACACCTGCACAAGCTCGGCATCATTTACCGAGACCTGAAACTGGAGAAT
GTGCTGCTGGACTCCGAGGGCACATTGTCCTCACGGACTTCGGGCTGAG
CAAGGAGTTCCTGACGGAGGAGAAAGAGCGGACCTTCTCCTTCTGTGGCA
CCATCGAGTACATGGCCCCCGAAATCATCCGTAGCAAGACGGGGCATGGC
AAGGCTGTGGACTGGTGGAGCCTGGGCATCTTGCTCTTCGAGCTGCTGAC
GGGGGCCTCGCCCTTCACCCTGGAGGGCGAGAGGAACACGCAGGCTGAGG
TGTCTCGACGGATCCTGAAGTGCTCCCCTCCCTTCCCCCCTCGGATCGGG
CCCGTGGCGCAGGACCTGCTGCAGCGGCTGCTTTGTAAGGATCCTAAGAA
GCGATTGGGCGCGGGCCCCAGGGGGCACAAGAAGTCCGGAACCATCCCT
TCTTCCAGGGCCTCGATTGGGTGGCTCTGGCTGCCAGGAAGATTCCAGCC
CCATTCCGGCCCCAAATCCGCTCAGAGCTGGATGTGGGCAACTTTGCGGA
GGAATTCACTCGGCTGGAGCCTGTCTACTCACCCCCTGGCAGCCCCCCAC
CTGGGGACCCCCGAATCTTTCAGGGATACTCCTTTGTGGCACCCTCCATT
CTCTTTGACCACAACAACGCGGTGATGACCGATGGGCTGGAAGCGCCTGG
TGCTGGAGACCGGCCAGGTCGGGCAGCGGTGGCCAGGAGCGCTATGATGC
AGCAGTACGAGCTGGACCTGCGGGAGCCTGCGCTGGGCCAGGGCAGCTTT
TCTGTGTGTCGCCGCTGCCGCCAGCGCCAGAGCGGCCAGGAGTTCGCAGT
CAAGATCCTCAGTCGCAGGCTGGAGGCGAACACGCAGCGCGAAGTGGCTG
CCCTGCGCCTGTGCCAGTCACACCCCAACGTGGTGAATCTGCACGAGGTG
CATCACGACCAGCTGCACACGTACCTGGTCCTGGAGCTGCTGCGGGGCGG
GGAGCTGCTGGAGCACATCCGCAAGAAGCGGCACTTCAGCGAGTCGGAAG
CAAGCCAGATCCTGCGCAGCCTCGTGTCGGCCGTGAGCTTCATGCACGAG
GAGGCGGGCGTGGTGCACCGCGACCTCAAGCCGGAGAACATCCTGTACGC
CGACGACACGCCCGGGCCCCGGTGAAAATCATCGACTTCGGGTTCGCGC
GGTTGCGGCCGCAGAGTCCCGGGGTGCCCATGCAGACGCCCTGCTTCACG
CTGCAGTACGCTGCCCCCGAGCTGCTGGCGCAGCAGGGCTACGACGAGTC
CTGCGACCTCTGGAGCCTGGGCGTCATTCTGTACATGATGCTGTCGGGGC
AGGTCCCCTTCCAGGGGCCTCTGGCCAGGGCGGGCAGAGCCAGGCGGCC
GAGATCATGTGCAAAATCCGCGAGGGGCGCTTCTCCCTTGACGGGGAGGC
CTGGCAGGGTGTATCCGAGGAAGCCAAGGAGCTGGTCCGAGGGCTCCTGA
CCGTGGACCCCGCCAAGCGGCTGAAGCTCGAGGGACTGCGGGCAGCTCG
TGGCTGCAGGACGGCAGCGCGCGCTCCTCGCCCCCGCTCCGGACGCCCGA
CGTGCTCGAGTCCTCTGGGCCCGCAGTGCGCTCGGGTCTCAACGCCACCT
TCATGGCATTCAACCGGGGCAAGCGGGAGGGCTTCTTCCTGAAGAGCGTG
GAGAATGCACCCCTCA
``` or (SEQ ID NO:8)

```
ACCGAAGCCAACCTGACCGGGCACGAGGAGAAGGTGAGCGTGGAGAACTT
CGAGCTGCTCAAGGTGCTGGGCACGGGAGCCTACGGCAAGGTGTTCCTGG
TGCGGAAGGCGGGCGGGCACGACGCGGGGAAGCTGTACGCCATGAAGGTG
CTGCGCAAGGCGGCGCTGGTGCAGCGCGCCAAGACGCAAGAGCACACGCG
CACCGAGCGCTCGGTGCTGGAGCTGGTGCGCCAGGCGCCCTTCCTGGTCA
CGCTGCACTACGCTTTCCAGACGGATGCCAAGCTGCACCTCATCCTGGAC
TATGTGAGCGGCGGGGAGATGTTCACCCACCTCTACCAGCGCCAGTACTT
CAAGGAGGCTGAGGTGCGCGTGTATGGGGGTGAGATCGTGCTGGCCCTGG
AACACCTGCACAAGCTCGGCATCATTTACCGAGACCTGAAACTGGAGAAT
GTGCTGCTGGACTCCGAGGGCACATTGTCCTCACGGACTTCGGGCTGAG
CAAGGAGTTCCTGACGGAGGAGAAAGAGCGGACCTTCTCCTTCTGTGGCA
CCATCGAGTACATGGCCCCCGAAATCATCCGTAGCAAGACGGGGCATGGC
AAGGCTGTGGACTGGTGGAGCCTGGGCATCTTGCTCTTCGAGCTGCTGAC
GGGGGCCTCGCCCTTCACCCTGGAGGGCGAGAGGAACACGCAGGCTGAGG
TGTCTCGACGGATCCTGAAGTGCTCCCCTCCCTTCCCCCCTCGGATCGGG
CCCGTGGCGCAGGACCTGCTGCAGCGGCTGCTTTGTAAGGATCCTAAGAA
GCGATTGGGCGCGGGCCCCAGGGGGCACAAGAAGTCCGGAACCATCCCT
TCTTCCAGGGCCTCGATTGGGTGGCTCTGGCTGCCAGGAAGATTCCAGCC
CCATTCCGGCCCCAAATCCGCTCAGAGCTGGATGTGGGCAACTTTGCGGA
GGAATTCACTCGGCTGGAGCCTGTCTACTCACCCCCTGGCAGCCCCCCAC
CTGGGGACCCCCGAATCTTTCAGGGATACTCCTTTGTGGCACCCTCCATT
CTCTTTGACCACAACAACGCGGTGATGACCGATGGGCTGGAAGCGCCTGG
TGCTGGAGACCGGCCAGGTCGGGCAGCGGTGGCCAGGAGCGCTATGATGC
AGGACTCGCCCTTCTTCCAGCAGTACGAGCTGGACCTGCGGGAGCCTGCG
CTGGGCCAGGGCAGCTTTTCTGTGTGTCGCCGCTGCCGCCAGCGCCAGAG
CGGCCAGGAGTTCGCAGTCAAGATCCTCAGTCGCAGGCTGGAGGCGAACA
CGCAGCGCGAAGTGGCTGCCCTGCGCCTGTGCCAGTCACACCCCAACGTG
GTGAATCTGCACGAGGTGCATCACGACCAGCTGCACACGTACCTGGTCCT
GGAGCTGCTGCGGGGCGGGGAGCTGCTGGAGCACATCCGCAAGAAGCGGC
ACTTCAGCGAGTCGGAAGCAAGCCAGATCCTGCGCAGCCTCGTGTCGGCC
GTGAGCTTCATGCACGAGGAGGCGGGCGTGGTGCACCGCGACCTCAAGCC
GGAGAACATCCTGTACGCCGACGACACGCCCGGGCCCCGGTGAAAATCA
TCGACTTCGGGTTCGCGCGGTTGCGGCCGCAGAGTCCCGGGGTGCCCATG
CAGACGCCCTGCTTCACGCTGCAGTACGCTGCCCCCGAGCTGCTGGCGCA
GCAGGGCTACGACGAGTCCTGCGACCTCTGGAGCCTGGGCGTCATTCTGT
ACATGATGCTGTCGGGGCAGGTCCCCTTCCAGGGGCCTCTGGCCAGGGC
GGGCAGAGCCAGGCGGCCGAGATCATGTGCAAAATCCGCGAGGGGCGCTT
CTCCCTTGACGGGGAGGCCTGGCAGGGTGTATCCGAGGAAGCCAAGGAGC
TGGTCCGAGGGCTCCTGACCGTGGACCCCGCCAAGCGGCTGAAGCTCGAG
GGACTGCGGGCAGCTCGTGGCTGCAGGACGGCAGCGCGCGCTCCTCGCC
CCCGCTCCGGACGCCCGACGTGCTCGAGTCCTCTGGGCCCGCAGTGCGCT
```

-continued

CGGGTCTCAACGCCACCTTCATGGCATTCAACCGGGGCAAGCGGGAGGGC

TTCTTCCTGAAGAGCGTGGAGAATGCACCCCTCA or (SEQ ID NO:9)

CACGCGTCCGGAGACGAGGATGAGGACGAGGGCTGCGCCGTGGAGCTGCA

GATCACCGAAGCCAACCTCACCGGGCATGAGGAGAAGGTGAGCGTGGAGA

ACTTCGCGCTGCTCAAGGTGCTGGGCACGGGAGCCTATGGGAAGGTGTTC

CTGGTGCGGAAGACGGGTGGGCACGACGCGGGCAAGCTCTATGCCATGAA

GGTGCTACGCAAGGCGGCGTTGGTGCAGCGCGCGAAGACACAGGAGCATA

CCCGCACCGAACGCTCGGTGCTGGAGCTGGTTCGCCAAGCACCCTTCCTG

GTCACACTGCACTACGCCTTCCAGACGGATGCCAAGCTGCACCTCATCCT

GGACTACGTGAGCGGTGGTGAGATGTTCACTCACCTCTACCAGCGCCAGT

ACTTCAAGGAGGCTGAGGTTCGAGTGTATGGGGGCGAGATTGTGCTGGCC

CTGGAACACCTGCACAAGCTGGGTATCATCTACCGGGACCTGAAGCTGGA

GAACGTCTTACTTGACTCAGAAGGTCACATCGTCCTTACAGACTTTGGGC

TGAGCAAGGAGTTCCTGACGGAGGAGAAAGAGCGGACCTTCTCCTTCTGT

GGCACAATCGAGTACATGGCTCCCGAAATCATCCGAAGCAAGGCTGGACA

TGGCAAGGCTGTGGACTGGTGGAGCCTGGGTATCCTGCTCTTCGAGCTGC

TGACAGGGGCCTCACCCTTCACACTGGAGGGAGAGAGGAACACTCAGGCT

GAGGTGTCCCGACGGATCTTGAAGTGCTCCCCTCCCTTCCCTCTCCGGAT

TGGGCCTGTGGCACAGGACCTGCTACAGCGGCTGCTGTGCAAGGACCCTA

AGAAGAGGTTGGGCGCAGGTCCCCAGGGTGCGCAGGAAGTCAAGAGTCAC

CCCTTCTTCAGGGTCTGGACTGGGTGGGCTCTGGCTGCCAGAAAGATCCC

AGCCCCATTCCGGCCCCAGATCCGCTCAGAGCTGGATGTGGGGAATTTTG

CGGAGGAATTCACCCGGCTGGAGCCCGTCTACTCCCCTGCAGGCAGCCCT

CCACCTGGGGACCCTCGGATCTTTCAGGGATACTCCTTCGTGGCTCCGTC

CATCCTCTTTGACCACAACAATGCAGTGATGGCTGATGTACTGCAGGCAC

CGGGTGCCGGATACAGGCCCGGCAGGGCAGCAGTTGCCAGGAGTGCCATG

ATGCAGGACTCGCCTTTCTTCCAGCAGTACGAACTGGACCTTCGGGAGCC

AGCGCTGGGGCAGGGCAGCTTCTCTGTGTGTCGGAGATGTAGGCAGCGCC

AGAGCGGCCAGGAGTTTGCTGTCAAGATCCTCAGCCGCAGGCTGGAGGAG

AACACTCAGCGAGAGGTGGCTGCTCTTCGCCTGTGCCAGTCACACCCCAA

CGTGGTGAATCTGCATGAGGTGCTTCATGACCAGCTACACACTTACCTGG

TCCTGGAGTTGCTGCGAGGCGGAGAGCTATTGGAACACATCCGCAAGAAG

CGGCTCTTCAGCGAGTCGGAGGCCAGCCAGATCCTTCGGAGCCTGGTTTC

GGCCGTGAGCTTCATGCACGAGGAGGCAGGCGTGGTGCACCGCGACCTGA

AACCCGAGAACATCTTGTACGCGGACGACACTCCCGGGGCCCCGGTGAAG

ATCATCGACTTCGGGTTCGCGCGACTGCGGCCCCAGAGCCCGGCAGAGCC

CATGCAGACTCCTTGCTTCACACTGCAGTACGCTGCACCCGAGCTGCTGG

-continued

CACAGCAGGGCTACGATGAGTCCTGCGATCTATGGAGCCTGGGTGTCATT

CTGTACATGATGCTGTCTGGCCAGGTTCCCTTCCAAGGGGCCTCCGGCCA

GGGTGGACAGAGTCAGGCAGCTGAGATCATGTGCAAGATCCGTGAAGGGC

GCTTCTCCCTGGACGGGGAAGCCTGGCAAGGTGTGTCGGAGGAAGCCAAG

GAGCTGGTCCGAGGGCTACTGACAGTCGACCCCGCCAAGCGGCTGAAGCT

GGAGGGGCTGCGTAGCAGCTCGTGGCTTCAGGACGGCAGCGCGCGCTCCT

CGCCCCCGCTCCGCACGCCGGATGTGCTGGAGTCCTCTGGGCCAGCTGTG

CGTTCCGGGCTCAATGCCACTTTCATGGCGTTCAACCGAGGCAAGCGCGA

GGGCTTCTTTCTCAAGAGTGTAGAGAATGCGCCTCTGGCCAAGAGGCGCA

AGCAGAAGCTCCGGAGCGCGGC or a variant, fragment, fusion or derivative thereof.

The above polynucleotides encode partial human (two splice variants) or mouse MSK2 respectively. It will be appreciated that sequences encoding full length mouse or human MSK2 may be obtained by routine use of methods well known to those skilled in the art, making use of the sequences shown above. Thus PCR methods may be used, particularly methods developed to generate 5' cDNA sequences (for example, the "RACE" method, as well known to those skilled in the art).

In a preferred embodiment, the polynucleotide comprises the sequence (SEQ ID NO:10)

CGAGCCGTGCGGCCAGAGCGGGAAAGAGACTCGTCTTTGCGTCCGAGTTC

TGGAGCCGCCGCACCCCGACTCCTGGGGCCGCGGCAGCGGCTGCGAGGGG

ACGGGCGTCCGCTGTCTCCTGGGTTCCCCTCGTAGCGACCCGCGGGATCG

GAAAAAAAGGAGAAGATGGAGGAGGAGGGTGGCAGCAGCGGCGGCGCCGC

GGGGACCAGCGCGGACGGCGGCGACGGAGGAGAGCAGCTCCTCACTGTCA

AGCACGAGCTGCGGACTGCTAATTTGACAGGACATGCTGAGAAGGTGGGA

ATAGAAATTTTGAGCTCCTGAAGGTCCTAGGAACTGGAGCTTATGGAAA

AGTATTTCTAGTTCGTAAAATAAGTGGCCATGATACTGGAAAGCTGTATG

CCATGAAAGTTTTGAAAAAGGCAACAATCGTTCAAAAGGCCAAAACCACA

GAGCATACAAGGACAGAACGACAAGTCCTGGAACACATTAGGCAGTCGCC

ATTTTTGGTAACATTACATTATGCTTTCCAGACAGAAACCAAACTTCATC

TCATTTTAGATTATATAAATGGTGGTGAACTTTTTACTCATCTTTCTCAA

AGAGAGCGTTTCACAGAGCATGAGGTGCAGATTTATGTTGGAGAGATTGT

GCTTGCCCTCGAACATCTCCACAAGTTGGGGATTATATATCGTGATATTA

AGCTTGAGAATATTCTACTTGATTCTAATGGCCATGTGGTGCTGACAGAT

TTTGGTCTGAGTAAGGAGTTTGTGGCTGATGAAACTGAAAGAGCATATTC

CTTTTGTGGAACTATTGAATACATGGCACCAGATATTGTCAGAGGGGGAG

ATTCAGGACATGACAAGGCAGTTGACTGGTGGAGTTTGGGTGTTCTAATG

TATGAATTACTAACTGGAGCATCTCCTTTCACTGTTGATGGAGAAAAAAA

TTCCCAAGCTGAGATATCTAGGAGAATATTAAAAAGTGAGCCTCCATATC

CCCAAGAAATGAGTGCTTTAGCGAAAGACCTAATTCAGCGTCTTTTGATG

-continued

AAAGATCCCAAGAAGAGATTGGGATGTGGTCCACGTGATGCAGATGAAAT

CAAAGAACATCTCTTCTTTCAGAAAATAAATTGGGATGATTTAGCCGCCA

AAAAAGTGCCTGCACCATTTAAGCCAGTCATTCGAGATGAATTAGATGTG

AGTAACTTTGCAGAAGAGTTCACAGAAATGGATCCCACTTATTCTCCCGC

AGCCCTGCCCCAGAGTTCTGAGAAGCTGTTTCAGGGCTATTCCTTTGTTG

CTCCTTCCATCCTATTCAAGCGTAATGCAGCTGTCATAGACCCTCTTCAG

TTTCACATGGGAGTTGAACGTCCTGGAGTGACAAATGTTGCCAGGAGTGC

AATGATGAAGGACTCTCCATTCTATCAACACTATGACCTAGATTTGAAGG

ACAAACCCTGGGAGAAGGTAGTTTTTCAATTTGTCGAAAGTGTGTGCAT

AAAAAAAGTAACCAAGCTTTTGCAGTCAAAATAATCAGCAAAAGGATGGA

AGCCAATACTCAAAAGGAAATAACAGCTCTGAAACTCTGTGAAGGACACC

CCAATATTGTGAAGTTGCATGAAGTTTTTCATGATCAGCTTCACACGTTT

CTAGTGATGGAACTTCTGAATGGAGGAGAACTGTTTGAGCGCATTAAGAA

AAAGAAGCACTTCAGTGAGACGGAAGCCAGCTACATCATGAGGAAGCTTG

TTTCAGCTGTAAGCCACATGCATGATGTTGGAGTGGTGCACAGGGATCTG

AAACCTGAGAATTTATTGTTCACCGATGAAAATGACAATTTGGAAATTAA

AATAATTGATTTTGGATTTGCACGGCTAAAGCCACCGGATAATCAGCCCC

TGAAGACTCCATGCTTCACCCTTCATTATGCCGCCCCAGAGCTCTTGAAT

CAGAACGGCTACGATGAGTCCTGTGACCTGTGGAGCTTGGGCGTCATTTT

GTACACAATGTTGTCAGGACAGGTTCCCTTCCAATCTCATGACCGAAGTT

TGACGTGTACCAGCGCGGTGGAAATCATGAAGAAAATTAAAAAGGGAGAT

TTCTCCTTTGAAGGAGAAGCCTGGAAGAATGTATCCCAAGAGGCTAAAGA

TTTGATCCAAGGACTTCTCACAGTAGATCAAACAAAAGGCTTAAAATGT

CTGGCTTGAGGTACAATGAATGGCTACAAGATGGAAGTCAGCTGTCCTCC

AATCCTCTGATGACTCCGGATATTCTAGGATCTTCCGGAGCTGCCGTGCA

TACCTGTGTGAAAGCAACCTTCCACGCCTTTAACAAATACAAGAGAGAGG

GGTTTTGCCTTCAGAATGTTGATAAGGCCCCTTTGGCTAAGAGAAGAAAA

ATGAAAAAGACTAGCACCAGTACCGAGACGCGCAGCAGTTCCAGTGAGAG

TTCCCATTCTTCTTCCTCTCATTCTCACGGTAAAACTACACCCACCAAGA

CACTGCAGCCCAGCAATCCTGCCGACAGCAATAACCCGGAGACCCTCTTC

CAGTTCTCGGACTCAGTAGCTTAGGCATGGTAGGAGTGTATCAGTGATCC

ATTGCACCTTTATTCCCTCAGCATATGCCTGAGGCGATCTTTTATGCTTT

TAAAAATGTTTCCCGTTGGTCTCATTGGAATCTGCCTCCTAATGATTTTT

TTTCAGGAAAACCTGTTTGGTTATCCTCATTCAAAAGCACTGGACAGAGA

ATGTTACTGTGAATAGAGCACATATTACTCTTTTTAGCAACCTAGCATGA

TGCCAACAAGACTATTTTTGAAAGAGCAAAGGTTCCTGTAAATTTAATTA

GGGCTAGATTTGAGCTGCTTGTAAGTCACAGGTTTTCCAGATGTCTGCCA

ACAAGAAATGACTCATACTGTGATGATACCTTTTGCTTTGCCTTGTGGAC

AATGTGGGTTTTTGAAATTTGCACCCTTCAAACAATGATTTATCAGAGAA

AGGGGTCTGTTTTCAAAAAAGATTCTGTAATGAATTTTATGTGTGGCATA

-continued

TACTTATTTCTTGAGAGAAGATTTTAACTTATTGTTTTTATTTTATGGTT

ACATATGATGATAACCTGCTATTATTAAACT or a variant, fragment, fusion or derivative thereof. The nucleotide sequence encoding MSK1 is shown in FIG. 1 together with the translation of the relevant open reading frame.

In another preferred embodiment the polynucleotide comprises the nucleotide sequence (SEQ ID NO:11)

ACCGAAGCCAACCTGACCGGGCACGAGGAGAAGGTGAGCGTGGAGAACTT

CGAGCTGCTCAAGGTGCTGGGCACGGGAGCCTACGGCAAGGTGTTCCTGG

TGCGGAAGGCGGGCGGGCACGACGCGGGGAAGCTGTACGCCATGAAGGTG

CTGCGCAAGGCGGCGCTGGTGCAGCGCGCCAAGACGCAAGAGCACACGCG

CACCGAGCGCTCGGTGCTGGAGCTGGTGCGCCAGGCGCCCTTCCTGGTCA

CGCTGCACTACGCTTTCCAGACGGATGCCAAGCTGCACCTCATCCTGGAC

TATGTGAGCGGCGGGGAGATGTTCACCCACCTCTACCAGCGCCAGTACTT

CAAGGAGGCTGAGGTGCGCGTGTATGGGGGTGAGATCGTGCTGGCCCTGG

AACACCTGCACAAGCTCGGCATCATTTACCGAGACCTGAAACTGGAGAAT

GTGCTGCTGGACTCCGAGGGCCACATTGTCCTCACGGACTTCGGGCTGAG

CAAGGAGTTCCTGACGGAGGAGAAAGAGCGGACCTTCTCCTTCTGTGGCA

CCATCGAGTACATGGCCCCCGAAATCATCCGTAGCAAGACGGGGCATGGC

AAGGCTGTGGACTGGTGGAGCCTGGGCATCTTGCTCTTCGAGCTGCTGAC

GGGGGCCTCGCCCTTCACCCTGGAGGGCGAGAGGAACACGCAGGCTGAGG

TGTCTCGACGGATCCTGAAGTGCTCCCCTCCCTTCCCCCCTCGGATCGGG

CCCGTGGCGCAGGACCTGCTGCAGCGGCTGCTTTGTAAGGATCCTAAGAA

GCGATTGGGCGCGGGCCCCAGGGGGCACAAGAAGTCCGGAACCATCCCT

TCTTCCAGGGCCTCGATTGGGTGGCTCTGGCTGCCAGGAAGATTCCAGCC

CCATTCCGCCCCAAATCCGCTCAGAGCTGGATGTGGGCAACTTTGCGGA

GGAATTCACTCGGCTGGAGCCTGTCTACTCACCCCCTGGCAGCCCCCCAC

CTGGGGACCCCGAATCTTTCAGGGATACTCCTTTGTGGCACCCTCCATT

CTCTTTGACCAACAACGCGGTGATGACCGATGGGCTGGAAGCGCCTGG

TGCTGGAGACCGGCCAGGTCGGGCAGCGGTGGCCAGGAGCGCTATGATGC

AGCAGTACGAGCTGGACCTGCGGGAGCCTGCGCTGGGCCAGGGCAGCTTT

TCTGTGTGTCGCCGCTGCCGCCAGCGCCAGAGCGGCCAGGAGTTCGCAGT

CAAGATCCTCAGTCGCAGGCTGGAGGCGAACACGCAGCGCGAAGTGGCTG

CCCTGCGCCTGTGCCAGTCACACCCCAACGTGGTGAATCTGCACGAGGTG

CATCACGACCAGCTGCACACGTACCTGGTCCTGGAGCTGCTGCGGGGCGG

GGAGCTGCTGGAGCACATCCGCAAGAAGCGGCACTTCAGCGAGTCGGAAG

CAAGCCAGATCCTGCGCAGCCTCGTGTCGGCCGTGAGCTTCATGCACGAG

GAGGCGGGCGTGGTGCACCGCGACCTCAAGCCGGAGAACATCCTGTACGC

CGACGACACGCCCGGGGCCCCGGTGAAAATCATCGACTTCGGGTTCGCGC

GGTTGCGGCCGCAGAGTCCCGGGGTGCCCATGCAGACGCCCTGCTTCACG

-continued

CTGCAGTACGCTGCCCCCGAGCTGCTGGCGCAGCAGGGCTACGACGAGTC
CTGCGACCTCTGGAGCCTGGGCGTCATTCTGTACATGATGCTGTCGGGGC
AGGTCCCCTTCCAGGGGGCCTCTGGCCAGGGCGGGCAGAGCCAGGCGGCC
GAGATCATGTGCAAAATCCGCGAGGGGCGCTTCTCCCTTGACGGGGAGGC
CTGGCAGGGTGTATCCGAGGAAGCCAAGGAGCTGGTCCGAGGGCTCCTGA
CCGTGGACCCCGCCAAGCGGCTGAAGCTCGAGGGACTGCGGGGCAGCTCG
TGGCTGCAGGACGGCAGCGCGCGCTCCTCGCCCCCGCTCCGGACGCCCGA
CGTGCTCGAGTCCTCTGGGCCCGCAGTGCGCTCGGGTCTCAACGCCACCT
TCATGGCATTCAACCGGGGCAAGCGGGAGGGCTTCTTCCTGAAGAGCGTG
GAGAATGCACCCCTCA or (SEQ ID NO:12)

ACCGAAGCCAACCTGACCGGGCACGAGGAGAAGGTGAGCGTGGAGAACTT
CGAGCTGCTCAAGGTGCTGGGCACGGGAGCCTACGGCAAGGTGTTCCTGG
TGCGGAAGGCGGGCGGGCACGACGCGGGGAAGCTGTACGCCATGAAGGTG
CTGCGCAAGGCGGCGCTGGTGCAGCGCGCCAAGACGCAAGAGCACACGCG
CACCGAGCGCTCGGTGCTGGAGCTGGTGCGCCAGGCGCCCTTCCTGGTCA
CGCTGCACTACGCTTTCCAGACGGATGCCAAGCTGCACCTCATCCTGGAC
TATGTGAGCGGCGGGGAGATGTTCACCCACCTCTACCAGCGCCAGTACTT
CAAGGAGGCTGAGGTGCGCGTGTATGGGGGTGAGATCGTGCTGGCCCTGG
AACACCTGCACAAGCTCGGCATCATTTACCGAGACCTGAAACTGGAGAAT
GTGCTGCTGGACTCCGAGGGCCACATTGTCCTCACGGACTTCGGGCTGAG
CAAGGAGTTCCTGACGGAGGAGAAAGAGCGGACCTTCTCCTTCTGTGGCA
CCATCGAGTACATGGCCCCGAAATCATCCGTAGCAAGACGGGGCATGGC
AAGGCTGTGGACTGGTGGAGCCTGGGCATCTTGCTCTTCGAGCTGCTGAC
GGGGGCCTCGCCCTTCACCCTGGAGGGCGAGAGGAACACGCAGGCTGAGG
TGTCTCGACGGATCCTGAAGTGCTCCCCTCCCTTCCCCCCTCGGATCGGG
CCCGTGGCGCAGGACCTGCTGCAGCGGCTGCTTTGTAAGGATCCTAAGAA
GCGATTGGGCGCGGGCCCCAGGGGCACAAGAAGTCCGGAACCATCCCT
TCTTCCAGGGCCTCGATTGGGTGGCTCTGGCTGCCAGGAAGATTCCAGCC
CCATTCCGGCCCCAAATCCGCTCAGAGCTGGATGTGGGCAACTTTGCGGA
GGAATTCACTCGGCTGGAGCCTGTCTACTCACCCCCTGGCAGCCCCCAC
CTGGGGACCCCGAATCTTTCAGGGATACTCCTTTGTGGCACCCTCCATT
CTCTTTGACCACAACAACGCGGTGATGACCGATGGGCTGGAAGCGCCTGG
TGCTGGAGACCGGCCAGGTCGGGCAGCGGTGGCCAGGAGCGCTATGATGC
AGGACTCGCCCTTCTTCCAGCAGTACGAGCTGGACCTGCGGGAGCCTGCG
CTGGGCCAGGGCAGCTTTTCTGTGTGTCGCCGCTGCCGCCAGCGCCAGAG
CGGCCAGGAGTTCGCAGTCAAGATCCTCAGTCGCAGGCTGGAGGCGAACA
CGCAGCGCGAAGTGGCTGCCCTGCGCCTGTGCCAGTCACACCCCAACGTG

-continued

GTGAATCTGCACGAGGTGCATCACGACCAGCTGCACACGTACCTGGTCCT
GGAGCTGCTGCGGGGCGGGAGCTGCTGGAGCACATCCGCAAGAAGCGGC
ACTTCAGCGAGTCGGAAGCAAGCCAGATCCTGCGCAGCCTCGTGTCGGCC
GTGAGCTTCATGCACGAGGAGGCGGGCGTGGTGCACCGCGACCTCAAGCC
GGAGAACATCCTGTACGCCGACGACACGCCCGGGGCCCCGGTGAAAATCA
TCGACTTCGGGTTCGCGCGGTTGCGGCCGCAGAGTCCCGGGGTGCCCATG
CAGACGCCCTGCTTCACGCTGCAGTACGCTGCCCCCGAGCTGCTGGCGCA
GCAGGGCTACGACGAGTCCTGCGACCTCTGGAGCCTGGGCGTCATTCTGT
ACATGATGCTGTCGGGGCAGGTCCCCTTCCAGGGGGCCTCTGGCCAGGGC
GGGCAGAGCCAGGCGGCCGAGATCATGTGCAAAATCCGCGAGGGGCGCTT
CTCCCTTGACGGGGAGGCCTGGCAGGGTGTATCCGAGGAAGCCAAGGAGC
TGGTCCGAGGGCTCCTGACCGTGGACCCCGCCAAGCGGCTGAAGCTCGAG
GGACTGCGGGGCAGCTCGTGGCTGCAGGACGGCAGCGCGCGCTCCTCGCC
CCCGCTCCGGACGCCCGACGTGCTCGAGTCCTCTGGGCCCGCAGTGCGCT
CGGGTCTCAACGCCACCTTCATGGCATTCAACCGGGGCAAGCGGGAGGGC
TTCTTCCTGAAGAGCGTGGAGAATGCACCCCTCA or (SEQ ID NO:13)

CACGCGTCCGGAGACGAGGATGAGGACGAGGGCTGCGCCGTGGAGCTGC
AGATCACCGAAGCCAACCTCACCGGGCATGAGGAGAAGGTGAGCGTGGA
GAACTTCGCGCTGCTCAAGGTGCTGGGCACGGGAGCCTATGGGAAGGTG
TTCCTGGTGCGGAAGACGGGTGGGCACGACGCGGGCAAGCTCTATGCCA
TGAAGGTGCTACGCAAGGCGGCGTTGGTGCAGCGCGCGAAGACACAGGA
GCATACCCGCACCGAACGCTCGGTGCTGGAGCTGGTTCGCCAAGCACCC
TTCCTGGTCACACTGCACTACGCCTTCCAGACGGATGCCAAGCTGCACC
TCATCCTGGACTACGTGAGCGGTGGTGAGATGTTCACTCACCTCTACCA
GCGCCAGTACTTCAAGGAGGCTGAGGTTCGAGTGTATGGGGGCGAGATT
GTGCTGGCCCTGGAACACCTGCACAAGCTGGGTATCATCTACCGGGACC
TGAAGCTGGAGAACGTCTTACTTGACTCAGAAGGTCACATCGTCCTTAC
AGACTTTGGGCTGAGCAAGGAGTTCCTGACGGAGGAGAAAGAGCGGACC
TTCTCCTTCTGTGGCACAATCGAGTACATGGCTCCCGAAATCATCCGAA
GCAAGGCTGGACATGGCAAGGCTGTGGACTGGTGGAGCCTGGGTATCCT
GCTCTTCGAGCTGCTGACAGGGCCTCACCCTTCACACTGGAGGGAGAG
AGGAACACTCAGGCTGAGGTGTCCCGACGGATCTTGAAGTGCTCCCCTC
CCTTCCCTCTCCGGATTGGGCCTGTGGCACAGGACCTGCTACAGCGGCT
GCTGTGCAAGGACCCTAAGAAGAGGTTGGGCGCAGGTCCCCAGGGTGCG
CAGGAAGTCAAGAGTCACCCCTTCTTCAGGGTCTGGACTGGGTGGGCTC
TGGCTGCCAGAAAGATCCCAGCCCCATTCCGGCCCCAGATCCGCTCAGA
GCTGGATGTGGGGAATTTTGCGGAGGAATTCACCCGGCTGGAGCCCGTC
TACTCCCCTGCAGGCAGCCCTCCACCTGGGGACCCTCGGATCTTTCAGG

-continued

```
GATACTCCTTCGTGGCTCCGTCCATCCTCTTTGACCACAACAATGCAGT
GATGGCTGATGTACTGCAGGCACCGGGTGCCGGATACAGGCCCGGCAGG
GCAGCAGTTGCCAGGAGTGCCATGATGCAGGACTCGCCTTTCTTCCAGC
AGTACGAACTGGACCTTCGGGAGCCAGCGCTGGGGCAGGGCAGCTTCTC
TGTGTGTCGGAGATGTAGGCAGCGCCAGAGCGGCCAGGAGTTTGCTGTC
AAGATCCTCAGCCGCAGGCTGGAGGAGAACACTCAGCGAGAGGTGGCTG
CTCTTCGCCTGTGCCAGTCACACCCCAACGTGGTGAATCTGCATGAGGT
GCTTCATGACCAGCTACACACTTACCTGGTCCTGGAGTTGCTGCGAGGC
GGAGAGCTATTGGAACACATCCGCAAGAAGCGGCTCTTCAGCGAGTCGG
AGGCCAGCCAGATCCTTCGGAGCCTGGTTTCGGCCGTGAGCTTCATGCA
CGAGGAGGCAGGCGTGGTGCACCGCGACCTGAAACCCGAGAACATCTTG
TACGCGGACGACACTCCCGGGGCCCCGGTGAAGATCATCGACTTCGGGT
TCGCGCGACTGCGGCCCCAGAGCCCGGCAGAGCCCATGCAGACTCCTTG
CTTCACACTGCAGTACGCTGCACCCGAGCTGCTGGCACAGCAGGGCTAC
GATGAGTCCTGCGATCTATGGAGCCTGGGTGTCATTCTGTACATGATGC
TGTCTGGCCAGGTTCCCTTCCAAGGGGCCTCCGGCCAGGGTGGACAGAG
TCAGGCAGCTGAGATCATGTGCAAGATCCGTGAAGGGCGCTTCTCCCTG
GACGGGGAAGCCTGGCAAGGTGTGTCGGAGGAAGCCAAGGAGCTGGTCC
GAGGGCTACTGACAGTCGACCCCGCCAAGCGGCTGAAGCTGGAGGGGCT
GCGTAGCAGCTCGTGGCTTCAGGACGGCAGCGCGCGCTCCTCGCCCCCG
CTCCGCACGCCGGATGTGCTGGAGTCCTCTGGGCCAGCTGTGCGTTCCG
GGCTCAATGCCACTTTCATGGCGTTCAACCGAGGCAAGCGCGAGGGCTT
CTTTCTCAAGAGTGTAGAGAATGCGCCTCTGGCCAAGAGGCGCAAGCAG
AAGCTCCGGAGCGCGGC
``` or a variant, fragment, fusion or derivative thereof.

The above polynucleotides encode partial human (two splice variants) or mouse MSK2 respectively.

A full length human MSK2 polypeptide sequence may be as follows and as given in GenBank entry accession number AJ010119 (Pierrat et al (1998) *J Biol Chem* 273 (45), 29661–29671) (SEQ ID NO:36):

```
MGDEDDDESCAVELRITEANLTGHEEKVSVENFELLKVLGTGAYGKVFLV
RKAGGHDAGKLYAMKVLRKAALVQRAKTQEHTRTERSVLELVRQAPFLVT
LHYAFQTDAKLHLILDYVSGGEMFTHLYQRQYFKEAEVRVYGGEIVLALE
HLNKLGIIYRDLKLENVLLDSEGHIVLTDFGLSKEFLTEEKERTFSFCGT
IEYMAPEIIRSKTGHGKAVDWWSLGILLFELLTGASPFTLEGERNTQAEV
SRRILKCSPPFPPRIGPVAQDLLQRLLCKDPKKRLGAPQGAQEVRNHPF
FQGLDWVALAARKIPAPFRPQIRSELDVGNFAEEFTRLEPVYSPPGSPPP
GDPRIFQGYSFVAPSILFDHNNAVMTDGLEAPGAGDRPGRAAVARSAMMQ
DSPFFQQYELDLREPALGQGSFSVCRRCRQRQSGQEFAVKILSRRLEANT
QREVAALRLCQSHPNVVNLHEVHHDQLHTYLVLELLRGGELLEHIRKKRH
FSESEASQILRSLVSAVSFMHEEAGVVHRDLKPENILYADDTPGAPVKII
DFGFARLRPQSPGVPMQTPCFTLQYAAPELLAQQGYDESCDLWSLGVILY
MMLSGQVPFQGASGQGGQSQAAEIMCKIREGRFSLDGEAWQGVSEEAKEL
VRGLLTVDPAKRLKLEGLRGSSWLQDGSARSSPPLRTPDVLESSGPAVRS
GLNATFMAFNRGKREGFFLKSVENAPLAKRRKQKLRSATASRRGSPAPAN
PGRAPVASKGAPRRANGPLPPS
```

A full length human MSK2 nucleotide sequence may be as follows and as given in GenBank entry accession number AJ010119 (Pierrat et al(1998) *J Biol Chem* 273 (45), 29661–29671) (SEQ ID NO:37):

```
GGAGCCGCCATGTAACCGGCGCCGCCCGGAGCCCGAGCCGCGCGGGCCCC
AGCGACCCGCCCGCCATGGGGGACGAGGACGACGATGAGAGCTGCGCCGT
GGAGCTGCGGATCACAGAAGCCAACCTGACCGGGCACGAGGAGAAGGTGA
GCGTGGAGAACTTCGAGCTGCTCAAGGTGCTGGGCACGGGAGCCTACGGC
AAGGTGTTCCTGGTGCGGAAGGCGGGCGGGCACGACGCGGGGAAGCTGTA
CGCCATGAAGGTGCTGCGCAAGGCGGCGCTGGTGCAGCGCGCCAAGACGC
AGGAGCACACGCGCACCGAGCGCTCGGTGCTGGAGCTGGTGCGCCAGGCG
CCCTTCCTGGTCACGCTGCACTACGCTTTCCAGACGGATGCCAAGCTGCA
CCTCATCCTGGACTATGTGAGCGGCGGGGAGATGTTCACCCACCTCTACC
AGCGCCAGTACTTCAAGGAGGCTGAGGTGCGCGTGTATGGGGGTGAGATC
GTGCTGGCCCTGGAACACCTGCACAAGCTCGGCATCATTTACCGAGACCT
GAAACTGGAGAATGTGCTGCTGGACTCCGAGGGCCACATTGTCCTCACGG
ACTTCGGGCTGAGCAAGGAGTTCCTGACGGAGGAGAAAGAGCGGACCTTC
TCCTTCTGTGGCACCATCGAGTACATGGCCCCCGAAATCATCCGTAGCAA
GACGGGGCATGGCAAGGCTGTGGACTGGTGGAGCCTGGGCATCTTGCTCT
TCGAGCTGCTGACGGGGGCCTCGCCCTTCACCCTGGAGGGCGAGAGGAAC
ACGCAGGCTGAGGTGTCTCGACGGATCCTGAAGTGCTCCCCTCCCTTCCC
CCCTCGGATCGGGCCCGTGGCGCAGGACCTGCTGCAGCGGCTGCTTTGTA
AGGATCCTAAGAAGCGATTGGGCGCGGGCCCCAGGGGGCACAAGAAGTC
CGGAACCATCCCTTCTTCCAGGGCCTCGATTGGGTGGCTCTGGCTGCCAG
GAAGATTCCAGCCCCATTCCGGCCCCAAATCCGCTCAGAGCTGGATGTGG
GCAACTTTGCGGAGGAATTCACTCGGCTGGAGCCTGTCTACTCACCCCCT
GGCAGCCCCCCACCTGGGGACCCCCGAATCTTTCAGGGATACTCCTTTGT
GGCACCCTCCATTCTCTTTGACCACAACAACGCGGTGATGACCGATGGGC
TGGAAGCGCCTGGTGCTGGAGACCGGCCAGGTCGGGCAGCGGTGGCCAGG
AGCGCTATGATGCAGGACTCGCCCTTCTTCCAGCAGTACGAGCTGGACCT
GCGGGAGCCTGCGCTGGGCCAGGGCAGCTTTTCTGTGTGTCGCCGCTGCC
GCCAGCGCCAGAGCGCCAGGAGTTCGCAGTCAAGATCCTCAGTCGCAGG
CTGGAGGCAACACGCAGCGCGAAGTGGCTGCCCTGCGCCTGTGCCAGTC
ACACCCCAACGTGGTGAATCTGCACGAGGTGCATCACGACCAGCTGCACA
```

-continued

```
CGTACCTGGTCCTGGAGCTGCTGCGGGCGGGGAGCTGCTGGAGCACATC

CGCAAGAAGCGGCACTTCAGCGAGTCGGAAGCAAGCCAGATCCTGCGCAG

CCTCGTGTCGGCCGTGAGCTTCATGCACGAGGAGGCGGGCGTGGTGCACC

GCGACCTCAAGCCGGAGAACATCCTGTACGCCGACGACACGCCCGGGCC

CCGGTGAAAATCATCGACTTCGGGTTCGCGCGGTTGCGGCCGCAGAGTCC

CGGGGTGCCCATGCAGACGCCCTGCTTCACGCTGCAGTACGCTGCCCCCG

AGCTGCTGGCGCAGCAGGGCTACGACGAGTCCTGCGACCTCTGGAGCCTG

GGCGTCATTCTGTACATGATGCTGTCGGGGCAGGTCCCCTTCCAGGGGGC

CTCTGGCCAGGGCGGGCAGAGCCAGGCGGCCGAGATCATGTGCAAAATCC

GCGAGGGGCGCTTCTCCCTTGACGGGGAGGCCTGGCAGGGTGTATCCGAG

GAAGCCAAGGAGCTGGTCCGAGGGCTCCTGACCGTGGACCCCGCCAAGCG

GCTGAAGCTCGAGGGACTGCGGGGCAGCTCGTGGCTGCAGGACGGCAGCG

CGCGCTCCTCGCCCCGCTCCGGACGCCCGACGTGCTCGAGTCCTCTGGG

CCCGCAGTGCGCTCGGGTCTCAACGCCACCTTCATGGCATTCAACCGGGG

CAAGCGGGAGGGCTTCTTCCTGAAGAGCGTGGAGAATGCACCCCTGGCCA

AGCGGCGGAAGCAGAAGCTGCGGAGCGCCACCGCCTCCCGCCGGGGCTCC

CCTGCACCAGCCAACCCGGGCCGAGCCCCGTCGCCTCCAAAGGGCCCC

CCGCCGAGCCAACGGCCCCTGCCCCCCTCCTAATCCCCACCACTGTGAC

CCCCTTCCCTCATAGGGGCTGTGACCTGGGAGCCCGGCTCACTCCCGGAG

GCCTCTGCCTGCGGCTGACCTGATCCCCAAGGGACTGTCCTTTCCTCTCC

TACCCCACCCCACTCCCAGACAGAGCAGAAGTATTTTTATAAGCAGAGAA

TTTTTTATGTCTTACCAGATAGAGTTGCAGGGAAGGGGGGCCTGCTGGG

GAGTGGGGTTTGGGGGGCCCTCTCCCAGGACACTGCCTCTTCTGGGCAGA

AGGCCCCTCCAGGGGGACTGCTCCAACAGGAAAGAGCCCCTCCCCCACTT

CTAAGCACTGAGTTAGGAGTGCTAACTCCTAAACTGGGACCCCCTACCCT

GTTCTCCCCTGAGGCCCCGTTCCTGGGAGGGGCACCCCTCAACTGTCACT

TTATGGACTGTCTGTGCAATTACGTCCACCAAAGACCCGTGTTGGGGGTA

CTGAAGGAGAGGCCCTGGGGGACCCTCTGAAGCATTTCTGCCTCACTTTA

TGTCATCTGCTTCTCCCCTGTTGGGGCTAAGGAAGGAGATAGGTGGCTCC

TAAAAGAGGAGGCCATCTTCTCACCCACCCCTTCCTCTTTGGCACAGCTA

CTCCTGGCTGGGGGTGGGGCCTTGGGGGTCTGGGCTGGGCATCCATGGTC

ACTGCCTCAGCCCAGCCAGGCTGTGCCTTTGACTTTAAAATAAAAGTCCA

CCCAGTGCTGTGTGTGGCAAAAAAAAAAAAA
```

It will be appreciated that an expressed sequence tag (EST) clone is not a recombinant polynucleotide as defined above as it lacks sequences necessary for the translation and therefore expression of the expressed sequence tag. EST sequences may be cloned in the vector Uni-ZAP XR, pT7T3D-Pac, pBluescript SK-, Lafinid BA or pCMV-SPORT2 vector.

A polynucleotide comprising a fragment of the recombinant polynucleotide encoding a polypeptide of the invention or a variant, fragment, fusion or derivative may also be useful. Preferably, the polynucleotide comprises a fragment which is at least 10 nucleotides in length, more preferably at least 14 nucleotides in length and still more preferably at least 18 nucleotides in length. Such polynucleotides are useful as PCR primers. A polynucleotide complementary to the polynucleotide (or a fragment thereof) encoding a polypeptide of the invention or a variant, fragment, fusion or derivative may also be useful. Such complementary polynucleotides are well known to those skilled in the art as antisense polynucleotides.

The polynucleotide or recombinant polynucleotide of the invention may be DNA or RNA, preferably DNA. The polynucleotide may or may not contain introns in the coding sequence; preferably the polynucleotide is a cDNA.

A "variation" of the polynucleotide includes one which is (i) usable to produce a protein or a fragment thereof which is in turn usable to prepare antibodies which specifically bind to the protein encoded by the said polynucleotide or (ii) an antisense sequence corresponding to the gene or to a variation of type (i) as just defined. For example, different codons can be substituted which code for the same amino acid(s) as the original codons. Alternatively, the substitute codons may code for a different amino acid that will not affect the activity or immunogenicity of the protein or which may improve or otherwise modulate its activity or immunogenicity. For example, site-directed mutagenesis or other techniques can be employed to create single or multiple mutations, such as replacements, insertions, deletions, and transpositions, as described in Botstein and Shortle, "Strategies and Applications of In Vitro Mutagenesis" *Science*, 229: 193–210 (1985), which is incorporated herein by reference. Since such modified polynucleotides can be obtained by the application of known techniques to the teachings contained herein, such modified polynucleotides are within the scope of the claimed invention.

Moreover, it will be recognised by those skilled in the art that the polynucleotide sequence (or fragments thereof) encoding a polypeptide of the invention can be used to obtain other polynucleotide sequences that hybridise with it under conditions of high stringency. Such polynucleotides includes any genomic DNA. Accordingly, the polynucleotide of the invention includes polynucleotide that shows at least 60%, preferably 70%, and more preferably at least 80% and most preferably at least 90% homology with the polynucleotide identified in the method of the invention, provided that such homologous polynucleotide encodes a polypeptide which is usable in at least some of the methods described below or is otherwise useful.

Percent homology can be determined by, for example, the GAP program of the University of Wisconsin Genetic Computer Group.

DNA—DNA, DNA-RNA and RNA—RNA hybridisation may be performed in aqueous solution containing between 0.1×SSC and 6×SSC and at temperatures of between 55° C. and 70° C. It is well known in the art that the higher the temperature or the lower the SSC concentration the more stringent the hybridisation conditions. By "high stringency" we mean 2×SSC and 65° C. 1×SSC is 0.15M NaCl/0.015M sodium citrate. Polynucleotides which hybridise at high stringency are included within the scope of the claimed invention.

"Variations" of the polynucleotide also include polynucleotide in which relatively short stretches (for example 20 to 50 nucleotides) have a high degree of homology (at least 80% and preferably at least 90 or 95%) with equivalent stretches of the polynucleotide of the invention even though the overall homology between the two polynucleotides may be much less. This is because important active or binding sites may be shared even when the general architecture of the protein is different.

A variety of methods have been developed to operably link polynucleotides, especially DNA, to vectors for example via complementary cohesive termini. Suitable methods are described in Sambrook et al(1989) Molecular Cloning, A Laboratory Manual, Cold Spring Harbor Laboratory, Cold Spring Harbor, N.Y.

A desirable way to modify the DNA encoding a polypeptide of the invention is to use the polymerase chain reaction as disclosed by Saiki et al(1988) Science 239, 487–491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al(1972) *Proc. Natl. Acad. Sci. USA* 69, 2110 and Sambrook et al(1989) Molecular Cloning, A Laboratory Manual, Cold Spring Harbor Laboratory, Cold Spring Harbor, N.Y. Transformation of yeast cells is described in Sherman et al(1986) Methods In Yeast Genetics, A Laboratory Manual, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al(1988) *Mol. Microbiol.* 2, 637–646 incorporated herein by reference. The greatest number of transformants is consistently recovered following electroporation of the DNA-cell mixture suspended in 2.5×PEB using 6250V per cm at 25:FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al(1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention provides a method of making the polypeptide of the invention or a variant, derivative, fragment or fusion thereof or a fusion of a variant, fragment or derivative the method comprising culturing a host cell comprising a recombinant polynucleotide or a replicable vector which encodes said polypeptide, and isolating said polypeptide or a variant, derivative, fragment or fusion thereof or a fusion of a variant, fragment or derivative from said host cell. Methods of cultivating host cells and isolating recombinant proteins are well known in the art.

The invention also includes a polypeptide, or a variant, fragment, derivative or fusion thereof, or fusion of a said variant or fragment or derivative obtainable by the above method of the invention.

A still further aspect of the invention provides an antibody reactive towards a polypeptide of the invention. Examples of such antibodies and of methods of preparing such antibodies are given in Example 1.

Antibodies reactive towards the said polypeptide of the invention may be made by methods well known in the art. In particular, the antibodies may be polyclonal or monoclonal.

Suitable monoclonal antibodies which are reactive towards the said polypeptide may be prepared by known techniques, for example those disclosed in "Monoclonal Antibodies: A manual of techniques", H Zola (CRC Press, 1988) and in "Monoclonal Hybridoma Antibodies: Techniques and Applications", SGR Hurrell (CRC Press, 1982).

In a preferred embodiment the antibody is raised using any suitable peptide sequence obtainable from the given amino acid sequence of MSK1 or MSK2 as appropriate. It is preferred if polyclonal antipeptide antibodies are made. Suitable peptides obtainable from MSK1 include LTVKHELRTANLTGHAEKV (SEQ ID NO:14)(corresponding to residues 26 to 44 of MSK1 and FKRNAAVID-PLQFHMGVER (SEQ ID NO:15) (corresponding to residues 384 to 402 of MSK1), as discussed in Example 1. A suitable peptide obtainable from MSK2 is FKRNAAVID-PLQFHMGVER (SEQ ID NO:15) (corresponding to residues 753–772 of MSK2).

It is particularly preferred if the antibody does not react substantially with another two-kinase domain protein kinase such as MAPKAP-K1a/b/c. Accordingly, it may be preferred if peptides based on the MSK1 or MSK2 sequence are used which vary significantly from any peptides found in any other stress-activated protein kinases such as MAPKAP-K1a/b/c. It may also be preferred that an antibody reacts with MSK1 but does not react substantially with MSK2, and vice versa.

Peptides in which one or more of the amino acid residues are chemically modified, before or after the peptide is synthesised, may be used providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys, beta-galactosidase and the 163–171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement.

The peptide of the invention may be linked to other antigens to provide a dual effect.

Peptides may be synthesised by the Fmoc-polyamide mode of solid-phase peptide synthesis as disclosed by Lu et al(1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of sidechain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A further aspect of the invention provides a method of identifying a drug-like compound or lead compound for the development of a drug-like compound that modulates the activity of a polypeptide as defined in the first aspect of the invention, the method comprising contacting a compound with the polypeptide or a suitable variant, fragment, derivative or fusion thereof or a fusion of a variant, fragment or derivative thereof and determining whether the protein kinase activity of the said polypeptide is changed compared to the activity of the said polypeptide or said variant, fragment, derivative or fusion thereof or a fusion of a variant, fragment or derivative thereof in the absence of said compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons molecular weight and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

The compound may act by interacting with the polypeptide of the invention and modulating, for example inhibiting, its activation by MAPK2 or SAPK2/p38, as discussed further below.

It will be understood that it will be desirable to identify compounds that may modulate the activity of the polypeptide in vivo. Thus it will be understood that reagents and conditions used in the method may be chosen such that the interactions between the said polypeptide and its substrate are substantially the same as between human MSK1 or MSK2 and their substrate or substrates in vivo. An example of a substrate of said MSK1 polypeptide is CREB or ATF1.

In one embodiment, the compound decreases the activity of said polypeptide. For example, the compound may bind substantially reversibly or substantially irreversibly to the active site of said polypeptide. In a further example, the compound may bind to a portion of said polypeptide that is not the active site so as to interfere with the binding of the said polypeptide to its substrate. In a still further example, the compound may bind to a portion of said polypeptide so as to decrease said polypeptide's activity by an allosteric effect. This allosteric effect may be an allosteric effect that is involved in the natural regulation of the said polypeptide's activity, for example in the activation of the said polypeptide by an "upstream activator" such as MAPK2 or SAPK2/p38.

The compound Ro318220 is an example of an inhibitor of MSK1 and MSK2 activity, as described in Example 1 and Example 5. This compound inhibits other protein kinases in addition to MSK1 and MSK2, but some of these other protein kinases, for example MAPKAP-K2 are largely unaffected at compound concentrations that ablate MSK1 activity, as described in Example 1.

In a further embodiment, the compound increases the activity of said polypeptide. For example, the compound may bind to a portion of said polypeptide that is not the active site so as to aid the binding of the said polypeptide to its substrate. In a still further example, the compound may bind to a portion of said polypeptide so as to increase said polypeptide's activity by an allosteric effect. This allosteric effect may be an allosteric effect that is involved in the natural regulation of the said polypeptide's activity for example in the activation of the said polypeptide by an "upstream activator" such as MAPK2 or SAPK2/p38.

Conveniently, the method makes use of the fact that MSK1 or MSK2 phosphorylates CREB or CREBtide or ATF1 or Crosstide as described in Example 1, but any suitable substrate may be used. Thus the phosphorylation of CREB or CREBtide or ATF1 of Crosstide may be measured using techniques well known to those skilled in the art.

Conveniently, the method makes use of an assay which may be substantially the same as that described in Example 1. In Example 1, phosphorylation of CREB or ATF1 by MSK1 is measured. It is preferred that the MSK1 or MSK2 is recombinant MSK1 or MSK2. It is preferred that the substrate, for example CREB or ATF1, is recombinant.

Alternatively, a change in the activity of the substrate may be measured. For example, the activity of CREB or ATF1 as a transcription factor may be measured. This may be done by measuring the binding of CREB or ATF1 to DNA containing the appropriate binding site, as well known in the art, or by measuring expression of an RNA from a promoter that is regulated by CREB or ATF1. This may be done in a whole cell system or using purified or partially purified components. Similarly, expression of an protein encoded by an RNA transcribed from a promoter regulated by CREB or ATF1 may be measured. The protein may be one that is physiologically regulated by CREB or ATF1 or may be a "reporter" protein, as well known to those skilled in the art (ie a recombinant construct may be used). A reporter protein may be one whose activity may easily be assayed, for example (β-galactosidase, chloramphenicol acetyltransferase or luciferase (see, for example, Tan et al(1996)).

Proteins that are physiologically regulated by CREB may be COX2 and IL-1. Thus, inhibition of CREB may be measured by measuring the expression of COX2 or IL-1 under circumstances when COX2 or IL-1 expression may be expected, as described in Example 5. Thus, COX2 may be expressed in RAW 264 murine macrophages or J774.2 macrophages on exposure of the macrophages to endotoxin, as described, for example, in Mitchell et al(1994) PNAS 90, 11693–11697 and Dubois et al(1998) *FASEB J* 12, 1063–1073. J774.2 and RAW 264 cells may be obtained from the European Collection of Animal Cell Culture, Salisbury, UK. The expression of COX2 or IL-1 may be measured by any convenient method, for example using PCR to detect the presence of COX2 or IL-1 mRNA, antibody based assays to detect COX2 or IL-1 protein or assays to detect COX2 enzyme activity, for example by measuring the amount of prostaglandins, for example PGE2 produced on exposing the cells to arachidonic acid (the substrate of COX2). Suitable assays may be described in Example 5, Mitchell et al(1994), Slater et al(1995) Am J Obstet Gynecol 172(1), 77–82, or in WO 94/14977. Prostaglandin metabolites rather than the direct products of COX2 may be measured, as prostaglandins may be unstable and rapidly metabolised.

It will be necessary to perform various control assays, as known to those skilled in the art, in order to determine that a compound is affecting the activation of CREB, rather than having some other effect on processes leading to whatever measurement is made. However, assays in which, for example, prostaglandin levels are measured, may be useful in assessing the usefulness of compounds in a whole cell or in vivo system and may be useful in evaluating the concept in different situations, for example, different models of disease. It will be appreciated that assays in which, for example, the effect of a compound on COX2 expression or activity is measured, may be used alongside or interpreted using the results from other assays in which the effect of the compound on the ability of, for example, MSK1 to phosphorylate CREB, for example, is measured more directly.

A still further aspect of the invention provides a method of identifying a compound which binds to CREB or ATF1 (or other substrate of the polypeptide as defined in the first aspect of the invention, preferably MSK1) and either enhances or prevents its activation by the polypeptide as defined in the first aspect of the invention, preferably MSK1, the method comprising determining whether a compound enhances or prevents the interaction of CREB or ATF1 (or other substrate of the polypeptide as defined in the first aspect of the invention, preferably MSK1) or a suitable fragment, variant, derivative or fusion thereof or a suitable fusion of a fragment, variant or derivative with the polypeptide as defined in the first aspect of the invention (preferably MSK1) or determining whether the compound substantially blocks activation of CREB or ATF1 (or other substrate of the polypeptide as defined in the first aspect of the invention, preferably MSK1) or a suitable fragment, variant, derivative or fusion thereof or a suitable fusion of a fragment, variant or derivative by the polypeptide as defined in the first aspect of the invention.

Suitable assays may be similar to those described above.

A still further aspect of the invention provides a method of identifying a compound which modulates the activation of the polypeptide as defined in the first aspect of the invention by an "upstream activator", for example MAPK2/ERK2 or SAPK2a/p38 or SAPK2b/p38β2. By "upstream activator" is meant a molecule that interacts with the polypeptide of the invention with the result that the protein kinase activity of the polypeptide of the invention is increased. It may be a polypeptide. Preferably, it is a physiological activator of native MSK1 or MSK2.

The method comprises determining whether a compound enhances or disrupts the interaction between (a) a polypeptide as defined in the first aspect of the invention or a suitable fragment, variant, derivative or fusion thereof or a suitable fusion of a fragment, variant or derivative and (b) an "upstream activator", for example MAPK2/ERK2, SAPK2a/p38 or SAPK2b/p38β2, or a suitable variant, derivative, fragment or fusion thereof or a suitable fusion of a variant, derivative or fragment, or determining whether the compound substantially blocks activation of the said polypeptide or a suitable variant, fragment, derivative or fusion thereof, or a fusion of a said fragment, derivative or fusion by an "upstream activator" or a suitable variant, derivative, fragment or fusion thereof. It will be appreciated that the compound may interact with or bind to either the upstream activator or to the polypeptide of the invention, or both.

Examples of compounds that are able to modulate the activation of MSK1 and MSK2 include inhibitors of SAPK2/p38, for example a pyridinylimidazole inhibitor of SAPK2/p38, as known to those skilled in the art, for example SB203580 or FHPI (4-(4-fluorophenyl)-2-2-(4-hydroxyphenyl)-5-(4-pyridyl)imidazole).

The term "pyridinylimidazole inhibitor" is well known to those skilled in the art, and encompasses compounds comprising a pyridyl ring and an imidazole ring with substituents which bind to and/or inhibit SAPK2a/p38 (or less preferably, are known to inhibit IL-1 production from monocytes) as set out in Gallagher et al (1997) *Bioorg Med Chem* 5(1), 49–64. Pyridinylimidazole inhibitors are also discussed, for example, in WO95/02591. Compounds of this type are known inhibitors of particular protein kinases and as cytokine-suppressive anti-inflammatory drugs (CSAIDs). Use of these compounds in investigating signalling pathways is reviewed in Cohen (1997) *Trends Cell Biol* 7, 354–361.

It will be appreciated that the numerical measure of binding affinity or inhibition $IC_{50}$ for a particular compound/protein combination will depend upon the exact assay system used. A pyridinylimidazole may be considered to be a pyridinylimidazole inhibitor if it has a binding $IC_{50}$ or kinase $IC_{50}$ for SAPK2a/p38 (CSBP) of less than 100 μM, preferably less than 10 μM, still more preferably less than 1 or 0.1 or 0.01 μM as set out in Gallagher et al. Examples of pyridinlyimidazole inhibitors include SB 202190 (a 2,4,5-triarylimidazole), SB 203580 (another 3,4,5-triarylimidazole) and derivatives such as the 3'-iodinated compound as described in Tong et al (1997) *Nature Structural Biology* 4(4), 311–316. A derivative in which the p-methylsulphinylphenyl group is removed may also act as an inhibitor. Substituents may be made at the N1 atom of the imidazole ring and substitutions made at the 2-position of the imidazole ring may be moved to the N1 atom without significant loss of potency.

Examples of compounds that are able to modulate the activation of MSK1 and MSK2 include inhibitors of MAPK2/ERK2 or inhibitors of activation of MAPK2/ERK2, for example inhibitors of MAPK kinase 1 (MKK1) activity or activation, for example PD98059 or U0126.

MAPK2/ERK2 is a known activator of MAPKAP-K1. It is shown here also to be an activator of the polypeptide of the invention, known as MSK1 or MSK2. By "activation of MSK1" it is meant that the ability of MSK1 to phosphorylate CREB or ATF1 (or alternative substrates as listed above) is increased following the treatment of MSK1, for example by MgATP and MAPK2/ERK2.

Expression of MAPK2/ERK2, SAPK2a/p38 and SAPK2b/p38β2 as activated GST fusions is described in Example 1, in which references are also given which describe the sequences of the above proteins.

Thus a further aspect of the invention is the use of MAPK2/ERK2, SAPK2a/p38 or SAPK2b/p38β2 for the activation of the polypeptide of the invention, for example MSK1 or MSK2.

A still further aspect of the invention provides a method of identifying a polypeptide that interacts with the protein kinase (polypeptide) of the invention, the method comprising (1) contacting (a) the said protein kinase as defined in the first aspect of the invention or a suitable variant fragment, derivative or fusion thereof or a fusion of a variant, fragment or derivative thereof with (b) a composition that may contain a polypeptide that interacts with the said protein kinase, (2) detecting the presence of a complex containing the said protein kinase and a polypeptide, and optionally (3) identifying any polypeptide bound to the said protein kinase.

In one embodiment, the composition may comprise material from cells. In particular, the cells may be selected from the following types: (1) cells which do not have MSK1 or MSK2 activity even when stimulated, (2) cells which have MSK1 or MSK2 activity after exposure to a stimulus, but which have not been so exposed and (3) cells of type 2 after exposure to the stimulus. Polypeptides that are found in a subset only of types 1–3 are of particular interest and may be characterised further. Such a peptide may be an activator of MSK1 or MSK2. Alternatively, it may be an inactivator of MSK1 or MSK2.

It will be appreciated that the method may be performed within a cell, for example using the yeast two hybrid system as is well known in the art. In this example, cDNAs copied from mRNA from the three cell types described above would be used.

It will further be appreciated that a transgenic animal in which a MSK1 or MSK2 gene is altered and/or a recombinant MSK1 or MSK2 gene is present, for example a rodent, in particular a mouse, may be useful in, for example, identifying a substrate of MSK1 or MSK2.

A still further aspect of the invention provides a method of identifying a compound which blocks the activation of the polypeptide as defined in the first aspect of the invention by an interacting polypeptide, for example MAPK2 or SAPK2a/p38 or SAPK2b/p38β2, the method comprising determining whether a compound enhances or disrupts the interaction between (a) a protein kinase as defined in the first aspect of the invention or a suitable fragment, variant, derivative or fusion thereof or a suitable fusion of a fragment, variant or derivative and (b) said interacting polypeptide or a suitable variant, derivative, fragment or fusion thereof or a suitable fusion of a variant, derivative or fragment, or determining whether the compound substantially blocks activation of the polypeptide according to the first aspect of the invention or a suitable variant, fragment, derivative or fusion thereof, or a fusion of a said fragment, derivative or fusion by said interacting polypeptide or a suitable variant, derivative, fragment or fusion thereof.

Conveniently, the said polypeptide according to the first aspect of the invention or fragment, derivative, variant or fusion thereof used in the method is one which is produced by recombinant DNA technology. Similarly, it is preferred if the CREB or ATF1 or fragment, derivative, variant or fusion thereof used in the method of identifying compounds that modulate activity of the said protein kinase is one which is produced by recombinant DNA technology. Similarly, it is preferred if MAPK2/ERK2, SAPK2a/p38 or SAPK2b/p38β2 or other "upstream activator" or fragment, derivative, variant or fusion thereof used in the method is one which is produced by recombinant DNA technology.

It will be appreciated that it may be necessary to activate the polypeptide of the invention prior to its use in assays. In a preferred embodiment the polypeptide of the invention (MSK1 or MSK2) is activated in vitro by treating the polypeptide with MAPK2/ERK2 and MgATP, as described in Example 1. It is particularly preferred if the MSK1 or MSK2 is the recombinant polypeptide produced according to the methods of the invention.

It will be appreciated that by "suitable" we mean that the said components in the method are those that have interactions or activities which are substantially the same as those of MSK1 or CREB or ATF1 or other substrates, or the upstream activator such as MAPK2/ERK2 or SAPK2a/p38 or SAPK2b/p38β2 as the case may be but which may be more convenient to use in an assay. For example, fusions of MSK1 or CREB are particularly useful since said fusion may contain a moiety which may allow the fusion to be purified readily.

It will be appreciated that the methods described may be performed in cells. "Reporter gene" constructs may be prepared by methods known to those skilled in the art, using the teaching herein. For example, a reporter gene construct may be made with a CREB or ATF1-dependent promoter sequence. This construct may be introduced together with an MSK1 or MSK2 construct into a cell line, in the parent cell line of which CREB or ATF1 is activated in response to known stimuli, and in which the endogenous MSK1 or MSK2 gene has been inactivated. Alternatively the reporter gene construct could be introduced into the cell line in which CREB or ATF1 is activated in response to known stimuli. The expression of the reporter gene will be dependent on the activity of MSK1 or MSK2 and thus the effect of compounds can be measured. In a further example, the reporter gene may be fatal to the cells, or alternatively may allow cells to survive under otherwise fatal conditions. Cell survival can then be measured, for example using calorimetric assays for mitochondrial activity, such as reduction of WST-1 (Boehringer). WST-1 is a formosan dye that undergoes a change in absorbance on receiving electrons via succinate dehydrogenase. In a further embodiment the yeast two-hybrid system is used.

The enhancement or disruption of the interaction between the said polypeptide of the invention and MSK1 or MSK2 or an interacting polypeptide as defined above, or suitable derivatives, fragments, fusions or variants can be measured in vitro using methods well known in the art of biochemistry and include any methods which can be used to assess protein—protein interactions.

The said interaction can also be measured within a cell, for example using the yeast two hybrid system as is well known in the art.

It will be appreciated that the invention provides screening assays for drugs which may be useful in modulating, for example either enhancing or inhibiting, the activity of MSK1 or MSK2 or its interactions with upstream activators. The compounds identified in the methods may themselves be useful as a drug or they may represent lead compounds for the design and synthesis of more efficacious compounds.

It will be appreciated that screening assays which are capable of high throughput operation will be particularly preferred. Examples may include the cell based assays described and protein—protein binding assays. A further example is an SPA-based (Scintillation Proximity Assay) system as described in Example 2.

A further aspect of the invention provides a compound identifiable by the screening methods of the invention, wherein the compound is not Ro318220, PD98059 or a known pyridinylimidazole inhibitor of SAPK2/p38, for example SB203580 or FHPI (4-(4-fluorophenyl)-2-2-(4-hydroxyphenyl)-5-(4-pyridyl)imidazole). The compound may be a compound that enhances or a compound that inhibits, the activity of MSK1 or MSK2. A still further aspect provides such a compound for use in medicine.

The transcription factor CREB is required for the production of IL-[and of the enzyme cyclo-oxygenase2 or prostaglandin synthase-2 (COX2/PGS-2) in vivo. We show here that CREB may be activated by MSK1/MSK2. Thus, inhibitors of MSK1 may have the effect of inhibitors of IL-1 and/or COX2 and may therefore have the same clinical indications as inhibitors of IL-1 activity and/or COX2.

IL-1 is an inflammatory mediator. COX2 is well known to those skilled in the art as a proinflammatory enzyme that is involved in the synthesis of the proinflammatory signalling molecules prostaglandins from arachidonic acid. Cyclooxygenase 1 (COX1) is a related enzyme that is constitutively expressed, whereas COX2 is expressed early in inflammation as a result of proinflammatory signalling pathways. Inhibitors of COX1, such as aspirin may reduce inflammation, but also have side-effects such as gastrointestinal damage, including ulcers. Much effort has therefore been directed to the development of selective inhibitors of COX2, such as Meloxicam. However, many COX2 inhibitors also have COX1 inhibitory activity.

Selective COX-2 inhibitors may have anti-inflammatory, analgesic and anti-pyretic activities comparable with non-steroidal anti-inflammatories (NSAIDs) which include COX-1 inhibitors, but may avoid the side-effects (for a review, see Botting (1996) Drug News & Perspec 9(2), 123–128).

Inhibitors of MSK1/MSK2 activity or activation (such as the compounds of the invention, discussed above) may therefore be useful in methods of treating the diseases or conditions discussed below in which IL-1, COX2 or prostaglandins have been implicated.

Such diseases and conditions include those in which inflammation or tissue injury is involved. Inflammatory diseases in which COX-2 inhibitors have been investigated include osteoarthritis, rheumatoid arthritis, ankylosing spondylitis and other rheumatologic and pain indications. Other diseases in which inflammation is involved and in which MSK1/MSK2 inhibitors may be useful include asthma, psoriasis, septic shock and inflammatory bowel disease. Prostaglandins have been implicated in uterine contractions and pain and in labour (see, for example, Pulkkinen (1993) Drugs 46(suppl 1), 129–133 and Slater et al(1995) Am J Obset Gynecol 172(1), 77–82). Further diseases in which MSK1/MSK2 inhibitors may be useful may be listed in WO 96/41645.

A further aspect of the invention is the use of any of the screening methods of the invention in the identification of a molecule that may be useful in treating inflammatory disease.

A further aspect of the invention is the use of any of the screening methods of the invention in the identification of a molecule that may be useful in treating a patient in need of modulation, for example reduction or an increase, in the activity of COX2 or IL-1.

It is believed that a compound identifiable by any of the screening methods of the invention may be useful in treating inflammatory disease. Inflammatory diseases include rheumatoid arthritis, psoriasis, septic shock, asthma and inflammatory bowel disease, and other diseases or conditions as discussed above.

Thus, a further aspect of the invention provides a method of treating a patient with an inflammatory disease the method comprising administering to the patient an effective amount of a compound identifiable by the screening methods of the invention, wherein the compound is not a known pyridinylimidazole inhibitor of SAPK2/p38, for example SB203580 or FHPI (4-(4-fluorophenyl)-2-2-(4-hydroxyphenyl)-5-(4-pyridyl)imidazole). The screening methods may identify compounds which either activate or inhibit. Compounds with either activity may be suitable but it is preferred that the compounds may inhibit phosphorylation mediated by MSK1 or MSK2.

A still further invention provides a use of a compound identifiable by the screening methods of the invention in the manufacture of a medicament for treating an inflammatory disease in a patient wherein the compound is not a known pyridinylimidazole inhibitor of SAPK2/p38, for example SB203580 or FHPI (4-(4-fluorophenyl)-2-2-(4-hydroxyphenyl)-5-(4-pyridyl)imidazole).

A further aspect of the invention provides a method of treating a patient a patient in need of modulation, for example reduction or an increase, of the activity of COX2 or IL-1 the method comprising administering to the patient an effective amount of a compound identifiable by the screening methods of the invention, wherein the compound is not a known pyridinylimidazole inhibitor of SAPK2/p38, for example SB203580 or FHPI (4-(4-fluorophenyl)-2-2-(4-hydroxyphenyl)-5-(4-pyridyl)imidazole). The screening methods may identify compounds which either activate or inhibit. Compounds with either activity may be suitable but it is preferred that the compounds may inhibit phosphorylation mediated by MSK1 or MSK2.

A still further invention provides a use of a compound identifiable by the screening methods of the invention in the manufacture of a medicament for treating a patient in need of modulation, for example reduction or an increase, of the activity of COX2 or IL-1, wherein the compound is not a known pyridinylimidazole inhibitor of SAPK2/p38, for example SB203580 or FHPI (4-(4-fluorophenyl)-2-2-(4-hydroxyphenyl)-5-(4-pyridyl)imidazole).

A still further aspect of the invention provides a method of treating a patient a patient in need of modulation, for example reduction or an increase (preferably reduction), of the activity of COX2, the method comprising administering to the patient (1) an inhibitor of the SAPK2/p38 cascade, for example a known pyridinylimidazole inhibitor of SAPK2/p38, for example SB203580 or FHPI (4-(4-fluorophenyl)-2-2-(4-hydroxyphenyl)-5-(4-pyridyl)imidazole) and (2) an inhibitor of the MAPK/ERK cascade, for example PD98059.

A still further aspect of the invention provides a use of (1) an inhibitor of the SAPK2/p38 cascade, for example a known pyridinylimidazole inhibitor of SAPK2/p38, for example SB203580 or FHPI (4-(4-fluorophenyl)-2-2-(4-hydroxyphenyl)-5-(4-pyridyl)imidazole) and (2) an inhibitor of the MAPK/ERK cascade, for example PD98059 in the manufacture of a medicament for treating a patient in need of modulation, for example reduction or an increase, of the activity of COX2.

A still further aspect of the invention provides a use of an inhibitor of the SAPK2/p38 cascade, for example a known pyridinylimidazole inhibitor of SAPK2/p38, for example SB203580 or FHPI (4-(4-fluorophenyl)-2-2-(4-hydroxyphenyl)-5-(4-pyridyl)imidazole) in the manufacture of a medicament for treating a patient in need of modulation, for example reduction or an increase, of the activity of COX2, wherein the patient is, has been or will be administered an inhibitor of the MAPK/ERK cascade, for example PD98059.

A still further aspect of the invention provides a use of an inhibitor of the MAPK/ERK cascade, for example PD98059, in the manufacture of a medicament for treating a patient in need of modulation, for example reduction or an increase, of the activity of COX2, wherein the patient is, has been or will be administered an inhibitor of the SAPK2/p38 cascade, for example a known pyridinylimidazole inhibitor of SAPK2/p38, for example SB203580 or FHPI (4-(4-fluorophenyl)-2-2-(4-hydroxyphenyl)-5-(4-pyridyl)imidazole).

It is further believed that such compounds identifiable by the screening methods of the invention are useful in treating disease in which apoptosis is involved. For example, such compounds may suppress apoptosis, which may aid cell survival during or following cell damaging processes. Examples of such diseases include, but are not limited to, ischaemic disease, for example stroke and myocardial infarction, neural injury and myocardial infarction.

COX-2 may be involved in long-term potentiation and synaptic plasticity, and expression may precede apoptotic cell death and be involved in neurodegenerative diseases such as Alzheimer's disease. Focal ischaemia may induce COX2 expression in cortical neurons that may be particularly likely to die following an ischaemic incident.

Some of the compounds of the invention may aid apoptosis, for example compounds that may lead to increased activation of CREB. Conditions in which aiding apoptosis may be of benefit include resolution of inflammation. Compounds of the invention that lead to decreased activation of CREB or ATF1 may inhibit apoptosis.

Thus, a further aspect of the invention provides a method of treating a patient with an ischaemic disease the method comprising administering to the patient an effective amount of a compound identifiable by the screening methods of the invention, wherein the compound is not a known pyridinylimidazole inhibitor of SAPK2/p38, for example SB203580 or FHPI (4-(4-fluorophenyl)-2-2-(4-hydroxyphenyl)-5-(4-pyridyl)imidazole).

A still further invention provides a use of a compound identifiable by the screening methods of the invention in the manufacture of a medicament for treating an ischaemic disease in a patient, wherein the compound is not a known pyridinylimidazole inhibitor of SAPK2/p38, for example SB203580 or FHPI (4-(4-fluorophenyl)-2-2-(4-hydroxyphenyl)-5-(4-pyridyl)imidazole).

COX2 may be involved in changes in pain perception following tissue injury (hyperalgesia and allodynia), thus inhibitors of MSK1 may be useful in analgesia. COX2 expression may be involved in migraine and therefore inhibitors of MSK1 may be useful in treating migraine. Thus a further aspect of the invention provides a method of treating a patient with migraine or in need of analgesia the method comprising administering to the patient an effective amount of a compound identifiable by the screening methods of the invention.

COX2 may be involved in cancer. Inhibiting COX2 may be useful in preventing or treating cancer. COX2 may promote angiogenesis. Inhibition of COX2 may have anticancer effects, for example in colon cancer, by increasing the level of arachidonic acid that in turn may stimulate the conversion of sphingomyelin to ceramide, which has been suggested as a mediator of apoptosis. Thus MSK1 inhibitors such as compounds of the invention described above may be useful in the treatment or prevention of cancer.

The compounds of the invention may also be useful in the treatment or prevention of Alzheimer's disease. NSAIDs and corticosteroids (also antiinflammatory) have been suggested to be useful in delaying the onset or slowing the progression of Azheimer's disease, even when used in low doses, sufficient for analgesic effect but less than used for antiinflammatory treatment. COX2 expression has been shown to be elevated in Alzheimer's disease brains and in glial cells in response to inflammatory mediators. Overexpression of COX2 in neurons in a transgenic mouse model may lead to (β-amyloid neurotoxicity in vitro, supporting a role for COX2 in Alzheimer's disease. Thus, MSK1 inhibitors may be useful in the treatment or prevention of Alzheimer's disease and other neurodegenerative diseases.

Fos may be involved in cell transformation and malignancy/cancer. Thus a further aspect of the invention provides a method of treating a patient with cancer, the method comprising administering to the patient an effective amount of a compound identifiable by the screening methods of the invention, wherein the compound is not PD98059. It is preferred that the compound is not Ro318220.

A still further aspect of the invention provides a use of a compound identifiable by the screening methods of the invention in the manufacture of a medicament for treating cancer, wherein the compound is not PD98059. It is preferred that the compound is not Ro318220.

The aforementioned compounds of the invention or a formulation thereof may be administered by any conventional method including oral and parenteral (e.g. subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

Thus, the invention also provides pharmaceutical compositions comprising the compound identifiable by the screening methods of the invention and a pharmaceutically acceptable carrier, wherein the compound is not PD98059, Ro318220 or a known pyridinylimidazole inhibitor of SAPK2/p38, for example SB203580 or FHPI (4-(4-fluorophenyl)-2-2-(4-hydroxyphenyl)-5-(4-pyridyl)imidazole).

Further aspects of the invention provide a use of a polypeptide (protein kinase) as defined in the first aspect of the invention in a screening assay for compounds which inhibit the activity of the said protein kinase or which block interactions of said protein kinase.

A further aspect of the invention provides a kit of parts that are useful in carrying out the screening methods. Thus a kit of parts may comprise a polypeptide of the invention and a substrate of said polypeptide, for example Crosstide (GRPRTSSFAEG) (SEQ ID NO:16), CREB or CREBtide (EILSRRPSYRK) (SEQ ID NO:18) or a CREB fusion protein, for example GST-CREB or ATF1 or a fusion protein thereof. The kit may alternatively comprise a polypeptide of the invention and a protein useful in activating the polypeptide of the invention as described above, for example MAPK2. The kit may comprise (1) a polypeptide of the invention, (2) a substrate of said polypeptide, as described above and (3) a protein useful in activating said polypeptide, as described above.

The present invention will now be described in more detail with reference to the following Figures and Examples.

FIGURE LEGENDS

FIG. 1. Nucleotide and deduced amino acid sequence of human MSK1. The underlined residues correspond to the kinase domains. The residues shown in bold type (Ser212, Ser360, Ser 377 and Thr581) are putative activating phosphorylation sites. The putative bipartite nuclear localization signal (Robins et al., 1991) between residues 726 to 745 (which is not present in MAPKAP-K1a/b) is denoted with asterisks. The stop Codon is denoted with a solid triangle.

Figure 2A:
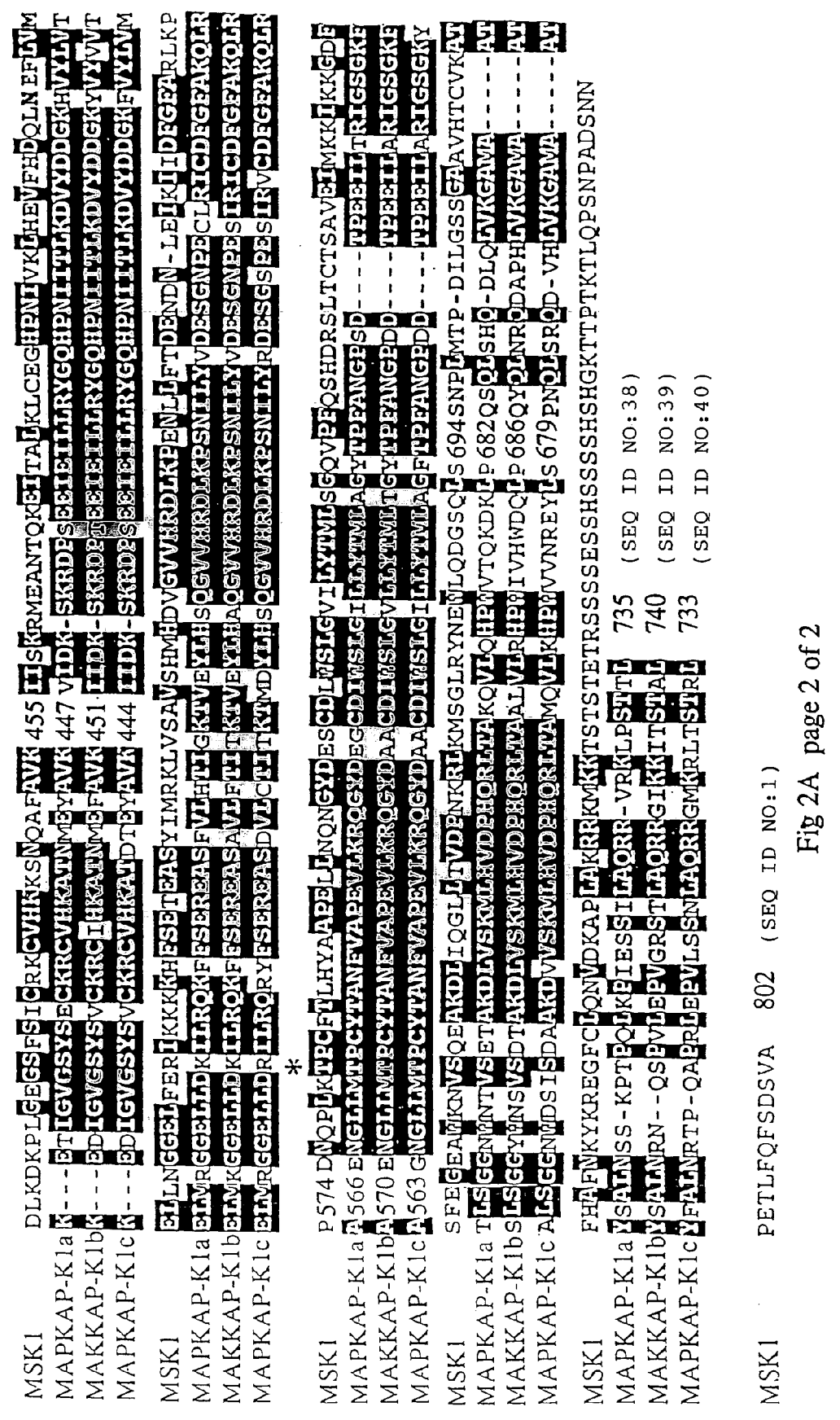

FIG. 2. Alignment of the amino acid sequences of MSK1 with closely related kinases. The alignment was carried out using the Clustal W program (Thompson et al., 1994). Identical residues are shaded in black. (A) Alignment of MSK1 with human MAPKAP-K1 isoforms. The residues corresponding to the key activating phosphorylation sites on MAPKAP-K1a (Ser222, Ser364, Ser381 and Thr 574) are marked with asterisks. (B) Alignment of the N-terminal (MSK1-N) and C-terminal (MSK1-C) kinase domains of MSK1 with the kinase domains of MAPKAP-K2/3 and MNK1. There is no significant homolgy in the non catalytic regions of these kinse. (C) Alignment of human MSK1 with partial mouse (mMSK2) and human MSK2 sequences. The putative activating phosphorylation sites are indicated with asterisks.

FIG. 3. Expression and purification of GST-MSK1 and its activation by MAPK2/ERK2 and SAPK2. (A) GST-MSK1 (2 μg protein) and GST-MAPKAP-K1a (2 μg protein) purified from unstimulated and TPA stimulated cells were electrophoresed on a 7.5% SDS-polyacrylamide gel and stained with Coomassie blue. The position of the molecular mass markers, β-galactosidase (116 kDa) and glycogen phosphorylase (97 kDa) are shown. The activity of each protein was assayed using the peptide substrate Crosstide (GRPRTSSFAEG) (SEQ ID NO:16). (B) GST-MSK1 or (C) GST-MAPKAP-K1a derived from unstimulated cells was incubated with either MAPK2/ERK2 (8 U/ml, open circles), SAPK2b/p38β (1 U/ml, closed squares), SAPK3/p38γ (1 U/ml, open triangles) or SAPK4/p38δ (1 U/ml, closed triangles), 10 mM Mg(Ac)$_2$ and 100 μM unlabelled ATP in Buffer B. At the times indicated, aliquots were removed, diluted 10-fold in Buffer B containing 1 mg/ml BSA, and assayed for activity towards Crosstide. In parallel experiments the activity of MAPK2/ERK2, and all the SAPK enzymes except SAPK1/JNK1(were assayed using myelin basic protein. SAPK1/JNK1(was assayed using ATF2 (data not shown). The results are presented as ±SEM for six determinations (two independent experiments). The error for each point is <15%. (D) GST-MSK1 was incubated with MAPK2/ERK2 and SAPK enzymes as above except that ([$^{32}$P]ATP was used. After 20 min, the reactions were terminated by the addition of SDS, the samples electrophoresed on a 7.5% polyacrylamide gel and the Coomassie Blue-staining bands corresponding to GST-MSK1 autoradiographed. Similar results were obtained in 2 separate experiments.

FIG. 4. Generation of antibodies that immunoprecipitate MSK1 specifically. (A) Activated GST-MSK1 purified from TPA stimulated 293 cells (50 μl at 1.0 U/ml) was incubated for 30 min at 4° C. on a shaking platform with protein G-Sepharose beads (5 μl) coupled to the indicated antibodies (5 μg) in the presence or absence of the indicated peptide immunogens (1 mM), and then centrifuged for 1 min at 13,000×g. The beads were washed as described in Materials and Methods and assayed for activity towards Crosstide. (B) and (C) As for A, except that activated GST-MAPKAP-K1a derived from TPA stimulated 293 cells (B) or MAPKAP-K1b (C) were immunoprecipitated with the indicated antibodies, and the washed immunoprecipitates were assayed for activity towards Crosstide.

Figure 5:
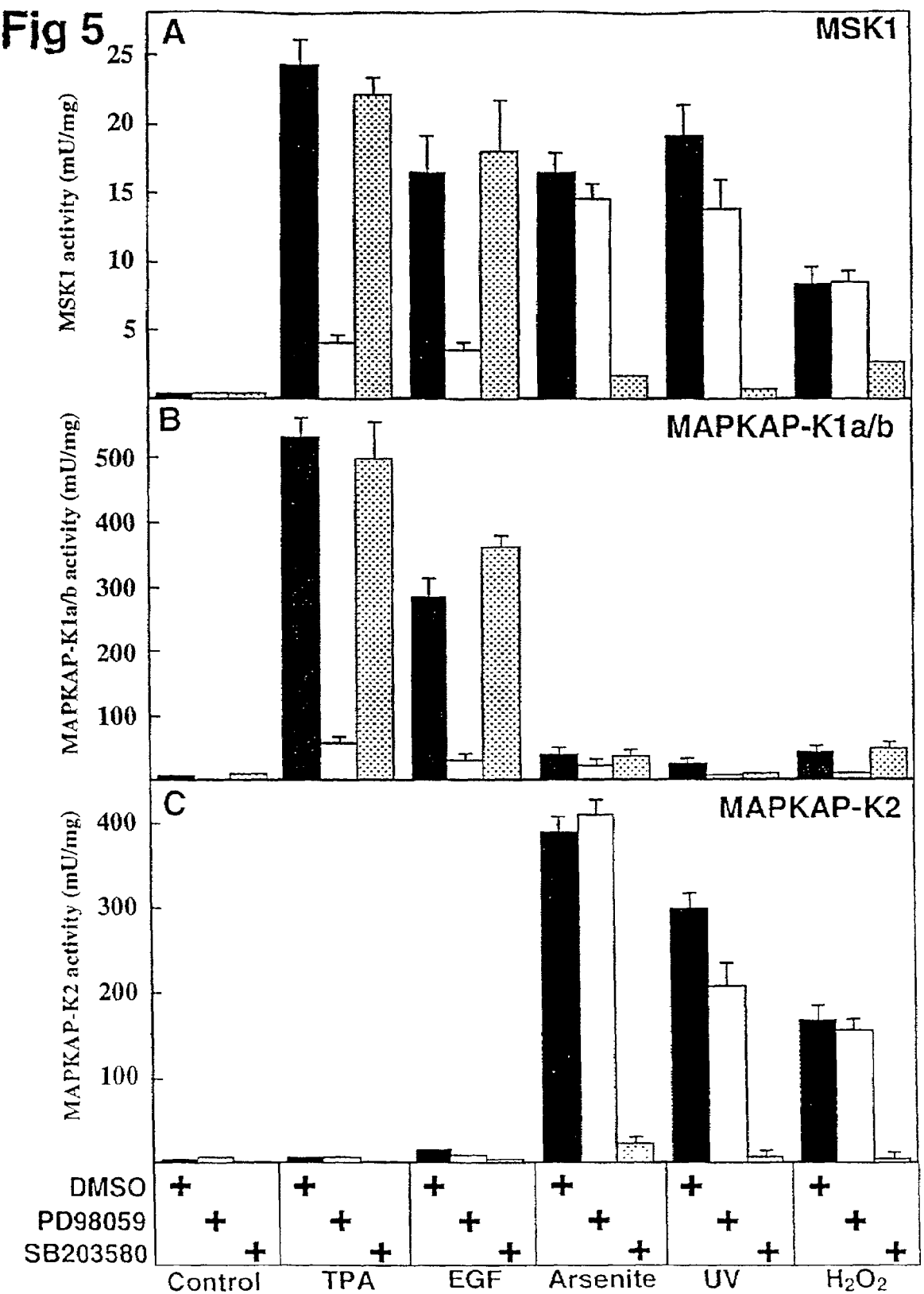

FIG. 5. Activation of endogenous MSK1 by TPA, EGF and cellular stresses. 293 cells were serum starved for 16 h, and then incubated in the presence of 50 μM PD 98059 (open bars), 10 (M SB 203580 (speckled bars) or the absence of either compound (solid bars) for 1 h. The cells were either left unstimulated (control) or stimulated with TPA (200 ng/ml, 10 min), EGF (100 ng/ml, 10 min), sodium arsenite (0.5 mM, 30 min) exposed to UV radiation (200 J/m$^2$ then left for 30 min at 37° C.) or H$_2$O$_2$ (2 mM, 30 min) in the continued presence or absence of inhibitors. The cells were lysed and MSK1 (A), MAPKAP-K1a/b (B) or MAPKAPK2 (C) was immunoprecipitated from the same lysate and assayed. The data are presented as the mean±SEM for two separate experiments with each determination carried out in triplicate.

Figure 6:
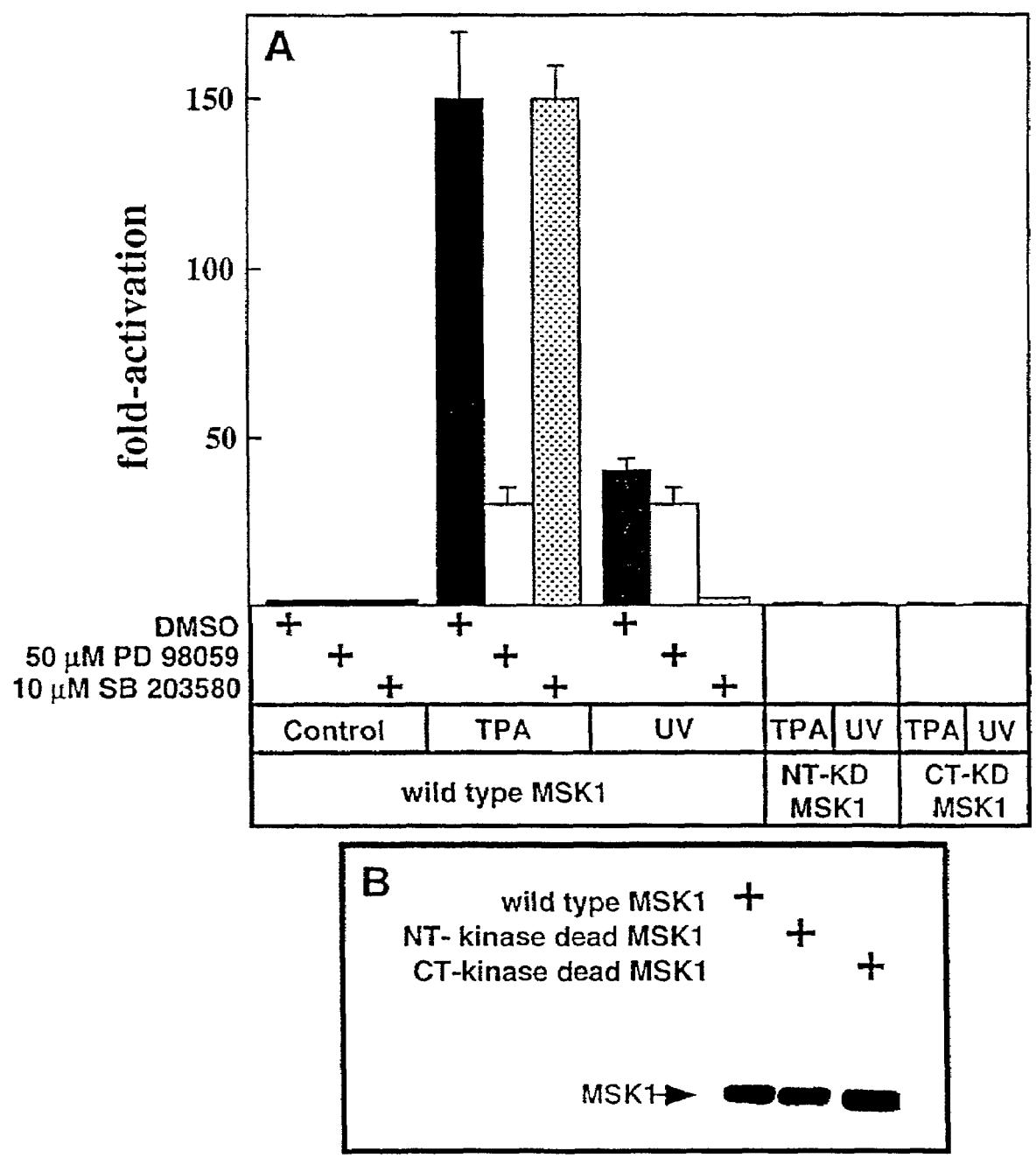

FIG. 6. Effect of mutation of MSK1 on activation by TPA and UV in 293 cells. 293 cells were transiently transfected with DNA constructs expressing Flag epitope tagged wild type MSK1, N-terminal (NT) "kinase dead" MSK1 and C-terminal (CT) "kinase dead" MSK1. The cells were incubated for 1 h with 50 µM PD 98059, 10 µM SB 203580 or in the absence of either compound. They were then stimulated for 10 min with TPA (200 ng/ml) or exposed to UV radiation (200 J/m$^2$ then left for 30 min at 37° C.) in the continued presence or absence of inhibitors. The cells were lysed and the MSK1 was immunoprecipitated from the lysates and assayed with Crosstide. The data are presented as the mean±SEM for three separate experiments with each determination carried out in triplicate (B) 2 µg of protein from each lysate was electrophoresed on a 10% SDS/polyacrylamide gel and immunoblotted using monoclonal Flag-antibody. No immunoreactive MSK1 protein was observed in untransfected cells (data not shown). The Flag epitope-tagged MSK1 comigrates with glycogen phosphorylase (apparent mass 97 kDa).

Figures 7A, 7B:
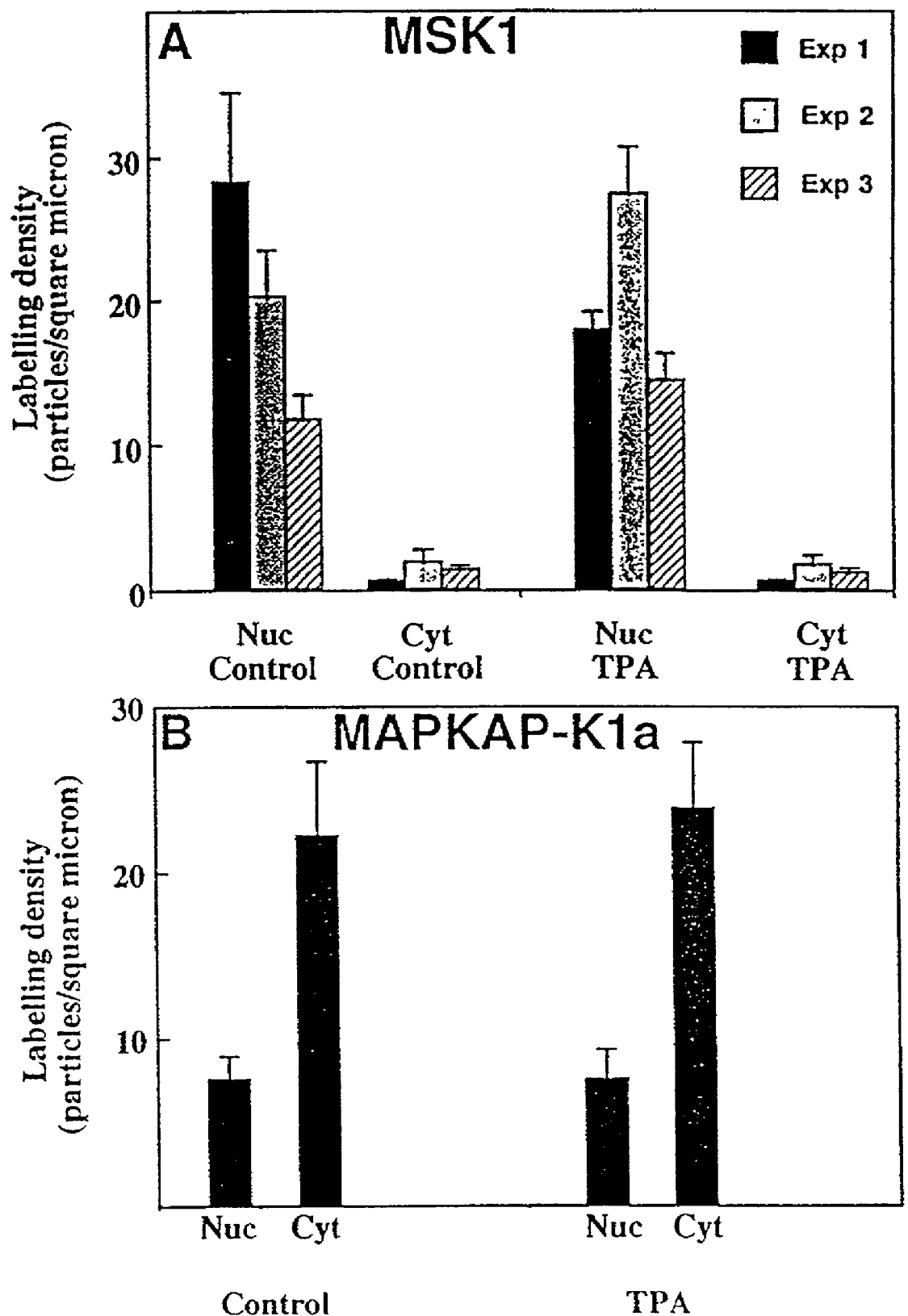
Figure 7:

FIG. 7. MSK1 is mainly localised in the nucleus of cells and MAPKAP-K1a in the cytosol. 293 cells expressing N-terminally Flag epitope tagged wild type MSK1 or N-terminally HA epitope-tagged MAPKAP-K1a were incubated in serum free medium for 16 h and then either left unstimulated, or stimulated with TPA (100 ng/ml, 10 min) before formaldehyde fixation, sectioning and immunogold labelling for the appropriate tag (Flag for MSK1 (A+B) and HA for MAPKAP-K1a (C). Quantitation of the concentration of MSK1 or MAPKAP-K1a in the nucleus (Nuc) and cytoplasm (Cyt) of cells was carried out as described in materials and methods. The results show that TPA stimulation has no detectable effect on MSK1 or MAPKAP-K1a localisation. Data is from three independent experiments. For MSK1 controls n=9, 9 and 14; for TPA n+10, 11 and 15. For MAPKAP-K1a controls total n=22; for TPA total n=9 (excluding cells with extensive clumps of immunoreactive material in the cytoplasm). Bars represent standard error of the mean calculated according to Cochran (1953). (C) Selected samples for MSK1 (C, unstimulated and D, TPA) and for MAPKAP-K1a (E, unstimulated) are shown to illustrate structures and labelling distributions. Bar is 500 nm.

FIG. 8. MSK1 phosphorylates CREB at Ser133. (A) Comparison of the substrate specificities of MSK1, MAPKAP-K1a and MAPKAP-K1b towards the indicated peptides and CREB. Phosphorylation and analysis was carried out as described in Materials and Methods. The standard errors for all reported kinetic constants were within <+20% (SEM), and the data is reported as mean values for 2 independent experiments. The Vmax values are reported as a percentage of the value obtained using Crosstide (GRPRTSSFAEG, peptide 1 (SEQ ID NO:16)) as a substrate. The peptide EILSRRPSYRK (SEQ ID NO:18) corresponding to residues 126–136 of CREB is termed CREBtide. The serine residues shown in bold correspond to the phosphorylated serine residues on the peptides. The Vmax values of MSK1, MAPKAP-K1a and MAPKAP-K1b towards Crosstide are 200 U/mg, 350 U/mg, and 800 U/mg respectively. (B) GST-MSK1 (solid bars), GST-MAPKAPK-1a (open bars), MAPKAP-K-1b (speckled bars) or GST-MAPKAP-K2 (diagonal bars) were assayed with the indicated substrates. Under the conditions used GST-MAPKAP-K2 phosphorylated Ser98 of 341 amino acid splice variant of CREB (Gonzalez et al., 1989) to a 10-fold higher level than Ser133 (data not shown). The phosphorylation of CREB by MAP-KAP-K2 shown in the figure is corrected to show only the contribution of Ser133 phosphorylation to the total incorporation of phosphate into CREB. The data are presented as the mean±SEM for three separate experiments with each determination carried out in triplicate (C)CREB that had been phosphorylated with MSK1 was digested with trypsin and chromatographed on a Vydac 218TP54 C18 column (Separations Group, Hesperia, Calif.) equilibrated in 0.1% (v/v) trifluoroacetic acid (TFA) in water. The column was developed with a linear acetonitrile gradient (diagonal line) at a flow rate of 0.8 ml/min and fractions of 0.4 ml were collected. 75% of the radioactivity applied to the column was recovered from the major $^{32}$P-containing peptide at 13% acetonitrile (the remainder of the radioactivity eluted as numerous minor peaks). The peptide map of CREB phosphorylated with MAPKAP-K1b was identical to that of CREB phosphorylated with MSK1 (data not shown).

Figure 9:
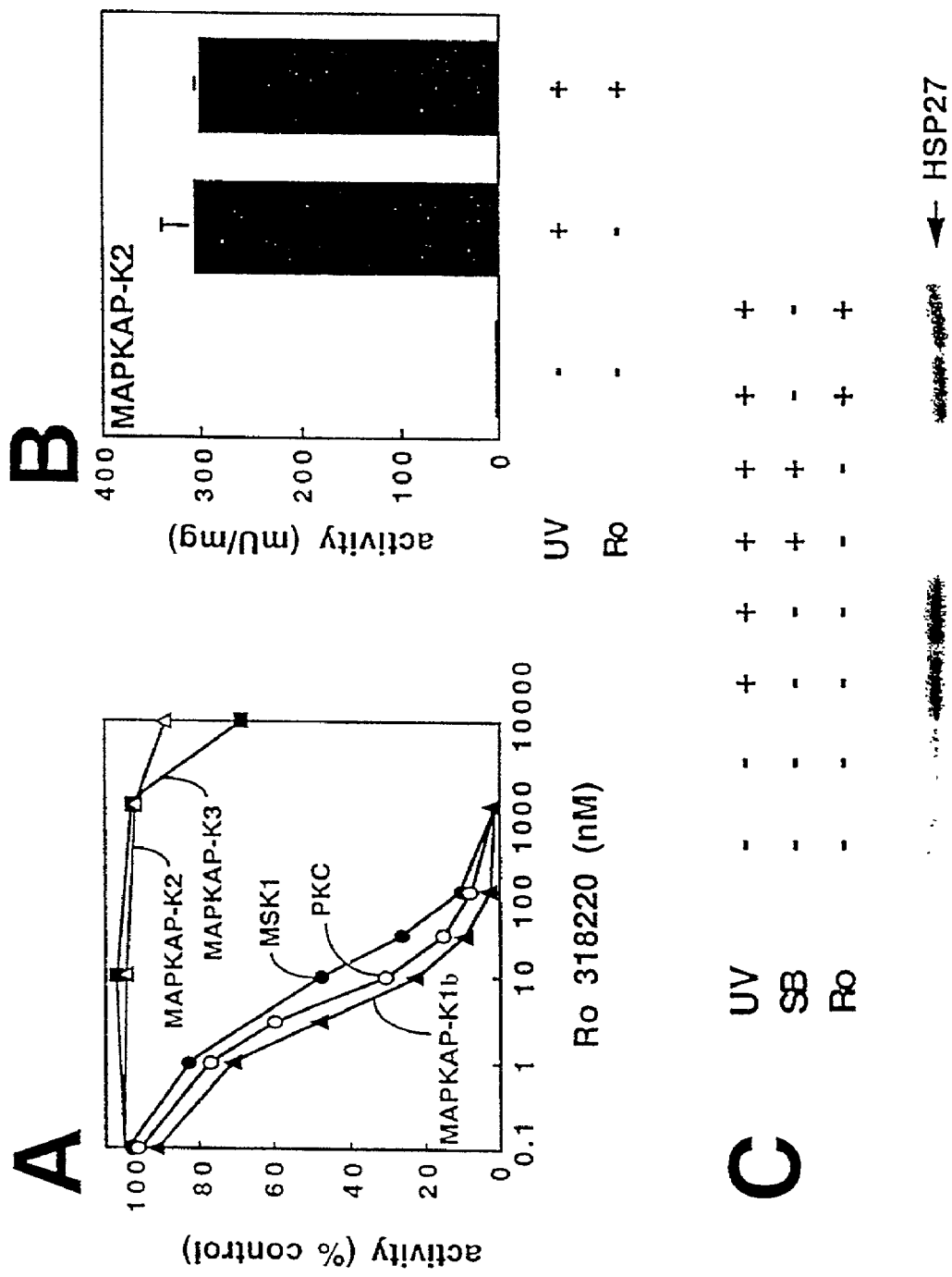

FIG. 9. Effect of Ro 318220 on the activity of MSK1. (A) Effect of Ro 318220 on GST-MSK1 (closed circles), mixed PKC isoforms (open circles) GST-MAPKAP-K1b and MAPKAP-K2 (open triangles) in vitro. The results are presented relative to control incubations in which the inhibitor was omitted and are shown as the average of 2 experiments with each determination carried out in triplicate. The error for each point is ±10%. (B) 293 cells were pre-treated for 1 h with 5 µM Ro 318220 (Ro) or in the absence of inhibitor (–), before being exposed to UV radiation (200 J/m$^2$) or left untreated (–) and then incubated for a further 30 min in the continued presence of Ro 318220. The cells were lysed MAPKAP-K2 was immunoprecipitated and assayed. The data are presented as the mean±SEM for two separate experiments with each determination carried out in triplicate. (C) as above except that 293 cells were incubated for 2 h in 32phosphate (0.1 mCi/ml) before treatment with inhibitors. Cells were then exposed to either UV radiation (200 J/m2) or left untreated (–), incubated for a further 20 min in the continued presence of inhibitors. Following cell lysis, HSP27 was immunoprecipitated from cell extracts (Cuenda et al., 1995) run on a 15% polyacrylamide gel and autoradiographed.

Figure 10:
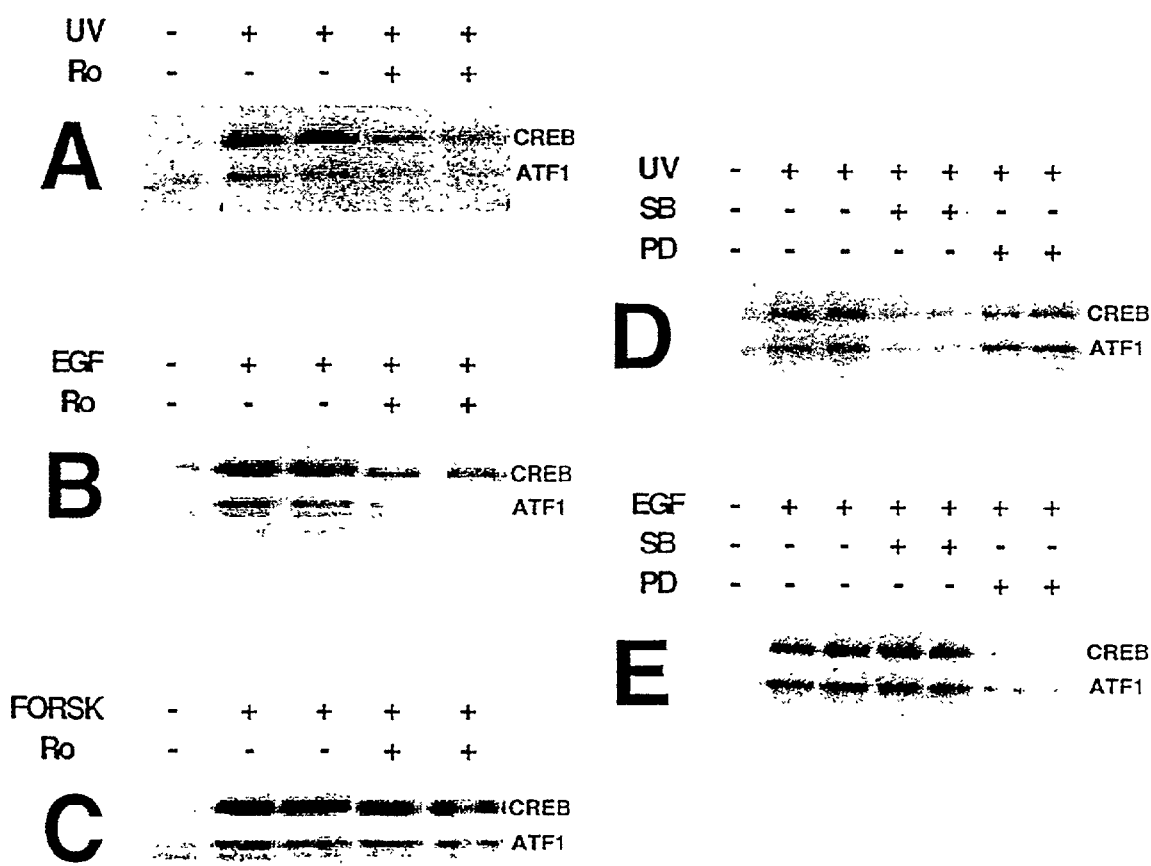

FIG. 10. Ro 318220 inhibits EGF and UV induced phosphorylation of CREB. 293 cells were pre-treated either in the presence or absence of 5 µM Ro 318220 (Ro), 10 µM SB 203580 (SB), 50 µM PD 98059 (PD), and then exposed to either (A, D) UV radiation (200 J/m$^2$, 30 min and then 30 min at 37° C.) (B, E) EGF (100 ng/ml, 15 min), (C) forskolin (20 µM, 15 min). The cells were lysed and proteins were separated on 10% acrylamide gels and immunoblotted using a phosphospecific antibody that recognised both CREB and ATF1 when phosphorylated on Ser133 and Ser63 respectively. The position of CREB and ATF1 on the blots is indicated.

Figure 11:
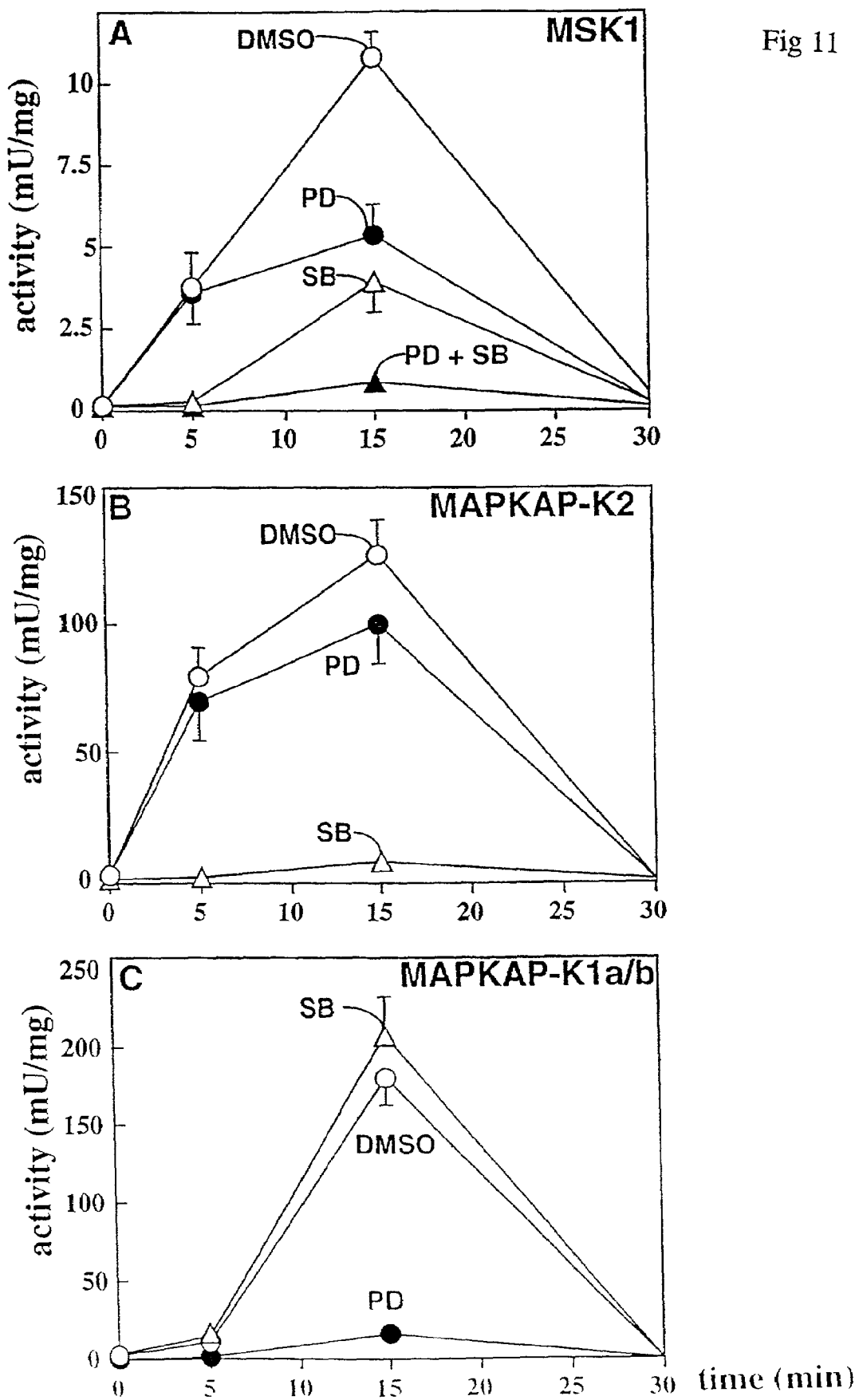

FIG. 11. Activation of MSK1 by TNF. HeLa cells were incubated for 2 h in serum free medium in the presence of 50 µM PD 98059 (solid circles), 10 µM SB 203580 (open triangles), 50 µM PD 98059 plus 10 µM SB 203580 (solid triangles) or in the absence of both compounds (open circles). The cells were then stimulated with TNF (10 ng/ml) for the times indicated in the continued presence or absence of inhibitors, lysed and MSK1 (A), MAPKAP-K2 (B), and MAPKAP-K1a/b (C) immunoprecipitated from the same lysate and assayed. The data are presented as the mean±SEM for two separate experiments with each determination carried out in triplicate.

FIG. 12. Effect of PD 98059, SB 203580 and Ro 318220 on TNF induced CREB phosphorylation. HeLa cells were incubated for 2 h in serum free medium in the presence or absence of 50 µM PD 98059 (PD), 10 µM SB 203580 (SB)

and 5 µM Ro 318220 (Ro) as indicated. The cells were then stimulated with TNF (10 ng/ml) for the times indicated in the continued presence or absence of inhibitors, lysed and the samples immunoblotted for phosphorylation of CREB and ATF1 as described in the legend to FIG. 11C. The position of CREB and ATF1 on the blots is indicated. The time of exposure (exp) of the blots before development is indicated.

Figure 13:
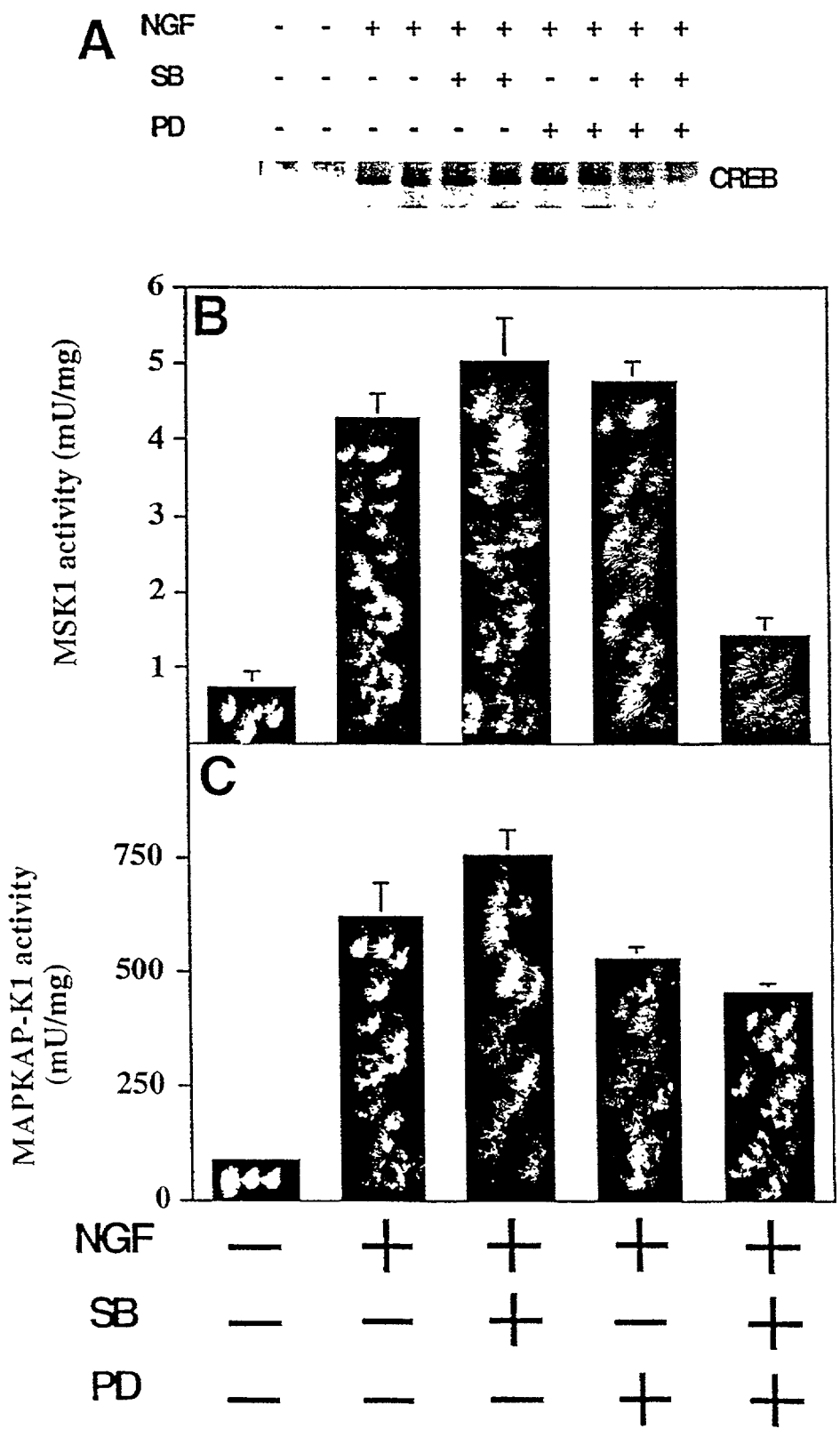

FIG. 13. Effect of PD 98059, SB 203580 and Ro 318220 on NGF-induced activation of CREB and MSK1 in PC12 cells. PC12 cells were incubated for 2 h in serum free medium in the presence or absence of 50 µM PD 98059 (PD) or 10 µM SB 203580 (SB). The cells were then stimulated with NGF (30 ng/ml) for 15 min in the continued presence or absence of inhibitors. After cell lysis aliquots were immunoblotted for phosphorylation of CREB (A) or used to assay MSK1 (B) or used MAPKAP-K1 (C) after their immunoprecipitation from the lysates.

FIG. 14. Effect of PD 98059, SB 203580 and Ro 318220 on arsenite and FGF-induced activation of CREB and MSK1 in SK-N-MC cells. SK-N-MC cells were incubated for 1 h in serum free medium in the presence or absence of 50 µM PD 98059 (PD), 10 µM SB 203580 (SB) and 5 µM Ro 318220 (Ro). The cells were then stimulated for 15 min with sodium arsenite (0.5 mM) or FGF (50 ng/ml) in the continued presence or absence of inhibitors. After cell lysis aliquots were assayed for either MSK1 (A), MAPKAP-K1 (B), MAPKAP-K2 (C) after their immunoprecipitation from the lysates or immunoblotted for phosphorylation of CREB and ATF1 (D).

Figure 15:
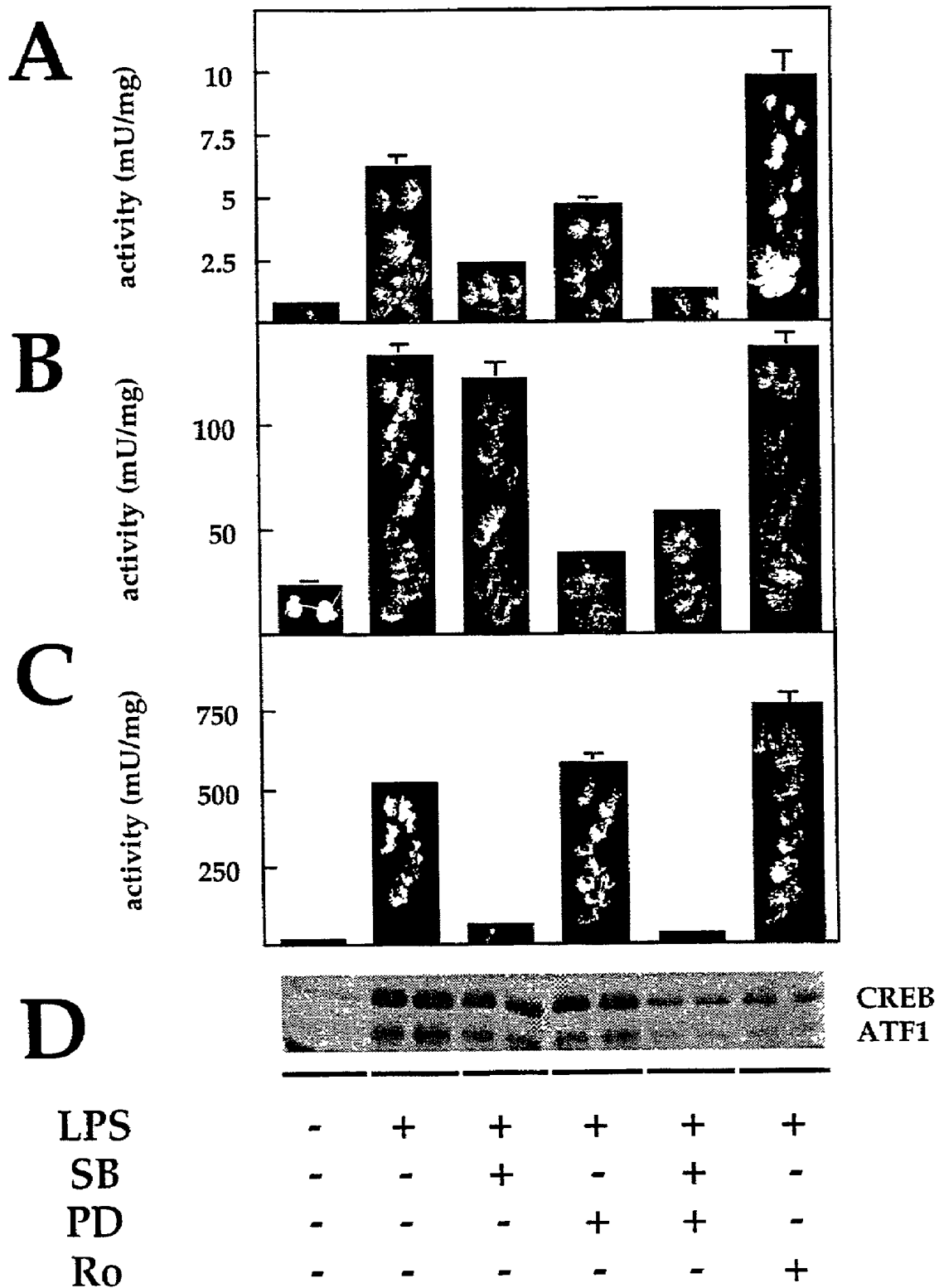

FIG. 15. Effect of PD 98059, SB203580 and Ro 318220 on LPS-induced activation of CREB and MSK1 in RAW macrophages. RAW 264 macrophages were incubated for 2 h in serum free medium, then for 1 h in the presence or absence of 50 µM PD 98059 (PD), 10 µM SB203580 (SB), or 5 µM Ro 318220 (Ro). The cells were then stimulated with LPS (100 ng/ml) for 1 h in the continued presence or absence of inhibitors. After cell lysis aliquots were assayed for either MSK1 (A), MAPKAP-K1 (B), MAPKAP-K2 (C) after their immunoprecipitation from the lysates or immunoblotted for phosphorylation of CREB and ATF1 (D).

FIG. 16. Amino acid and nucleotide sequences of human MSK2 and a splice variant of human MSK2.

Figure 17:
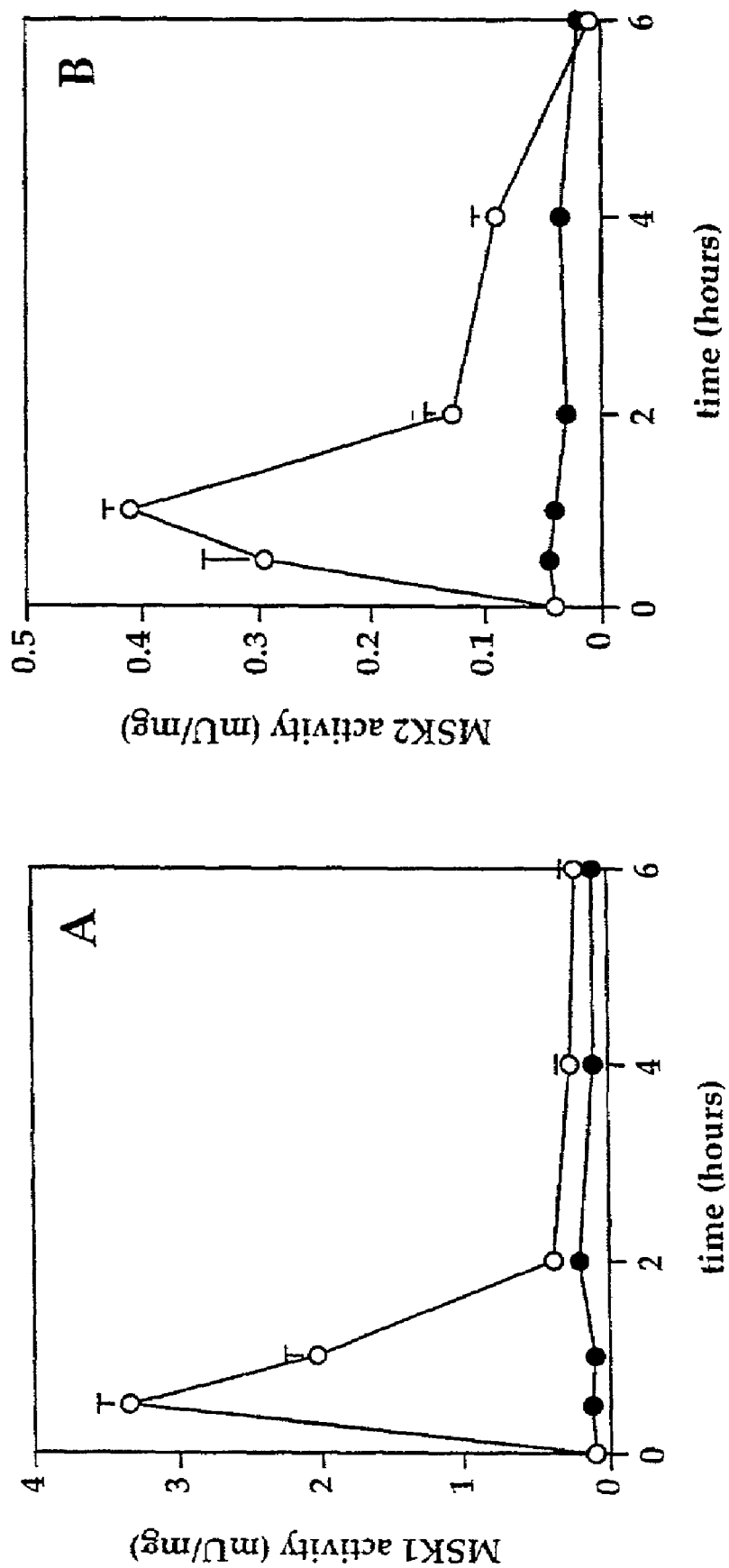

FIG. 17. Activation of MSKI and MSK2 by LPS in RAW 264 macrophages. Macrophages were stimulated for the times indicated with (open symbols) and without (closed symbols) 100 ng/ml LPS. MSK1 activity (A) or MSK2 activity (B) were then measured after immunoprecipitation from the lysates. The results are presented as the mean±SEM for two determinations from two separate dishes. Similar results were obtained in two further experiments.

FIG. 18. Effect of inhibitors on the LPS-induced activation of protein kinases in RAW 264 macrophages. Macrophages were incubated for 1 h in the presence or absence 10 µM UO 126 (U) and/or 10 µM SB 203580 (SB), or 5 TM Ro 318220 (Ro), then stimulated for 1 h with or without 100 ng/ml LPS in the continued presence or absence of the inhibitors. MSK1(A), MSK2 (B), MAPKAP-KI (C) and MAPKAP-K2 (D) were then assayed after immunoprecipitation from the lysates. The results are presented as the mean±SEM for two determinations from two separate dishes. Similar results were obtained in two further experiments.

Figure 19:
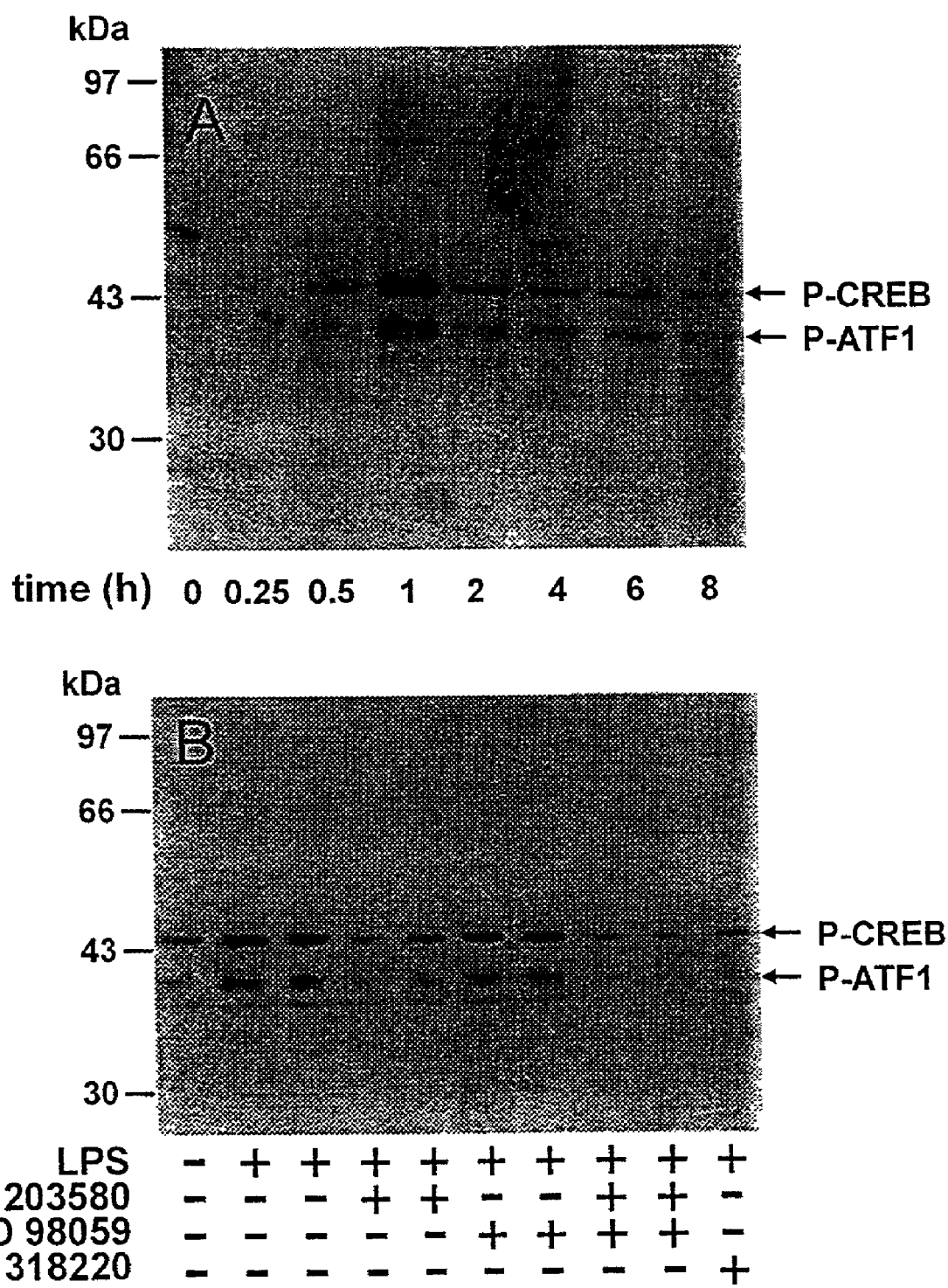

FIG. 19. LPS-induced CREB and ATF1 phosphorylation in RAW264 macrophages. (A) Macrophages were stimulated for the times indicated with LPS (100 ng/ml). After cell lysis, aliquots of the lysate (30 Tg protein) were denatured in SDS, electrophoresed on a 10% polyacrylamide gel, transferred to a nitrocellulose membrane, and immunoblotted with a phospho-CREB antibody. The positions of the molecular mass markers glycogen phosphorylase (97 kDa), bovine serum albumin (66 kDa), ovalbumin (43 kDa) and carbonic anhydrase (30 kDa) are indicated. Similar results were obtained in three further experiments. (B) As in A, except that the macrophages were incubated for 1 h in the presence or absence of 50 TM PD 98059 and/or 10 TM SB 203580 (SB), or 5 TM Ro 318220 (Ro), then stimulated for 1 h in the absence or presence of 100 ng/ml LPS and in the continued presence or absence of the inhibitors. Similar results were obtained in three further experiments.

Figure 20:
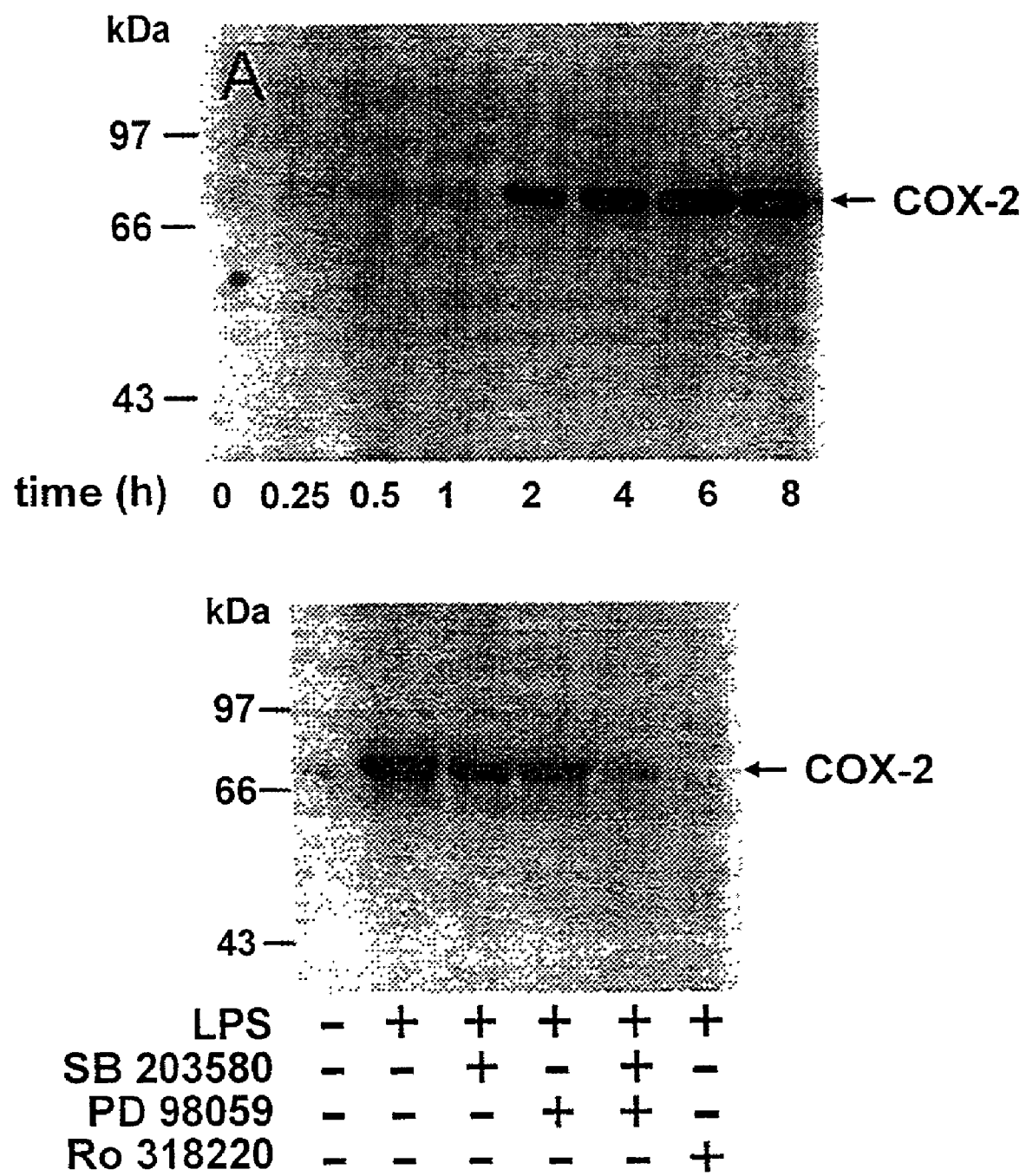

FIG. 20. LPS-stimulated induction of COX2 protein in RAW264 macrophages. (A) Macrophages were stimulated for the times indicated with LPS (100 ng/ml). After cell lysis, aliquots of the lysate (30 Tg protein) were immunoblotted with a COX-2 antibody (see legend to FIG. 19 for details and molecular mass markers). Similar results were obtained in three further experiments. (B) As in A, except that the macrophages were incubated for 1 h in the presence or absence of 50 TM PD 98059 (PD) and/or 10 TM SB 203580 (SB), or 5 TM Ro 318220 (Ro), then stimulated for 4 h in the absence or presence of 100 ng/ml LPS and in the continued presence or absence of the inhibitors. Similar results were obtained in three further experiments.

Figure 21:
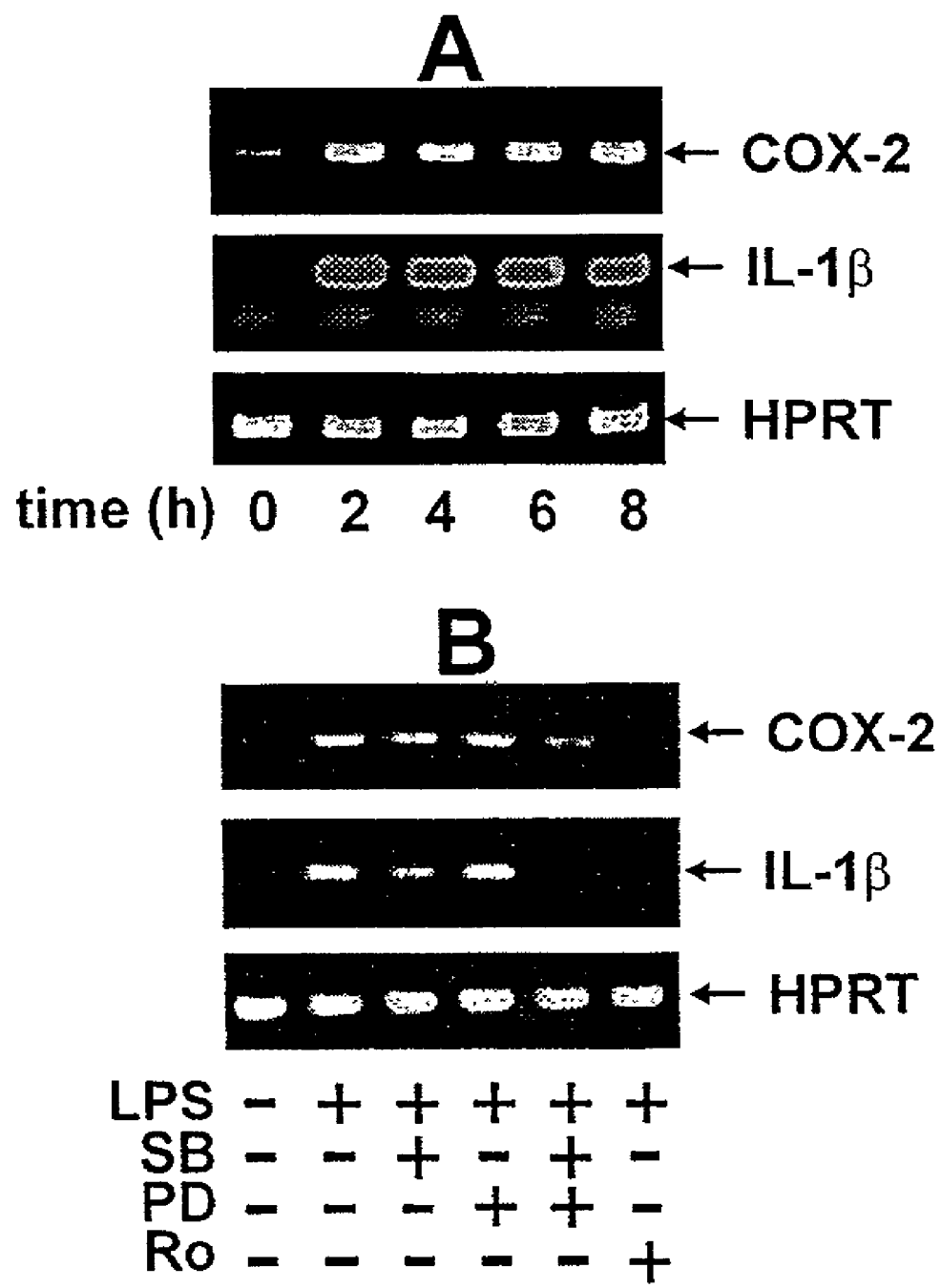

FIG. 21. Effect of PD 98059 and SB 203580 on gene transcription in RAW 264 macrophages. (A) Cells were stimulated for the times indicated with LPS (100 ng/ml). Total RNA was extracted at each time point and mRNA encoding IL-1, COX-2 and HRPT was determined using the reverse transcriptase polymerase chain reaction (Section 2.6). (B) As in A, except that the macrophages were incubated for 1 h in the presence or absence of PD 98059 (50 TM) and/or SB 203580 (10 TM), or Ro 318220 (5 TM), then stimulated for 3 h in the absence or presence of LPS, and in the continued presence or absence of the inhibitors. RTPCR was performed using oligonucleotides encoding fragments of IL-1, COX-2 and HPRT. Similar results were obtained in two further experiments.

Figure 22:
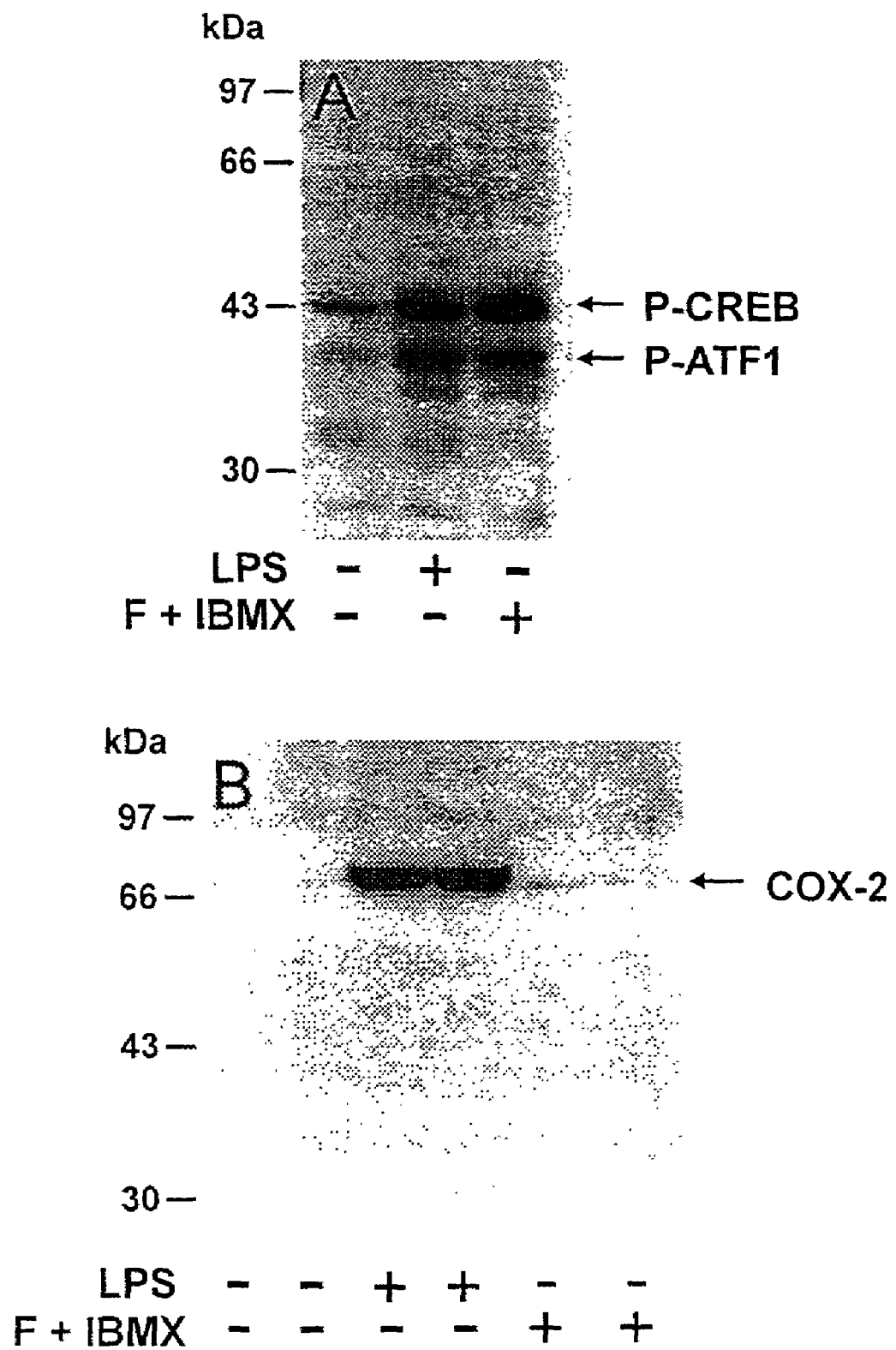

FIG. 22. Effect of forskolin on CREB phosphorylation and COX-2 induction in RAW264 macrophages. (A) Macrophages were stimulated for 1 h with LPS (100 ng/ml) or for 15 min with forskolin (F) (20 TM) plus IBMX (10 TM). After cell lysis, aliquots of the lysate (30 Tg protein) were immunoblotted with a phospho-specific CREB antibody (see legend to FIG. 19 for details and molecular mass markers). (B) Macrophages were stimulated for 3 h with LPS (100 ng/ml), or forskolin (20 TM) plus IBMX (10 TM), and immunoblotting performed with a specific COX-2 antibody (materials & methods section). The marker proteins are as in FIG. 19. Similar results were obtained in two further experiments.

EXAMPLE 1

Mitogen and Stress Activated Protein Kinase (MSK1), a Novel Two-Kinase Domain Enzyme That is Directly Activated by MAPK and SAPK2/p38 and Which may Mediate the Activation of CREB We have identified a novel mitogen and stress-activated protein kinase (MSK1) and a closely related homologue (MSK2) that contain two protein kinase domains in a single polypeptide. MSK1 (802 residues) displays 43% overall amino acid sequence identity to MAP kinase-activated protein kinase-1 (MAPKAP-K1, also termed p90 RSK) another "two kinase domain" enzyme. The N-and C-terminal kinase domains of MSK1 are 54% and 44% identical to the corresponding domains in MAPKAP-K1, and the four key activating phosphorylation sites in MAPKAP-K1 are conserved in MSK1. Like MAPKAP-K1, MSK1 is activated in vitro by MAPK2/ERK2 but, unlike MAPKAP-K1, it is also activated by stress-activated protein kinase2a (SAPK2a, also termed p38) and SAPK2b/p38β2. Consistent with these findings, endogenous MSK1 is activated in 293 cells by either polypeptide growth factor/phorbol ester stimulation or by exposure to UV radiation, oxidative and chemical stress, whereas MAPKAP-K1 is only activated significantly by growth factor/phorbol ester stimulation. The activation of MSK1 by growth factor/phorbol ester stimulation is prevented by the drug PD 98059, which suppresses activation of the MAPK cascade, while the activation of MSK1 by UV radiation, oxidative and chemical stress is largely prevented by SB 203580, a specific inhibitor of SAPK2a/p38 and SAPK2b/p38β. In HeLa cells, both PD 98059 and SB 203580 are required to suppress the activation of MSK1 by TNF, NGF and FGF, respectively, because this agonist activates both the MAPK/ERK and the SAPK2/p38 cascades. The activation of MSK1 is abolished by making single inactivating mutations in either the N-terminal or C-terminal kinase domain. MSK1 is localised in the nucleus of unstimulated or stimulated cells, whereas MAPKAP-K1a is largely cytosolic under the same conditions. MSK1 phosphorylates the transcription factor CREB at Ser133 with a Km value far lower than PKA, MAPKAP-K1 and MAPKAP-K2. A peptide corresponding to the sequence surrounding Ser133 is phosphorylated with a remarkably low Km value (<0.1 µM). The effects of SB 203580, PD 98059 and Ro 318220 on agonist-induced activation of CREB and ATF1 in four cell lines mirror the effects of these inhibitors on MSK1 activation and exclude a role for MAPKAP-K2, MAPKAP-K3 and MAPKAP-K1 in this process. These findings together with other observations, suggest that MSK1 may mediate the growth factor and stress-induced activation of CREB.

Results

Identification of MSK1 as a novel MAPKAP-K1 related kinase. We used the DNA sequence encoding the N-terminal kinase domain of MAPKAP-K1 to interrogate the NCBI EST database. This search identified one EST (AA1 158571) encoding a full length cDNA clone of a novel member of this subfamily, hereafter termed MSK1. The open reading frame encoded a protein of 802 amino acids with a molecular mass of 89.9 kDa. There is a stop codon immediately 5' to the predicted initiating ATG codon. The MSK1 polypeptide domain possessed two protein kinase domains (FIG. 1) both of which contained the eleven subdomains characteristic of all protein kinases (Hanks et al., 1988). MSK1 showed greatest similarity to the three isoforms of the MAPKAP-K1, which also possess two kinase domains (FIG. 2A). The N terminal and C-terminal kinase domains of MSK1 were 54% and 44% identical to the corresponding kinase domains of MAPKAP-K1. The overall identity between MAPKAP-K1 and MSK1 was 43%. We identified 14 human EST clones encoding fragments of MSK1 that are derived from many tissues (Table 1), indicating that MSK1 is a widely expressed enzyme.

TABLE 1

Genbank accession numbers for human MSK1 ESTs

| Tissue from which EST derives | |
| --- | --- |
| AA314565, AA305163 | colon carcinoma |
| AA134359, AA134358 | colon |
| AA699729, R11235, T97584, T97538, R11183 | fetal liver spleen |
| W04930 | fetal lung |
| AA158572, AA158571 | pancreas |
| AA322270 | cerebellum |
| H09985, HO 9986, F05701, HSC0jE081 | infant brain |
| N31641, N57096 | placenta |
| AA255846, AA255996 | germinal centre B cell |
| AA897221 | mixed |
| Genbank accession numbers for mouse MSK1 ESTs | |
| AA472165 | mammary gland |
| AA389168, AA061016 | embryo |
| AA444366 | heart |
| Genbank accession numbers for human MSK2 ESTs | |
| H41647 | adult brain |
| R17109 | fat cell |
| T19765 | cardiovascular system |
| R71969, AA631897, AA505842 | breast tumor |
| AA443601 | ovary tumor |
| AA678670 | Gessler Wilms tumor |
| AA5706681 | prostate tumor |
| AA594559, AA576979, AA568895 | colon tumor |
| AA857431 | pharynx carcinoma |
| Genbank accession numbers for mouse MSK2 ESTs | |
| AA472165 | mammary gland |
| AA389168 | embryo |
| AA061016 | fetus |
| AA657108 | myotubes |
| AA267490 | lymph node |
| AA444366 | heart |

Northern blot analysis of human tissues revealed that MSK1 was expressed as a 4 kb transcript in all tissues examined (heart, brain, placenta, lung, liver, kidney and pancreas) with the highest levels observed in brain, muscle and placenta (data not shown). An alignment of the N and C-terminal kinase domains of MSK1 with other protein kinases that are activated by MAPK family members is shown in FIG. 2B.

We also found EST cDNA clones (Table 1) encoding a further protein kinase whose amino acid sequence was 75% identical to MSK1, but also only 40% identical to MAPKAPK1, and which we have termed MSK2. The near full length coding sequence of murine MSK2 and the partial sequence of human MSK2 aligned with MSK1 are presented in FIG. 2C. The murine and human MSK2 sequences share 90% amino acid sequence identity. We identified 8 human EST cDNA clones encoding fragments of MSK2 that were derived from a number of cells and tissues. Six of these were tumour cell lines. Northern Blot analysis of human tissues revealed that MSK2 was expressed as a 3 kb transcript with a similar distribution to that of MSK1 (results not shown).

Activation of MSK1 in vitro by MAPK2/ERK2 and SAPK2/p38. The four key activating phosphorylation sites present in MAPKAP-K1a (see Introduction) are conserved in MSK1 and MSK2 (FIG. 2). Two of the four sites in MAPKAP-K1 (Ser 360 and Thr 581), which are followed by proline residues, are phosphorylated by MAPK (FIG. 2C). These observations suggested that MSK1 and MSK2 may be activated by one or more MAPKs. In order to compare the activation of MSK1 and MAPKAP-K1a by MAPKs, both enzymes were expressed in human embryonic kidney 293 cells as fusion proteins with glutathione S-transferase (GST)

at the amino terminus (hereafter termed GST-MSK1 and GST-MAPKAP-K1a). Both proteins were purified on glutathione-Sepharose and showed a single major Coomassie Blue-staining band when subjected to SDS/polyacrylamide gel electrophoresis (FIG. 3A). The apparent molecular mass of GST-MSK1 estimated by SDS/polyacrylamide gel electrophoresis (116 kDa), was slightly larger than GST-MAPKAP-K1a (FIG. 3A) which is consistent with the latter enzyme being 62 amino acids shorter (FIG. 2A).

MAPKAP-K1 is known to have a high activity towards the peptide named Crosstide (GRPRTSSFAEG) (SEQ ID NO:16) (Alessi et al., 1996a). GST-MSK1 and GST-MAPKAP-K1a purified from 293 cells that had been serum starved overnight possessed a low activity towards this substrate (2-4 U/mg), which was enhanced over 100-fold by incubation with MgATP and activated MAPK2/ERK2 (FIGS. 3B and 3C). GST-MSK1 could also be activated similarly by SAPK2a/p38 and SAPK2b/p38β (FIG. 4A), whereas MAPKAP-K1a could not(FIG. 3C). SAPK1/JNK1γ and SAPK3/p38β did not activate either GST-MSK1 or GST-MAPKAP-K1a. SAPK4/p38δ was a weak activator of GST-MSK1 and did not activate GST-MAPKAP-K1a. The ability of MAPK2/ERK2 (data not shown) and SAPK2/p38 (FIG. 3D) to activate GST-MSK1 correlated with the extent of phosphorylation of this enzyme.

Endogenous MSK1 is activated in vivo by EGF and TPA through the MAPK/ERK pathway and by stressful stimuli through the SAPK2/p38 pathway. The experiments presented in FIG. 3 raised the possibility that MSK1 might be activated in response to stimuli that activate the SAPK2/p38 isoforms, as well as stimuli that activate the classical MAPK/ERK cascade. In order to examine this possibility three MSK1 antibodies were raised, one against residues 26 to 44 (antibody "A"), a second against residues 384 to 402 (antibody "B") and a third against residues 716 to 734 (antibody "C"). All three antibodies immunoprecipitated MSK1 quantitatively (not shown) and immunoprecipitation of expressed MSK1 (FIG. 4A) or endogenous MSK1 in cell lysates (not shown) was prevented by incubation with the appropriate peptide immunogen.

The MAPKAP-K1 antibody used in this study immunoprecipitates both MAPKAP-K1a and MAPKAP-K1b (FIGS. 4B and 4C, Alessi et al., 1995), but did not immunoprecipitate MSK1 (FIG. 4A). Furthermore, non of the MSK1 antibodies immunoprecipitated MAPKAP-K1a or MAP-KAP-K1b (FIGS. 4B and 4C). The peptide sequence used to raise MSK1 antibody "A" is not conserved in MSK2, and the 19 residue peptides used to raise antibodies "B" and "C" possess only 9 and 12 conserved residues with MSK2 respectively. All three MSK1 antibodies immunoprecipitated similar levels of MSK1 activity in both 293 cells exposed to EGF, TPA or stresses, or in HeLa cells stimulated with TNF (data not shown). These results indicate that MSK2 is not co-immunoprecipitated with MSK1.

Endogenous MSK1 was immunoprecipitated with antibody "A" from the lysates of 293 cells previously stimulated with EGF, 12-O-tetradecanoylphorbol 13-acetate (TPA) or exposed to cellular stresses (sodium arsenite, UV radiation or hydrogen peroxide). These experiments demonstrated that MSK1 was potently activated by all of these stimuli (FIG. 5A). Interestingly, the activation of MSK1 by EGF and TPA was largely prevented by PD 98059, a specific inhibitor of the activation of MAP kinase kinase-1 (Alessi et al., 1995), but not by SB 203580, a specific inhibitor of SAPK2a/p38 and SAPK2b/p38β, (Cuenda et al., 1995). In contrast, the activation of MSK1 by stressful stimuli was largely inhibited by SB 203580, but not by PD 98059 (FIG. 5A). Identical results were obtained when antibody "B" or antibody "C" were used instead of antibody "A" (data not shown).

EGF and TPA stimulation of cells potently activated MAPKAP-K1a/b in 293 cells and, like the activation of MSK1, this was largely suppressed by PD 98059, but not by SB 203580 (FIG. 5B). Stressful stimuli did not induce significant activation of MAPKAP-K1a/b (FIG. 5B) but induced a large activation of MAPKAP-K2 that was prevented by SB 203580, but not by PD 98059 (FIG. 5C). MAPKAP-K2 was not activated significantly by EGF or TPA (FIG. 5C).

The activation of MSK1 by TPA and UV radiation requires both kinase domains. In order to establish which kinase domain of MSK1 was required for its activation in vivo, we transfected 293 cells with DNA expression constructs encoding wild type MSK1 (WT-MSK1), a mutant MSK1 in which the N-terminal kinase domain should be inactivated by a point mutation (NT kinase-dead MSK1) and a further mutant in which the C-terminal kinase domain should be inactivated (CT kinase-dead MSK1). All the constructs possessed an N-terminal "flag" tag (see Methods) to enable their immunoprecipitation and assay from cell lysates. Stimulation of the cells with TPA or exposure to UV radiation induced 200-fold and 30-fold activation of the wild type MSK1, respectively. Similar to the results with the endogenous MSK1, the activation of transfected MSK1 by TPA was prevented by PD 98059 but not by SB 203580, while the UV-induced activation was prevented by SB 203580 but unaffected by PD 98059 (FIG. 6A). The transfected, wild type enzyme was also activated 50-100 fold by EGF, basic FGF and serum, and activation was prevented by PD 98059 but not SB 203580 (data not shown). These observations confirm the results obtained by immunoprecipitation of the endogenous protein kinase; ie that MSK1 can be activated in cells by either the classical MAP kinase cascade or via the SAPK2a/p38 pathway.

In contrast neither the NT kinase dead mutant nor the CT-kinase dead mutant of MSK1 possessed detectable activity either before or after cell stimulation with TPA or exposure to UV radiation (FIG. 6A). Both the "kinase dead" MSK1 mutants were expressed at the same level as the wild type MSK1 protein (FIG. 6B). These observations also establish that the MSK1 activity measured in FIG. 6 is due to MSK1 itself and not a contaminant kinase that is co-immunoprecipitated with MSK1.

MSK1 is localised in nuclei and MAPKAP-K1a in the cytoplasm. The subcellular location of wild type MSK1 that was overexpressed in 293 cells was investigated by quantitative immunoelectron microscopy (FIG. 7). MSK1 was largely located in the nucleus of unstimulated cells. The density of MSK1 in the nuclear compartment was 12 to 30-fold higher than in the cytoplasm (FIGS. 7A and 7C). Activation of MSK1 by stimulation with TPA (FIGS. 7A and 7D) or by exposure to UV radiation (data not shown) did not induce any change in the subcellular location of MSK1. MSK1 possesses a putative bipartite nuclear localization signal (Robins et al., 1991) between residues 726 to 748 (FIG. 1) which is not present in MAPKAP-K1a/b. Consistent with this observation MAPKAP-K1a, when overexpressed in cells, was largely localised in the cytoplasm (FIG. 7B). Moreover, no significant translocation of MAPKAP-K1a to the nucleus was observed following TPA stimulation of cells (FIGS. 7B and 7E) which induces 100-fold activation of this kinase (data not shown).

MSK1 is an extremely efficient CREB kinase in vitro. The substrate specificities of MSK1 and MAPKAP-K1a were compared after expression of the GST fusion proteins in 293 cells, followed by TPA stimulation and purification from the cell lysates (FIG. 3A). The specific activity of GST-MSK1 at a saturating concentration of Crosstide (GRPRTSSFAEG (SEQ ID NO:16), Peptide 1 FIG. 8A) was found to be similar to that of MAPKAP-K1a (see legend to FIG. 8). The Km for Crosstide was 2–3 µM for MSK1, MAPKAP-K1a or MAPKAP-K1b. Crosstide is phosphorylated efficiently by MAPKAP-K1 because it contains two arginies located three and five residues N-terminal to the serine that is phosphorylated. For this reason, the peptide KKRNRTLSVA (SEQ ID NO:17) (Peptide 2, FIG. 8A) is phosphorylated by MAPKAP-K1a/b with almost identical Km and Vmax values as for Crosstide. This peptide was found to be phosphorylated even more efficiently by MSK1, the Km value being 0.2 µM. Changing the arginine at position n-3 in KKRNRTLSVA (SEQ ID NO:17) to lysine (Peptide 3 FIG. 8A) increased the Km about 100-fold for MSK1, as well as for MAPKAP-K1a/b. However, changing the arginine at position n-5 to leucine (Peptide 4 FIG. 8A) did not increase the Km for MSK1 significantly, although the Km for MAPKAP-K1a/b was increased five fold. These experiments indicate that MSK1 requires an arginine at position n-3, but not a basic residue at n-5.

It has been reported that MAPKAP-K1b (Xing et al., 1996) and MAPKAP-K2 (Tan et al., 1996) mediate the activation of the transcription factor CREB by growth factors and stressful stimuli, respectively. In view of the predominantly nuclear localisation of MSK1, it was therefore of interest to compare the efficiency with which it phosphorylated CREB compared to these other protein kinases. These experiments led to the surprising finding that CREB is an astonishingly good substrate for MSK1, being phosphorylated with a Km of 2 µM and with a Vmax similar to Crosstide or KKRNRTLSVA (SEQ ID NO:17). In contrast, CREB was phosphorylated by PKA with a Km of 17 µM under the same conditions (data not shown), while the Km was too high to be measured when phosphorylation was catalysed by MAPKAP-K1a/b (FIG. 8A) or MAPKAP-K2 (data not shown). As a result, when the activities of MSK1, MAPKAP-K1a/b and MAPKAP-K2 were matched towards Crosstide and/or the peptide KKLNRTLSVA (SEQ ID NO:35), the rate of phosphorylation of 5(M CREB by MSK1 was 30-fold higher than MAPKAP-K1a, 12-fold higher than MAPKAP-K1b and 60-fold higher than MAPKAP-K2 (FIG. 8B). In contrast, MAPKAP-K2 was much more active towards heat shock protein 27 (one of its physiological substrates, Cuenda et al., 1995) than MSK1 or MAPKAP-K1a/b (FIG. 8B).

The residue on CREB phosphorylated by MSK1 was established by tryptic digestion, followed by chromatography of the digest on a C 18 column. One major $^{32}$P-labelled peptide was observed that eluted at 15% acetonitrile (FIG. 8C). This peptide contained phosphoserine, and when subjected to solid phase sequencing, $^{32}$P-radioactivity was released after the third cycle of Edman degradation (data not shown). Its identity was established by MALDI-TOF mass spectrometry which revealed that the molecular weight of the peptide (758.33) was identical to that of the expected tryptic phosphopeptide comprising residues 131–135 and phosphorylated at Ser133 (calculated mass 758.36). MAPKAP-K1b, which is known to phosphorylate the same residue (Xing et al., 1996), labelled the same tryptic peptide as MSK1 (data not shown).

Consistent with the results obtained with the CREB protein, a synthetic peptide (termed CREBtide) corresponding to residues 126 to 136 of CREB (EILSRRPSYRK (SEQ ID NO:18), peptide 5, FIG. 8A) was phosphorylated with a Km value too low to be measured (<0.1 µM). In contrast, MAPKAP K1a and MAPKAP-K1b phosphorylated this peptide rather poorly with Km values that were at least 200-fold higher (FIG. 8A).

Evidence that MAPKAP-K2 does not mediate the phosphorylation of CREB and ATF1 by UV radiation or EGF in 293 cells. The staurosporine analogue Ro 318220 inhibits all the PKC isoforms (Davis et al., 1989) as well MAPKAP-K1a/b, with $IC_{50}$ values ranging from 10 to 30 nM (Alessi 1997, FIG. 9A). In the present work, Ro 318220 was found to be an equally potent inhibitor of MSK1 activity in vitro (FIG. 9A). Ro 318220 does not significantly inhibit MAPKAP-K2 in vitro even at 10 µM (FIG. 11A), nor does it affect the activation of MAPKAP-K2 in vivo in response to UV radiation (FIG. 9B). Furthermore, incubation of cells with Ro 318220 did not significantly affect the UV induced phosphorylation of HSP27, a physiological substrate for MAPKAP-K2 (Cuenda et al., 1995, FIG. 9C). In parallel experiments, the phosphorylation of HSP27 by UV radiation was blocked by SB203580. The cyclic AMP dependent protein kinase which mediates phosphorylation of CREB and ATF1 induced by agonists which increase cyclicAMP levels such forskolin (Gonzalez and Montminy 1989) is also not significantly inhibited by 10 µM Ro 318220 (Davis et al., 1989)

The results presented in FIG. 9 offered an opportunity to evaluate the role of MAPKAP-K2 in mediating the phosphorylation of CREB at Ser133 (and its close relative ATF1 at Ser63). We observed that CREB and ATF1 became rapidly phosphorylated following exposure of 293 cells to UV radiation or following treatment with EGF, and that phosphorylation was largely inhibited by 5 µM Ro 318220 (FIGS. 10A and 10B). In contrast phosphorylation of CREB and ATF1 induced by forskolin, which induces CREB phosphorylation through the cyclic AMP dependent protein kinase (Gonzalez et al., 1989), was unaffected by 5 µM Ro 318220 (FIG. 10C). Like the activation of MSK1, the UV radiation-induced phosphorylation of CREB and ATF1 was inhibited by SB 203580, but not by PD 98059 (FIG. 10D), while EGF-induced CREB phosphorylation was prevented by PD 98059 and not SB203580 (FIG. 10E).

Evidence that neither MAPKAP-K2 or MAPKAP-K1 mediated the phosphorylation of CREB and ATF1 by TNF in HeLa cells. Endogenous MSK1 was rapidly (but transiently) activated by tumour necrosis factor (TNF) in HeLa cells. Interestingly, the effect of SC 203580 and PD 98059 on the activation of MSK1 varied with the time of stimulation. After 5 min, activation was completely inhibited by SB 203580, but unaffected by PD 98059. However, after 15 min the activation of MSK1 was partially blocked by either SB 203580 or PD 98059, and almost completely suppressed if both drugs were added together (FIG. 11A). These observations are explained by the different rates of activation of the SAPK2/p38 and MAPK/ERK cascades. Thus, after 5 min of TNF stimulation, the SAPK2 pathway is activated as judged by the activation of MAPKAP-K2 (which is inhibited by SB 203580 but not by PD 98059). In contrast, the MAPK/ERK cascade is not activated after 5 min, as judged by lack of activation of MAPKAP-K1a/b (FIGS. 11B and 11C). However, both the MAPK/ERK and SAPK2/p38 cascades are activated after 15 min of TNF stimulation, as judged by the activation of both MAPKAP-K1a/b and MAPKAP-K2. The activation of MAPKAP-K1a/b after 15 min is suppressed by PD 98059, but not by SB 203580 (FIGS. 11B and 11C).

Stimulation of HeLa cells with TNF rapidly induced the phosphorylation of CREB and ATF1. After 5 min, the phosphorylation of CREB and ATF1 was prevented by SB 203580 but unaffected by PD 98059 (FIG. 12A). After 15 min, TNF-induced phosphorylation of CREB was partially suppressed by SB 203580, slightly suppressed by PD 98059 and completely prevented in the presence of both compounds (FIG. 12B). The effects of SB 203580 and PD 98059 on the activation of CREB were therefore similar to their effects on TNF-induced MSK1 activation (FIG. 11). TNF-induced CREB phosphorylation was completely blocked by 5 µM Ro 318220 (FIG. 12C), but the activation of MAPKAP-K2 was unaffected by this drug (data not shown).

Evidence that CREB phosphorylation as Ser133 in PC12 cells correlates with activation of MSK1 rather than MAPKAP-K1 or MAPKAP-K2. NGF stimulation of a PC12 cell line induced the phosphorylation of CREB (FIG. 13A) and the activation of MSK1 (FIG. 13B). The phosphorylation of CREB and the activation of MSK1 were not significantly affected by incubation of the cells with either PD98059 or SB 203580, but strongly inhibited in the presence of both drugs (FIG. 13). These results indicate that inhibition of both the MAPK/ERK and SAPK2/p38 pathways is needed to prevent CREB phosphorylation at Ser133 and MSK1 activation in these cells, and this is considered further under Discussion.

Like MSK1, MAPKAP-K1 was also activated five-fold by NGF but, in contrast to MSK1, activation of MAPKAP-K1 was unaffected by SB 203580, only partially inhibited by PD 98059 and not further inhibited by a combination of both drugs. Thus MAPKPA-K1 activity did not correlate with CREB phosphorylation. As reported previously (Rouse et al., 1994) NGF did not induce any significant activation of MAPKAP-K2 activation in PC23 cells. Moreover, NGF-induced CREB phosphorylation was suppressed by 5 µM Ro 318220 (data not shown), again excluding a role for MAPKAP-K2/K3.

Evidence that CREB phosphorylation at Ser 133 in SK-N-MC cells correlates with activation of MSK1 rather than MAPKAP-K1 or MAPKAP-K2. Earlier work from this laboratory showed that the phosphorylation of CREB at Ser133 in SK-N-MC cells, induced by either sodium arsenite or FGF, is suppressed by SB 203580 (Tan et al., 1996). In the present work we confirmed that the sodium arsenite-induced activation of CREB and MSK1 in these cells is prevented by SB 203580, but not by PD 98059. However, the FGF-induced phosphorylation of CREB was only inhibited slightly by either SB 203580 or PD 98059 and the presence of both drugs was needed to completely suppress CREB phsophorylation (FIG. 14D). Similarly, the FGF-induced activation of MSK1 in these cells is also only partially suppressed in the presence of either SB 203580 or PD 98059 and prevented in the presence of both compounds (FIG. 14A).

In contrast to MSK1, the activation of MAPKAP-K2 by sodium arsenite and FGF was completely prevented by SB203580 but not by PD 98059 (FIG. 14C) and Ro 318220 (which does not affect the activation or activity of MAPKAP-K2) largely suppressed phosphorylation of CREB at Ser133. These findings indicate that MAPKAP-K2 activity is not rate-limiting for CREB phosphorylation at Ser133. To avoid any confusion it should be noted that Ro 318220 is a reversible inhibitor of MSK1 activity and does not affect MSK1 activation in cells (FIG. 14A). Once the cells have been lysed and MSK1 immunoprecipitated from the lysates, the Ro 318220 inhibitor has been removed, thus MSK1 is no longer inhibited.

In contrast to MSK1, the activation of MAPKAP-K1 by FGF was abolished by PD 98059 but not by SB 203580 (FIG. 14B). However, PD 98059 (in the absence of SB 203580) did not significantly suppress the phosphorylation of CREB at Ser133.

Bacterial endotoxin stimulates MKS1 and CREB phosphorylation in the RAW 264 mouse macrophage cell line. As shown in FIG. 15, LPS stimulation of RAW 264 macrophages leads to MSK1 and CREB/ATF1 phosphorylation. 50 µM PD 98059 or 10 (M SB203580 appear to inhibit the phosphorylation of MSK1 and of CREB/ATF1.

Discussion.

We here present the sequence of a novel, widely expressed protein kinase, termed MSK1 (FIG. 1), and the nearly complete sequence of a close relative, MSK2 (FIGS. 2 and 16 and Table 1). MSK1 and MSK2 are most similar (40% overall amino acid sequence identity) to the isoforms of MAPKAP-K1, which they also resemble in possessing two protein kinase domains within a single polypeptide (FIG. 2). The N-terminal kinase domain of MAPKAP-K1 phosphorylates exogenous substrates, while the only known role of the C-terminal domain is to activate the N-terminal domain (see Introduction). The importance of the C-terminal kinase domain of MAPKAP-K1 is indicated by the finding that an inactivating mutation suppresses the activation of the N-terminal kinase domain by 85–90% (Leighton et al., 1996). In contrast, an inactivating mutation in the C-terminal kinase domain of MSK1 (like an inactivating mutation in the N-terminal kinase domain) completely abolishes activation (FIG. 8). If it is assumed that the mechanism of activation of MSK1 is analogous to that of MAPKAP-K1, as suggested by the conservation of the four key phosphorylation sites (FIG. 2), then this indicates that the C-terminal kinase domain of MSK1 is essential for activation of the N-terminal domain. MSK1 is activated in vivo by either the MAPK/ERK cascade or the SAPK2/p38 pathway. This was established by the finding that PD 98059 largely suppresses the activation of endogenous or transfected MSK1 by growth factors and phorbol esters, while SB 203580 suppresses activation induced by exposure to UV radiation or oxidative stress (FIG. 5 and FIG. 6). Consistent with these findings, MSK1 can be activated in vitro by either MAPK2/ERK2 or by SAPK2/p38 (FIG. 3). Several signals, such as TNF in HeLa cells (FIG. 110, FGF in SK-N-MC cells (FIG. 14) and NGF in PC12 cells (FIG. 13) activate both the MAPK2/ERK2 and SAPK2/p38 cascades, and both signalling pathways contribute to the activation of MSK1 in these cells. Why MSK1 and MNK1 (Fukunaga & Hunter, 1997 and Waskiewicz et al., 1997) can be activated in vitro by both MAP kinase family members while MAPKAP-K1 can only be activated by MAPK2/ERK2 is unclear. Presumably, MAPKAP-K1 either lacks a motif required for recognition by SAPK2/p38 or contains a motif that prevents recognition by these enzymes.

The finding that MSK1 is activated in vivo by signals that trigger activation of the MAPK/ERK cascade or the SAPK2/p38 pathway implies that, like MNK1, it plays a role in integrating the effects of different extracellular signals. The substrates of MSK1 are therefore likely to be proteins that become phosphorylated in response to both mitogenic and stress signals. Two such proteins are the transcription factors CREB and ATF1 (see Introduction), and we have found that CREB is a remarkably good substrate for MSK1 in vitro (FIG. 8). MSK1 phosphorylates CREB only at Ser133, the activation site that becomes phosphorylated in vivo in response to mitogens or stress signals. The Km for phosphorylation of CREB by MSK1 is much lower than for phosphorylation by PKA<MAPKAP-K1 or MAPKAP-K2 (FIG. 8). MSK1 phosphorylates CREBtide at the equivalent residue and with a remarkably low Km value estimated to be below 0.1 μM (FIG. 8A). To our knowledge, this is the lowest Km for any peptide substrate of any protein kinase that has so far been identified. These observations suggest that MSK1 (and/or MSK2) may mediate the activation of CREB by mitogenic and stress stimuli, and the nuclear location of MSK1 (FIG. 7) is consistent with such a role.

MAPKAP-K2 may mediate the activation of CREB by stress signals or FGF in the neuronal cell line SK-N-MC (Tan et al., 1996). However, in the present work, neither the activation of MAPKAP-K2 in vivo nor its activity in vitro (FIGS. 9 and 14) were affected by Ro 318220 up to 10 μM; yet 5 μM Ro 318220 suppressed CREB phosphorylation at Ser133 in response to all the signals that activate MAPKAP-K2 in SK-N-MC cells and other cell lines (FIGS. 10, 12 and 14). In addition, we have found that MAPKAP-K2 phosphorylates the alternatively spliced CREB2 variant (Gonzalez et al., 1989) much more rapidly at Ser98 than at Ser133, but no phosphorylation of CREB at Ser98 is observed after stimulation by agonists that activate MAPKAP-K2 strongly. These results demonstrate that MAPKAP-K2/K3 activity is not rate-limiting for stress-induced activation of CREB activation in SK-N-MC cells. The only other protein kinase known to be activated by stressful stimuli and which phosphorylates CREB at Ser133 is MSK1. MSK1 phosphorylates CREB far more efficiently than MAPKAP-K2 in vitro (FIG. 8) and is potently inhibited by Ro318220 (FIG. 9). For these reasons, MSK1 (and/or MSK2) is currently the best candidate to mediate the stress-induced CREB phosphorylation at Ser133.

MSK1 and MAPKAP-K1 are both activated by MAPKs/ERKs after cell stimulation by growth factors or phorbol esters, they both phosphorylate CREB at Ser133 and they are both inhibited potently by Ro 318220. This raises the question of whether growth factor/phorbol ester induced activation of CREB is mediated by MSK1 or a MAPKAP-K1 isoform. It has been reported that MAPKAP-K1b is a much more efficient CREB kinase than MAPKAP-K1a (Xing et al., 1996) and that MAPKAP-K1b is the major CREB kinase detectable in lysates prepared from NGF-stimulated PC 12 cells (Ginty et al., 1994; Xing et al., 1996). However, in our hands, MAPKAP-K1a and MAPKAP-K1b phosphorylated CREB or CREBtide with similar kinetics (FIG. 8) and neither was remotely as efficient as MSK1 (FIG. 8).

Furthermore, there are numerous examples where the major protein kinase detected biochemically has subsequently been shown not to be the relevant enzyme in vivo towards a particular substrate. For example, MAPKAP-K1 is the major insulin-stimulated protein kinase in extracts prepared from L6 myotubes that phosphorylates and inactivates glycogen synthase kinase-3 (Cross et al., 1994), and yet subsequent work using PD 98059 excluded its involvement in this process (Cross et al., 1995). The reason why MSK1 was not detected previously by biochemical analysis may be due to the much lower abundance of MSK1 activity compared to the MAPKAP-K1 and MAPKAP-K2 activities in the cells examined. The low abundance of MSK1 activity in cells compared with MAPKAP-K1 and MAPKAP-K2 may explain why MSK1 activity was not detectable by previous biochemical analysis (Xing et al., 1996 and Tan et al., 1996).

Recently Xing et al., (1998) have reported that both SB 203580 and PD 98059 are required to prevent the NGF-induced phosphorylation of CREB in PC12 cells. We have confirmed this observation (FIG. 13A) and also demonstrated that NGF activates MSK1 in these cells (FIG. 13 B). Like the phosphorylation of CREB, the activation of MSK1 by NGF is only significantly inhibited in these cells in the presence of both SB 203580 and PD 98059. These observations indicate that activation of either the MAPK/ERK cascade or the SAPK2/p38 pathway is sufficient to produce maximal activation of MSK1 and CREB phosphorylation at Ser 133. In contrast, the NGR-induced activation of MAPKAP-K1 isoforms is unaffected by SB 203580 and only partially inhibited by PD 98059 (in the absence or presence of SB 203580). Thus MAPKAP-K1 isoforms alone cannot account for the NGF-induced phosphorylation of CREB at Ser133.

The phosphorylation of CREB at Ser133 also correlated much better with the activation of MSK1 in TNF-stimulated HeLa cells (compare FIGS. 11 and 12) and FGF-treated SK-N-MC cells (FIG. 14). In both situations, the MAPK and SAPK2/p38 pathways were activated and suppression of CREB phosphorylation at Ser133, as well as the activation of MSK1, required the presence of both SB 203580 and PD 98059. In SK-N-MC and HeLa cells, PD 98059 completely suppressed the activation of MAPKAP-K1 by FGF and TNF, respectively, but only had a small effect on CREB phosphorylation induced by these agonists.

In summary, while a role for one or more MAPKAP-K1 isoforms (or an as yet unidentified protein kinase) in the activation of CREB by growth factors/phorbol esters cannot be entirely excluded, our results suggest that MSK1 (and/or MSK2) mediates the activation of CREB by these stimuli.

Materials and Methods

Materials. Peptides for protein kinase assays were synthesised at Dundee by Mr. F. B. Caudwell (MRC unit), and those used to used to raise antibodies were synthesized by Dr G. Blomberg (University of Bristol, U.K.). Protein G-Sepharose and glutathione Sepharose was purchased from Pharmacia (Milton Keynes, UK), alkylated trypsin from Promega (Southampton, UK), tissue culture reagents, microcystin-LR, and EGF, Life Technologies Inc. (Paisley, UK), 12-O-tetradecanoylphorbol 13-acetate (TPA) from Sigma-Aldrich (Poole, Dorset, UK), sodium arsenite and hydrogen peroxide ($H_2O_2$, Aristar grade) from E. Merck (Lutterworth, UK), SB 203580 and PD 98059 from Calbiochem (Nottingham, UK) and the pCR 2.1-TOPO cloning vector from Invitrogen (Leek, Netherlands). Activated GST-MAPK2/ERK2 (Alessi et al., 1994), GST-SAPK1/JNK1((Lawler et al., 1997), GST-SAPK2a/p38α, GST-SAPK2b/p38β and GST-SAPK3/p38γ (Cuenda et al., 1997), GST-SAPK4/p38δ (Goedert et al., 1997), GST-MAPKAP-K2 (Ben-Levy et al., 1995) and GST-MAPKAP-K3 (Clifton et al., 1996) were expressed in bacteria and maximally activated in vitro using the appropriate upstream kinase kinase as described previously. MAPKAP-K1b was purified from rabbit skeletal muscle by Dr N. Morrice in the MRC Unit as previously described (Sutherland et al., 1993). GST-MAPKAP kinase-2 was expressed in bacteria and activated in vitro using GST-MAPK as described previously (BenLevy et al., 1995). PKA was prepared from bovine heart as known to those skilled in the art.

Antibodies. The MSK1 "A", MSK1 "B" and MSK "C" antibodies were raised in sheep against the peptides LTVKHELRTANLTGHAEKV (SEQ ID NO:14) (corresponding to residues 26 to 44 of MSK1), FKRNAAVID-PLQFHMGVER (SEQ ID NO:15) (corresponding to residues 384 to 402 of MSK1) and KATFHAFNKYKREGFCLQN (SEQ ID NO:19) (corresponding to residues 716 to 734 of MSK1) respectively. Antibodies that immunoprecipitate MAPKAP-K2 specifically (Clifton et al., 1996), or both MAPKAP-K1a and MAPKAP-K1b (Alessi et al., 1995) were raised in sheep against the peptides KEDKERWEDVKEEMTS (SEQ ID NO:20) (residues 343–358 of human MAPKAP-K2) and RNQSPVLEPVGRSTLAQRRGIKK (SEQ ID NO:21) (residues 712 to 734 of human MAPKAP-K1b). All the antibodies used in this study were affinity-purified on CH-Sepharose columns to which the appropriate peptides were coupled covalently, and are available commercially from UBI (Lake Placid, USA). A monoclonal antibody recognising the Flag epitope was purchased from Anachem (Luton, UK), a rabbit polyclonal antibody recognizing HSP27 was purchased from Stressgen (York, UK).

Buffer solutions. Buffer A—50 mM Tris-HCl pH 7.5, 1 mM EGTA, 1 mm EDTA, 1% (by mass) Triton-X 100, 1 mM sodium orthovanadate, 50 mM sodium fluoride, 5 mM sodium pyrophosphate, 0.27 M sucrose, 1 (M microcystin-LR, 0.1% (by vol) (β-mercaptoethanol and "complete" proteinase inhibitor cocktail (one tablet per 50 ml Boehringer Mannheim, Lewes, UK).

Buffer B—50 mM Tris-HCl pH 7.5, 0.1 mM EGTA, 10 mM β-mercaptoethanol.

Cloning of MSK1 and MSK2. The sequence of MSK1 was obtained by sequencing the human EST cDNA (AA15 8571) obtained from the I.M.A.G.E. consortium (Lennon et al., 1996). The mouse and human MSK2 sequences were obtained from sequencing some of the EST cDNA clones shown in Table 1. The mouse MSK2 sequence was obtained by sequencing EST inserts: AA472165; AA389168. The human MSK2 sequence was obtained by sequencing EST inserts: H46268; AA568895. DNA sequencing was carried out on an Applied Biosystems 373A automatic DNA sequencer using the Taq dye terminator cycle sequencing kit.

Preparation of DNA expression constructs encoding GST-MSK1, Flag-MSK1 and GST-MAPKAP-K1a. A DNA construct expressing human MSK1 with the FLAG DYKD-DDDK epitope tag at the N-terminus (Flag-MSK1) was prepared as follows:—A PCR reaction was carried out using, as a template, the MSK1 cDNA and the oligonucleotides (SEQ ID NO:22) 5'GAGATCTGCCACCATGGA-CTACAAGGACGACGATGACAAGGAGGAGGAGGG-TGGCAGCAGCGGCG-3' (incorporating a BglII site which is underlined) and 5'-GGATCCATTTCTGTGAACTCT-TCTG-3'(SEQ ID NO:23). The resulting PCR product was ligated into pTopo vector. A triple ligation was then set up to generate a full length FLAG-MSK 1 construct in the pCMV5 mammalian expression (Anderson et al., 1989) vector by excision of the N-terminal MSK1 PCR product from the pTopo vector as an EcoR1-EcoRV fragment and ligating this together with the C-terminal EcoRV-KpnI fragment of MSK1 into the EcoR1-KpnI sites of the pCMV5 vector. A GST-MSK1 expression construct was prepared by subcloning the Flag-MSK1 cDNA from the pCMV5 vector as a BglII-KpnI fragment into the BamHI and KpnI sites of the pEBG2T (Sanchez et al., 1994) expression vector. Full length Flag MSK1 mutants (in the pCMV5 vector) in which either the N-terminal or C-terminal kinase domains have been inactivated were prepared by changing the conserved Asp195 and Asp565 residues in subdomain VII of the kinase domain to Ala. This was achieved using the PCR-based megaprimer strategy. A GST-MAPKAP-K1a expression construct was prepared by subcloning of HA-MAPKAP-K1a from the pGEX4T.1 vector described in (Dalby et al., 1998) as a NotI—NotI fragment into the NotI site of the pEBG2T expression vector. The structures of all of the expression constructs were verified by DNA sequencing, after purification from bacteria using Quiagen plasmid Mega kit according to the manufacturer's protocol.

Expression of GST-MSK1 and GST-MAPKAP-K1a. Twenty 10 cm diameter dishes of human embryonic kidney 293 cells were cultured and each dish transfected with 20 µg of DNA encoding either GST-MSK1 or GST-MAPKAP-K1a using a modified calcium phosphate method (Alessi et al., 1996b). 24 h after transfection, the cells were serum starved for 16 h and either left unstimulated or stimulated with TPA (200 ng/ml, 15 min) and each dish of cells lysed in 1 ml of ice-cold Buffer A. The 20 lysates were pooled, centrifuged at 4° C. for 10 min at 13,000×g and the supernatant incubated for 60 min on a rotating platform with 1 ml of glutathione-Sepharose previously equilibrated in Buffer A. The suspension was centrifuged for 1 min at 3000×g, the beads washed three times with 10 ml of Buffer A containing 0.5 M NaCl, and then a further three times with 10 ml of Buffer B containing 0.27 M sucrose. GST-MSK1 or GST-MAPKAP-K1a were eluted from the resin at ambient temperature with three 1 ml portions of Buffer B containing 20 mM glutathione and 0.27 M Sucrose. The combined eluates (0.5 mg/ml protein for GST-MSK1, and 0.1 mg/ml GST-MAPKAP-K1a) were divided into aliquots, snap frozen in liquid nitrogen, and stored at −80° C.

Cell Culture, stimulation and cell lysis. Human embryonic kidney 293 cells and HeLa cells were cultured to confluence and incubated for 16 h in Dulbecco's Modified Eagle's Medium from which foetal calf serum was omitted. HeLa and SK-N-MC cells were cultured to confluence on 10 cm diameter dishes and incubated for 2 h in Dulbecco's Modified Eagle's Medium from which foetal calf serum was omitted. PC12 cells expressing high levels of the NGF receptor which start to differentiate within a few hours of addition of NGF were cultured and incubated for 2 h in Dulbecco's Modified Eagle's Medium from which foetal calf serum was omitted (Rouse et al., 1994). Due to the high levels of the NGF receptor in these cells the PD 98059 inhibitor only partially suppresses the NGF-induced activation of MAPK (Alessi et al., 1995). The cells were then incubated for the times indicated in the figure legends with 50 µM PD 98059, 10 µM SB 203580, 5 µ Ro 318220 or the equivalent volume of DMSO as a control, stimulated as indicated in the figure legends and the cells lysed in 1.0 ml of ice cold Buffer A. The lysates were frozen immediately in liquid nitrogen and stored at −80° C. until use. Protein concentrations were determined (Bradford et al., 1976) using bovine serum albumin as a standard.

Immunoprecipitation and assay of MSK1, MAPKAP-K2 and MAPKAP-K1. The amount of cell lysate used for each immunoprecipitation was: MSK1 (500 µg protein), MAPKAP-K2 (50 µg protein) and MAPKAP-K1a/b (50 µg protein). The lysates were incubated at 4° C. for 30 min on a shaking platform with 5 µg of each antibody coupled to 5 µl of protein G-Sepharose. The immunoprecipitates were washed twice with 1 ml of Buffer A containing 0.5 M NaCl, and once with 1 ml of Buffer B. The standard MSK1 or MAPKAP-K1a/b assay (50 µl) contained: washed Protein G-Sepharose immunoprecipitate, 50 mm Tris/HCl pH 7.5, 0.1 mM EGTA, 0.1% (by vol) 2-mercaptoethanol, 2.5 µM PKI (peptide inhibitor of cyclic-AMP-dependent protein kinase), Crosstide (30 µM), 10 mM Mg(Ac)$_2$ and 0.1 nM [($^{32}$P]ATP (100–200 cpm/pmol). The assays were carried out for 10 min at 30° C., the assay tubes being agitated continuously to keep the immunoprecipitate in suspension, then terminated and analysed as described (Alessi et al., 1994). MAPKAP-K2 was assayed in the same way except that the peptide KKLNRTLSVA (SEQ ID NO:35) (30 μM) was used as substrate. One unit of activity was that amount of enzyme which catalysed the phosphorylation of 1 nmol of peptide substrate in 1 min.

Expression of CREB. The *E. coli* strain BL21, transformed with a DNA construct encoding the 341 amino acid splice variant of CREB (Gonzalez et al., 1989), kindly provided to us by M. J. Comb (New England Biolabs, Boston, USA), were induced with 0.3 mM isopropyl-(-D-thiogalactoside for 5 h at 37° C. The GST-CREB was purified on glutathione-Sepharose as described previously for GST-MAPK2/ERK2 (Alessi et al., 1994), and dialysed against Buffer B containing 50% glycerol and stored at −20° C. The preparation showed two major bands at 62 kDa and 43 kDa as well as a number of minor bands. Only the 62 kDa and the 43 kDa bands were phosphorylated by MAPKAP-K1 and MSK1. The protein concentration of CREB was estimated by comparing the intensity of the 62 kDa and 43 kDa bands relative to a bovine serum albumin standard.

Immunoblotting for phosphorylated CREB and ATF1. Cell extracts were prepared and immunoblotting of these carried out as described (Tan et al., 1996) using a phospho-specific antibody recognizing CREB phosphorylated on Ser 133 and ATF1 phosphorylated on Ser63 purchased from UBI (Lake Placid, USA). Detection of phosphorylated CREB and ATF1 proteins was performed using the enhanced chemiluminescence reagent (Amersham).

Phosphorylation of CREB and HSP27 by MSK1 and MAPKAP-K1a/b (see FIG. 8). MSK1 and MAPKAP-K1a expressed as GST fusion proteins were purified from TPA stimulated 293 cells (FIG. 3) and MAPKAP-K1b was purified from rabbit skeletal muscle (Sutherland et al., 1993). The peptides indicated in FIG. 8 as well as CREB and HSP27 were incubated at 30° C. with 2 U/ml GST-MSK1, GST-MAPKAP-K1a or GST-MAPKAP-K1b in Buffer B containing 10 mM Mg(Ac)$_2$, 100 (M [($^{32}$P]ATP (1×10$^6$ cpm/nmole), 10 μM PKI and 1 (M microcystin-LR. After incubation for 10 min incorporation of phosphate into peptides was determined using P81 phosphocellulose paper (Alessi et al., 1994), and the incorporation of phosphate into CREB and HSP27 was measured by addition of trichloroactetic acid (0.2 vol of 100%), and the sample was then incubated for 1 h on ice. The suspension was centrifuged for 10 min at 13,000×g, the supernatant discarded and the pellet washed five times with 0.2 ml of ice cold water. The $^{32}$P-radioactivity incorporated was then determined by Cerenkov counting. In order to map the site in CREB phosphorylated by MSK1 and GST-MAPKAP-K1b, the pellet was resuspended in 0.3 ml of 50 mM Tris/HCl pH 8.0, 0.1% (by vol) reduced Triton-X 100 containing 2 μg of alkylated trypsin, after incubation for 16 h at 30° C., the digest centrifuged for 5 min at 13,000×g. The supernatant, containing 95% of the $^{32}$P-radioactivity, was chromatographed on a Vydac C18 column as described in the legend to FIG. 8. Michaelis constants (Km) and Vmax values were determined from double reciprocal plots of 1/V against 1/S, where V is the initial rate of phosphorylation, and S is the substrate concentration.

Transfection of MSK1 into 293 cells. 293 cells were cultured on 10 cm diameter dishes and transfected with the pCMV5 vector encoding the Flag epitope tagged MSK1 constructs using a modified calcium phosphate method (Alessi et al., 1996b). 24 h post-transfection, the cells were deprived of serum for 16 h, stimulated with TPA or exposed to UV radiation, the cells were then lysed in 1 ml of ice cold Buffer A, centrifuged at 13,000×g for 5 min, and the Flag tagged MSK1 protein immunoprecipitated from aliquots of lysate (containing 25 μg protein) using 2 μg of FLAG antibody coupled to 5 (1 of Protein G-Sepharose.

Immunoprecipitates were incubated, washed and assayed for MSK1 activity as described above.

Immunoelectron Microscopy. Cells were fixed in 8% paraformaldehyde in 0.2M Pipes pH 7.2 for at least one day, scraped using a rubber policeman and embedded as a pellet in 10% pig skin gelatin. Blocks were soaked in 2.1 M sucrose/PBS for at least 15 minutes before mounting on iron stubs and freezing in liquid nitrogen. Ultrathin cryosections were then prepared on an Reichert Ultracut E cryomicrotome at −100° C. and mounted on carbon/formvar coated grids. Grids were incubated first on 0.5% fish skin gelatin/PBS (5 min), followed by anti FLAG mouse monoclonal antibodies (15(g/ml); then rabbit antimouse antibodies (2 μg/ml Southern Biotechnology Associates Inc. Birmingham Ala., USA) and lastly on protein A-8 nm gold complex prepared as previously described (Lucocq 1993). PBS washes followed each of the affinity reagents which were themselves diluted in 0.5% fish skin gelatin/PBS. Finally, after washes in distilled water the sections were contrasted in methyl cellulose/uranyl acetate.

Labelling was quantified as follows. At a magnification of 15,000×micrographs were taken of labelled cell profiles possessing both cytoplasm and nucleus (these nuclear weighted sections allowed data from these compartments in individual cells to be compared). Cytoplasm and nuclear areas were estimated using point counting with a square lattice grid of 1 cm line spacing and gold labelling counted (Lucocq, 1994). Coefficients of error were calculated according to Cochran 1953.

REFERENCES

Alessi D. R., Cohen P., Ashworth A., Cowley S., Leevers S. J. and Marshall C. J. (1994) Assay and expression of Mtogen-Activated Protein-Kinase, MAP Kinase Kinase, and RAF. Methods in Enzymol. 255, 279–290.

Alessi D. R., Cuenda A., Cohen P., Dudley D. T. and Saltiel A. R. (1995) PD-098059 is a specific inhibitor of the activation of mitogen-activated protein-kinase kinase in-vitro and in-vivo. J. Biol. Chem., 270, 27489–27494.

Alessi, D. R., Caudwell, F. B., Andjelkovic, M., Hemmings, B. A. and Cohen, P. (1996a). Molecular basis for the substrate specificity of protein kinase B; comparison with MAPKAP kinase-1 and p70 S6 kinase. FEBS Lett. 399, 333–338.

Alessi, D. R., Andjelkovic, M., Caudwell, F. B., Cron, P., Morrice, N. Cohen, P. and Hemmings, B. (1996b) Mechanism of activation of protein kinase B by insulin and IGF 1. EMBO J. 15, 6541–6551.

Alessi, D. R. (1997) The protein kinase C inhibitors Ro 318220 and GF 109203X are equally potent inhibitors of MAPKAP kinase-1((Rsk-2) and p70 S6 Kinase. FEBS Lett. 402, 121–123.

Anderson, S., Davie, D. N., Dahlbäck, H., Jörnvall, H. and Russell, D. W. (1989) Cloning, structure, and expression of the mitochondrial cytochrome-(−450 sterol 26-hydroxylase, a bile-acid biosynthetic enzyme. J. Biol. Chem. 264, 8222–8229.

Ben-Levy, R., Leighton, I. A., Doza, Y. N., Attwood, P., Morrice, N., Marshall, C. J. and Cohen, P., (1995) Identification of novel phosphorylation sites required for activation of MAPKAP kinase-2. EMBO J. 14, 5920–5930.

Bradford, M. M. (1976) A rapid and sensitive method for the quantitation of microgram quantities of protein utilizing the principle of protein-dye binding. Anal Biochem, 72, 248–254.

Bjorbaek C., Zhao Y. and Moller D. E. (1995) Divergent functional roles for p90(RSK) kinase domains. J. Biol. Chem. 270, 18848–18852.

Chen R. H., Samecki C. and Blenis J. (1992) Nuclear-localization and regulation of ERK-encoded and RSK-encoded protein-kinases. Mol. Cell.Biol. 12, 915–927.

Clifton A. D., Young P. R. and Cohen P. (1996). A comparison of the substrate-specificity of MAPKAP kinase-2 and MAPKAP kinase-3 and their activation by cytokines and cellular stress FEBS Lett. 392, 209–214.

Cochran, W. C. (1953) "Sampling techniques". Wiley and Sons, New York.

Cohen P. (1997) The search for physiological substrates of MAP and SAP kinases in mammalian cells. Trends Cell Biol. 7, 353–361.

Cross, D. A. E, Alessi D. R, Cohen P, Andjelkovic M and Hemmings B. A (1995) Inhibition of glycogen-synthase kinase-3 by insulin is mediated by protein-kinase-B. Nature 378, 785–789.

Cross, D. A. E., Alessi D. R, Vandenheede, J. R, McDowell, H. E., Hundal, H. S. and Cohen, P. The inhibition of glycogen-synthase kinase-3 by insulin or insulin like growth factor 1 in the rat skeletal muscle cell line 16 is blocked by wortmannin, but not by rapamycin. Biochemical J 303, 21–26.

Cuenda, A., Rouse, J., Doza, Y. N., Meier, R., Young, P. R., Cohen, P. and Lee, J. C. (1995) SB 203580 is a specific inhibitor of a MAP kinase homologue which is stimulated by cellular stresses and interleukin-1. FEBS Lett. 364, 229–233.

Cuenda A., Cohen P., BueeScherrer V. and Goedert M. (1997). Activation of stressactivated protein kinase-3 (SAPK3) by cytokines and cellular stresses is mediated via SAPKK3 (MKK6); Comparison of the specificities of SAPK3 and SAPK2 (RK/p38). EMBO J. 16, 295–305.

Dalby K. N., Morrice N., Caudwell F. B., Avruch J. and Cohen P. (1998) Identification of regulatory phosphorylation sites in mitogen-activated protein kinase (MAPK)-activated protein kinase-1a/p90(rsk) that are inducible by MAPK. J. Biol. Chem. 273, 1496–1505.

Davis P. D., Hill C. H., Keech E., Lawton G., Nixon J. S., Sedgwick A. D., Wadsworth J., Westmacott D. and Wilkinson S. E. (1989). Potent selective inhibitors of protein kinase-C. FEBS Lett. 259, 61–63.

Freshney N. W., Rawlinson L., Guesdon F., Jones E., Cowley S., Hsuan J. and Saklatvala J. (1994) Interleukin-1 activates a novel protein-kinase cascade that results in the phosphorylation of HSP27. Cell 78, 1039–1049.

Fukunaga R. and Hunter T. (1997). MNK1, a new MAP kinase-activated protein kinase, isolated by a novel expression screening method for identifying protein kinase substrates. EMBO J. 16, 1921–1933.

Ginty D. D,. Bonni A., and Greenberg M. E. (1994). Nerve growth-factor activates a Ras-dependent protein-kinase that stimulates c-Fos transcription through phosphorylation of CREB. Cell 77, 713–725.

Goedert M., Cuenda A., Craxton M., Jakes R. and Cohen P. (1997). Activation of the novel stress-activated protein kinase SAPK4 by cytokines and cellular stresses is mediated by SKK3 (MKK6) Comparison of its substrate specificity with that of other SAP kinases EMBO J. 16, 3563–357 1.

Gonzalez G. A., Yamamoto K. K., Fischer W. H., Karr D., Menzel P., Biggs W., Vale W. W. and Montminy M. R. (1989). A cluster of phosphorylation sites on the cyclic AMP-regulated nuclear factor CREB predicted by its sequence. Nature 337, 749–752.

Gonzalez, G. A. and Montminy, M. R. (1989) Cyclic AMP stimulates somatostatin gene transcription by phosphorylation of CREB at Ser133. Cell, 59, 675–680.

Hanks, S. K., Quinn, A. M. and Hunter, T. (1988) The protein-kinase family conserved features and deduced phylogeny of the catalytic domains. Science 241, 42–52.

Lawler S., Cuenda A., Goedert M. and Cohen P. (1997). SKK4, a novel activator of stress-activated protein kinase-1 (SAPK1/JNK). FEBS Lett. 414, 153–158.

Lennon, G. G., Auffray, C., Polymeropoulos, N. and Soares, M. B. (1996) The I.M.A.G.E. consortium: An integrated molecular analysis of genomes and their expression. Genomics 33, 151–152.

Leighton I. A., Dalby K. N., Caudwell F. B., Cohen P. T. W. and Cohen P. (1996) Comparison of the specificities of p70 S6 kinase and MAPKAP kinase-1 identifies a relatively specific substrate for p70 S6 kinase. The N-terminal kinase domain of MAPKAP kinase-1 is essential for peptide phosphorylation. FEBS Lett. 375, 289–293.

Lucocq, J. M. (1993) Particulate markers for immunoelectron microscopy. Chap. 8. In "Fine structure immunocytochemistry".

Lucocq J. M. (1994) Quantitation of gold labelling and antigens in immunolabelled ultrathin sections. Journal of Anatomy 184, 1–13.

Iordanov M., Bender K., Ade T., Schmid W., Sachsenmaier C., Engel K., Gaestel M., Rahmsdorf H. J. and Herrlich P. (1997) CREB is activated by UVC through a p38/HOG-1-dependent protein kinase. EMBO J. 16, 1009–1022.

Mclaughlin M. M., Kumar S., Mcdonnell P. C., Vanhorn S., Lee J. C., Livi G. P. and Young P. R. (1996) Identification of Mitogen-Activated Protein (MAP) Kinase-Activated Protein Kinase-3, a novel substrate of CSBP p38 MAP kinase. J. Biol. Chem. 271, 8488–8492.

Pende M, Fisher T. L., Simpson P. B., Russell J. T., Blenis J. and Gallo V (1997). Neurotransmitter- and growth factor-induced cAMP response element binding protein phosphorylation in glial cell progenitors: Role of calcium ions, protein kinase C, and mitogen activated protein kinase/ribosomal S6 kinase pathway. J. Neurosci. 17, 1291–1301.

Robbins J., Dilworth S. M., Laskey R. A. and Dingwall C. (1991). Two interdependent basic domains in nucleoplasmin nuclear targeting sequence: Identification of a class of bipartite nuclear targeting sequence. Cell, 64, 615–623.

Rouse, J., Cohen, P., Trigon, S., Morange, M., Alonso-Llamazares A., Zamanilo, D., Hunt, T. and Nebreda, A. (1994) A novel kinase cascade triggered by stress and heatshock that stimulates MAPKAP kinase-2 and phosphorylation of the small heat-shock proteins. Cell 78, 1027–1037.

Sanchez, I., Hughes, R. T., Mayer, B. J., Yee, K., Woodgett, J. R., Avruch, J., Kyriakis, J. M. and Zon, L. I. (1994) Role of SAPK/ERK kinase-1 in the stress-activated pathway regulating transcription factor c-Jun. Nature, 372, 794–798.

Sturgill T. W., Ray L. B., Erikson E. and Maller J. L. (1988) Insulin-Stimulated MAP-2 Kinase phosphorylates and activates Ribosomal-Protein S6 Kinase-II. Nature, 334, 715–718.

Sutherland C., Campbell D. G., Cohen P. (1993) Identification of insulin-stimulated protein kinase-1 as the rabbit equivalent of RSK2. Identification of 2 threonines phosphorylated during activation by Mitogen-Activated Protein-kinase. Eur. J. Biochem.212, 581–588.

Tan Y., Rouse J., Zhang A. H., Catiati S., Cohen P. and Comb M. J. (1996). FGF and stress regulate CREB and ATF-1 via a pathway involving p38 Map Kinase and MAPKAP kinase-2. EMBO J. 15, 4629–4642.

Thompson, J. D., Higgins, D. G. and Gibson, T. J. (1994), Clustal-W—improving the sensitivity of progressive multiple sequence alignment through sequence weighting, position specific gap penalties and weight matrix choice. Nuc. Acid Res. 22, 4673–4680.

Trivier E., Decesare D., Jacquot S., Pannetier S., Zackai E., Young I., Mandel J. L., Sassone-Corsi P. and Hanauer A. (1996). Mutations in the kinase RSK-2 associated with Coffin-Lowry Syndrome. Nature 384, 567–570.

Vik T. A. and Ryder J. W. (1997) Identification of serine 380 as the major site of autophosphorylation of *Xenopus* pp90rsk. Biochem. Biophys. Res. Comm. 235, 398–402.

Wang, X., Flynn, A., Waskiewicz, A. J., Webb, B. L. J., Vries, R. G., Baines, I. A., Cooper, J. A. and Proud, C. G. (1998) The phosphorylation of eukaryotic initiation factor eIF4E in response to phorbol esters, cell stress, and cytokines is mediated by distinct MAP kinase pathways. J. Biol. Chem. 271, 9373–9377.

Waskiewicz A. J., Flynn A., Proud C. G. and Cooper J. A. (1997). Mitogen-activated protein kinases activate the serine/threonine kinases MNK1 and MNK2. EMBO J. 16, 19091920.

Xing J., Ginty D. D., and Greenberg M. E. (1996) Coupling of the Ras-MAPK pathway to gene activation by Rsk2, a growth factor-regulated CREB kinase. Science 273, 959–963.

Xing, J., Kornhauser, J. M., Xia, Z, Thiele, E. A. and Greenber, M. E. (1998) Nerve Growth Factor activates Extracellular Signal-Regulated Kinase and p38 Mitogen-Activated Protein Kinase pathways to stimulate CREB serine 133 phosphorylation. Mol Cell Biol. 1988, 1946–1955.

Zhao Y., Bjorbaek C., Weremowicz S., Morton C. C. and Moller D. E. (1995) RSK3 encodes a novel PP90(RSK) isoform with a unique N-terminal sequence-growth factor stimulated kinase function and nuclear translocation. Mol. Cell. Biol. 15, 4353–4363 1.

EXAMPLE 2

Alternative Assays

A Scintillation Proximity Assay (SPA) system (Amersham International) is used to assess the incorporation of $^{32}P$ radioactivity into CREB or CREBtide. In this system, the sample is mixed with beads comprising scintillant and antibodies that bind CREB or CREBtide. Conveniently this is done in a 96-well format. The plate is then counted using a suitable scintillation counter, using known parameters for $^{32}P$ SPA assays. Only $^{32}P$ that is in proximity to the scintillant, i.e. only that bound to CREB or CREBtide that is then bound by the antibody, is detected.

EXAMPLE 3

Assay for Compounds which Modulate MSK1 Activity

An assay is set up with CREB, as described in Example 1 or Example 2. Compounds are tested in the assay and those that give rise to inhibition or activation of MSK1 are selected for further study. To confirm that any effects observed are not due to effects on CREB, compounds are tested for effects on the ability of MSK1 to phosphorylate another substrate such as a peptide substrate, for example Crosstide, that is structurally dissimilar to CREB. Those compounds that have similar effects on the phosphorylation of CREB and the peptide substrate are selected. Compounds may also be tested for effects on activated and inactive CREB.

EXAMPLE 4

Assay for Polypeptides that Interact with MSK1

A yeast two hybrid assay system is set up to identify polynucleotides encoding polypeptides that are capable of associating with MSK1 in a stable enough manner to allow transcriptional activation to occur. The polynucleotides are (in separate experiments) cDNAs copied from mRNA from cells that are capable of expressing MSK1, before or after stimulation capable of activating MSK1, and from cells which do not express MSK1. Interactions which are found in a subset only of these cell types are of particular interest.

The polypeptide encoded by the polynucleotide is determined by sequencing the insert by the Sanger method as described in Example 1 to obtain a predicted amino acid sequence.

EXAMPLE 5

Role of MAP Kinase Cascades in Mediating Induction of Cyclooxygenase-2 and Interleukin-1 by Lipopolysaccharide in RAW 264 Macrophages Lipopolysaccharide (LPS) stimulation of RAW264 macrophages triggered the activation of mitogen and stress-activated protein kinases-1 and –2 (MSK1, MSK2) and their putative substrates, the transcription factors CREB and ATF1. The activation of MSK1/MSK2 was prevented by preincubating the cells with a combination of two drugs that suppress activation of the classical MAP kinase cascade and SAPK2a/p38, respectively, but inhibition was only partial in the presence of either inhibitor. The LPS-stimulated activation of CREB and ATF1, the transcription of the cyclooxygenase-2 (COX-2) and interleukin-1J genes (whose promoters contain a CRE), and the induction of the COX-2 protein, were prevented by the same drug combination, as well as by Ro 318220, a potent inhibitor of MSK1/MSK2. Our results demonstrate that two different MAP kinase cascades are rate limiting for the LPS-induced activation of CREB/ATF1, and transcription of the COX-2 and IL-1 genes. They also suggest that MSK1/MSK2 may play an important role in these processes and hence are attractive targets for novel anti-inflammatory drugs.

Materials and Methods

Materials. Reagents and antibiotics for cell culture were purchased from Life Technologies (Paisley U.K.), PD 98059 from New England Biolabs (Baverly, USA), Ro 318220 and SB 203580 from Calbiochem (Nottingham, U.K.), forskolin and 3-isobutyl-1-methylxanthine (IBMX) from Sigma (Poole, U.K.), "complete" proteinase inhibitor cocktail from Boehringer (Lewes, U.K.), affinity-purified polyclonal goat anti-COX-2 antibody from Santa Cruz Biotechnology (Santa Cruz, Calif.), affinity-purified polyclonal rabbit anti-phospho-CREB from Upstate Biotechnology Inc. (Lake Placid, N.Y.), [K-$^{32}P$]-ATP and ECL reagent from Amsterdam (Bucks, UK), RNeasy Mini Kit from QIAGEN Ltd (West Sussex, U.K.) and the access RT-PCR System from Promega (Southampton, U.K.). Murine RAW 264 macrophages were obtained from the European Cell Culture Collection (Wilts, UK), while LPS and U0126 were gifts from Dr. John Lee (SmithKline Beecham, Pa. USA) and Dr Sue Cartlidge (Zeneca Pharmaceuticals, Cheshire, U.K.).

Cell culture and stimulation. RAW 264 macrophages were maintained in a 95% air/5% $CO_2$ atmosphere in Dulbecco's modified Eagle's medium (DMEM) plus 10% (v/v) heat-inactivated foetal calf serum, 100 U/ml penicillin, 100 mg/ml streptomycin. The day before stimulation, the macrophages were plated at a density of $2 \times 10^6$ cells per 6 cm plate and 2 h before stimulation, the medium removed and replaced with 2 ml of DMEM. The cells were then stimulated with 100 ng/ml LPS, or 20 TM forskolin plus 10 TM IBMX, for the times indicated in the figure legends. Where indicated, SB 203590 (10 TM) and/or PD 98059 (50 Tm), or U0126 (10 TM) or Ro 318220 (5 TM), were added 1 h before stimulation.

Cell lysis. After stimulation, the medium was aspirated and the cells were solubilized in 0.2 ml of ice cold lysis buffer (50 mM Tris-acetate pH 7.0, 1 mM EDTA, 1 mM EGTA, 1% (w/v) Triton X-100, 1 mM sodium orthovanadate, 10 mM sodium glycerophosphate, 50 mM NaF, 5 mM sodium pyrophosphate, 0.27 M sucrose, 2 TM microcystin-LR, 1 mM benzamidine, 0.1% (v/v) 2-mercaptoethanol and "complete" proteinase inhibitor cocktail—one tablet per 50 ml). The samples were then snap frozen in liquid nitrogen and stored in aliquots at $-80°$ C. until analysis. Protein concentrations were determined according to [7].

Immunoblotting. For immunoblotting of CREB, nuclear cell extracts were prepared as described [2] and immunoblotting performed using a phospho-specific antibody recognising CREB phosphorylated on Ser 133 and ATF1 phosphorylated on Ser 63. For immunoblotting of COX-2, cell lysate (30 Tg protein) was denatured in SDS, electrophoresed on 10% polyacrylamide gel, transferred to a nitrocellulose membrane, and immunoblotted with anti-COX-2 antibody (1.0 mg/ml). Detection of phosphorylated CREB and ATF1 and COX-2 was performed using the enhanced chemiluminescence reagent (ECL).

Immunoprecipitation and assay of protein kinases. All antibodies were raised as described in Example 1. MSK2 was immunoprecipitated from cell lysates (1 mg protein) with an antibody raised against the peptide RAPVASKGAPRRANGPLPPS corresponding to residues 753–772 of MSK2. The immunoprecipitates were washed and assayed at 30° C. as described in Example 1. One unit of MSK1 or MSK2 activity was defined as that amount which catalyses the incorporation of 1 nmol of phosphate into the peptide GRPRTSSFAEG in 1 min. MAP kinase-activated protein (MAPKAP-K1, also known as p90RSK) was immunoprecipitated from cell lysates (50 Tg protein) with an antibody raised against the peptide RNQSPV-LEPVGRSTLAQRRGIKK corresponding to residues 605–627 of murine MAPKAP-K1b (RSK2 isoform). This antibody immunoprecipitates MAPKAP-K1a (RSK1) as well as MAPKAP-K1b [8]. The immunoprecipitates were washed and assayed at 30° C. as described [8]. One unit of MAPKAP-K1 activity was defined as that amount which catalyses the incorporation of 1 nmol of phosphate into [G245,G246]S6-(218–249)] (a peptide closely related to the C-terminus of ribosomal protein S6) in 1 min. MAPKAP-K2 was immunoprecipitated in an identical manner to MAP-KAP-K1 using an antibody raised against the peptide MTSALATMRVDYEQIK corresponding to residues 356–371 of the human protein. This antibody immunprecipitates MAPKAP-K3, as well as MAPKAP-K2 [9]. MAPKAP-K2 was assayed as described [10] and one unit was that amount of enzyme which catalyses the incorporation of 1 nmol of phosphate into the peptide KKLNRTLSVA in 1 min.

Reverse transcripts polymerase chain reactions. Total RNA was prepared from LPS-stimulated or control RAW 264 cells using the Rneasy Mini Kit according to the manufacturer's protocol. Total RNA was measured and 100 ng was reverse transcribed using Promega AMV reverse transcriptase (5 U/ml) with the oligonucleotides GTTG-GATACAGGCCAGACTTTGTTG and GAGGGTAG-GCTGGCCTATAGGCT (coding for the "housekeeping gene" hypoxanthine guanine phosphoribosyl transferase, HPRT), AAGCTCTCCACCTCAATGGACAG and CTCAAACTCCACTTTGCTCT TGA (coding for the IL-1 gene) and CAGCAAATCCTTGCTGTTCC and TGGGCAAAGAATGCAAACATC (coding for the COX-2 gene). Conditions for PCR amplification of the resulting first-stand DNA template were 94° C. denaturing for 30 sec, 60° C. annealing for 1 min, 68° C. extension for 1 min, 30 cycles using thermostable Tfl DNA polymerase (SU/ml), and 1 mM $MgSO_4$. The PCR products showed a single band of 352 bp for HPRT and a single band of 515 bp for COX-2.

Results

The LPS-induced activation of MSK1 and MSK2 is mediated by two different MAP kinase cascades. LPS activates both the classical MAPK cascade and SAPK2a/p38 pathway in macrophages as shown by the activation of MAPKAP-K1 (also called p90 RSK) and MAPKAP-K2, respectively [11]. The activation of both enzymes is transient, peaking after 30–60 min before declining to near basal levels after 2 h [11]. In the present study similar findings have been made for MSK1 and MSK2. The activity of these enzymes is negligible in unstimulated macrophages, but greatly elevated after stimulation with LPS. Activation peaks after 30–60 min and declines thereafter (FIGS. 17A and 17B).

In order to identify which signal transduction pathway(s) mediates the activation of MSK1 and MSK2 we examined the effects of SB. 203580 (Section 1) and UO126 which, like PD 98059 (Section 1), inhibits the activation/activity of MKK1 [12]. These studies revealed that a concentration of UO126 that completely suppresses the activation of MAP-KAP-K1 (FIG. 18C), only inhibits the activation of MSK1 and MSK2 partially (FIGS. 18A and 18B). Similarly, MSK1 and MSK2 are only inhibited partially by SB 203580 (FIGS. 18A and 18B) at concentrations that completely block the activation of MAPKAP-K2 (FIG. 18D). In contrast, the activation of MSK1 and MSK2 is almost completely suppressed if macrophages are incubated in the presence of both UO126 and SB 203580 (FIGS. 18A and 18B). These observations indicated that the LPS-induce activation of MSK1 and MSK2 is mediated by two different MAP kinase cascades.

The LPS-induced phosphorylation of CREB and ATF1 is mediated by two different MAP kinase cascades. Two putative physiological substrates for MSK1/MSK2 are the transcription factors CREB and ATF1. As shown in FIG. 19A, LPS induces the phosphorylation of CREB and Ser 133 and the phosphorylation of AFT1 at Ser63. Like the activation of MSK1 and MSK2, the phosphorylation of CREB and ATF1 peak after 1 h peak and return to near basal levels after 2 h. Similarly, the LPS-induced phosphorylation of CREB and AFT1 is partially inhibited by SB 203580, partially inhibited by PD 98059, and completely inhibited in the presence of both drugs (FIG. 19B).

The LPS-stimulated induction of COX-2 and IL-1 is mediated by two different MAP kinase cascades. The COX-2 promoter contains a CRE[5]. We therefore decided to examine whether the signaling pathways that mediate that LPS-stimulated induction of this enzyme are the same as those required to activate CREB. The COX-2 protein is undetectable in unstimulated macrophages, but strongly induced 2 h after exposure to LPS. Induction is maximal after 4 h and maintained for at least 8 h (FIG. 20A). The induction of COX-2 is partially inhibited by SB 203580, partially inhibited by PD 98059 and almost completely suppressed in the presence of both drugs (FIG. 20B).

In order to confirm these results by an independent method, we studied the effect of LPS on COX-2 gene transcription. LPS strongly induces COX-2 mRNA, which reaches a maximum level after 2 h stimulation that is sustained for at least 8 h (FIG. 21A). The induction of COX-2 mRNA is partially suppressed by SB 203580, partially suppressed by PD 98059 and almost completely suppressed in the presence of both inhibitors (FIG. 21B).

We also examined the signal transduction pathways that mediate the induction of the proinflammatory cytokine IL-1, whose promoter also contains a CRE. The time course of induction of IL-1 gene transcription is indistinguishable from that of COX-2 gene (FIG. 21A). Interestingly, the induction of IL-1 mRNA is also partially inhibited by PD 98059 partially inhibited by SB 203580 and completely inhibited in the presence of both drugs (FIG. 21B).

In contrast, the mRNA encoding the "housekeeping" gene HPRT is unaffected by LPS, PD 98059 and/or SB 203580 (FIG. 21).

Effect of Ro 318220 on LPS-induced activities. Ro 318220 is a potent inhibitor of MSK1 and several other protein kinases, but many other protein kinases, such as MAPKAP-K2, are unaffected at drug concentrations that ablate MSK1 activity ([1,3], discussed further below). Ro 318220 (5 TM) does not affect the LPS-induced activation of MSK1 and MSK2, MAPKAP-K1or MAPKAP-K2 (FIG. 18), demonstrating that none of the "upstream" protein kinases in these signaling pathways are inhibited by this compound. However, Ro 318220 (5TM) completely prevents the LPS-induced phosphorylation of CREB at Ser133 and ATF1 at Ser63 (FIG. 19). The same concentration of Ro 318220 also suppresses the LSP-stimulated induction of the COX-2 protein (FIG. 4B) and the transcription of the COX-2 and IL-1 (FIG. 21B) genes. In contrast, the mRNA encoding HPRT are unaffected by Ro 318220.

Activation of CREB is insufficient to induce the synthesis of COX-2 or IL-1. The phosphorylation of CREB at Ser 133 and ATF-1 at Ser63 is also catalysed by PKA in vivo and can therefore be induced by agonists, that elevate the intracellular concentration of cyclic AMP, such as forskolin. Stimulation of macrophages with forskolin triggers a similar phosphorylation of CREB and ATF-1 to that induced by LPS (FIG. 22). However, this is not suppressed by PD 98059 plus SB 203580, or by Ro 318220 (data not shown). In contrast to LPS, forskolin does not induce the appearance of a significant amount of COX-2 protein. This finding is considered further below.

Discussion.

In this paper we establish that MSK1 and the closely related MSK2 are present in RAW 264 macrophages and that both kinases are transiently activated in response to LPS (FIG. 17). The rates of activation and inactivation are similar to those of MAPKAP-K1 and MAPKAP-K2 which are convenient "downstream" reporters of the activation of the classical MAP kinase cascade and the SAPK2a/p38 pathway respectively. The LPS-induced activation of MSK1 and MSK2 is partially inhibited by drugs that prevent activation of the classical MAP kinase cascade, partially inhibited by SB 203580 (an inhibitor of SAPK2a/p38) and inhibited almost completely when macrophages are incubated in the presence of both types of drug (FIG. 18). The activity of MSK2 in macrophages is much lower than that of MSK1, and this is also the case in 293, HeLa and PC 12 cells (results not shown).

Transcription factors CREB and ATF1 may be physiological substrates of MSK1 (see Example 1) and MSK2 [13] and the present study is also consistent with this hypothesis. Thus CREB and ATF1 were transiently phosphorylated with similar kinetics to the activation/inactivation of MSK1 and MSK2, phosphorylation was prevented by incubating macrophages with inhibitors of both the classical MAP kinase cascade and SAPK2a/p38, but only partially by inhibition of one of these pathways. Moreover, the phosphorylation of CREB was also prevented by Ro 318220 (FIG. 3B) at concentrations that inhibit MSK1 and MSK2, but only a few other protein kinases. MAPKAP-K2, MAPKAP-K3 and PKA also phosphorylate CREB and ATF1 at Ser133 and Ser63, respectively. However, these protein kinases cannot be rate-limiting for the LPS-induced activation of CREB and ATF1, in contrast to previous reports [1, 2], because they are unaffected in vivo by the concentrations of Ro 318220 used in these experiments (see Example 1 and [1]).

Two genes in macrophages that contain a CRE are those encoding COX-2 [5] and IL-1J [6]. We have found that the LPS-induced transcription of these genes and the synthesis of COX-2 protein is prevented by exactly the same combinations of inhibitors that prevent the activation of CREB; i.e. SB 203580 plus PD 98059 or Ro 318220. These results suggest that MSK1/MSK2 may stimulate transcription of the COX-2 and IL-1J genes, at least in part, by phosphorylating CREB. However another transcription factor, C/EBPJ, has also been reported to paly a critical role in activation of the COX-2 [14] and IL-1,β [15] genes in certain cell lines. Moreover C/EBPJ is reported to be activated by the MAPK/ERK catalysed phosphorylation of a particular threonine residue in NIH 3T3 cells [16], as well as by SAPK2/p38 in 3T3-L1 preadipocytes [17]. Thus PD 98059/UO126 and SB 203580 may suppress the transcription of COX-2 and IL-1J by inhibiting the activation of C/EPBJ as well as the activation of CREB. The requirement for C/EPBβ as well as Creb may explain why activation of CREB alone, induced by cyclic AMP-elevating agents, is insufficient to induce significant transcription of the COX-2 gene. Experiments to address these possibilities are in progress, but direct phosphorylation of C/EBPJ by MAPKs/ERKs and SAPK2a/p38 cannot account for the effects of Ro 318220 on COX-2 and IL-1J gene transcription, since these MAP kinase family members ([3] and results not show) and the signaling pathways that lead to their activation (FIG. 18) are resistant to this drug.

REFERENCES

1. Deak, M., Clifton, A. D., Lucocq, J. M. and Alessi, D. R. (1998) *EMBO J.* 17, 4426–444 1.
2. Tan, Y., Rouse, J., Zhang, A. H., Cariati, S., Cohen, P, and Comb, M. J. (1996) *EMBO J.* 15, 4629–4642
3. Alessi, D. R. (1997) *FEBS Letter* 402, 121–123.

4. Dubois, R. N., Abramson, S. B., Crofford, L., Gupta, R. A., Simon, L. S., Van de Putte, L. B. A. and Lipsky, P. E. (1998) *FASEB J.* 12,1063–1073.
5. Appleby, S. B., Ristimaki, A., Neilson, K., Narko K. and Hla T. (1994) *Biochem J.* 302, 723–727.
6. Chandra, G., Cogswell, J. P., Miller, L. R., Godlevski, M. M., Stinnett, S. W., Noel, S. L., Kadwell, S. H., Kost, T. A. and Gray, J. G. (1995) *J. Immunol* 155, 4535–4543.
7. Bradford, M. M. (1976) *Anal Biochem* 72, 248–254.
8. Alessi, D. R., Cuenda, A., Cohen, P., Dudley, D. T. and Saltiel, A. R. (1995) *J. Biol. Chem.* 270, 274–89–27494.
9. Cuenda, A., Rouse, J., Doza, Y. N., Meier, R., Cohen, P., Gallagher, T. F., Young, P. R. and Lee, J. C. (1995) *FEBS Lett.* 364, 229–233.
10. Stokoe, D., Caudwell, B., Cohen, P. T. W. and Cohen, P. (1993) *Biochem J.* 296, 842–849.
11. Caivano, M. (1998) *FEBS Letter* 429, 249–253.
12. Favata, M. F., Horiuchi, K. Y., Manos, E. J., Daulerio, A. J., Stradley, D. A., Feeser, W. S., Van Dyk, D. E., Pitts, W. J., Earl, R. A., Hobbs, F., Copeland, R. A., Magolda, R. L., Scherle, P. A. and Trzaskos, J. M. (1998) *J. Biol. Chem.* 273, 19623–18632.
13. Pierrat, B., da Silva Correia, J., Mary, J-L., Tomas-Zuber, M. and Lesslauer, W. (1998) *J. Biol. Chem.* 273, 29661–29671.
14. Kim, Y. and Fischer, S. M. (1998) *J. Biol. Chem.* 273, 27686–27694.
15. Tsukada, J., Saito, K., Waterman, W. R., Webb A. C. and Auron, P. E. (1994) *Mol. Cell. Biol.* 14, 7285–7297.
16. Nakajiima, T., Kinshita, S., Sasagawa, T., Sasaki, K., Naruto, M., Kishiimoto, T. and Akira, S. (1993) *Proc. Natl. Acad. Sci, USA* 90, 2207–2211.
17. Engelman, J. A., Lisanti, M. P. and Scherer, P. E. (1998) *J. Biol. Chem.* 273, 32111–32120.

The invention claimed is:

1. A substantially pure polypeptide comprising SEQ ID NO: 1 or a variant, fragment or fusion thereof, or a fusion of said variant or fragment, wherein said variant has at least about 90% amino acid identity with SEQ ID NO:1 and wherein said polypeptide, variant or fragment thereof or a fusion of said variant or fragment has protein kinase activity and is activated by both MAPK2 and SAPK2.

2. A recombinant polynucleotide comprising a nucleic acid sequence which encodes the polypeptide as defined in claim 1.

3. An isolated polynucleotide encoding a fusion of the polypeptide according to claim 1.

4. A vector suitable for replication in a mammalian/eukaryotic cell comprising a polynucleotide encoding the polypeptide according to claim 1.

5. The polynucleotide or vector according to any one of claims 2 to 4 which contains no introns.

6. An isolated host cell comprising a recombinant polynucleotide or a replicable vector as defined in any one of claims 2 to 4.

7. A method of making a polypeptide, or a variant, fragment, or fusion thereof or a fusion of said variant or fragment, the method comprising culturing a host cell which expresses a polypeptide according to claim 1, or a variant, fragment, or fusion thereof according to claim 1 or a fusion of said variant or fragment according to claim 1 and isolating said polypeptide or a variant, fragment, or fusion thereof or a fusion of said variant or fragment.

8. A The polypeptide according to claim 1, or a variant, fragment, or fusion thereof according to claim 1 or a fusion of said variant or fragment according to claim 1 produced by the method of claim 7.

9. A method of identifying a compound that modulates the activity of a polypeptide as defined in claim 1, the method comprising contacting a compound with said polypeptide as defined in claim 1 or a variant, fragment, or fusion thereof as defined in claim 1 or a fusion of a variant or fragment thereof as defined in claim 1 and determining whether the activity of said polypeptide, variant, fragment or fusion is changed compared to the activity of said polypeptide, variant, fragment or fusion in the absence of said compound.

10. A method according to claim 9 in which the activity is decreased.

11. A method according to claim 9 in which the activity is increased.

12. A method of identifying a compound which binds to CREB and either enhances or prevents its activation by the polypeptide as defined in claim 1, the method comprising determining whether the compound enhances or prevents the interaction of CREB or a fragment, variant, or fusion thereof or a fusion of a fragment or variant with the polypeptide as defined in claim 1 or determining whether the compound substantially blocks activation of CREB or a fragment, variant, or fusion thereof or a fusion of a fragment or variant by the polypeptide as defined in claim 1.

13. A method of identifying a compound which blocks the activation of a polypeptide as defined in claim 1 by an interacting polypeptide, the method comprising determining whether a compound blocks the interaction between (a) a polypeptide as defined in claim 1 or a fragment, variant, or fusion thereof according to claim 1 or a fusion of a fragment or variant according to claim 1 and (b) the interacting polypeptide, or a variant, fragment or fusion thereof or a fusion of a variant or fragment, or determining whether the compound substantially blocks activation of said polypeptide according to claim 1 or a variant, fragment, or fusion thereof according to claim 1, or a fusion of said fragment or fusion according to claim 1 by the interacting polypeptide or a variant, fragment or fusion thereof.

14. A method of identifying a polypeptide that interacts with a polypeptide as defined in claim 1, the method comprising 1) contacting a) the polypeptide as defined in claim 1 with b) a composition that may contain such an interacting polypeptide, 2) detecting the presence of a complex containing the polypeptide as defined in claim 1 and an interacting polypeptide, and optionally 3) identifying any interacting polypeptide bound to the said polypeptide as defined in claim 1.

15. A kit comprising a polypeptide as defined in claim 1.

16. A kit according to claim 15 further comprising a substrate of said polypeptide, wherein the substrate is Crosstide (SEQ ID NO:16), CREBtide (SEQ ID NO:18), CREB, ATF1 or a CREB or ATF1 fusion protein.

17. A kit according to claim 15 further comprising a protein for activating said polypeptide.

* * * * *

SEQUENCE LISTING

<160> NUMBER OF SEQ ID NOS: 45

<210> SEQ ID NO 1
<211> LENGTH: 802
<212> TYPE: PRT
<213> ORGANISM: Homo sapiens

<400> SEQUENCE: 1

```
Met Glu Glu Glu Gly Gly Ser Ser Gly Gly Ala Ala Gly Thr Ser Ala
1               5                   10                  15

Asp Gly Gly Asp Gly Gly Glu Gln Leu Leu Thr Val Lys His Glu Leu
            20                  25                  30

Arg Thr Ala Asn Leu Thr Gly His Ala Glu Lys Val Gly Ile Glu Asn
        35                  40                  45

Phe Glu Leu Leu Lys Val Leu Gly Thr Gly Ala Tyr Gly Lys Val Phe
    50                  55                  60

Leu Val Arg Lys Ile Ser Gly His Asp Thr Gly Lys Leu Tyr Ala Met
65                  70                  75                  80

Lys Val Leu Lys Lys Ala Thr Ile Val Gln Lys Ala Lys Thr Thr Glu
                85                  90                  95

His Thr Arg Thr Glu Arg Gln Val Leu Glu His Ile Arg Gln Ser Pro
            100                 105                 110

Phe Leu Val Thr Leu His Tyr Ala Phe Gln Thr Glu Thr Lys Leu His
        115                 120                 125

Leu Ile Leu Asp Tyr Ile Asn Gly Gly Glu Leu Phe Thr His Leu Ser
    130                 135                 140

Gln Arg Glu Arg Phe Thr Glu His Glu Val Gln Ile Tyr Val Gly Glu
145                 150                 155                 160

Ile Val Leu Ala Leu Glu His Leu His Lys Leu Gly Ile Ile Tyr Arg
                165                 170                 175

Asp Ile Lys Leu Glu Asn Ile Leu Leu Asp Ser Asn Gly His Val Val
            180                 185                 190

Leu Thr Asp Phe Gly Leu Ser Lys Glu Phe Val Ala Asp Glu Thr Glu
        195                 200                 205

Arg Ala Tyr Ser Phe Cys Gly Thr Ile Glu Tyr Met Ala Pro Asp Ile
    210                 215                 220

Val Arg Gly Gly Asp Ser Gly His Asp Lys Ala Val Asp Trp Trp Ser
225                 230                 235                 240
```

-continued

```
Leu Gly Val Leu Met Tyr Glu Leu Leu Thr Gly Ala Ser Pro Phe Thr
            245                 250                 255

Val Asp Gly Glu Lys Asn Ser Gln Ala Glu Ile Ser Arg Arg Ile Leu
        260                 265                 270

Lys Ser Glu Pro Pro Tyr Pro Gln Glu Met Ser Ala Leu Ala Lys Asp
            275                 280                 285

Leu Ile Gln Arg Leu Leu Met Lys Asp Pro Lys Lys Arg Leu Gly Cys
290                 295                 300

Gly Pro Arg Asp Ala Asp Glu Ile Lys Glu His Leu Phe Phe Gln Lys
305                 310                 315                 320

Ile Asn Trp Asp Asp Leu Ala Ala Lys Lys Val Pro Ala Pro Phe Lys
                325                 330                 335

Pro Val Ile Arg Asp Glu Leu Asp Val Ser Asn Phe Ala Glu Glu Phe
            340                 345                 350

Thr Glu Met Asp Pro Thr Tyr Ser Pro Ala Ala Leu Pro Gln Ser Ser
            355                 360                 365

Glu Lys Leu Phe Gln Gly Tyr Ser Phe Val Ala Pro Ser Ile Leu Phe
        370                 375                 380

Lys Arg Asn Ala Ala Val Ile Asp Pro Leu Gln Phe His Met Gly Val
385                 390                 395                 400

Glu Arg Pro Gly Val Thr Asn Val Ala Arg Ser Ala Met Met Lys Asp
            405                 410                 415

Ser Pro Phe Tyr Gln His Tyr Asp Leu Asp Leu Lys Asp Lys Pro Leu
            420                 425                 430

Gly Glu Gly Ser Phe Ser Ile Cys Arg Lys Cys Val His Lys Lys Ser
        435                 440                 445

Asn Gln Ala Phe Ala Val Lys Ile Ile Ser Lys Arg Met Glu Ala Asn
    450                 455                 460

Thr Gln Lys Glu Ile Thr Ala Leu Lys Leu Cys Glu Gly His Pro Asn
465                 470                 475                 480

Ile Val Lys Leu His Glu Val Phe His Asp Gln Leu His Thr Phe Leu
                485                 490                 495

Val Met Glu Leu Leu Asn Gly Gly Glu Leu Phe Glu Arg Ile Lys Lys
            500                 505                 510

Lys Lys His Phe Ser Glu Thr Glu Ala Ser Tyr Ile Met Arg Lys Leu
        515                 520                 525

Val Ser Ala Val Ser His Met His Asp Val Gly Val Val His Arg Asp
            530                 535                 540

Leu Lys Pro Glu Asn Leu Leu Phe Thr Asp Glu Asn Asp Asn Leu Glu
545                 550                 555                 560

Ile Lys Ile Ile Asp Phe Gly Phe Ala Arg Leu Lys Pro Pro Asp Asn
                565                 570                 575

Gln Pro Leu Lys Thr Pro Cys Phe Thr Leu His Tyr Ala Ala Pro Glu
            580                 585                 590

Leu Leu Asn Gln Asn Gly Tyr Asp Glu Ser Cys Asp Leu Trp Ser Leu
        595                 600                 605

Gly Val Ile Leu Tyr Thr Met Leu Ser Gly Val Pro Phe Gln Ser
            610                 615                 620

His Asp Arg Ser Leu Thr Cys Thr Ser Ala Val Glu Ile Met Lys Lys
625                 630                 635                 640

Ile Lys Lys Gly Asp Phe Ser Phe Glu Gly Glu Ala Trp Lys Asn Val
                645                 650                 655
```

-continued

```
Ser Gln Glu Ala Lys Asp Leu Ile Gln Gly Leu Leu Thr Val Asp Pro
                660                 665                 670

Asn Lys Arg Leu Lys Met Ser Gly Leu Arg Tyr Asn Glu Trp Leu Gln
            675                 680                 685

Asp Gly Ser Gln Leu Ser Ser Asn Pro Leu Met Thr Pro Asp Ile Leu
        690                 695                 700

Gly Ser Ser Gly Ala Ala Val His Thr Cys Val Lys Ala Thr Phe His
705                 710                 715                 720

Ala Phe Asn Lys Tyr Lys Arg Glu Gly Phe Cys Leu Gln Asn Val Asp
                725                 730                 735

Lys Ala Pro Leu Ala Lys Arg Lys Met Lys Lys Thr Ser Thr Ser
            740                 745                 750

Thr Glu Thr Arg Ser Ser Ser Glu Ser Ser His Ser Ser Ser Ser
        755                 760                 765

His Ser His Gly Lys Thr Thr Pro Thr Lys Thr Leu Gln Pro Ser Asn
770                 775                 780

Pro Ala Asp Ser Asn Asn Pro Glu Thr Leu Phe Gln Phe Ser Asp Ser
785                 790                 795                 800

Val Ala

<210> SEQ ID NO 2
<211> LENGTH: 705
<212> TYPE: PRT
<213> ORGANISM: Mus musculus

<400> SEQUENCE: 2

Thr Glu Ala Asn Leu Thr Gly His Glu Glu Lys Val Ser Val Glu Asn
1               5                   10                  15

Phe Glu Leu Leu Lys Val Leu Gly Thr Gly Ala Tyr Gly Lys Val Phe
                20                  25                  30

Leu Val Arg Lys Ala Gly Gly His Asp Ala Gly Lys Leu Tyr Ala Met
            35                  40                  45

Lys Val Leu Arg Lys Ala Ala Leu Val Gln Arg Ala Lys Thr Gln Glu
        50                  55                  60

His Thr Arg Thr Glu Arg Ser Val Leu Glu Leu Val Arg Gln Ala Pro
65                  70                  75                  80

Phe Leu Val Thr Leu His Tyr Ala Phe Gln Thr Asp Ala Lys Leu His
                85                  90                  95

Leu Ile Leu Asp Tyr Val Ser Gly Gly Glu Met Phe Thr His Leu Tyr
            100                 105                 110

Gln Arg Gln Tyr Phe Lys Glu Ala Glu Val Arg Val Tyr Gly Gly Glu
        115                 120                 125

Ile Val Leu Ala Leu Glu His Leu His Lys Leu Gly Ile Ile Tyr Arg
130                 135                 140

Asp Leu Lys Leu Glu Asn Val Leu Leu Asp Ser Glu Gly His Ile Val
145                 150                 155                 160

Leu Thr Asp Phe Gly Leu Ser Lys Glu Phe Leu Thr Glu Glu Lys Glu
                165                 170                 175

Arg Thr Phe Ser Phe Cys Gly Thr Ile Glu Tyr Met Ala Pro Glu Ile
            180                 185                 190

Ile Arg Ser Lys Thr Gly His Gly Lys Ala Val Asp Trp Trp Ser Leu
        195                 200                 205

Gly Ile Leu Leu Phe Glu Leu Leu Thr Gly Ala Ser Pro Phe Thr Leu
210                 215                 220
```

-continued

```
Glu Gly Glu Arg Asn Thr Gln Ala Glu Val Ser Arg Arg Ile Leu Lys
225                 230                 235                 240

Cys Ser Pro Pro Phe Pro Pro Arg Ile Gly Pro Val Ala Gln Asp Leu
            245                 250                 255

Leu Gln Arg Leu Leu Cys Lys Asp Pro Lys Lys Arg Leu Gly Ala Gly
        260                 265                 270

Pro Gln Gly Ala Gln Glu Val Arg Asn His Pro Phe Phe Gln Gly Leu
    275                 280                 285

Asp Trp Val Ala Leu Ala Ala Arg Lys Ile Pro Ala Pro Phe Arg Pro
290                 295                 300

Gln Ile Arg Ser Glu Leu Asp Val Gly Asn Phe Ala Glu Glu Phe Thr
305                 310                 315                 320

Arg Leu Glu Pro Val Tyr Ser Pro Pro Gly Ser Pro Pro Pro Gly Asp
                325                 330                 335

Pro Arg Ile Phe Gln Gly Tyr Ser Phe Val Ala Pro Ser Ile Leu Phe
            340                 345                 350

Asp His Asn Asn Ala Val Met Thr Asp Gly Leu Glu Ala Pro Gly Ala
        355                 360                 365

Gly Asp Arg Pro Gly Arg Ala Ala Val Ala Arg Ser Ala Met Met Gln
370                 375                 380

Gln Tyr Glu Leu Asp Leu Arg Glu Pro Ala Leu Gly Gln Gly Ser Phe
385                 390                 395                 400

Ser Val Cys Arg Arg Cys Arg Gln Arg Gln Ser Gly Gln Glu Phe Ala
                405                 410                 415

Val Lys Ile Leu Ser Arg Arg Leu Glu Ala Asn Thr Gln Arg Glu Val
            420                 425                 430

Ala Ala Leu Arg Leu Cys Gln Ser His Pro Asn Val Val Asn Leu His
        435                 440                 445

Glu Val His His Asp Gln Leu His Thr Tyr Leu Val Leu Glu Leu Leu
    450                 455                 460

Arg Gly Gly Glu Leu Leu Glu His Ile Arg Lys Lys Arg His Phe Ser
465                 470                 475                 480

Glu Ser Glu Ala Ser Gln Ile Leu Arg Ser Leu Val Ser Ala Val Ser
                485                 490                 495

Phe Met His Glu Glu Ala Gly Val Val His Arg Asp Leu Lys Pro Glu
            500                 505                 510

Asn Ile Leu Tyr Ala Asp Asp Thr Pro Gly Ala Pro Val Lys Ile Ile
        515                 520                 525

Asp Phe Gly Phe Ala Arg Leu Arg Pro Gln Ser Pro Gly Val Pro Met
    530                 535                 540

Gln Thr Pro Cys Phe Thr Leu Gln Tyr Ala Ala Pro Glu Leu Leu Ala
545                 550                 555                 560

Gln Gln Gly Tyr Asp Glu Ser Cys Asp Leu Trp Ser Leu Gly Val Ile
                565                 570                 575

Leu Tyr Met Met Leu Ser Gly Gln Val Pro Phe Gln Gly Ala Ser Gly
            580                 585                 590

Gln Gly Gly Gln Ser Gln Ala Ala Glu Ile Met Cys Lys Ile Arg Glu
        595                 600                 605

Gly Arg Phe Ser Leu Asp Gly Glu Ala Trp Gln Gly Val Ser Glu Glu
    610                 615                 620

Ala Lys Glu Leu Val Arg Gly Leu Leu Thr Val Asp Pro Ala Lys Arg
625                 630                 635                 640
```

```
Leu Lys Leu Glu Gly Leu Arg Gly Ser Ser Trp Leu Gln Asp Gly Ser
            645                 650                 655

Ala Arg Ser Ser Pro Pro Leu Arg Thr Pro Asp Val Leu Glu Ser Ser
        660                 665                 670

Gly Pro Ala Val Arg Ser Gly Leu Asn Ala Thr Phe Met Ala Phe Asn
            675                 680                 685

Arg Gly Lys Arg Glu Gly Phe Phe Leu Lys Ser Val Glu Asn Ala Pro
    690                 695                 700

Leu
705

<210> SEQ ID NO 3
<211> LENGTH: 711
<212> TYPE: PRT
<213> ORGANISM: Mus musculus

<400> SEQUENCE: 3

Thr Glu Ala Asn Leu Thr Gly His Glu Glu Lys Val Ser Val Glu Asn
1               5                  10                  15

Phe Glu Leu Leu Lys Val Leu Gly Thr Gly Ala Tyr Gly Lys Val Phe
            20                  25                  30

Leu Val Arg Lys Ala Gly Gly His Asp Ala Gly Lys Leu Tyr Ala Met
        35                  40                  45

Lys Val Leu Arg Lys Ala Ala Leu Val Gln Arg Ala Lys Thr Gln Glu
    50                  55                  60

His Thr Arg Thr Glu Arg Ser Val Leu Glu Leu Val Arg Gln Ala Pro
65                  70                  75                  80

Phe Leu Val Thr Leu His Tyr Ala Phe Gln Thr Asp Ala Lys Leu His
                85                  90                  95

Leu Ile Leu Asp Tyr Val Ser Gly Gly Glu Met Phe Thr His Leu Tyr
            100                 105                 110

Gln Arg Gln Tyr Phe Lys Glu Ala Glu Val Arg Val Tyr Gly Gly Glu
        115                 120                 125

Ile Val Leu Ala Leu Glu His Leu His Lys Leu Gly Ile Ile Tyr Arg
    130                 135                 140

Asp Leu Lys Leu Glu Asn Val Leu Leu Asp Ser Glu Gly His Ile Val
145                 150                 155                 160

Leu Thr Asp Phe Gly Leu Ser Lys Glu Phe Leu Thr Glu Glu Lys Glu
                165                 170                 175

Arg Thr Phe Ser Phe Cys Gly Thr Ile Glu Tyr Met Ala Pro Glu Ile
            180                 185                 190

Ile Arg Ser Lys Thr Gly His Gly Lys Ala Val Asp Trp Trp Ser Leu
        195                 200                 205

Gly Ile Leu Leu Phe Glu Leu Leu Thr Gly Ala Ser Pro Phe Thr Leu
    210                 215                 220

Glu Gly Glu Arg Asn Thr Gln Ala Glu Val Ser Arg Arg Ile Leu Lys
225                 230                 235                 240

Cys Ser Pro Pro Phe Pro Pro Arg Ile Gly Pro Val Ala Gln Asp Leu
                245                 250                 255

Leu Gln Arg Leu Leu Cys Lys Asp Pro Lys Lys Arg Leu Gly Ala Gly
            260                 265                 270

Pro Gln Gly Ala Gln Glu Val Arg Asn His Pro Phe Phe Gln Gly Leu
        275                 280                 285

Asp Trp Val Ala Leu Ala Ala Arg Lys Ile Pro Ala Pro Phe Arg Pro
    290                 295                 300
```

-continued

```
Gln Ile Arg Ser Glu Leu Asp Val Gly Asn Phe Ala Glu Glu Phe Thr
305                 310                 315                 320

Arg Leu Glu Pro Val Tyr Ser Pro Gly Ser Pro Pro Gly Asp
            325                 330                 335

Pro Arg Ile Phe Gln Gly Tyr Ser Phe Val Ala Pro Ser Ile Leu Phe
            340                 345                 350

Asp His Asn Asn Ala Val Met Thr Asp Gly Leu Glu Ala Pro Gly Ala
            355                 360                 365

Gly Asp Arg Pro Gly Arg Ala Ala Val Ala Arg Ser Ala Met Met Gln
        370                 375                 380

Asp Ser Pro Phe Phe Gln Gln Tyr Glu Leu Asp Leu Arg Glu Pro Ala
385                 390                 395                 400

Leu Gly Gln Gly Ser Phe Ser Val Cys Arg Arg Cys Arg Gln Arg Gln
                405                 410                 415

Ser Gly Gln Glu Phe Ala Val Lys Ile Leu Ser Arg Arg Leu Glu Ala
            420                 425                 430

Asn Thr Gln Arg Glu Val Ala Ala Leu Arg Leu Cys Gln Ser His Pro
        435                 440                 445

Asn Val Val Asn Leu His Glu Val His His Asp Gln Leu His Thr Tyr
    450                 455                 460

Leu Val Leu Glu Leu Leu Arg Gly Gly Glu Leu Leu Glu His Ile Arg
465                 470                 475                 480

Lys Lys Arg His Phe Ser Glu Ser Glu Ala Ser Gln Ile Leu Arg Ser
                485                 490                 495

Leu Val Ser Ala Val Ser Phe Met His Glu Glu Ala Gly Val Val His
            500                 505                 510

Arg Asp Leu Lys Pro Glu Asn Ile Leu Tyr Ala Asp Asp Thr Pro Gly
        515                 520                 525

Ala Pro Val Lys Ile Ile Asp Phe Gly Phe Ala Arg Leu Arg Pro Gln
    530                 535                 540

Ser Pro Gly Val Pro Met Gln Thr Pro Cys Phe Thr Leu Gln Tyr Ala
545                 550                 555                 560

Ala Pro Glu Leu Leu Ala Gln Gln Gly Tyr Asp Glu Ser Cys Asp Leu
                565                 570                 575

Trp Ser Leu Gly Val Ile Leu Tyr Met Met Leu Ser Gly Gln Val Pro
            580                 585                 590

Phe Gln Gly Ala Ser Gly Gln Gly Gly Gln Ser Gln Ala Ala Glu Ile
        595                 600                 605

Met Cys Lys Ile Arg Glu Gly Arg Phe Ser Leu Asp Gly Glu Ala Trp
    610                 615                 620

Gln Gly Val Ser Glu Glu Ala Lys Glu Leu Val Arg Gly Leu Leu Thr
625                 630                 635                 640

Val Asp Pro Ala Lys Arg Leu Lys Leu Glu Gly Leu Arg Gly Ser Ser
                645                 650                 655

Trp Leu Gln Asp Gly Ser Ala Arg Ser Ser Pro Pro Leu Arg Thr Pro
            660                 665                 670

Asp Val Leu Glu Ser Ser Gly Pro Ala Val Arg Ser Gly Leu Asn Ala
        675                 680                 685

Thr Phe Met Ala Phe Asn Arg Gly Lys Arg Glu Gly Phe Phe Leu Lys
    690                 695                 700

Ser Val Glu Asn Ala Pro Leu
705                 710
```

```
<210> SEQ ID NO 4
<211> LENGTH: 473
<212> TYPE: PRT
<213> ORGANISM: Mus musculus
<220> FEATURE:
<221> NAME/KEY: MISC_FEATURE
<222> LOCATION: (365)..(365)
<223> OTHER INFORMATION: residue 365 is unknown

<400> SEQUENCE: 4
```

Arg Ile Leu Lys Cys Ser Pro Pro Phe Pro Pro Arg Ile Gly Pro Val
1               5                   10                  15

Ala Gln Asp Leu Leu Gln Arg Leu Leu Cys Lys Asp Pro Lys Lys Arg
            20                  25                  30

Leu Gly Ala Gly Pro Gln Gly Ala Gln Glu Val Arg Asn His Pro Phe
        35                  40                  45

Phe Gln Gly Leu Asp Trp Val Ala Leu Ala Ala Arg Lys Ile Pro Ala
    50                  55                  60

Pro Phe Arg Pro Gln Ile Arg Ser Glu Leu Asp Val Gly Asn Phe Ala
65                  70                  75                  80

Glu Glu Phe Thr Arg Leu Glu Pro Val Tyr Ser Pro Pro Gly Ser Pro
                85                  90                  95

Pro Pro Gly Asp Pro Arg Ile Phe Gln Gly Tyr Ser Phe Val Ala Pro
            100                 105                 110

Ser Ile Leu Phe Asp His Asn Asn Ala Val Met Thr Asp Gly Leu Glu
        115                 120                 125

Ala Pro Gly Ala Gly Asp Arg Pro Gly Arg Ala Ala Val Ala Arg Ser
    130                 135                 140

Ala Met Met Gln Asp Ser Pro Phe Phe Gln Gln Tyr Glu Leu Asp Leu
145                 150                 155                 160

Arg Glu Pro Ala Leu Gly Gln Gly Ser Phe Ser Val Cys Arg Arg Cys
                165                 170                 175

Arg Gln Arg Gln Ser Gly Gln Glu Phe Ala Val Lys Ile Leu Ser Arg
            180                 185                 190

Arg Leu Glu Ala Asn Thr Gln Arg Glu Val Ala Ala Leu Arg Leu Cys
        195                 200                 205

Gln Ser His Pro Asn Val Val Asn Leu His Glu Val His His Asp Gln
    210                 215                 220

Leu His Thr Tyr Leu Val Leu Glu Leu Leu Arg Gly Gly Glu Leu Leu
225                 230                 235                 240

Glu His Ile Arg Lys Lys Arg His Phe Ser Glu Ser Glu Ala Ser Gln
                245                 250                 255

Ile Leu Arg Ser Leu Val Ser Ala Val Ser Phe Met His Glu Glu Ala
            260                 265                 270

Gly Val Val His Arg Asp Leu Lys Pro Glu Asn Ile Leu Tyr Ala Asp
        275                 280                 285

Asp Thr Pro Gly Ala Pro Val Lys Ile Ile Asp Phe Gly Phe Ala Arg
    290                 295                 300

Leu Arg Pro Pro Gly Val Pro Met Gln Thr Pro Cys Phe Thr Leu Gln
305                 310                 315                 320

Tyr Ala Ala Pro Glu Leu Leu Ala Gln Gln Gly Tyr Asp Glu Ser Cys
                325                 330                 335

Asp Leu Trp Ser Leu Gly Val Ile Leu Tyr Met Met Leu Ser Gly Gln
            340                 345                 350

Val Pro Phe Gln Gly Ala Ser Gly Gln Gly Gly Gln Xaa Gln Ala Ala
        355                 360                 365

```
Glu Ile Met Cys Lys Ile Arg Glu Gly Arg Phe Ser Leu Asp Gly Glu
    370                 375                 380

Ala Trp Gln Gly Val Ser Glu Glu Ala Lys Glu Leu Val Arg Gly Leu
385                 390                 395                 400

Leu Thr Val Asp Pro Ala Lys Arg Leu Lys Leu Glu Gly Leu Arg Gly
                405                 410                 415

Ser Ser Trp Leu Gln Asp Gly Ser Ala Arg Ser Ser Pro Pro Leu Arg
            420                 425                 430

Thr Pro Asp Val Leu Glu Ser Ser Gly Pro Ala Val Arg Ser Gly Leu
        435                 440                 445

Asn Ala Thr Phe Met Ala Phe Asn Arg Gly Lys Arg Glu Gly Phe Phe
    450                 455                 460

Leu Lys Ser Val Glu Asn Ala Pro Leu
465                 470

<210> SEQ ID NO 5
<211> LENGTH: 740
<212> TYPE: PRT
<213> ORGANISM: Homo sapiens

<400> SEQUENCE: 5

His Ala Ser Gly Asp Glu Asp Glu Asp Glu Gly Cys Ala Val Glu Leu
1               5                   10                  15

Gln Ile Thr Glu Ala Asn Leu Thr Gly His Glu Glu Lys Val Ser Val
            20                  25                  30

Glu Asn Phe Ala Leu Leu Lys Val Leu Gly Thr Gly Ala Tyr Gly Lys
        35                  40                  45

Val Phe Leu Val Arg Lys Thr Gly Gly His Asp Ala Gly Lys Leu Tyr
    50                  55                  60

Ala Met Lys Val Leu Arg Lys Ala Ala Leu Val Gln Arg Ala Lys Thr
65                  70                  75                  80

Gln Glu His Thr Arg Thr Glu Arg Ser Val Leu Glu Leu Val Arg Gln
                85                  90                  95

Ala Pro Phe Leu Val Thr Leu His Tyr Ala Phe Gln Thr Asp Ala Lys
            100                 105                 110

Leu His Leu Ile Leu Asp Tyr Val Ser Gly Gly Glu Met Phe Thr His
        115                 120                 125

Leu Tyr Gln Arg Gln Tyr Phe Lys Glu Ala Glu Val Arg Val Tyr Gly
    130                 135                 140

Gly Glu Ile Val Leu Ala Leu Glu His Leu His Lys Leu Gly Ile Ile
145                 150                 155                 160

Tyr Arg Asp Leu Lys Leu Glu Asn Val Leu Leu Asp Ser Glu Gly His
                165                 170                 175

Ile Val Leu Thr Asp Phe Gly Leu Ser Lys Glu Phe Leu Thr Glu Glu
            180                 185                 190

Lys Glu Arg Thr Phe Ser Phe Cys Gly Thr Ile Glu Tyr Met Ala Pro
        195                 200                 205

Glu Ile Ile Arg Ser Lys Ala Gly His Gly Lys Ala Val Asp Trp Trp
    210                 215                 220

Ser Leu Gly Ile Leu Leu Phe Glu Leu Leu Thr Gly Ala Ser Pro Phe
225                 230                 235                 240

Thr Leu Glu Gly Glu Arg Asn Thr Gln Ala Glu Val Ser Arg Arg Ile
                245                 250                 255

Leu Lys Cys Ser Pro Pro Phe Pro Leu Arg Ile Gly Pro Val Ala Gln
            260                 265                 270
```

-continued

```
Asp Leu Leu Gln Arg Leu Leu Cys Lys Asp Pro Lys Lys Arg Leu Gly
        275                 280                 285

Ala Gly Pro Gln Gly Ala Gln Glu Val Lys Ser His Pro Phe Phe Arg
        290                 295                 300

Val Trp Thr Gly Trp Ala Leu Ala Ala Arg Lys Ile Pro Ala Pro Phe
305                 310                 315                 320

Arg Pro Gln Ile Arg Ser Glu Leu Asp Val Gly Asn Phe Ala Glu Glu
                    325                 330                 335

Phe Thr Arg Leu Glu Pro Val Tyr Ser Pro Ala Gly Ser Pro Pro Pro
                340                 345                 350

Gly Asp Pro Arg Ile Phe Gln Gly Tyr Ser Phe Val Ala Pro Ser Ile
            355                 360                 365

Leu Phe Asp His Asn Asn Ala Val Met Ala Asp Val Leu Gln Ala Pro
        370                 375                 380

Gly Ala Gly Tyr Arg Pro Gly Arg Ala Ala Val Ala Arg Ser Ala Met
385                 390                 395                 400

Met Gln Asp Ser Pro Phe Phe Gln Gln Tyr Glu Leu Asp Leu Arg Glu
                    405                 410                 415

Pro Ala Leu Gly Gln Gly Ser Phe Ser Val Cys Arg Arg Cys Arg Gln
                420                 425                 430

Arg Gln Ser Gly Gln Glu Phe Ala Val Lys Ile Leu Ser Arg Arg Leu
            435                 440                 445

Glu Glu Asn Thr Gln Arg Glu Val Ala Ala Leu Arg Leu Cys Gln Ser
        450                 455                 460

His Pro Asn Val Val Asn Leu His Glu Val Leu His Asp Gln Leu His
465                 470                 475                 480

Thr Tyr Leu Val Leu Glu Leu Leu Arg Gly Gly Glu Leu Leu Glu His
                    485                 490                 495

Ile Arg Lys Lys Arg Leu Phe Ser Glu Ser Glu Ala Ser Gln Ile Leu
                500                 505                 510

Arg Ser Leu Val Ser Ala Val Ser Phe Met His Glu Glu Ala Gly Val
            515                 520                 525

Val His Arg Asp Leu Lys Pro Glu Asn Ile Leu Tyr Ala Asp Asp Thr
        530                 535                 540

Pro Gly Ala Pro Val Lys Ile Ile Asp Phe Gly Phe Ala Arg Leu Arg
545                 550                 555                 560

Pro Gln Ser Pro Ala Glu Pro Met Gln Thr Pro Cys Phe Thr Leu Gln
                    565                 570                 575

Tyr Ala Ala Pro Glu Leu Leu Ala Gln Gln Gly Tyr Asp Glu Ser Cys
                580                 585                 590

Asp Leu Trp Ser Leu Gly Val Ile Leu Tyr Met Met Leu Ser Gly Gln
            595                 600                 605

Val Pro Phe Gln Gly Ala Ser Gly Gln Gly Gln Ser Gln Ala Ala
        610                 615                 620

Glu Ile Met Cys Lys Ile Arg Glu Gly Arg Phe Ser Leu Asp Gly Glu
625                 630                 635                 640

Ala Trp Gln Gly Val Ser Glu Glu Ala Lys Glu Leu Val Arg Gly Leu
                    645                 650                 655

Leu Thr Val Asp Pro Ala Lys Arg Leu Lys Leu Glu Gly Leu Arg Ser
                660                 665                 670

Ser Ser Trp Leu Gln Asp Gly Ser Ala Arg Ser Ser Pro Pro Leu Arg
            675                 680                 685
```

```
Thr Pro Asp Val Leu Glu Ser Ser Gly Pro Ala Val Arg Ser Gly Leu
    690                 695                 700

Asn Ala Thr Phe Met Ala Phe Asn Arg Gly Lys Arg Glu Gly Phe Phe
705                 710                 715                 720

Leu Lys Ser Val Glu Asn Ala Pro Leu Ala Lys Arg Arg Lys Gln Lys
                725                 730                 735

Leu Arg Ser Ala
        740

<210> SEQ ID NO 6
<211> LENGTH: 3131
<212> TYPE: DNA
<213> ORGANISM: Homo sapiens

<400> SEQUENCE: 6
cgagccgtgc ggccagagcg ggaaagagac tcgtctttgc gtccgagttc tggagccgcc      60
gcaccccgac tcctggggcc gcggcagcgg ctgcgagggg acgggcgtcc gctgtctcct     120
gggttcccct cgtagcgacc cgcgggatcg gaaaaaaagg agaagatgga ggaggagggt     180
ggcagcagcg gcggcgccgc ggggaccagc gcggacggcg gcgacggagg agagcagctc     240
ctcactgtca agcacgagct gcggactgct aatttgacag acatgctgga aggtgggga      300 atagaaaatt ttgagctcct gaaggtccta ggaactggag cttatggaaa agtatttcta     360
gttcgtaaaa taagtggcca tgatactgga aagctgtatg ccatgaaagt tttgaaaaag     420
gcaacaatcg ttcaaaaggc caaaaccaca gagcatacaa ggacagaacg acaagtcctg     480
gaacacatta ggcagtcgcc atttttggta acattacatt atgctttcca gacagaaacc     540
aaacttcatc tcattttaga ttatataaat ggtggtgaac tttttactca tctttctcaa     600
agagagcgtt tcacagagca tgaggtgcag atttatgttg gagagattgt gcttgccctc     660
gaacatctcc acaagttggg gattatatat cgtgatatta gcttgagaa tattctactt     720 gattctaatg gccatgtggt gctgacagat tttggtctga gtaaggagtt tgtggctgat     780
gaaactgaaa gagcatattc cttttgtgga actattgaat acatggcacc agatattgtc     840 agaggggag attcaggaca tgacaaggca gttgactggt ggagtttggg tgttctaatg     900
tatgaattac taactggagc atctcctttc actgttgatg gagaaaaaaa ttcccaagct     960
gagatatcta ggagaatatt aaaaagtgag cctccatatc cccaagaaat gagtgcttta    1020
gcgaaagacc taattcagcg tctttttgatg aaagatccca agaagagatt gggatgtggt    1080
ccacgtgatg cagatgaaat caaagaacat ctcttctttc agaaaataaa ttgggatgat    1140
ttagccgcca aaaagtgcc tgcaccattt aagccagtca ttcgagatga attagatgtg    1200
agtaactttg cagaagagtt cacagaaatg gatcccactt attctcccgc agccctgccc    1260
cagagttctg agaagctgtt tcagggctat tcctttgttg ctccttccat cctattcaag    1320
cgtaatgcag ctgtcataga ccctcttcag tttcacatgg agttgaacg tcctggagtg    1380 acaaatgttg ccaggagtgc aatgatgaag gactctccat tctatcaaca ctatgaccta    1440
gatttgaagg acaaacccct gggagaaggt agttttttcaa tttgtcgaaa gtgtgtgcat    1500
aaaaaaagta ccaagctttt tgcagtcaaa ataatcagca aaggatggaa agccaatact    1560
caaaaggaaa taacagctct gaaactctgt gaaggacacc ccaatattgt gaagttgcat    1620 gaagttttc atgatcagct tcacacgttt ctagtgatgg aacttctgaa tggaggagaa    1680
ctgtttgagc gcattaagaa aaagaagcac ttcagtgaga cggaagccag ctacatcatg    1740
aggaagcttg tttcagctgt aagccacatg catgatgttg gagtggtgca cagggatctg    1800
```

-continued

```
aaacctgaga atttattgtt caccgatgaa aatgacaatt tggaaattaa aataattgat    1860
tttggatttg cacggctaaa gccaccggat aatcagcccc tgaagactcc atgcttcacc    1920
cttcattatg ccgccccaga gctcttgaat cagaacggct acgatgagtc ctgtgacctg    1980
tggagcttgg gcgtcatttt gtacacaatg ttgtcaggac aggttccctt ccaatctcat    2040
gaccgaagtt tgacgtgtac cagcgcggtg gaaatcatga agaaaattaa aagggagat    2100
ttctcctttg aaggagaagc ctggaagaat gtatcccaag aggctaaaga tttgatccaa    2160
ggacttctca cagtagatcc aaacaaaagg cttaaaatgt ctggcttgag gtacaatgaa    2220
tggctacaag atggaagtca gctgtcctcc aatcctctga tgactccgga tattctagga    2280
tcttccggag ctgccgtgca tacctgtgtg aaagcaacct ccacgcctt taacaaatac     2340
aagagagagg ggttttgcct tcagaatgtt gataaggccc ctttggctaa gagaagaaaa    2400
atgaaaaaga ctagcaccag taccgagacg cgcagcagtt ccagtgagag ttcccattct    2460
tcttcctctc attctcacgg taaaactaca cccaccaaga cactgcagcc cagcaatcct    2520
gccgacagca ataacccgga gaccctcttc cagttctcgg actcagtagc ttaggcatgg    2580
taggagtgta tcagtgatcc attgcacctt tattccctca gcatatgcct gaggcgatct    2640
tttatgcttt taaaaatgtt tcccgttggt ctcattggaa tctgcctcct aatgattttt    2700
tttcaggaaa acctgtttgg ttatcctcat tcaaaagcac tggacagaga atgttactgt    2760
gaatagagca catattactc tttttagcaa cctagcatga tgccaacaag actatttttg    2820
aaagagcaaa ggttcctgta aatttaatta gggctagatt tgagctgctt gtaagtcaca    2880
ggttttccag atgtctgcca acaagaaatg actcatactg tgatgatacc ttttgctttg    2940
ccttgtggac aatgtgggtt tttgaaattt gcacccttca aacaatgatt tatcagagaa    3000
aggggtctgt tttcaaaaaa gattctgtaa tgaatttat gtgtggcata tacttatttc      3060
ttgagagaag atttttaactt attgttttta ttttatggtt acatatgatg ataacctgct   3120
attattaaac t                                                                     3131
```

<210> SEQ ID NO 7
<211> LENGTH: 3131
<212> TYPE: DNA
<213> ORGANISM: Homo sapiens

<400> SEQUENCE: 7

```
cgagccgtgc ggccagagcg ggaaagagac tcgtctttgc gtccgagttc tggagccgcc      60
gcaccccgac tcctggggcc gcggcagcgg ctgcgagggg acgggcgtcc gctgtctcct     120
gggttcccct cgtagcgacc cgcgggatcg gaaaaaaagg agaagatgga ggaggagggt    180
ggcagcagcg gcggcgccgc ggggaccagc gcggacggcg gcgacggagg agagcagctc    240
ctcactgtca gcacgagct gcggactgct aatttgacag gacatgctga gaaggtggga     300
atagaaaatt ttgagctcct gaaggtccta ggaactggag cttatggaaa agtatttcta   360
gttcgtaaaa taagtggcca tgatactgga aagctgtatg ccatgaaagt tttgaaaaag   420
gcaacaatcg ttcaaaaggc caaaaccaca gagcatacaa ggacagaacg acaagtcctg   480
gaacacatta ggcagtcgcc attttttggta acattacatt atgctttcca gacagaaacc   540
aaacttcatc tcatttaga ttatataaat ggtggtgaac tttttactca tctttctcaa    600
agagagcgtt tcacagagca tgaggtgcag atttatgttg agagattgt gcttgccctc    660
gaacatctcc acaagttggg gattatatat cgtgatatta gcttgagaa tattctactt   720
gattctaatg ccatgtggt gctgacagat tttggtctga gtaaggagtt tgtggctgat   780
```

```
gaaactgaaa gagcatattc cttttgtgga actattgaat acatggcacc agatattgtc    840 agaggggag  attcaggaca tgacaaggca gttgactggt ggagtttggg tgttctaatg    900
tatgaattac taactggagc atctccttttc actgttgatg gagaaaaaaa ttcccaagct   960
gagatatcta ggagaatatt aaaaagtgag cctccatatc cccaagaaat gagtgcttta  1020
gcgaaagacc taattcagcg tcttttgatg aaagatccca agaagagatt gggatgtggt  1080
ccacgtgatg cagatgaaat caaagaacat ctcttctttc agaaaataaa ttgggatgat  1140
ttagccgcca aaaagtgcc  tgcaccattt aagccagtca ttcgagatga attagatgtg   1200
agtaactttg cagaagagtt cacagaaatg gatcccactt attctcccgc agccctgccc  1260
cagagttctg agaagctgtt tcagggctat tcctttgttg ctccttccat cctattcaag  1320
cgtaatgcag ctgtcataga ccctcttcag tttcacatgg gagttgaacg tcctggagtg  1380
acaaatgttg ccaggagtgc aatgatgaag gactctccat tctatcaaca ctatgaccta  1440
gatttgaagg acaaaccct  gggagaaggt agttttttcaa tttgtcgaaa gtgtgtgcat  1500
aaaaaaagta accaagcttt tgcagtcaaa ataatcagca aaaggatgga agccaatact  1560
caaaaggaaa taacagctct gaaactctgt gaaggacacc ccaatattgt gaagttgcat  1620 gaagttttc  atgatcagct tcacacgttt ctagtgatgg aacttctgaa tggaggagaa  1680
ctgtttgagc gcattaagaa aaagaagcac ttcagtgaga cggaagccag ctacatcatg  1740
aggaagcttg tttcagctgt aagccacatg catgatgttg gagtggtgca cagggatctg  1800
aaacctgaga atttattgtt caccgatgaa atgacaatt  tggaaattaa aataattgat  1860
tttggatttg cacggctaaa gccaccggat aatcagcccc tgaagactcc atgcttcacc  1920
cttcattatg ccgccccaga gctcttgaat cagaacggct acgatgagtc ctgtgacctg  1980
tggagcttgg gcgtcatttt gtacacaatg ttgtcaggac aggttcccctt ccaatctcat  2040 gaccgaagtt tgacgtgtac cagcgcggtg gaaatcatga agaaaattaa aagggagat   2100 ttctcctttg aaggagaagc ctggaagaat gtatcccaag aggctaaaga tttgatccaa  2160
ggacttctca cagtagatcc aaacaaaagg cttaaaatgt ctggcttgag gtacaatgaa  2220
tggctacaag atggaagtca gctgtcctcc aatcctctga tgactccgga tattctagga  2280
tcttccggag ctgccgtgca tacctgtgtg aaagcaaacct tccacgcctt taacaaatac  2340
aagagagagg ggttttgcct tcagaatgtt gataaggccc ctttggctaa gagaagaaaa  2400
atgaaaaaga ctagcaccag taccgagacg cgcagcagtt ccagtgagag ttcccattct  2460
tcttcctctc attctcacgg taaaactaca cccaccaaga cactgcagcc cagcaatcct  2520
gccgacagca ataacccgga gaccctcttc cagttctcgg actcagtagc ttaggcatgg  2580
taggagtgta tcagtgatcc attgcaacctt tattccctca gcatatgcct gaggcgatct  2640
tttatgcttt taaaaatgtt tcccgttggt ctcattggaa tctgcctcct aatgatttt   2700 tttcaggaaa acctgtttgg ttatcctcat tcaaaagcac tggacagaga atgttactgt  2760
gaatagagca catattactc tttttagcaa cctagcatga tgccaacaag actatttttg  2820
aaagagcaaa ggttcctgta aatttaatta gggctagatt tgagctgctt gtaagtcaca  2880
ggttttccag atgtctgcca acaagaaatg actcatactg tgatgatacc ttttgctttg  2940
ccttgtggac aatgtgggtt tttgaaattt gcacccttca aacaatgatt tatcagaaaa  3000
aggggtctgt tttcaaaaaa gattctgtaa tgaattttat gtgtggcata tacttatttc  3060
ttgagagaag attttaactt attgttttta tttatggtt  acatatgatg ataacctgct  3120
attattaaac t                                                         3131
```

<210> SEQ ID NO 8
<211> LENGTH: 2134
<212> TYPE: DNA
<213> ORGANISM: Homo sapiens

<400> SEQUENCE: 8

| | | | | | |
|---|---|---|---|---|---|
| accgaagcca | acctgaccgg | gcacgaggag | aaggtgagcg | tggagaactt | cgagctgctc | 60 |
| aaggtgctgg | gcacgggagc | ctacggcaag | gtgttcctgg | tgcggaaggc | gggcgggcac | 120 |
| gacgcgggga | agctgtacgc | catgaaggtg | ctgcgcaagg | cggcgctggt | gcagcgcgcc | 180 |
| aagacgcaag | agcacacgcg | caccgagcgc | tcggtgctgg | agctggtgcg | ccaggcgccc | 240 |
| ttcctggtca | cgctgcacta | cgcttttcag | acggatgcca | agctgcacct | catcctggac | 300 |
| tatgtgagcg | gcggggagat | gttcacccac | ctctaccagc | gccagtactt | caaggaggct | 360 |
| gaggtgcgcg | tgtatggggg | tgagatcgtg | ctggccctgg | aacacctgca | caagctcggc | 420 |
| atcatttacc | gagacctgaa | actggagaat | gtgctgctgg | actccgaggg | ccacattgtc | 480 |
| ctcacggact | tcgggctgag | caaggagttc | ctgacggagg | agaaagagcg | gaccttctcc | 540 |
| ttctgtggca | ccatcgagta | catggcccc | gaaatcatcc | gtagcaagac | ggggcatggc | 600 |
| aaggctgtgg | actggtggag | cctgggcatc | ttgctcttcg | agctgctgac | ggggggcctcg | 660 |
| cccttcaccc | tggagggcga | gaggaacacg | caggctgagg | tgtctcgacg | gatcctgaag | 720 |
| tgctcccctc | ccttccccc | tcggatcggg | cccgtgcgc | aggacctgct | gcagcggctg | 780 |
| ctttgtaagg | atcctaagaa | gcgattgggc | gcggggcccc | aggggcaca | agaagtccgg | 840 |
| aaccatccct | tcttccaggg | cctcgattgg | gtggctctgg | ctgccaggaa | gattccagcc | 900 |
| ccattccggc | cccaaaatccg | ctcagagctg | gatgtgggca | actttgcgga | ggaattcact | 960 |
| cggctgagc | ctgtctactc | accccctggc | agcccccac | ctggggaccc | ccgaatcttt | 1020 |
| cagggatact | cctttgtggc | accctccatt | ctctttgacc | acaacaacgc | ggtgatgacc | 1080 |
| gatgggctga | agcgcctgg | tgctggagac | cggccaggtc | gggcagcggt | ggccaggagc | 1140 |
| gctatgatgc | aggactcgcc | cttcttccag | cagtacgagc | tggacctgcg | ggagcctgcg | 1200 |
| ctgggccagg | gcagcttttc | tgtgtgtcgc | cgctgccgcc | agcgccagag | cggccaggag | 1260 |
| ttcgcagtca | agatcctcag | tcgcaggctg | gaggcgaaca | cgcagcgcga | agtggctgcc | 1320 |
| ctgcgcctgt | gccagtcaca | ccccaacgtg | gtgaatctgc | acgaggtgca | tcacgaccag | 1380 |
| ctgcacacgt | acctggtcct | ggagctgctg | cggggcgggg | agctgctgga | gcacatccgc | 1440 |
| aagaagcggc | acttcagcga | gtcggaagca | agccagatcc | tgcgcagcct | cgtgtcggcc | 1500 |
| gtgagcttca | tgcacgagga | ggcgggcgtg | gtgcaccgcg | acctcaagcc | ggagaacatc | 1560 |
| ctgtacgccg | acgacacgcc | cggggccccg | gtgaaaatca | tcgacttcgg | gttcgcgcgg | 1620 |
| ttgcggccgc | agagtcccgg | ggtgcccatg | cagacgccct | gcttcacgct | gcagtacgct | 1680 |
| gccccgagc | tgctggcgca | gcagggctac | gacgagtcct | gcgacctctg | gagcctgggc | 1740 |
| gtcattctgt | acatgatgct | gtcggggcag | gtccccttcc | aggggcctc | tggccagggc | 1800 |
| gggcagagcc | aggcggccga | gatcatgtgc | aaaatccgcg | aggggcgctt | ctcccttgac | 1860 |
| ggggaggcct | ggcagggtgt | atccgaggaa | gccaaggagc | tggtccgagg | gctcctgacc | 1920 |
| gtggaccccg | ccaagcggct | gaagctcgag | ggactgcggg | gcagctcgtg | gctgcaggac | 1980 |
| ggcagcgcgc | gctcctcgcc | cccgctccgg | acgcccgacg | tgctcgagtc | ctctgggccc | 2040 |
| gcagtgcgct | cgggtctcaa | cgccaccttc | atggcattca | accggggcaa | gcgggagggc | 2100 |
| ttcttcctga | agagcgtgga | gaatgcaccc | ctca | | | 2134 |

-continued

<210> SEQ ID NO 9
<211> LENGTH: 2222
<212> TYPE: DNA
<213> ORGANISM: Mus musculus

<400> SEQUENCE: 9

| | | | | | |
|---|---|---|---|---|---|
| cacgcgtccg | gagacgagga | tgaggacgag | ggctgcgccg | tggagctgca | gatcaccgaa | 60 |
| gccaacctca | ccgggcatga | ggagaaggtg | agcgtggaga | acttcgcgct | gctcaaggtg | 120 |
| ctgggcacgg | gagcctatgg | gaaggtgttc | ctggtgcgga | gacgggtgg | gcacgacgcg | 180 |
| ggcaagctct | atgccatgaa | ggtgctacgc | aaggcggcgt | tggtgcagcg | cgcgaagaca | 240 |
| caggagcata | cccgcaccga | acgctcggtg | ctggagctgg | ttcgccaagc | acccttcctg | 300 |
| gtcacactgc | actacgcctt | ccagacggat | gccaagctgc | acctcatcct | ggactacgtg | 360 |
| agcggtggtg | agatgttcac | tcacctctac | cagcgccagt | acttcaagga | ggctgaggtt | 420 |
| cgagtgtatg | ggggcgagat | tgtgctggcc | ctggaacacc | tgcacaagct | gggtatcatc | 480 |
| taccgggacc | tgaagctgga | gaacgtctta | cttgactcag | aaggtcacat | cgtccttaca | 540 |
| gactttgggc | tgagcaagga | gttcctgacg | gaggagaaag | agcggacctt | ctccttctgt | 600 |
| ggcacaatcg | agtacatggc | tcccgaaatc | atccgaagca | aggctggaca | tggcaaggct | 660 |
| gtggactggt | ggagcctggg | tatcctgctc | ttcgagctgc | tgacaggggc | ctcacccttc | 720 |
| acactggagg | gagagaggaa | cactcaggct | gaggtgtccc | gacggatctt | gaagtgctcc | 780 |
| cctcccttcc | ctctccggat | tgggcctgtg | gcacaggacc | tgctacagcg | gctgctgtgc | 840 |
| aaggaccctc | agaagaggtt | gggcgcaggt | ccccagggtg | cgcaggaagt | caagagtcac | 900 |
| cccttcttca | gggtctggac | tgggtgggct | ctggctgcca | gaaagatccc | agccccattc | 960 |
| cggccccaga | tccgctcaga | gctggatgtg | gggaattttg | cggaggaatt | cacccggctg | 1020 |
| gagcccgtct | actcccctgc | aggcagccct | ccacctgggg | accctcggat | ctttcaggga | 1080 |
| tactccttcg | tggctccgtc | catcctcttt | gaccacaaca | atgcagtgat | ggctgatgta | 1140 |
| ctgcaggcac | cgggtgccgg | atacaggccc | ggcagggcag | cagttgccag | gagtgccatg | 1200 |
| atgcaggact | cgccttttctt | ccagcagtac | gaactggacc | ttcgggagcc | agcgctgggg | 1260 |
| cagggcagct | tctctgtgtg | tcggagatgt | aggcagcgcc | agagcggcca | ggagtttgct | 1320 |
| gtcaagatcc | tcagccgcag | gctggaggag | aacactcagc | gagaggtggc | tgctcttcgc | 1380 |
| ctgtgccagt | cacaccccaa | cgtggtgaat | ctgcatgagg | tgcttcatga | ccagctacac | 1440 |
| acttacctgg | tcctggagtt | gctgcgaggc | ggagagctat | tggaacacat | ccgcaagaag | 1500 |
| cggctcttca | gcgagtcgga | ggccagccag | atccttcgga | gcctggtttc | ggccgtgagc | 1560 |
| ttcatgcacg | aggaggcagg | cgtggtgcac | cgcgacctga | acccgagaa | catcttgtac | 1620 |
| gcggacgaca | ctcccggggc | cccggtgaag | atcatcgact | tcgggttcgc | gcgactgcgg | 1680 |
| ccccagagcc | cggcagagcc | catgcagact | ccttgcttca | cactgcagta | cgctgcaccc | 1740 |
| gagctgctgg | cacagcaggg | ctacgatgag | tcctgcgatc | tatggagcct | gggtgtcatt | 1800 |
| ctgtacatga | tgctgtctgg | ccaggttccc | ttccaagggg | cctccggcca | gggtggacag | 1860 |
| agtcaggcag | ctgagatcat | gtgcaagatc | cgtgaagggc | gcttctccct | ggacggggaa | 1920 |
| gcctggcaag | tgtgtcgga | ggaagccaag | gagctggtcc | gagggctact | gacagtcgac | 1980 |
| cccgccaagc | ggctgaagct | ggaggggctg | cgtagcagct | cgtggcttca | ggacggcagc | 2040 |
| gcgcgctcct | cgcccccgct | ccgcacgccg | gatgtgctgg | agtcctctgg | gccagctgtg | 2100 |
| cgttccgggc | tcaatgccac | tttcatggcg | ttcaaccgag | gcaagcgcga | gggcttcttt | 2160 |

-continued

| ctcaagagtg tagagaatgc gcctctggcc aagaggcgca agcagaagct ccggagcgcg | 2220 |
| gc | 2222 |

<210> SEQ ID NO 10
<211> LENGTH: 3131
<212> TYPE: DNA
<213> ORGANISM: Homo sapiens

<400> SEQUENCE: 10

| cgagccgtgc ggccagagcg ggaaagagac tcgtctttgc gtccgagttc tggagccgcc | 60 |
| gcaccccgac tcctgggggcc gcggcagcgg ctgcgagggg acgggcgtcc gctgtctcct | 120 |
| gggttcccct cgtagcgacc cgcgggatcg gaaaaaaagg agaagatgga ggaggaggt | 180 |
| ggcagcagcg gcggcgccgc ggggaccagc gcggacggcg gcgacggagg agagcagctc | 240 |
| ctcactgtca agcacgagct gcggactgct aatttgacag gacatgctga aaggtggga | 300 |
| atagaaaatt ttgagctcct gaaggtccta ggaactggac cttatggaaa agtatttcta | 360 |
| gttcgtaaaa taagtggcca tgatactgga aagctgtatg ccatgaaagt tttgaaaaag | 420 |
| gcaacaatcg ttcaaaaggc caaaaccaca gagcatacaa ggacagaacg acaagtcctg | 480 |
| gaacacatta ggcagtcgcc attttggta acattacatt atgctttcca gacagaaacc | 540 |
| aaacttcatc tcattttaga ttatataaat ggtggtgaac tttttactca tcttttctcaa | 600 |
| agagagcgtt tcacagagca tgaggtgcag atttatgttg gagagattgt gcttgccctc | 660 |
| gaacatctcc acaagttggg gattatatat cgtgatatta agcttgagaa tattctactt | 720 |
| gattctaatg gccatgtggt gctgacagat tttggtctga gtaaggagtt tgtggctgat | 780 |
| gaaactgaaa gagcatattc cttttgtgga actattgaat acatggcacc agatattgtc | 840 |
| agaggggggag attcaggaca tgacaaggca gttgactggt ggagtttggg tgttctaatg | 900 |
| tatgaattac taactggagc atctcctttc actgttgatg gagaaaaaa ttcccaagct | 960 |
| gagatatcta ggagaatatt aaaagtgag cctccatatc cccaagaaat gagtgcttta | 1020 |
| gcgaaagacc taattcagcg tctttttgatg aaagatccca agaagagatt gggatgtggt | 1080 |
| ccacgtgatg cagatgaaat caaagaacat ctcttcttc agaaaataaa ttgggatgat | 1140 |
| ttagccgcca aaaagtgcc tgcaccattt aagccagtca ttcgagatga attagatgtg | 1200 |
| agtaactttg cagaagagtt cacagaaatg gatcccactt attctcccgc agccctgccc | 1260 |
| cagagttctg agaagctgtt tcagggctat tcctttgttg ctccttccat cctattcaag | 1320 |
| cgtaatgcag ctgtcataga ccctcttcag tttcacatgg gagttgaacg tcctggagtg | 1380 |
| acaaatgttg ccaggagtgc aatgatgaag gactctccat tctatcaaca ctatgaccta | 1440 |
| gatttgaagg acaaacccct gggagaaggt agttttttcaa tttgtcgaaa gtgtgtgcat | 1500 |
| aaaaaaagta accaagcttt tgcagtcaaa ataatcagca aaaggatgga agccaatact | 1560 |
| caaaaggaaa taacagctct gaaactctgt gaaggacacc ccaatattgt gaagttgcat | 1620 |
| gaagttttttc atgatcagct tcacacgttt ctagtgatgg aacttctgaa tggaggagaa | 1680 |
| ctgtttgagc gcattaagaa aaagaagcac ttcagtgaga cggaagccag ctacatcatg | 1740 |
| aggaagcttg tttcagctgt aagccacatg catgatgttg gagtggtgca cagggatctg | 1800 |
| aaacctgaga atttattgtt caccgatgaa aatgacaatt ggaaattaa ataattgat | 1860 |
| tttggatttg cacggctaaa gccaccggat aatcagcccc tgaagactcc atgcttcacc | 1920 |
| cttcattatg ccgccccaga gctcttgaat cagaacggct acgatgagtc ctgtgacctg | 1980 |
| tggagcttgg gcgtcatttt gtacacaatg ttgtcaggac aggttcccctt ccaatctcat | 2040 |

-continued

```
gaccgaagtt tgacgtgtac cagcgcggtg gaaatcatga agaaaattaa aaagggagat    2100
ttctcctttg aaggagaagc ctggaagaat gtatcccaag aggctaaaga tttgatccaa    2160
ggacttctca cagtagatcc aaacaaaagg cttaaaatgt ctggcttgag gtacaatgaa    2220
tggctacaag atggaagtca gctgtcctcc aatcctctga tgactccgga tattctagga    2280
tcttccggag ctgccgtgca tacctgtgtg aaagcaacct tccacgcctt taacaaatac    2340
aagagagagg ggttttgcct tcagaatgtt gataaggccc ctttggctaa gagaagaaaa    2400
atgaaaaaga ctagcaccag taccgagacg cgcagcagtt ccagtgagag ttcccattct    2460
tcttcctctc attctcacgg taaaactaca cccaccaaga cactgcagcc cagcaatcct    2520
gccgacagca ataacccgga gaccctcttc cagttctcgg actcagtagc ttaggcatgg    2580
taggagtgta tcagtgatcc attgcacctt tattccctca gcatatgcct gaggcgatct    2640
tttatgcttt taaaaatgtt tcccgttggt ctcattggaa tctgcctcct aatgattttt    2700
tttcaggaaa acctgtttgg ttatcctcat tcaaaagcac tggacagaga atgttactgt    2760
gaatagagca catattactc tttttagcaa cctagcatga tgccaacaag actattttg    2820 aaagagcaaa ggttcctgta aatttaatta gggctagatt tgagctgctt gtaagtcaca    2880
ggttttccag atgtctgcca acaagaaatg actcatactg tgatgatacc ttttgctttg    2940
ccttgtggac aatgtgggtt tttgaaattt gcacccttca aacaatgatt tatcagagaa    3000
aggggtctgt tttcaaaaaa gattctgtaa tgaattttat gtgtggcata tacttatttc    3060
ttgagagaag attttaactt attgttttta ttttatggtt acatatgatg ataacctgct    3120
attattaaac t                                                        3131
```

<210> SEQ ID NO 11
<211> LENGTH: 2116
<212> TYPE: DNA
<213> ORGANISM: Homo sapiens

<400> SEQUENCE: 11

```
accgaagcca acctgaccgg gcacgaggag aaggtgagcg tggagaactt cgagctgctc      60
aaggtgctgg gcacgggagc ctacggcaag gtgttcctgg tgcggaaggc gggcgggcac     120
gacgcgggga gctgtacgc catgaaggtg ctgcgcaagg cggcgctggt gcagcgcgcc     180
aagacgcaag agcacacgcg caccgagcgc tcggtgctgg agctggtgcg ccaggcgccc     240
ttcctggtca cgctgcacta cgcttttccag acggatgcca agctgcacct catcctggac     300
tatgtgagcg gcgggagat gttcacccac ctctaccagc gccagtactt caaggaggct     360
gaggtgcgcg tgtatggggg tgagatcgtg ctgccctgg aacacctgca caagctcggc     420
atcatttacc gagacctgaa actggagaat gtgctgctgg actccgaggg ccacattgtc     480
ctcacggact tcgggctgag caaggagttc ctgacggagg agaaagagcg gaccttctcc     540
ttctgtggca ccatcgagta catggccccc gaaatcatcc gtagcaagac ggggcatggc     600
aaggctgtgg actggtggag cctgggcatc ttgctcttcg agctgctgac ggggggcctcg     660 cccttcaccc tggagggcga gaggaacacg caggctgagg tgtctcgacg gatcctgaag     720
tgctcccctc ccttcccccc tcggatcggg cccgtggcgc aggacctgct gcagcggctg     780 cttttgtaagg atcctaagaa gcgattgggc gcggggcccc aggggcaca agaagtccgg     840 aaccatccct tcttccaggg cctcgattgg gtggctctgg ctgccaggaa gattccagcc     900
ccattccggc cccaaatccg ctcagagctg gatgtgggca actttgcgga ggaattcact     960
cggctggagc ctgtctactc accccctggc agccccccac ctggggaccc ccgaatcttt    1020
```

-continued

| | |
|---|---|
| cagggatact cctttgtggc accctccatt ctctttgacc acaacaacgc ggtgatgacc | 1080 |
| gatgggctgg aagcgcctgg tgctggagac cggccaggtc gggcagcggt ggccaggagc | 1140 |
| gctatgatgc agcagtacga gctggacctg cgggagcctg cgctgggcca gggcagcttt | 1200 |
| tctgtgtgtc gccgctgccg ccagcgccag agcggccagg agttcgcagt caagatcctc | 1260 |
| agtcgcaggc tggaggcgaa cacgcagcgc gaagtggctg ccctgcgcct gtgccagtca | 1320 |
| caccccaacg tggtgaatct gcacgaggtg catcacgacc agctgcacac gtacctggtc | 1380 |
| ctggagctgc tgcggggcgg ggagctgctg gagcacatcc gcaagaagcg gcacttcagc | 1440 |
| gagtcggaag caagccagat cctgcgcagc ctcgtgtcgg ccgtgagctt catgcacgag | 1500 |
| gaggcgggcg tggtgcaccg cgacctcaag ccggagaaca tcctgtacgc cgacgacacg | 1560 |
| cccgggcccc cggtgaaaat catcgacttc ggttcgcgc ggttgcggcc gcagagtccc | 1620 |
| ggggtgccca tgcagacgcc ctgcttcacg ctgcagtacg ctgcccccga gctgctggcg | 1680 |
| cagcagggct acgacgagtc ctgcgacctc tggagcctgg gcgtcattct gtacatgatg | 1740 |
| ctgtcggggc aggtccccct tccaggggcc tctggccagg gcgggcagag ccaggcggcc | 1800 |
| gagatcatgt gcaaaatccg cgaggggcgc ttctcccttg acggggaggc ctggcagggt | 1860 |
| gtatccgagg aagccaagga gctggtccga gggctcctga ccgtggaccc cgccaagcgg | 1920 |
| ctgaagctcg agggactgcg gggcagctcg tggctgcagg acggcagcgc gcgctcctcg | 1980 |
| cccccgctcc ggacgcccga cgtgctcgag tcctctgggc ccgcagtgcg ctcgggtctc | 2040 |
| aacgccacct tcatggcatt caaccggggc aagcgggagg gcttcttcct gaagagcgtg | 2100 |
| gagaatgcac ccctca | 2116 |

<210> SEQ ID NO 12
<211> LENGTH: 2134
<212> TYPE: DNA
<213> ORGANISM: Homo sapiens

<400> SEQUENCE: 12

| | |
|---|---|
| accgaagcca acctgaccgg gcacgaggag aaggtgagcg tggagaactt cgagctgctc | 60 |
| aaggtgctgg gcacgggagc ctacggcaag gtgttcctgg tgcggaaggc gggcgggcac | 120 |
| gacgcgggga gctgtacgc catgaaggtg ctgcgcaagg cggcgctggt gcagcgcgcc | 180 |
| aagacgcaag agcacacgcg caccgagcgc tcggtgctgg agctggtgcg ccaggcgccc | 240 |
| ttcctggtca cgctgcacta cgctttccag acggatgcca agctgcacct catcctggac | 300 |
| tatgtgagcg gcggggagat gttcacccac ctctaccagc gccagtactt caaggaggct | 360 |
| gaggtgcgcg tgtatggggg tgagatcgtg ctggccctgg aacacctgca caagctcggc | 420 |
| atcatttacc gagacctgaa actggagaat gtgctgctga ctccgagggg ccacattgtc | 480 |
| ctcacggact tcgggctgag caaggagttc ctgacggagg agaaagagcg gaccttctcc | 540 |
| ttctgtggca ccatcgagta catggcccc gaaatcatcc gtagcaagac ggggcatggc | 600 |
| aaggctgtgg actggtggag cctgggcatc ttgctcttcg agctgctgac ggggggcctcg | 660 |
| cccttcaccc tggagggcga gaggaacacg caggctgagg tgtctcgacg gatcctgaag | 720 |
| tgctccccctc ccttcccccc tcggatcggg cccgtggcgc aggacctgct gcagcggctg | 780 |
| ctttgtaagg atcctaagaa gcgattgggc gcggggcccc aggggcaca agaagtccgg | 840 |
| aaccatccct tcttccaggg cctcgattgg gtggctctgg ctgccaggaa gattccagcc | 900 |
| ccattccggc cccaaatccg ctcagagctg gatgtgggca actttgcgga ggaattcact | 960 |
| cggctggagc ctgtctactc accccctggc agccccccac ctggggaccc ccgaatctt | 1020 |

| | |
|---|---|
| caggaatact cctttgtggc accctccatt ctctttgacc acaacaacgc ggtgatgacc | 1080 |
| gatgggctgg aagcgcctgg tgctggagac cggccaggtc gggcagcggt ggccaggagc | 1140 |
| gctatgatgc aggactcgcc cttcttccag cagtacgagc tggacctgcg ggagcctgcg | 1200 |
| ctgggccagg gcagctttc tgtgtgtcgc cgctgccgcc agcgccagag cggccaggag | 1260 |
| ttcgcagtca agatcctcag tcgcaggctg gaggcgaaca cgcagcgcga agtggctgcc | 1320 |
| ctgcgcctgt gccagtcaca ccccaacgtg gtgaatctgc acgaggtgca tcacgaccag | 1380 |
| ctgcacacgt acctggtcct ggagctgctg cggggcgggg agctgctgga gcacatccgc | 1440 |
| aagaagcggc acttcagcga gtcggaagca agccagatcc tgcgcagcct cgtgtcggcc | 1500 |
| gtgagcttca tgcacgagga ggcgggcgtg gtgcaccgcg acctcaagcc ggagaacatc | 1560 |
| ctgtacgccg acgacacgcc cggggccccg gtgaaaatca tcgacttcgg gttcgcgcgg | 1620 |
| ttgcggccgc agagtcccgg ggtgcccatg cagacgccct gcttcacgct gcagtacgct | 1680 |
| gcccccgagc tgctggcgca gcagggctac gacgagtcct cgacctctg agcctgggc | 1740 |
| gtcattctgt acatgatgct gtcggggcag gtccccttcc aggggcctc tggccagggc | 1800 |
| gggcagagcc aggcggccga gatcatgtgc aaaatccgcg aggggcgctt ctcccttgac | 1860 |
| ggggaggcct ggcagggtgt atccgaggaa gccaaggagc tggtccgagg gctcctgacc | 1920 |
| gtggaccccg ccaagcggct gaagctcgag ggactgcggg gcagctcgtg gctgcaggac | 1980 |
| ggcagcgcgc gctcctcgcc cccgctccgg acgcccgacg tgctcgagtc ctctgggccc | 2040 |
| gcagtgcgct cgggtctcaa cgccaccttc atggcattca accggggcaa gcgggagggc | 2100 |
| ttcttcctga agagcgtgga gaatgcaccc ctca | 2134 |

<210> SEQ ID NO 13
<211> LENGTH: 2222
<212> TYPE: DNA
<213> ORGANISM: Mus musculus

<400> SEQUENCE: 13

| | |
|---|---|
| cacgcgtccg agacgagga tgaggacgag ggctgcgccg tggagctgca gatcaccgaa | 60 |
| gccaacctca ccgggcatga ggagaaggtg agcgtggaga acttcgcgct gctcaaggtg | 120 |
| ctgggcacgg gagcctatgg gaaggtgttc ctggtgcgga agacgggtgg gcacgacgcg | 180 |
| ggcaagctct atgccatgaa ggtgctacgc aaggcggcgt tggtgcagcg cgcgaagaca | 240 |
| caggagcata cccgcaccga acgctcggtg ctggagctgg ttcgccaagc acccttcctg | 300 |
| gtcacactgc actacgcctt ccagacggat gccaagctgc acctcatcct ggactacgtg | 360 |
| agcggtggtg agatgttcac tcacctctac cagcgccagt acttcaagga ggctgaggtt | 420 |
| cgagtgtatg ggggcgagat tgtgctggcc ctggaacacc tgcacaagct gggtatcatc | 480 |
| taccgggacc tgaagctgga gaacgtctta cttgactcag aaggtcacat cgtccttaca | 540 |
| gactttgggc tgagcaagga gttcctgacg gaggagaaag agcggacctt ctccttctgt | 600 |
| ggcacaatcg agtacatggc tcccgaaatc atccgaagca aggctggaca tggcaaggct | 660 |
| gtggactggt ggagctgggg tatcctgctc ttcgagctgc tgacagggc ctcacccttc | 720 |
| acactggagg gagagaggaa cactcaggct gaggtgtccc gacggatctt gaagtgctcc | 780 |
| cctcccttcc ctctccggat tgggcctgtg gcacaggacc tgctacagcg gctgctgtgc | 840 |
| aaggaccta agaagaggtt gggcgcaggt ccccagggtg cgcaggaagt caagagtcac | 900 |
| cccttcttca gggtctggac tggtgggct ctggctgcca gaaagatccc agccccattc | 960 |
| cggccccaga tccgctcaga gctggatgtg gggaattttg cggaggaatt cacccggctg | 1020 |

```
gagcccgtct actccctgc aggcagccct ccacctgggg accctcggat ctttcaggga    1080
tactccttcg tggctccgtc catcctcttt gaccacaaca atgcagtgat ggctgatgta    1140
ctgcaggcac cgggtgccgg atacaggccc ggcagggcag cagttgccag gagtgccatg    1200
atgcaggact cgcctttctt ccagcagtac gaactggacc ttcgggagcc agcgctgggg    1260
cagggcagct tctctgtgtg tcggagatgt aggcagcgcc agagcggcca ggagtttgct    1320
gtcaagatcc tcagccgcag gctggaggag aacactcagc gagaggtggc tgctcttcgc    1380
ctgtgccagt cacaccccaa cgtggtgaat ctgcatgagg tgcttcatga ccagctacac    1440
acttacctgg tcctggagtt gctgcgaggc ggagagctat tggaacacat ccgcaagaag    1500
cggctcttca gcgagtcgga ggccagccag atccttcgga gcctggtttc ggccgtgagc    1560
ttcatgcacg aggaggcagg cgtggtgcac cgcgacctga acccgagaa catcttgtac    1620 gcggacgaca ctcccggggc cccggtgaag atcatcgact tcgggttcgc gcgactgcgg    1680
ccccagagcc cggcagagcc catgcagact ccttgcttca cactgcagta cgctgcaccc    1740
gagctgctgg cacagcaggg ctacgatgag tcctgcgatc tatggagcct gggtgtcatt    1800
ctgtacatga tgctgtctgg ccaggttccc ttccaagggg cctccggcca gggtggacag    1860
agtcaggcag ctgagatcat gtgcaagatc cgtgaagggc gcttctccct ggacggggaa    1920
gcctggcaag gtgtgtcgga ggaagccaag gagctggtcc gagggctact acagtcgac    1980 cccgccaagc ggctgaagct ggagggctg cgtagcagct cgtggcttca ggacggcagc    2040
gcgcgctcct cgcccccgct ccgcacgccg gatgtgctgg agtcctctgg ccagctgtg    2100 cgttccgggc tcaatgccac tttcatggcg ttcaaccgag gcaagcgcga gggcttcttt    2160
ctcaagagtg tagagaatgc gcctctggcc aagaggcgca agcagaagct ccggagcgcg    2220
gc                                                                   2222
```

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: petide

<400> SEQUENCE: 14

Leu Thr Val Lys His Glu Leu Arg Thr Ala Asn Leu Thr Gly His Ala
1               5                   10                  15

Glu Lys Val

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence:peptide

<400> SEQUENCE: 15

Phe Lys Arg Asn Ala Ala Val Ile Asp Pro Leu Gln Phe His Met Gly
1               5                   10                  15

Val Glu Arg

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: peptide

```
<400> SEQUENCE: 16

Gly Arg Pro Arg Thr Ser Ser Phe Ala Glu Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 17

Lys Lys Arg Asn Arg Thr Leu Ser Val Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 18

Glu Ile Leu Ser Arg Arg Pro Ser Tyr Arg Lys
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence:peptide

<400> SEQUENCE: 19

Lys Ala Thr Phe His Ala Phe Asn Lys Tyr Lys Arg Glu Gly Phe Cys
1               5                   10                  15

Leu Gln Asn

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence:peptide

<400> SEQUENCE: 20

Lys Glu Asp Lys Glu Arg Trp Glu Asp Val Lys Glu Glu Met Thr Ser
1               5                   10                  15

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence:peptide

<400> SEQUENCE: 21

Arg Asn Gln Ser Pro Val Leu Glu Pro Val Gly Arg Ser Thr Leu Ala
1               5                   10                  15

Gln Arg Arg Gly Ile Lys Lys
                20
```

```
<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence:pcr primer

<400> SEQUENCE: 22
gagatactgc caccatggac tacaaggacg acgatgacaa ggaggaggag ggtggcagca      60
gcggcg                                                                66

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: pcr primer

<400> SEQUENCE: 23
ggatccattt ctgtgaactc ttctg                                           25

<210> SEQ ID NO 24
<211> LENGTH: 19
<212> TYPE: PRT
<213> ORGANISM: Artificial Sequence
<220> FEATURE:
<223> OTHER INFORMATION: Desription of Artificial Sequence: peptide

<400> SEQUENCE: 24

Arg Ala Pro Val Ala Ser Lys Gly Ala Pro Arg Arg Ala Asn Pro Leu
1               5                   10                  15

Pro Pro Ser

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: peptide

<400> SEQUENCE: 25

Met Thr Ser Ala Leu Ala Thr Met Arg Val Asp Tyr Glu Gln Ile Lys
1               5                   10                  15

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:pcr primer

<400> SEQUENCE: 26
gttggataca ggccagactt tgttg                                           25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:pcr primer

<400> SEQUENCE: 27
gagggtaggc tggcctatag gct                                             23
```

```
<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:pcr primer

<400> SEQUENCE: 28
aagctctcca cctcaatgga cag                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:pcr primer

<400> SEQUENCE: 29
ctcaaactcc actttgctct tga                                              23

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:pcr primer

<400> SEQUENCE: 30
cagcaaatcc ttgctgttcc                                                  20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:pcr primer

<400> SEQUENCE: 31
tgggcaaaga atgcaaacat c                                                21

<210> SEQ ID NO 32
<211> LENGTH: 285
<212> TYPE: PRT
<213> ORGANISM: Homo sapiens

<400> SEQUENCE: 32

Ile Glu Asn Phe Glu Leu Leu Lys Val Leu Gly Thr Gly Ala Tyr Gly
1               5                   10                  15

Lys Val Phe Leu Val Arg Lys Ile Ser Gly His Asp Thr Gly Lys Leu
            20                  25                  30

Tyr Ala Met Lys Val Leu Lys Lys Ala Thr Ile Val Gln Lys Ala Lys
        35                  40                  45

Thr Thr Glu His Thr Arg Thr Glu Arg Gln Val Leu Glu His Ile Arg
    50                  55                  60

Gln Ser Pro Phe Leu Val Thr Leu His Tyr Ala Phe Gln Thr Glu Thr
65                  70                  75                  80

Lys Leu His Leu Ile Leu Asp Tyr Ile Asn Gly Gly Glu Leu Phe Thr
                85                  90                  95

His Leu Ser Gln Arg Glu Arg Phe Thr Glu His Glu Val Gln Ile Tyr
            100                 105                 110

Val Gly Glu Ile Val Leu Ala Leu Glu His Leu His Lys Leu Gly Ile
        115                 120                 125
```

```
Ile Tyr Arg Asp Ile Lys Leu Glu Asn Ile Leu Leu Asp Ser Asn Gly
    130                 135                 140

His Val Val Leu Thr Asp Phe Gly Leu Ser Lys Glu Phe Val Ala Asp
145                 150                 155                 160

Glu Thr Glu Arg Ala Tyr Ser Phe Cys Gly Thr Ile Glu Tyr Met Ala
                165                 170                 175

Pro Asp Ile Val Arg Gly Gly Asp Ser Gly His Asp Lys Ala Val Asp
                180                 185                 190

Trp Trp Ser Leu Gly Val Leu Met Tyr Glu Leu Leu Thr Gly Ala Ser
            195                 200                 205

Pro Phe Thr Val Asp Gly Glu Lys Asn Ser Gln Ala Glu Ile Ser Arg
            210                 215                 220

Arg Ile Leu Lys Ser Glu Pro Pro Tyr Pro Gln Glu Met Ser Ala Leu
225                 230                 235                 240

Ala Lys Asp Leu Ile Gln Arg Leu Leu Met Lys Asp Pro Lys Lys Arg
                245                 250                 255

Leu Gly Cys Gly Pro Arg Asp Ala Asp Glu Ile Lys Glu His Leu Phe
                260                 265                 270

Phe Gln Lys Ile Asn Trp Asp Asp Leu Ala Ala Lys Lys
                275                 280                 285

<210> SEQ ID NO 33
<211> LENGTH: 282
<212> TYPE: PRT
<213> ORGANISM: Homo sapiens

<400> SEQUENCE: 33

Tyr Asp Leu Asp Leu Lys Asp Lys Pro Leu Gly Glu Gly Ser Phe Ser
1               5                   10                  15

Ile Cys Arg Lys Cys Val His Lys Lys Ser Asn Gln Ala Phe Ala Val
                20                  25                  30

Lys Ile Ile Ser Lys Arg Met Glu Ala Asn Thr Gln Lys Glu Ile Thr
            35                  40                  45

Ala Leu Lys Leu Cys Glu Gly His Pro Asn Ile Val Lys Leu His Glu
        50                  55                  60

Val Phe His Asp Gln Leu His Thr Phe Leu Val Met Glu Leu Leu Asn
65                  70                  75                  80

Gly Gly Glu Leu Phe Glu Arg Ile Lys Lys Lys His Phe Ser Glu
                85                  90                  95

Thr Glu Ala Ser Tyr Ile Met Arg Lys Leu Val Ser Ala Val Ser His
                100                 105                 110

Met His Asp Val Gly Val Val His Arg Asp Leu Lys Pro Glu Asn Leu
            115                 120                 125

Leu Phe Thr Asp Glu Asn Asp Asn Leu Glu Ile Lys Ile Ile Asp Phe
130                 135                 140

Gly Phe Ala Arg Leu Lys Pro Pro Asp Asn Gln Pro Leu Lys Thr Pro
145                 150                 155                 160

Cys Phe Thr Leu His Tyr Ala Ala Pro Glu Leu Leu Asn Gln Asn Gly
                165                 170                 175

Tyr Asp Glu Ser Cys Asp Leu Trp Ser Leu Gly Val Ile Leu Tyr Thr
                180                 185                 190

Met Leu Ser Gly Gln Val Pro Phe Gln Ser His Asp Arg Ser Leu Thr
            195                 200                 205

Cys Thr Ser Ala Val Glu Ile Met Lys Lys Ile Lys Lys Gly Asp Phe
210                 215                 220
```

-continued

Ser Phe Glu Gly Glu Ala Trp Lys Asn Val Ser Gln Glu Ala Lys Asp
225                 230                 235                 240

Leu Ile Gln Gly Leu Leu Thr Val Asp Pro Asn Lys Arg Leu Lys Met
            245                 250                 255

Ser Gly Leu Arg Tyr Asn Glu Trp Leu Gln Asp Gly Ser Gln Leu Ser
            260                 265                 270

Ser Asn Pro Leu Met Thr Pro Asp Ile Leu
        275                 280

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence:peptide

<400> SEQUENCE: 34

Lys Lys Arg Asn Lys Thr Leu Ser Val Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 35

Lys Lys Leu Asn Arg Thr Leu Ser Val Ala
1               5                   10

<210> SEQ ID NO 36
<211> LENGTH: 772
<212> TYPE: PRT
<213> ORGANISM: Homo sapiens

<400> SEQUENCE: 36

Met Gly Asp Glu Asp Asp Glu Ser Cys Ala Val Glu Leu Arg Ile
1               5                   10                  15

Thr Glu Ala Asn Leu Thr Gly His Glu Glu Lys Val Ser Val Glu Asn
            20                  25                  30

Phe Glu Leu Leu Lys Val Leu Gly Thr Gly Ala Tyr Gly Lys Val Phe
        35                  40                  45

Leu Val Arg Lys Ala Gly Gly His Asp Ala Gly Lys Leu Tyr Ala Met
    50                  55                  60

Lys Val Leu Arg Lys Ala Ala Leu Val Gln Arg Ala Lys Thr Gln Glu
65                  70                  75                  80

His Thr Arg Thr Glu Arg Ser Val Leu Glu Leu Val Arg Gln Ala Pro
                85                  90                  95

Phe Leu Val Thr Leu His Tyr Ala Phe Gln Thr Asp Ala Lys Leu His
            100                 105                 110

Leu Ile Leu Asp Tyr Val Ser Gly Gly Glu Met Phe Thr His Leu Tyr
        115                 120                 125

Gln Arg Gln Tyr Phe Lys Glu Ala Glu Val Arg Val Tyr Gly Gly Glu
    130                 135                 140

Ile Val Leu Ala Leu Glu His Leu His Lys Leu Gly Ile Ile Tyr Arg
145                 150                 155                 160

Asp Leu Lys Leu Glu Asn Val Leu Leu Asp Ser Glu Gly His Ile Val
                165                 170                 175

-continued

```
Leu Thr Asp Phe Gly Leu Ser Lys Glu Phe Leu Thr Glu Glu Lys Glu
            180                 185                 190
Arg Thr Phe Ser Phe Cys Gly Thr Ile Glu Tyr Met Ala Pro Glu Ile
        195                 200                 205
Ile Arg Ser Lys Thr Gly His Gly Lys Ala Val Asp Trp Trp Ser Leu
    210                 215                 220
Gly Ile Leu Leu Phe Glu Leu Leu Thr Gly Ala Ser Pro Phe Thr Leu
225                 230                 235                 240
Glu Gly Glu Arg Asn Thr Gln Ala Glu Val Ser Arg Arg Ile Leu Lys
                245                 250                 255
Cys Ser Pro Pro Phe Pro Pro Arg Ile Gly Pro Val Ala Gln Asp Leu
            260                 265                 270
Leu Gln Arg Leu Leu Cys Lys Asp Pro Lys Lys Arg Leu Gly Ala Gly
        275                 280                 285
Pro Gln Gly Ala Gln Glu Val Arg Asn His Pro Phe Phe Gln Gly Leu
    290                 295                 300
Asp Trp Val Ala Leu Ala Ala Arg Lys Ile Pro Ala Pro Phe Arg Pro
305                 310                 315                 320
Gln Ile Arg Ser Glu Leu Asp Val Gly Asn Phe Ala Glu Glu Phe Thr
                325                 330                 335
Arg Leu Glu Pro Val Tyr Ser Pro Pro Gly Ser Pro Pro Gly Asp
            340                 345                 350
Pro Arg Ile Phe Gln Gly Tyr Ser Phe Val Ala Pro Ser Ile Leu Phe
        355                 360                 365
Asp His Asn Asn Ala Val Met Thr Asp Gly Leu Glu Ala Pro Gly Ala
    370                 375                 380
Gly Asp Arg Pro Gly Arg Ala Ala Val Ala Arg Ser Ala Met Met Gln
385                 390                 395                 400
Asp Ser Pro Phe Phe Gln Gln Tyr Glu Leu Asp Leu Arg Glu Pro Ala
                405                 410                 415
Leu Gly Gln Gly Ser Phe Ser Val Cys Arg Arg Cys Arg Gln Arg Gln
            420                 425                 430
Ser Gly Gln Glu Phe Ala Val Lys Ile Leu Ser Arg Arg Leu Glu Ala
        435                 440                 445
Asn Thr Gln Arg Glu Val Ala Ala Leu Arg Leu Cys Gln Ser His Pro
    450                 455                 460
Asn Val Val Asn Leu His Glu Val His His Asp Gln Leu His Thr Tyr
465                 470                 475                 480
Leu Val Leu Glu Leu Leu Arg Gly Gly Glu Leu Leu Glu His Ile Arg
                485                 490                 495
Lys Lys Arg His Phe Ser Glu Ser Glu Ala Ser Gln Ile Leu Arg Ser
            500                 505                 510
Leu Val Ser Ala Val Ser Phe Met His Glu Glu Ala Gly Val Val His
        515                 520                 525
Arg Asp Leu Lys Pro Glu Asn Ile Leu Tyr Ala Asp Thr Pro Gly
    530                 535                 540
Ala Pro Val Lys Ile Ile Asp Phe Gly Phe Ala Arg Leu Arg Pro Gln
545                 550                 555                 560
Ser Pro Gly Val Pro Met Gln Thr Pro Cys Phe Thr Leu Gln Tyr Ala
                565                 570                 575
Ala Pro Glu Leu Leu Ala Gln Gln Gly Tyr Asp Glu Ser Cys Asp Leu
            580                 585                 590
```

-continued

```
Trp Ser Leu Gly Val Ile Leu Tyr Met Met Leu Ser Gly Gln Val Pro
            595                 600                 605
Phe Gln Gly Ala Ser Gln Gly Gly Gln Ser Gln Ala Ala Glu Ile
        610                 615                 620
Met Cys Lys Ile Arg Glu Gly Arg Phe Ser Leu Asp Gly Glu Ala Trp
625                 630                 635                 640
Gln Gly Val Ser Glu Glu Ala Lys Glu Leu Val Arg Gly Leu Leu Thr
                645                 650                 655
Val Asp Pro Ala Lys Arg Leu Lys Leu Glu Gly Leu Arg Gly Ser Ser
            660                 665                 670
Trp Leu Gln Asp Gly Ser Ala Arg Ser Ser Pro Pro Leu Arg Thr Pro
        675                 680                 685
Asp Val Leu Glu Ser Ser Gly Pro Ala Val Arg Ser Gly Leu Asn Ala
    690                 695                 700
Thr Phe Met Ala Phe Asn Arg Gly Lys Arg Glu Gly Phe Phe Leu Lys
705                 710                 715                 720
Ser Val Glu Asn Ala Pro Leu Ala Lys Arg Lys Gln Lys Leu Arg
                725                 730                 735
Ser Ala Thr Ala Ser Arg Arg Gly Ser Pro Ala Pro Ala Asn Pro Gly
            740                 745                 750
Arg Ala Pro Val Ala Ser Lys Gly Ala Pro Arg Ala Asn Gly Pro
        755                 760                 765
Leu Pro Pro Ser
    770
```

<210> SEQ ID NO 37
<211> LENGTH: 3131
<212> TYPE: DNA
<213> ORGANISM: Homo sapiens

<400> SEQUENCE: 37

```
ggagccgcca tgtaaccggc gccgcccgga gcccgagccg cgcgggcccc agcgacccgc      60
ccgccatggg ggacgaggac gacgatgaga gctgcgccgt ggagctgcgg atcacagaag     120
ccaacctgac cgggcacgag gagaaggtga gcgtggagaa cttcgagctg ctcaaggtgc     180
tgggcacggg agcctacggc aaggtgttcc tggtgcggaa ggcgggcggg cacgacgcgg     240
ggaagctgta cgccatgaag gtgctgcgca aggcggcgct ggtgcagcgc gccaagacgc     300
aggagcacac gcgcaccgag cgctcggtgc tggagctggt gcgccaggcg cccttcctgg     360
tcacgctgca ctacgctttc cagacggatg ccaagctgca cctcatcctg gactatgtga     420
gcggcgggga gatgttcacc cacctctacc agcgccagta cttcaaggag ctgaggtgc      480
gcgtgtatgg gggtgagatc gtgctggccc tggaacacct gcacaagctc ggcatcattt     540
accgagacct gaaactggag aatgtgctgc tggactccga gggccacatt gtcctcacgg     600
acttcgggct gagcaaggag ttcctgacgg aggagaaaga gcggaccttc tccttctgtg     660
gcaccatcga gtacatggcc ccgaaatca tccgtagcaa gacggggcat ggcaaggctg     720
tggactggtg gagcctgggc atcttgctct tcgagctgct gacgggggcc tcgcccttca     780
ccctggaggg cgagaggaac acgcaggctg aggtgtctcg acggatcctg aagtgctccc     840
ctccccttcc ccctcggatc gggccgtgg cgcaggacct gctgcagcgg ctgctttgta     900
aggatcctaa gaagcgattg ggcgcggggc ccagggggc acaagaagtc cggaaccatc     960
ccttcttcca gggcctcgat tgggtggctc tggctgccag gaagattcca gccccattcc    1020
ggccccaaat ccgctcagag ctggatgtgg gcaactttgc ggaggaattc actcggctgg    1080
```

-continued

```
agcctgtcta ctcaccccct ggcagcccccc cacctgggga cccccgaatc tttcagggat   1140
actcctttgt ggcaccctcc attctctttg accacaacaa cgcggtgatg accgatgggc   1200
tggaagcgcc tggtgctgga gaccggccag gtcgggcagc ggtggccagg agcgctatga   1260
tgcaggactc gcccttcttc cagcagtacg agctggacct gcgggagcct gcgctgggcc   1320
agggcagctt ttctgtgtgt cgccgctgcc gccagcgcca gagcggccag gagttcgcag   1380
tcaagatcct cagtcgcagg ctggaggcga acacgcagcg cgaagtggct gccctgcgcc   1440
tgtgccagtc acacccccaac gtggtgaatc tgcacgaggt gcatcacgac cagctgcaca   1500
cgtacctggt cctggagctg ctgcggggcg ggagctgct ggagcacatc cgcaagaagc   1560
ggcacttcag cgagtcggaa gcaagccaga tcctgcgcag cctcgtgtcg gccgtgagct   1620
tcatgcacga ggaggcgggc gtggtgcacc gcgacctcaa gccggagaac atcctgtacg   1680
ccgacgacac gcccggggcc ccggtgaaaa tcatcgactt cgggttcgcg cggttgcggc   1740
cgcagagtcc cggggtgccc atgcagacgc cctgcttcac gctgcagtac gctgcccccg   1800
agctgctggc gcagcagggc tacgacgagt cctgcgacct ctggagcctg gcgtcattc    1860
tgtacatgat gctgtcgggg caggtcccct tccagggggc ctctggccag ggcgggcaga   1920
gccaggcggc cgagatcatg tgcaaaatcc gcgaggggcg cttctccctt gacggggagg   1980
cctggcaggg tgtatccgag gaagccaagg agctggtccg agggctcctg accgtggacc   2040
ccgccaagcg gctgaagctc gagggactgc ggggcagctc gtggctgcag gacggcagcg   2100
cgcgctcctc gccccccgctc cggacgcccc acgtgctcga gtcctctggg cccgcagtgc   2160
gctcgggtct caacgccacc ttcatggcat tcaaccgggg caagcgggag ggcttcttcc   2220
tgaagagcgt ggagaatgca cccctggcca agcggcggaa gcagaagctg cggagcgcca   2280
ccgcctcccg ccgggggctcc cctgcaccag ccaacccggg ccgagccccc gtcgcctcca   2340
aaggggccccc ccgccgagcc aacggccccc tgccccccctc ctaatcccca ccactgtgac   2400
cccctccccct cataggggct gtgacctggg agcccggctc actccggag gcctctgcct   2460
gcggctgacc tgatccccaa gggactgtcc ttcctctcc tacccccaccc cactcccaga   2520
cagagcagaa gtatttttat aagcagagaa ttttttatgt cttaccagat agagttgcag   2580
ggaagggggg gcctgctggg gagtgggtt tggggggccc tctcccagga cactgcctct   2640
tctgggcaga aggcccctcc aggggggactg ctccaacagg aaagagcccc tcccccactt   2700
ctaagcactg agttaggagt gctaactcct aaactgggac cccctaccct gttctcccct   2760
gaggccccgt tcctgggagg ggcacccctc aactgtcact ttatggactg tctgtgcaat   2820
tacgtccacc aaagacccgt gttggggta ctgaaggaga ggccctgggg gaccctctga   2880
agcatttctg cctcacttta tgtcatctgc ttctcccctg ttggggctaa ggaaggagat   2940
aggtggctcc taaaagagga ggccatcttc tcacccaccc cttcctctttt ggcacagcta   3000
ctcctggctg ggggtggggc cttggggggtc tgggctgggc atccatggtc actgcctcag   3060
cccagccagg ctgtgccttt gactttaaaa taaaagtcca cccagtgctg tgtgtggcaa   3120
aaaaaaaaaaa a   3131
```

<210> SEQ ID NO 38
<211> LENGTH: 735
<212> TYPE: PRT
<213> ORGANISM: Homo sapiens -continued

<400> SEQUENCE: 38

```
Met Pro Leu Ala Gln Leu Lys Glu Pro Trp Pro Leu Met Glu Leu Val
1               5                   10                  15

Pro Leu Asp Pro Glu Asn Gly Gln Thr Ser Gly Glu Glu Ala Gly Leu
            20                  25                  30

Gln Pro Ser Lys Asp Glu Gly Val Leu Lys Glu Ile Ser Ile Thr His
        35                  40                  45

His Val Lys Ala Gly Ser Glu Lys Ala Asp Pro Ser His Phe Glu Leu
    50                  55                  60

Leu Lys Val Leu Gly Gln Gly Ser Phe Gly Lys Val Phe Leu Val Arg
65                  70                  75                  80

Lys Val Thr Arg Pro Asp Ser Gly His Leu Tyr Ala Met Lys Val Leu
                85                  90                  95

Lys Lys Ala Thr Leu Lys Val Arg Asp Arg Val Arg Thr Lys Met Glu
            100                 105                 110

Arg Asp Ile Leu Ala Asp Val Asn His Pro Phe Val Val Lys Leu His
        115                 120                 125

Tyr Ala Phe Gln Thr Glu Gly Lys Leu Tyr Leu Ile Leu Asp Phe Leu
    130                 135                 140

Arg Gly Gly Asp Leu Phe Thr Arg Leu Ser Lys Glu Val Met Phe Thr
145                 150                 155                 160

Glu Glu Asp Val Lys Phe Tyr Leu Ala Glu Leu Ala Leu Gly Leu Asp
                165                 170                 175

His Leu His Ser Leu Gly Ile Ile Tyr Arg Asp Leu Lys Pro Glu Asn
            180                 185                 190

Ile Leu Leu Asp Glu Glu Gly His Ile Lys Leu Thr Asp Phe Gly Leu
        195                 200                 205

Ser Lys Glu Ala Ile Asp His Glu Lys Lys Ala Tyr Ser Phe Cys Gly
    210                 215                 220

Thr Val Glu Tyr Met Ala Pro Glu Val Val Asn Arg Gln Gly His Ser
225                 230                 235                 240

His Ser Ala Asp Trp Trp Ser Tyr Gly Val Leu Met Phe Glu Met Leu
                245                 250                 255

Thr Gly Ser Leu Pro Arg Gln Gly Lys Asp Arg Lys Glu Thr Met Thr
            260                 265                 270

Leu Ile Leu Lys Ala Lys Leu Gly Met Pro Gln Phe Leu Ser Thr Glu
        275                 280                 285

Ala Gln Ser Leu Leu Arg Ala Leu Phe Lys Arg Asn Pro Ala Asn Arg
    290                 295                 300

Leu Gly Ser Gly Pro Asp Gly Ala Glu Glu Ile Lys Arg His Val Phe
305                 310                 315                 320

Tyr Ser Thr Ile Asp Trp Asn Lys Leu Tyr Arg Arg Glu Ile Thr Pro
                325                 330                 335

Pro Phe Lys Pro Ala Val Ala Gln Pro Asp Asp Thr Phe Tyr Phe Asp
            340                 345                 350

Thr Glu Phe Thr Ser Arg Thr Pro Lys Asp Ser Pro Gly Ile Pro Pro
        355                 360                 365

Ser Ala Gly Ala His Gln Leu Phe Arg Gly Phe Ser Phe Val Ala Thr
    370                 375                 380

Gly Leu Met Glu Asp Asp Gly Lys Pro Arg Ala Pro Gln Ala Pro Leu
385                 390                 395                 400

His Ser Val Val Gln Gln Leu His Gly Lys Asn Leu Val Phe Ser Asp
                405                 410                 415
```

```
Gly Tyr Val Val Lys Glu Thr Ile Gly Val Gly Ser Tyr Ser Glu Cys
            420                 425                 430
Lys Arg Cys Val His Lys Ala Thr Asn Met Glu Tyr Ala Val Lys Val
            435                 440                 445
Ile Asp Lys Ser Lys Arg Asp Pro Ser Glu Ile Glu Ile Leu Leu
450                 455                 460
Arg Tyr Gly Gln His Pro Asn Ile Ile Thr Leu Lys Asp Val Tyr Asp
465                 470                 475                 480
Asp Gly Lys His Val Tyr Leu Val Thr Glu Leu Met Arg Gly Gly Glu
            485                 490                 495
Leu Leu Asp Lys Ile Leu Arg Gln Lys Phe Phe Ser Glu Arg Glu Ala
            500                 505                 510
Ser Phe Val Leu His Thr Ile Gly Lys Thr Val Glu Tyr Leu His Ser
            515                 520                 525
Gln Gly Val Val His Arg Asp Leu Lys Pro Ser Asn Ile Leu Tyr Val
            530                 535                 540
Asp Glu Ser Gly Asn Pro Glu Cys Leu Arg Ile Cys Asp Phe Gly Phe
545                 550                 555                 560
Ala Lys Gln Leu Arg Ala Glu Asn Gly Leu Leu Met Thr Pro Cys Tyr
            565                 570                 575
Thr Ala Asn Phe Val Ala Pro Glu Val Leu Lys Arg Gln Gly Tyr Asp
            580                 585                 590
Glu Gly Cys Asp Ile Trp Ser Leu Gly Ile Leu Leu Tyr Thr Met Leu
            595                 600                 605
Ala Gly Tyr Thr Pro Arg Ala Asn Gly Pro Ser Asp Thr Pro Glu Glu
            610                 615                 620
Ile Leu Thr Arg Ile Gly Ser Gly Lys Phe Thr Leu Ser Gly Gly Asn
625                 630                 635                 640
Trp Asn Thr Val Ser Glu Thr Ala Lys Asp Leu Val Ser Lys Met Leu
            645                 650                 655
His Val Asp Pro His Gln Arg Leu Thr Ala Lys Gln Val Leu Gln His
            660                 665                 670
Pro Trp Val Thr Gln Lys Asp Lys Leu Pro Gln Ala Gln Leu Ser His
            675                 680                 685
Gln Asp Leu Gln Leu Val Lys Gly Ala Met Ala Ala Thr Tyr Ser Ala
            690                 695                 700
Leu Asn Ser Ser Lys Pro Thr Pro Gln Leu Lys Pro Ile Glu Ser Ser
705                 710                 715                 720
Ile Leu Ala Gln Arg Arg Val Arg Lys Leu Pro Ser Thr Thr Leu
            725                 730                 735

<210> SEQ ID NO 39
<211> LENGTH: 740
<212> TYPE: PRT
<213> ORGANISM: Homo sapiens

<400> SEQUENCE: 39

Met Pro Leu Ala Gln Leu Ala Asp Pro Trp Gln Lys Met Ala Val Glu
1               5                   10                  15
Ser Pro Ser Asp Ser Ala Glu Asn Gly Gln Gln Ile Met Asp Glu Pro
            20                  25                  30
Met Gly Glu Glu Glu Ile Asn Pro Gln Thr Glu Glu Val Ser Ile Lys
            35                  40                  45
Glu Ile Ala Ile Thr His His Val Lys Glu Gly His Glu Lys Ala Asp
        50                  55                  60
```

-continued

```
Pro Ser Gln Phe Glu Leu Leu Lys Val Leu Gly Gln Ser Phe Gly
 65                  70                  75                  80

Lys Val Phe Leu Val Lys Lys Ile Ser Gly Ser Asp Ala Arg Gln Leu
                 85                  90                  95

Tyr Ala Met Lys Val Leu Lys Lys Ala Thr Leu Lys Val Arg Asp Arg
            100                 105                 110

Val Arg Thr Lys Met Glu Arg Asp Ile Leu Val Glu Val Asn His Pro
        115                 120                 125

Phe Ile Val Lys Leu His Tyr Ala Phe Gln Thr Glu Gly Lys Leu Tyr
    130                 135                 140

Leu Ile Leu Asp Phe Leu Arg Gly Gly Asp Leu Phe Thr Arg Leu Ser
145                 150                 155                 160

Lys Glu Val Met Phe Thr Glu Glu Asp Val Lys Phe Tyr Leu Ala Glu
                165                 170                 175

Leu Ala Leu Ala Leu Asp His Leu His Ser Leu Gly Ile Ile Tyr Arg
            180                 185                 190

Asp Leu Lys Pro Glu Asn Ile Leu Leu Asp Glu Glu Phe His Ile Lys
        195                 200                 205

Leu Thr Asp Phe Gly Leu Ser Lys Glu Ser Ile Asp His Glu Lys Lys
    210                 215                 220

Ala Tyr Ser Phe Cys Gly Thr Val Glu Tyr Met Ala Pro Glu Val Val
225                 230                 235                 240

Asn Arg Arg Gly His Thr Gln Ser Ala Asp Trp Trp Ser Phe Gly Val
                245                 250                 255

Leu Met Phe Glu Met Leu Thr Gly Thr Leu Pro Phe Gln Gly Lys Asp
            260                 265                 270

Arg Lys Glu Thr Met Thr Met Ile Leu Lys Ala Lys Leu Gly Met Pro
        275                 280                 285

Gln Phe Leu Ser Pro Glu Ala Gln Ser Leu Leu Arg Met Leu Phe Lys
    290                 295                 300

Arg Asn Pro Ala Asn Arg Leu Gly Ala Gly Pro Asp Gly Val Glu Glu
305                 310                 315                 320

Ile Lys Arg His Ser Phe Phe Ser Thr Ile Asp Trp Asn Lys Leu Tyr
                325                 330                 335

Arg Arg Glu Ile His Pro Pro Phe Lys Pro Ala Thr Gly Arg Pro Glu
            340                 345                 350

Asp Thr Phe Tyr Phe Asp Pro Glu Phe Thr Ala Lys Thr Pro Lys Asp
        355                 360                 365

Ser Pro Gly Ile Pro Pro Ser Ala Asn Ala His Gln Leu Phe Arg Gly
    370                 375                 380

Phe Ser Phe Val Ala Ile Thr Ser Asp Asp Glu Ser Gln Ala Met Gln
385                 390                 395                 400

Thr Val Gly Val His Ser Ile Val Gln Gln Leu His Arg Asn Ser Ile
                405                 410                 415

Gln Phe Thr Asp Gly Tyr Glu Val Lys Glu Asp Ile Gly Val Gly Ser
            420                 425                 430

Tyr Ser Val Cys Lys Arg Cys Ile His Lys Ala Thr Asn Met Glu Phe
        435                 440                 445

Ala Val Lys Ile Ile Asp Lys Ser Lys Arg Asp Pro Thr Glu Glu Ile
    450                 455                 460

Glu Ile Leu Leu Arg Tyr Gly Gln His Pro Asn Ile Ile Thr Leu Lys
465                 470                 475                 480
```

```
Asp Val Tyr Asp Asp Gly Lys Tyr Val Tyr Val Thr Glu Leu Met
                485                 490                 495

Lys Gly Gly Glu Leu Leu Asp Lys Ile Leu Arg Gln Lys Phe Phe Ser
            500                 505                 510

Glu Arg Glu Ala Ser Ala Val Leu Phe Thr Ile Thr Lys Thr Val Glu
            515                 520                 525

Tyr Leu His Ala Gln Gly Val Val His Arg Asp Leu Lys Pro Ser Asn
            530                 535                 540

Ile Leu Tyr Val Asp Glu Ser Gly Asn Pro Glu Ser Ile Arg Ile Cys
545                 550                 555                 560

Asp Phe Gly Phe Ala Lys Gln Leu Arg Ala Glu Asn Gly Leu Leu Met
                565                 570                 575

Thr Pro Cys Tyr Thr Ala Asn Phe Val Ala Pro Glu Val Leu Lys Arg
                580                 585                 590

Gln Gly Tyr Asp Ala Ala Cys Asp Ile Trp Ser Leu Gly Val Leu Leu
                595                 600                 605

Tyr Thr Met Leu Thr Gly Tyr Thr Pro Phe Ala Asn Gly Pro Asp Asp
            610                 615                 620

Thr Pro Glu Glu Ile Leu Ala Arg Ile Gly Ser Gly Lys Phe Ser Leu
625                 630                 635                 640

Ser Phe Phe Tyr Trp Asn Ser Val Ser Asp Thr Ala Lys Asp Leu Val
                645                 650                 655

Ser Lys Met Leu His Val Asp Pro His Gln Arg Leu Thr Ala Ala Leu
            660                 665                 670

Val Leu Arg His Pro Trp Ile Val His Trp Asp Gln Leu Pro Gln Tyr
            675                 680                 685

Gln Leu Asn Arg Gln Asp Ala Pro His Leu Val Lys Gly Ala Met Ala
            690                 695                 700

Ala Thr Tyr Ser Ala Leu Asn Arg Asn Gln Ser Pro Val Leu Glu Pro
705                 710                 715                 720

Val Gly Arg Ser Thr Leu Ala Gln Arg Arg Gly Ile Lys Lys Ser Ile
                725                 730                 735

Thr Thr Ala Leu
            740

<210> SEQ ID NO 40
<211> LENGTH: 733
<212> TYPE: PRT
<213> ORGANISM: Homo sapiens

<400> SEQUENCE: 40

Met Asp Leu Ser Met Lys Lys Phe Ala Val Arg Arg Phe Phe Ser Val
1               5                   10                  15

Tyr Leu Arg Arg Lys Ser Arg Ser Lys Ser Ser Ser Leu Ser Arg Leu
            20                  25                  30

Glu Glu Glu Gly Val Val Lys Glu Ile Asp Ile Ser His His Val Lys
            35                  40                  45

Glu Gly Phe Glu Lys Ala Asp Pro Ser Gln Phe Glu Leu Leu Lys Val
        50                  55                  60

Leu Gly Gln Gly Tyr Ser Gly Lys Val Phe Leu Val Arg Lys Val Lys
65                  70                  75                  80

Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110
```

```
Leu Ala Glu Val Asn His Pro Phe Ile Val Lys Leu His Tyr Ala Phe
        115                 120                 125

Gln Thr Glu Gly Lys Leu Tyr Leu Ile Leu Asp Phe Leu Arg Gly Gly
        130                 135                 140

Asp Leu Phe Thr Arg Leu Ser Lys Glu Val Met Phe Thr Glu Glu Asp
145                 150                 155                 160

Val Lys Phe Tyr Leu Ala Glu Leu Ala Leu Ala Leu Asp His Leu His
                165                 170                 175

Ser Leu Gly Ile Ile Tyr Arg Asp Leu Lys Pro Glu Asn Ile Leu Leu
            180                 185                 190

Asp Glu Glu Gly His Ile Lys Ile Thr Asp Arg Gly Leu Ser Lys Glu
        195                 200                 205

Ala Ile Asp His Asp Lys Arg Ala Tyr Ser Phe Cys Gly Thr Ile Glu
        210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Arg Glu Met Leu Thr Gly Ser
                245                 250                 255

Leu Pro Phe Gln Gly Lys Asp Arg Lys Glu Thr Met Ala Leu Ile Leu
            260                 265                 270

Lys Ala Lys Leu Gly Met Pro Gln Phe Leu Ser Gly Glu Ala Gln Ser
        275                 280                 285

Leu Leu Arg Ala Leu Phe Lys Arg Asn Pro Cys Asn Arg Leu Gly Ala
        290                 295                 300

Gly Ile Asp Gly Val Glu Glu Ile Lys Arg His Pro Phe Phe Val Thr
305                 310                 315                 320

Ile Asp Trp Asn Thr Leu Tyr Arg Lys Glu Ile Lys Pro Pro Phe Lys
                325                 330                 335

Pro Ala Leu Gly Arg Pro Glu Asp Thr Phe His Phe Asp Pro Glu Phe
            340                 345                 350

Thr Ala Arg Thr Pro Thr Asp Ser Pro Gly Val Pro Pro Ser Ala Asn
        355                 360                 365

Ala His His Leu Phe Arg Gly Arg Ser Arg Val Ala Ser Ser Leu Ile
        370                 375                 380

Gln Glu Pro Ser Gln Gln Asp Leu His Lys Val Pro Val His Pro Ile
385                 390                 395                 400

Val Gln Gln Leu His Gly Asn Asn Ile His Phe Thr Asp Gly Tyr Glu
                405                 410                 415

Ile Lys Glu Asp Ile Gly Val Gly Ser Tyr Ser Val Cys Lys Arg Cys
            420                 425                 430

Val His Lys Ala Thr Asp Thr Glu Tyr Ala Val Lys Ile Ile Asp Lys
        435                 440                 445

Ser Lys Arg Asp Pro Ser Glu Glu Ile Glu Ile Leu Leu Arg Tyr Gly
        450                 455                 460

Gln His Pro Asn Ile Ile Thr Leu Lys Asp Val Tyr Asp Asp Gly Lys
465                 470                 475                 480

Phe Val Tyr Leu Val Met Glu Leu Met Arg Gly Gly Glu Leu Leu Asp
                485                 490                 495

Arg Ile Leu Arg Gln Arg Tyr Phe Ser Glu Arg Glu Ala Ser Asp Val
            500                 505                 510

Leu Cys Thr Ile Thr Lys Thr Met Asp Tyr Leu His Ser Gln Gly Val
        515                 520                 525
```

-continued

```
Val His Arg Asp Leu Lys Pro Ser Asn Ile Leu Tyr Arg Asp Glu Ser
            530                 535                 540

Gly Ser Pro Glu Ser Ile Arg Val Cys Asp Phe Gly Phe Ala Lys Gln
545                 550                 555                 560

Leu Arg Ala Gly Asn Gly Leu Leu Met Thr Pro Cys Tyr Thr Ala Asn
                565                 570                 575

Phe Val Ala Pro Glu Val Leu Lys Arg Gln Gly Tyr Asp Ala Ala Cys
                580                 585                 590

Asp Ile Trp Ser Leu Gly Ile Leu Leu Tyr Thr Met Leu Ala Gly Phe
                595                 600                 605

Thr Pro Phe Ala Asn Gly Pro Asp Asp Thr Pro Glu Glu Ile Leu Ala
            610                 615                 620

Arg Ile Gly Ser Gly Lys Tyr Ala Leu Ser Gly Gly Asn Trp Asp Ser
625                 630                 635                 640

Ile Ser Asp Ala Ala Lys Asp Val Val Ser Lys Met Leu His Val Lys
                645                 650                 655

Pro His Gln Arg Leu Thr Ala Met Gln Val Leu Lys His Pro Trp Val
                660                 665                 670

Val Asn Arg Glu Tyr Leu Ser Pro Asn Gln Leu Ser Arg Gln Asp Val
                675                 680                 685

His Leu Val Lys Gly Ala Met Ala Ala Thr Tyr Phe Ala Leu Asn Arg
            690                 695                 700

Thr Pro Gln Ala Pro Arg Leu Glu Pro Val Leu Ser Ser Asn Leu Ala
705                 710                 715                 720

Gln Arg Arg Gly Met Lys Arg Leu Thr Ser Thr Arg Leu
                725                 730
```

<210> SEQ ID NO 41
<211> LENGTH: 279
<212> TYPE: PRT
<213> ORGANISM: Homo sapiens

<400> SEQUENCE: 41

```
Tyr Lys Val Thr Ser Gln Val Leu Gly Leu Gly Ile Asn Gly Lys Val
1               5                   10                  15

Leu Gln Ile Phe Asn Lys Arg Thr Gln Glu Lys Phe Ala Leu Lys Met
                20                  25                  30

Leu Gln Asp Cys Pro Lys Ala Arg Arg Glu Val Glu Leu His Trp Arg
            35                  40                  45

Ala Ser Gln Cys Pro His Ile Val Arg Ile Val Asp Val Tyr Glu Asn
        50                  55                  60

Leu Tyr Ala Gly Arg Lys Cys Leu Leu Ile Val Met Glu Cys Leu Asp
65                  70                  75                  80

Gly Gly Glu Leu Phe Ser Arg Ile Gln Asp Arg Gly Asp Gln Ala Phe
                85                  90                  95

Thr Glu Arg Glu Ala Ser Glu Ile Met Lys Ser Ile Gly Glu Ala Ile
            100                 105                 110

Gln Tyr Leu His Ser Ile Asn Ile Ala His Arg Asp Val Lys Pro Glu
        115                 120                 125

Asn Leu Leu Tyr Thr Ser Lys Arg Pro Asn Ala Ile Leu Lys Leu Thr
    130                 135                 140

Asp Phe Gly Phe Ala Lys Glu Thr Thr Ser His Asn Ser Leu Thr Thr
145                 150                 155                 160

Pro Cys Tyr Thr Pro Tyr Tyr Val Ala Pro Glu Val Leu Gly Pro Glu
                165                 170                 175
```

```
Lys Tyr Asp Lys Ser Cys Asp Met Trp Ser Leu Gly Val Ile Met Tyr
            180                 185                 190

Ile Leu Leu Cys Gly Tyr Pro Pro Phe Tyr Ser Asn His Gly Leu Ala
        195                 200                 205

Ile Ser Pro Met Lys Thr Arg Ile Arg Met Gly Gln Tyr Glu Phe Pro
    210                 215                 220

Asn Pro Glu Trp Ser Glu Val Ser Glu Glu Val Lys Met Leu Ile Arg
225                 230                 235                 240

Asn Leu Leu Lys Thr Glu Pro Thr Gln Arg Met Thr Ile Thr Glu Phe
                245                 250                 255

Met Asn His Pro Trp Ile Met Gln Ser Thr Lys Val Pro Gln Thr Pro
            260                 265                 270

Leu His Thr Ser Arg Val Leu
            275

<210> SEQ ID NO 42
<211> LENGTH: 196
<212> TYPE: PRT
<213> ORGANISM: Homo sapiens

<400> SEQUENCE: 42

Val Gln Leu Ser Lys Gln Val Leu Gly Leu Gly Val Asn Gly Lys Val
1               5                   10                  15

Leu Glu Cys Phe His Arg Arg Thr Gly Gln Lys Cys Ala Leu Lys Leu
            20                  25                  30

Leu Tyr Asp Ser Pro Lys Ala Arg Gln Glu Val Asp His Trp Gln
        35                  40                  45

Ala Ser Gly Gly Pro His Ile Val Cys Ile Leu Asp Val Tyr Glu Gly
    50                  55                  60

Phe Ala Lys Glu Thr Thr Gln Asn Ala Leu Gln Thr Pro Cys Tyr Thr
65                  70                  75                  80

Pro Tyr Tyr Val Ala Pro Glu Val Leu Gly Pro Glu Lys Tyr Asp Lys
                85                  90                  95

Ser Cys Asp Met Trp Ser Leu Gly Val Ile Met Tyr Ile Leu Leu Cys
            100                 105                 110

Gly Phe Pro Pro Phe Tyr Ser Asn Thr Gly Gln Ala Ile Ser Pro Gly
        115                 120                 125

Met Lys Arg Arg Ile Arg Leu Gly Gln Tyr Gly Phe Pro Asn Pro Glu
    130                 135                 140

Trp Ser Glu Val Ser Glu Asp Ala Lys Gln Leu Ile Arg Leu Leu Leu
145                 150                 155                 160

Lys Thr Asp Pro Thr Glu Arg Leu Thr Ile Thr Gln Phe Met Asn His
                165                 170                 175

Pro Trp Ile Asn Gln Ser Met Val Val Pro Gln Thr Pro Leu His Thr
            180                 185                 190

Ala Arg Val Leu
        195

<210> SEQ ID NO 43
<211> LENGTH: 297
<212> TYPE: PRT
<213> ORGANISM: Homo sapiens
```

<400> SEQUENCE: 43

| | | | | | | | | | | | | | | |
|---|---|---|---|---|---|---|---|---|---|---|---|---|---|---|
|Tyr|Lys|Leu|Thr|Ser|Glu|Leu|Gly|Glu|Gly|Ala|Tyr|Ala|Lys|Val|
|1| | | |5| | | |10| | | | |15| |
|Gln|Gly|Ala|Val|Ser|Leu|Gln|Asn|Gly|Lys|Glu|Tyr|Ala|Val|Lys|Ile|
| | | |20| | | | |25| | | | |30| |
|Ile|Glu|Lys|Gln|Ala|Gly|His|Ser|Arg|Ser|Arg|Val|Phe|Arg|Glu|Val|
| | | |35| | | | |40| | | | |45| |
|Glu|Thr|Leu|Tyr|Gln|Cys|Gln|Gly|Asn|Lys|Asn|Ile|Leu|Glu|Leu|Ile|
| |50| | | | |55| | | | |60| | | |
|Glu|Phe|Phe|Glu|Phe|Tyr|Leu|Val|Phe|Glu|Lys|Leu|Gln|Gly|Gly|Ser|
|65| | | | |70| | | | |75| | | | |80|
|Ile|Leu|Ala|His|Ile|Gln|Lys|Gln|Lys|His|Phe|Asn|Glu|Arg|Glu|Ala|
| | | | |85| | | | |90| | | | |95| |
|Ser|Arg|Val|Val|Arg|Asp|Val|Ala|Ala|Leu|Asp|Phe|Leu|His|Thr|
| | | | |100| | | | |105| | | | |110| |
|Lys|Gly|Ile|Ala|His|Arg|Asp|Leu|Lys|Pro|Glu|Asn|Ile|Leu|Cys|Glu|
| | | | |115| | | | |120| | | | |125| |
|Ser|Pro|Glu|Lys|Val|Ser|Pro|Val|Lys|Ile|Cys|Asp|Phe|Asp|Leu|Gly|
| | | |130| | | | |135| | | | |140| |
|Ser|Gly|Met|Lys|Leu|Asn|Asn|Ser|Cys|Thr|Pro|Ile|Thr|Thr|Pro|Glu|
|145| | | | |150| | | | |155| | | | |160|
|Leu|Thr|Thr|Pro|Cys|Gly|Ser|Ala|Glu|Tyr|Met|Ala|Pro|Glu|Val|Val|
| | | | |165| | | | |170| | | | |175| |
|Glu|Val|Phe|Thr|Asp|Gln|Ala|Thr|Phe|Tyr|Asp|Lys|Arg|Cys|Lys|Leu|
| | | |180| | | | |185| | | | |190| |
|Trp|Ser|Leu|Gly|Val|Val|Leu|Tyr|Ile|Met|Leu|Ser|Gly|Tyr|Pro|Pro|
| | | |195| | | | |200| | | | |205| |
|Phe|Val|Gly|His|Cys|Gly|Ala|Asp|Cys|Gly|Trp|Asp|Arg|Gly|Glu|Val|
| | | |210| | | | |215| | | | |220| |
|Cys|Arg|Val|Cys|Gln|Asn|Lys|Leu|Phe|Glu|Ser|Ile|Gln|Glu|Gly|Lys|
|225| | | | |230| | | | |235| | | | |240|
|Tyr|Glu|Phe|Pro|Asp|Lys|Asp|Trp|Ala|His|Ile|Ser|Ser|Glu|Ala|Lys|
| | | | |245| | | | |250| | | | |255| |
|Asp|Leu|Ile|Ser|Lys|Leu|Leu|Val|Arg|Asp|Ala|Lys|Gln|Arg|Leu|Ser|
| | | |260| | | | |265| | | | |270| |
|Ala|Ala|Gln|Val|Leu|Gln|His|Pro|Trp|Val|Gln|Gly|Gln|Ala|Pro|Glu|
| | | |275| | | | |280| | | | |285| |
|Lys|Gly|Leu|Pro|Thr|Pro|Gln|Val|Leu|
| |290| | | | |295| | |

<210> SEQ ID NO 44
<211> LENGTH: 740
<212> TYPE: PRT
<213> ORGANISM: Mus musculus

<400> SEQUENCE: 44

| | | | | | | | | | | | | | | |
|---|---|---|---|---|---|---|---|---|---|---|---|---|---|---|
|His|Ala|Ser|Gly|Asp|Glu|Asp|Glu|Asp|Glu|Phe|Cys|Ala|Val|Glu|Leu|
|1| | | |5| | | | |10| | | | |15| |
|Gln|Ile|Thr|Glu|Ala|Asn|Leu|Thr|Gly|His|Glu|Glu|Lys|Val|Ser|Val|
| | | |20| | | | |25| | | | |30| |
|Glu|Asn|Phe|Ala|Leu|Leu|Lys|Val|Leu|Gly|Thr|Phe|Tyr|Gly|Lys|
| | | |35| | | | |40| | | | |45| |
|Val|Phe|Leu|Val|Arg|Lys|Thr|Gly|Gly|His|Asp|Ala|Gly|Lys|Leu|Tyr|
| |50| | | | |55| | | | |60| | | |

-continued

```
Ala Met Lys Val Leu Arg Lys Ala Ala Leu Val Gln Arg Ala Lys Thr
 65                  70                  75                  80

Gln Glu His Thr Arg Thr Glu Arg Ser Val Leu Glu Leu Val Arg Gln
                 85                  90                  95

Ala Pro Phe Leu Val Thr Leu His Tyr Ala Phe Gln Thr Asp Ala Lys
            100                 105                 110

Leu His Leu Ile Leu Asp Tyr Val Ser Gly Gly Glu Met Phe Thr His
            115                 120                 125

Leu Tyr Gln Arg Gln Tyr Phe Lys Glu Ala Glu Val Arg Val Tyr Gly
    130                 135                 140

Gly Glu Ile Val Leu Ala Leu Glu His Leu His Lys Leu Gly Ile Ile
145                 150                 155                 160

Tyr Arg Asp Leu Lys Leu Glu Asn Val Leu Leu Asp Ser Glu Gly His
                165                 170                 175

Ile Val Leu Thr Asp Phe Gly Leu Ser Lys Glu Phe Leu Thr Glu Glu
            180                 185                 190

Lys Glu Arg Thr Phe Ser Phe Cys Gly Thr Ile Glu Tyr Met Ala Pro
        195                 200                 205

Glu Ile Ile Arg Ser Lys Ala Gly His Gly Lys Ala Val Asp Trp Trp
    210                 215                 220

Ser Leu Gly Ile Leu Leu Phe Glu Leu Leu Thr Gly Ala Ser Pro Phe
225                 230                 235                 240

Thr Leu Glu Gly Glu Arg Asn Thr Gln Ala Glu Val Ser Arg Arg Ile
                245                 250                 255

Leu Lys Cys Ser Pro Pro Phe Pro Leu Arg Ile Gly Pro Val Ala Gln
            260                 265                 270

Asp Leu Leu Gln Arg Leu Leu Cys Lys Asp Pro Lys Lys Arg Leu Gly
        275                 280                 285

Ala Gly Pro Gln Gly Ala Gln Glu Val Lys Ser His Pro Phe Phe Arg
    290                 295                 300

Val Trp Thr Gly Trp Ala Leu Ala Ala Arg Lys Ile Pro Ala Pro Phe
305                 310                 315                 320

Arg Pro Gln Ile Arg Ser Glu Leu Asp Val Gly Asn Phe Ala Glu Glu
                325                 330                 335

Phe Thr Arg Leu Glu Pro Val Tyr Ser Pro Ala Gly Ser Pro Pro Pro
            340                 345                 350

Gly Asp Pro Arg Ile Phe Gln Gly Tyr Ser Phe Val Ala Pro Ser Ile
        355                 360                 365

Leu Phe Asp His Asn Asn Ala Val Met Ala Asp Val Leu Gln Ala Pro
    370                 375                 380

Gly Ala Gly Tyr Arg Pro Gly Arg Ala Ala Val Ala Arg Ser Ala Met
385                 390                 395                 400

Met Gln Asp Ser Pro Phe Phe Gln Gln Tyr Glu Leu Asp Leu Arg Glu
                405                 410                 415

Pro Ala Leu Gly Gln Gly Ser Phe Ser Val Cys Arg Cys Arg Gln
            420                 425                 430

Arg Gln Ser Gly Gln Glu Phe Ala Val Lys Ile Leu Ser Arg Arg Leu
        435                 440                 445

Glu Glu Asn Thr Gln Arg Glu Val Ala Ala Leu Arg Leu Cys Gln Ser
    450                 455                 460

His Pro Asn Val Val Asn Leu His Glu Val Leu His Asp Gln Leu His
465                 470                 475                 480
```

-continued

```
Thr Tyr Leu Val Leu Glu Leu Arg Gly Glu Leu Leu Glu His
            485                 490                 495

Ile Arg Lys Lys Arg Leu Phe Ser Glu Ser Glu Ala Ser Gln Ile Leu
            500                 505                 510

Arg Ser Leu Val Ser Ala Val Ser Phe Met His Glu Glu Ala Gly Val
            515                 520                 525

Val His Arg Asp Leu Lys Pro Glu Asn Ile Leu Tyr Ala Asp Asp Thr
530                 535                 540

Pro Gly Ala Pro Val Lys Ile Ile Asp Phe Gly Phe Ala Arg Leu Arg
545                 550                 555                 560

Pro Gln Ser Pro Ala Glu Pro Met Gln Thr Pro Cys Phe Thr Leu Gln
                565                 570                 575

Tyr Ala Ala Pro Glu Leu Leu Ala Gln Gln Gly Tyr Asp Glu Ser Cys
                580                 585                 590

Asp Leu Trp Ser Leu Gly Val Ile Leu Tyr Met Met Leu Ser Gly Gln
                595                 600                 605

Val Pro Phe Gln Gly Ala Ser Gly Gln Gly Gln Ser Gln Ala Ala
610                 615                 620

Glu Ile Met Cys Lys Ile Arg Glu Gly Arg Phe Ser Leu Asp Gly Glu
625                 630                 635                 640

Ala Trp Gln Gly Val Ser Glu Glu Ala Lys Glu Leu Val Arg Gly Leu
                645                 650                 655

Leu Thr Val Asp Pro Ala Lys Arg Leu Lys Leu Glu Gly Leu Arg Ser
                660                 665                 670

Ser Ser Trp Leu Gln Asp Gly Ser Ala Arg Ser Ser Pro Pro Leu Arg
            675                 680                 685

Thr Pro Asp Val Leu Glu Ser Ser Gly Pro Ala Val Arg Ser Gly Leu
            690                 695                 700

Asn Ala Thr Phe Met Ala Phe Asn Arg Gly Lys Arg Glu Gly Phe Phe
705                 710                 715                 720

Leu Lys Ser Val Glu Asn Ala Pro Leu Ala Lys Arg Arg Lys Gln Lys
                725                 730                 735

Leu Arg Ser Ala
            740
```

<210> SEQ ID NO 45
<211> LENGTH: 510
<212> TYPE: PRT
<213> ORGANISM: Homo sapiens
<220> FEATURE:
<221> NAME/KEY: misc_feature
<222> LOCATION: (373)..(373)
<223> OTHER INFORMATION: residue 373 is unknown

<400> SEQUENCE: 45

```
Gln Thr Glu Val Ser Arg Arg Ile Leu Lys Cys Ser Pro Phe Pro
1               5                   10                  15

Pro Arg Ile Gly Pro Val Ala Gln Asp Leu Leu Gln Arg Leu Leu Cys
            20                  25                  30

Lys Asp Pro Lys Lys Arg Leu Gly Ala Gly Pro Gln Gly Ala Gln Glu
            35                  40                  45

Val Arg Asn His Pro Phe Phe Gln Gly Leu Asp Trp Val Ala Leu Ala
        50                  55                  60

Ala Arg Lys Ile Pro Ala Pro Phe Arg Pro Gln Ile Arg Ser Glu Leu
65                  70                  75                  80
```

-continued

```
Asp Val Gly Asn Phe Ala Glu Glu Phe Thr Arg Leu Glu Pro Val Tyr
                85                  90                  95

Ser Pro Pro Gly Ser Pro Pro Gly Asp Pro Arg Ile Phe Gln Gly
            100                 105                 110

Tyr Ser Phe Val Ala Pro Ser Ile Leu Phe Asp His Asn Asn Ala Val
            115                 120                 125

Met Thr Asp Gly Leu Glu Ala Pro Gly Ala Gly Asp Arg Pro Gly Arg
    130                 135                 140

Ala Ala Val Ala Arg Ser Ala Met Met Gln Asp Ser Pro Phe Phe Gln
145                 150                 155                 160

Gln Tyr Glu Leu Asp Leu Arg Glu Pro Ala Leu Gly Gln Gly Ser Phe
                165                 170                 175

Ser Val Cys Arg Arg Cys Arg Gln Arg Gln Ser Gly Gln Glu Phe Ala
            180                 185                 190

Val Lys Ile Leu Ser Arg Arg Leu Glu Ala Asn Thr Gln Arg Glu Val
            195                 200                 205

Ala Ala Leu Arg Leu Cys Gln Ser His Pro Asn Val Val Asn Leu His
    210                 215                 220

Glu Val His His Asp Gln Leu His Thr Tyr Leu Val Leu Glu Leu Leu
225                 230                 235                 240

Arg Gly Gly Glu Leu Leu Glu His Ile Arg Lys Lys Arg His Phe Ser
                245                 250                 255

Glu Ser Glu Ala Ser Gln Ile Leu Arg Ser Leu Val Ser Ala Val Ser
            260                 265                 270

Phe Met His Glu Glu Ala Gly Val Val His Arg Asp Leu Lys Pro Glu
    275                 280                 285

Asn Ile Leu Tyr Ala Asp Asp Thr Pro Gly Ala Pro Val Lys Ile Ile
            290                 295                 300

Asp Phe Gly Phe Ala Arg Leu Arg Pro Gln Ser Pro Gly Val Pro Met
305                 310                 315                 320

Gln Thr Pro Cys Phe Thr Leu Gln Tyr Ala Ala Pro Glu Leu Leu Ala
                325                 330                 335

Gln Gln Gly Tyr Asp Glu Ser Cys Asp Leu Trp Ser Leu Gly Val Ile
            340                 345                 350

Leu Tyr Met Met Leu Ser Gly Gln Val Pro Phe Gln Gly Ala Ser Gly
    355                 360                 365

Gln Gly Gly Gln Xaa Gln Ala Ala Glu Ile Met Cys Lys Ile Arg Glu
    370                 375                 380

Gly Arg Phe Ser Leu Asp Gly Glu Ala Trp Gln Gly Val Ser Glu Glu
385                 390                 395                 400

Ala Lys Glu Leu Val Arg Gly Leu Leu Thr Val Asp Pro Ala Lys Arg
                405                 410                 415

Leu Lys Leu Glu Gly Leu Arg Gly Ser Ser Trp Leu Gln Asp Gly Ser
            420                 425                 430

Ala Arg Ser Ser Pro Pro Leu Arg Thr Pro Asp Val Leu Glu Ser Ser
    435                 440                 445

Gly Pro Ala Val Arg Ser Gly Leu Asn Ala Thr Phe Met Ala Phe Asn
450                 455                 460

Arg Gly Lys Arg Glu Gly Phe Phe Leu Lys Ser Val Glu Asn Ala Pro
465                 470                 475                 480
```

```
Leu Asn Cys His Phe Met Asp Cys Leu Cys Asn Tyr Val His Gln Arg
                485                 490                 495

Pro Val Leu Gly Val Leu Lys Glu Arg Pro Trp Gly Thr Leu
            500                 505                 510
```